United States Patent
Banine et al.

(10) Patent No.: US 10,580,545 B2
(45) Date of Patent: Mar. 3, 2020

(54) BEAM DELIVERY APPARATUS AND METHOD

(71) Applicant: ASML Netherlands B.V., Veldhoven (NL)

(72) Inventors: Vadim Yevgenyevich Banine, Veldhoven (NL); Petrus Rutgerus Bartraij, Veldhoven (NL); Ramon Pascal Van Gorkom, Veldhoven (NL); Lucas Johannes Peter Ament, Veldhoven (NL); Pieter Willem Herman De Jager, Veldhoven (NL); Gosse Charles De Vries, Veldhoven (NL); Rilpho Ludovicus Donker, Veldhoven (NL); Wouter Joep Engelen, Veldhoven (NL); Olav Waldemar Vladimir Frijns, Veldhoven (NL); Leonardus Adrianus Gerardus Grimminck, Veldhoven (NL); Andelko Katalenic, Veldhoven (NL); Erik Roelof Loopstra, Veldhoven (NL); Han-Kwang Nienhuys, Veldhoven (NL); Andrey Alexandrovich Nikipelov, Veldhoven (NL); Michael Jozef Mathijs Renkens, Veldhoven (NL); Franciscus Johannes Joseph Janssen, Veldhoven (NL); Borgert Kruizinga, Veldhoven (NL)

(73) Assignee: ASML Netherlands B.V., Veldhoven (NL)

( * ) Notice: Subject to any disclaimer, the term of this patent is extended or adjusted under 35 U.S.C. 154(b) by 0 days.

(21) Appl. No.: 14/917,623

(22) PCT Filed: Sep. 24, 2014

(86) PCT No.: PCT/EP2014/070335
§ 371 (c)(1),
(2) Date: Mar. 9, 2016

(87) PCT Pub. No.: WO2015/044182
PCT Pub. Date: Apr. 2, 2015

(65) Prior Publication Data
US 2016/0225477 A1 Aug. 4, 2016

Related U.S. Application Data

(60) Provisional application No. 61/882,336, filed on Sep. 25, 2013, provisional application No. 61/897,046, (Continued)

(30) Foreign Application Priority Data

Dec. 20, 2013 (EP) .................................. 13199009
Jan. 16, 2014 (EP) .................................. 14151497
(Continued)

(51) Int. Cl.
*G03F 7/20* (2006.01)
*G21K 1/06* (2006.01)

(52) U.S. Cl.
CPC ......... *G21K 1/067* (2013.01); *G03F 7/70025* (2013.01)

(58) Field of Classification Search
None
See application file for complete search history.

(56) References Cited

U.S. PATENT DOCUMENTS

| 3,204,101 A | 8/1965 | Brumfield et al. |
| 4,778,263 A | 10/1988 | Foltyn |

(Continued)

FOREIGN PATENT DOCUMENTS

| DE | 3818129 A1 | 11/1989 |
| DE | 10358225 B3 | 6/2005 |

(Continued)

OTHER PUBLICATIONS

Flavell, et al., "4GLS—the UK's fourth generation light source at Daresbury: new prosepcts in biological surface science," Journal of Physics: Condensed Matter 16, Jun. 18, 2004; pp. S2405-S2412.
(Continued)

*Primary Examiner* — Andrew Smyth
(74) *Attorney, Agent, or Firm* — Sterne, Kessler, Goldstein & Fox P.L.L.C.

(57) ABSTRACT

A delivery system for use within a lithographic system. The beam delivery system comprises optical elements arranged to receive a radiation beam from a radiation source and to reflect portions of radiation along one or more directions to form a one or more branch radiation beams for provision to one or more tools.

38 Claims, 73 Drawing Sheets

Related U.S. Application Data filed on Oct. 29, 2013, provisional application No. 61/905,053, filed on Nov. 15, 2013.

(30) Foreign Application Priority Data

| | | | |
|---|---|---|---|
| Jan. 24, 2014 | (EP) | ................................... | 14152443 |
| Feb. 20, 2014 | (EP) | ................................... | 14155980 |
| Apr. 23, 2014 | (EP) | ................................... | 14165675 |
| Jun. 4, 2014 | (EP) | ................................... | 14171050 |
| Jun. 4, 2014 | (EP) | ................................... | 14171051 |
| Jun. 18, 2014 | (EP) | ................................... | 14172951 |
| Jun. 23, 2014 | (EP) | ................................... | 14173446 |

(56) References Cited

U.S. PATENT DOCUMENTS

| | | | |
|---|---|---|---|
| 4,999,839 A | | 3/1991 | Deacon |
| 5,068,751 A | | 11/1991 | Braat et al. |
| 5,161,238 A | | 11/1992 | Mehmke |
| 5,222,112 A | | 6/1993 | Terasawa et al. |
| 5,317,618 A | | 5/1994 | Nakahara et al. |
| 5,557,347 A | | 9/1996 | Johnson |
| 5,572,563 A | | 11/1996 | Kasumi et al. |
| 5,867,239 A | | 2/1999 | Sahouani et al. |
| 5,969,441 A | * | 10/1999 | Loopstra ................ B23Q 1/621 310/12.06 |
| 6,028,660 A | | 2/2000 | Van Der Laan et al. |
| 6,081,581 A | | 6/2000 | Hasegawa |
| 6,331,710 B1 | * | 12/2001 | Wang .................... G02B 13/143 250/492.2 |
| 6,398,374 B1 | * | 6/2002 | Chapman ............ G03F 7/70075 359/364 |
| 6,753,946 B2 | | 6/2004 | Mulkens et al. |
| 6,754,302 B2 | * | 6/2004 | Kitaoka ................. B82Y 10/00 378/34 |
| 6,842,293 B1 | | 1/2005 | Yin et al. |
| 7,129,807 B2 | | 10/2006 | Rossmanith et al. |
| 7,209,286 B2 | | 4/2007 | Mann et al. |
| 7,248,667 B2 | * | 7/2007 | Weiss ..................... B82Y 10/00 250/492.2 |
| 8,848,167 B2 | | 9/2014 | Lippert et al. |
| 9,823,572 B2 | | 11/2017 | Nikipelov et al. |
| 2002/0018189 A1 | * | 2/2002 | Mulkens ............. G03F 7/70558 355/30 |
| 2002/0141533 A1 | * | 10/2002 | Kitaoka ................. B82Y 10/00 378/34 |
| 2003/0160949 A1 | | 8/2003 | Komatsuda et al. |
| 2003/0179919 A1 | | 9/2003 | Goldberg et al. |
| 2003/0189696 A1 | | 10/2003 | Sumiyoshi et al. |
| 2003/0219094 A1 | | 11/2003 | Basting et al. |
| 2004/0051954 A1 | * | 3/2004 | Bristol ................... G02B 5/1838 359/634 |
| 2004/0114122 A1 | | 6/2004 | Teeuwen |
| 2004/0184019 A1 | | 9/2004 | Totzeck et al. |
| 2005/0122495 A1 | * | 6/2005 | Kaplan ............... G03F 7/70258 355/52 |
| 2005/0213070 A1 | | 9/2005 | Scharnweber |
| 2005/0219498 A1 | | 10/2005 | Mori |
| 2005/0224702 A1 | | 10/2005 | Koehler et al. |
| 2006/0001890 A1 | | 1/2006 | Poultney |
| 2006/0127811 A1 | | 6/2006 | Josephina Moors et al. |
| 2006/0138350 A1 | | 6/2006 | Banine et al. |
| 2007/0152171 A1 | | 7/2007 | Goldstein et al. |
| 2007/0248127 A1 | | 10/2007 | Shiraishi |
| 2008/0151221 A1 | | 6/2008 | Sogard |
| 2008/0240182 A1 | | 10/2008 | Smith et al. |
| 2009/0153975 A1 | | 6/2009 | O'Reilly et al. |
| 2009/0154642 A1 | | 6/2009 | Bykanov et al. |
| 2009/0213356 A1 | | 8/2009 | Gruner et al. |
| 2009/0218521 A1 | | 9/2009 | Sogard et al. |
| 2009/0224179 A1 | | 9/2009 | Shirai |
| 2010/0045410 A1 | | 2/2010 | Beckenbach et al. |
| 2010/0117009 A1 | | 5/2010 | Moriya et al. |
| 2010/0149548 A1 | * | 6/2010 | Shmarev .......... G01N 21/95607 356/517 |
| 2011/0014799 A1 | | 1/2011 | Dinger et al. |
| 2011/0109890 A1 | | 5/2011 | Komatsuda |
| 2011/0222040 A1 | | 9/2011 | Steinhoff et al. |
| 2012/0002294 A1 | | 1/2012 | Dobschal et al. |
| 2012/0044473 A1 | * | 2/2012 | Lippert ................... G02B 1/10 355/66 |
| 2012/0212724 A1 | | 8/2012 | Osaka |
| 2012/0242968 A1 | | 9/2012 | Layh et al. |
| 2012/0281816 A1 | | 11/2012 | Kuroda et al. |
| 2013/0010352 A1 | | 1/2013 | Chan et al. |
| 2013/0148203 A1 | | 6/2013 | Debus et al. |
| 2016/0147161 A1 | | 5/2016 | Nikipelov et al. |

FOREIGN PATENT DOCUMENTS

| | | | | |
|---|---|---|---|---|
| DE | 102008031650 A1 | | 2/2010 | |
| EP | 0927595 A1 | | 7/1999 | |
| EP | 1223468 A1 | | 7/2002 | |
| EP | 1324138 A2 | * | 7/2003 | ......... G03F 7/70275 |
| EP | 1324138 A2 | * | 7/2003 | ......... G03F 7/70275 |
| EP | 1347271 A1 | | 9/2003 | |
| EP | 1376192 A2 | | 1/2004 | |
| EP | 1469347 A1 | | 10/2004 | |
| EP | 1580603 A2 | | 9/2005 | |
| EP | 1324138 A3 | * | 12/2007 | ......... G03F 7/70275 |
| EP | 1324138 A3 | * | 12/2007 | ......... G03F 7/70275 |
| EP | 1914583 A2 | | 4/2008 | |
| EP | 2454633 A1 | | 5/2012 | |
| GB | 1075205 A | | 7/1967 | |
| JP | H05-234857 A | | 9/1993 | |
| JP | H07-174896 A | | 7/1995 | |
| JP | H07272670 A | | 10/1995 | |
| JP | H1092717 A | | 4/1998 | |
| JP | 2001004931 A | | 1/2001 | |
| JP | 2001313435 A | * | 11/2001 | |
| JP | 2001313435 A | * | 11/2001 | |
| JP | 2002-299221 A | | 10/2002 | |
| JP | 2003-218026 A | | 7/2003 | |
| JP | 2009119491 A | * | 6/2009 | |
| JP | 2009119491 A | * | 6/2009 | |
| JP | 2010-197630 A | | 9/2010 | |
| JP | 2010-199562 A | | 9/2010 | |
| JP | 2012-069925 A | | 4/2012 | |
| JP | 2016-528528 A | | 9/2016 | |
| KR | 20100029651 A | | 3/2010 | |
| TW | 594044 B | | 6/2004 | |
| TW | 2007-41366 A | | 11/2007 | |
| WO | WO 01/82001 A1 | | 11/2001 | |
| WO | WO 03/077011 A1 | | 9/2003 | |
| WO | WO 2013/072352 A1 | | 5/2013 | |
| WO | WO 2011/096428 A1 | | 6/2013 | |
| WO | WO 2014/023660 A1 | | 2/2014 | |

OTHER PUBLICATIONS

Svetina, et al., "An active optics system for EUV/Soft x-ray beam shaping," Proceedings of SPIE, vol. 8503, (2012); pp. 850302-01-850302-8.

Hahn, et al., "Concept of electron beam diagnostic for the VUV SASE FEL at the TESLA Test Facility (TTF FEL) at DESY," Nuclear Instruments and Methods in Physics Research A 429 (1999); pp. 276-280.

Byrd, et al., "Design and manufacture of optical system for use in ultraviolet lithography with the free electron laser," Proceedings of SPIE, vol. 1868, Aug. 13, 1993; pp. 180-195.

(56) References Cited

OTHER PUBLICATIONS

Elleaume, et al., "Design considerations for a 1 Å SASE undulator," Nuclear Instruments and Methods in Physics Research A 455 (2000); pp. 503-523.

Newnam, B., "Development of free-electron lasers for XUV projection lithography," Proceedings of SPIE, vol. 1227, Jan. 14, 1990; pp. 116-133.

Azima, et al., "Experimental Layout of 30 nm High Harmonic Laser Seeding at Flash," Proceedings of EPAC08, Jun. 23, 2008; pp. 127-129.

Newnam, B., "Extreme ultraviolet free-electron laser-based projection," Optical Engineering, vol. 30, No. 8, Aug. 1991; pp. 1100-1108.

Zangrando, et al., "First results from the commissioning of the FERMI@Elettra free electron laser by means of the Photon Analysis Delivery and Reduction System (PADReS)," Proceedings of SPIE, vol. 8078, (2011); pp. 807801-1-807801-11.

Freund, et al., "Free-Electron Lasers: Vacuum Electronic Generators of Coherent Radition," Proceedings of the IEEE, vol. 87, No. 5, May 1999; pp. 782-803.

Raimondi, et al., "K-B bendable system optimization at FERMI@Elettra FEL: impact of different spatial wavelengths on the spot size," Proceedings of SPIE, vol. 8848, (2013); pp. 88480B-1 0 88480B-8.

Stevenson, et al., "Metrological gratings and moire fringe detection methods for displacement transducers," IEE Proceedings, vol. 136, Pt. A, No. 5, Sep. 1989; pp. 243-253.

Decker, et al., "Multiple FELs From the One LCLS Undulator," Proceedings of FEL2011, Aug. 2011; pp. 629-632.

Svetina, et al., "A beam-shaping system for TIMEX beamline," Nuclear Instruments and Methods in Physics Research A 635 (2011); pp. S12-S15.

Csonka, P., "Rotation and Shape of High Altitude Reflectors Controlled from the Ground," IEEE Transaction on Aerospace and Electronic Systems, vol. 19, No. 2, Mar. 1983; pp. 215-220.

Zangrando, et al., "The photon analysis, delivery, and reduction system at the FERMI@Elettra free electron laser user facility," Review of Scientific Instruments 80 (2009); pp. 113110-1-113110-5.

Oberta, et al., "The SwissFEL facility and its preliminary optics beamline layout," Proceedings of SPIE, vol. 8078, (2011); pp. 807805-1-807805-13.

Yu, et al., "The DUV-FEL Development Program," Brookhaven National Laboratory, Jun. 2001; 5 pages.

Cirmi, et al., "Cut-off scaling of high-harmonic generation driven by a femtosecond visible optical parametric amplifier," Journal of Physics B: Atomic, Molecular, and Optical Physics 45 (2012); 10 pages.

Di Mitri, et al., "FERMI@Elettra, a seeded free electron laser source for a broad scientific user program," Proceedings of SPIE, vol. 8078, (2011); pp. 807802-1-807802-13.

International Search Report and Written Opinion of the International Searching Authority directed to related International Patent Application No. PCT/EP2014/070335, dated Aug. 12, 2015; 73 pages.

International Preliminary Report on Patentability directed to related International Patent Application No. PCT/EP2014/070335, dated Mar. 29, 2016; 50 pages.

* cited by examiner

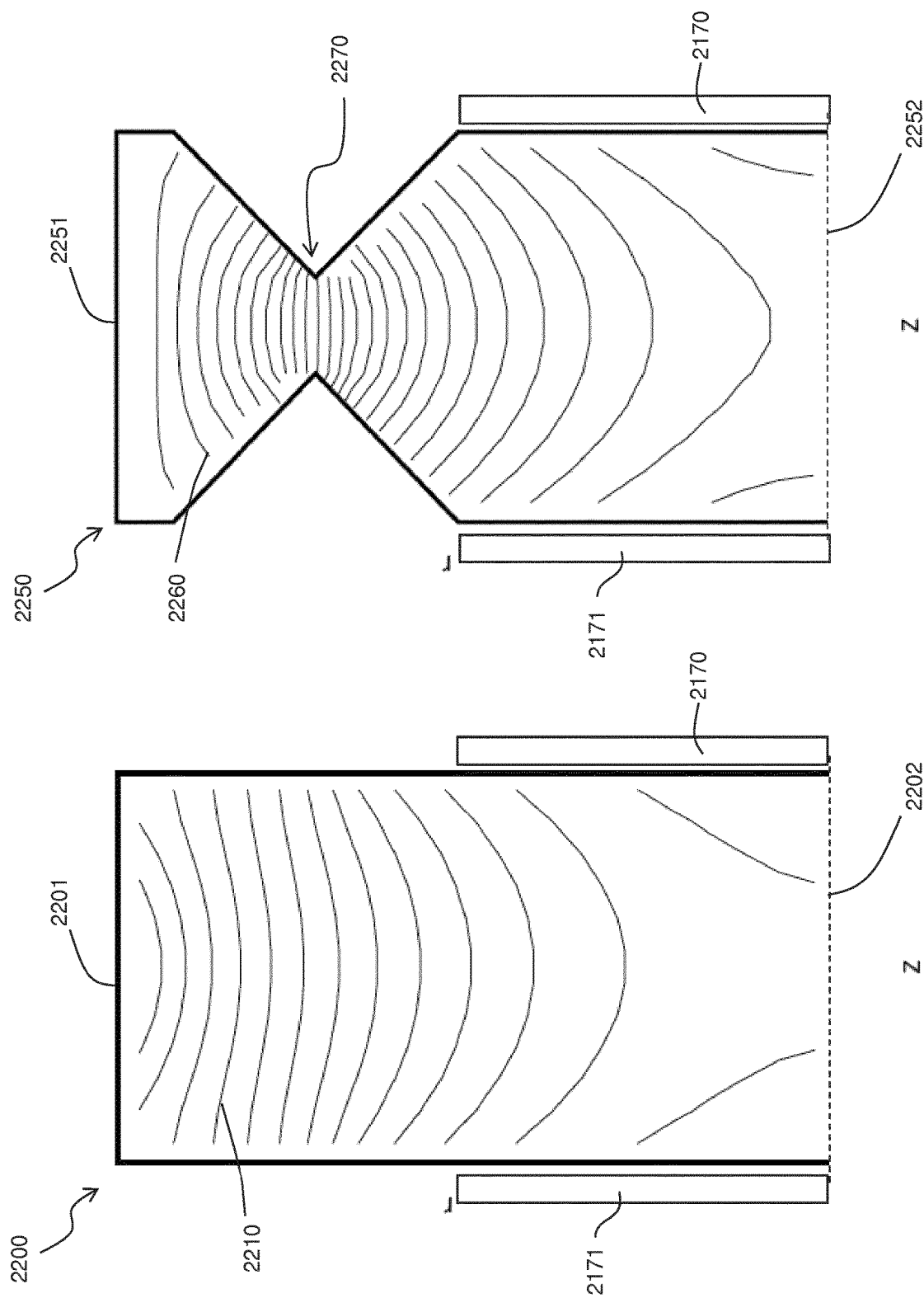

BEAM DELIVERY APPARATUS AND METHOD

CROSS-REFERENCE TO RELATED APPLICATIONS

This application claims the benefit of U.S. provisional application 61/882,336 which was filed on 25 Sep. 2013, and U.S. provisional application 61/897,046 which was filed on 29 Oct. 2013, and U.S. provisional 61/905,053 which was filed on 15 Nov. 2013, and EP application EP13199009.5 which was filed on 20 Dec. 2013, and EP application EP14152443.9 which was filed on 24 Jan. 2014, and EP application EP14151497.6 which was filed on 16 Jan. 2014, and EP application EP14155980.7 which was filed on 20 Feb. 2014, and EP application EP14165675.1 which was filed on 23 Apr. 2014, and EP application EP14171051.7 which was filed on 4 Jun. 2014, and EP application EP14172951.7 which was filed on 18 Jun. 2014, and EP application EP14171050.9 which was filed on 4 Jun. 2014, and EP application EP14173446.7 which was filed on 23 Jun. 2014 and which are incorporated herein in its entirety by reference.

FIELD

The present invention relates to a beam delivery apparatus. Particularly, but not exclusive, the present invention has application within lithographic systems that incorporate one or more free electron lasers.

BACKGROUND

A lithographic system comprises a radiation source and at least one lithographic apparatus. A lithographic apparatus is a machine constructed to apply a desired pattern onto a substrate. A lithographic apparatus can be used, for example, in the manufacture of integrated circuits (ICs). A lithographic apparatus may for example project a pattern from a patterning device (e.g. a mask) onto a layer of radiation-sensitive material (resist) provided on a substrate.

The wavelength of radiation used by a lithographic apparatus to project a pattern onto a substrate determines the minimum size of features which can be formed on that substrate. A lithographic apparatus which uses EUV radiation, being electromagnetic radiation having a wavelength within the range 4-20 nm, may be used to form smaller features on a substrate than a conventional lithographic apparatus (which may for example use electromagnetic radiation with a wavelength of 193 nm).

A lithographic apparatus may be provided with radiation from a radiation source which forms part of a lithographic system. A plurality of lithographic apparatus may be supplied by a single radiation source. The radiation source may comprise at least one free electron laser which emits EUV radiation.

It is desirable to provide a beam delivery apparatus or method that is suitable for a radiation source for providing one or more tools with radiation and which obviates or mitigates one or more of the problems associated with known beam delivery apparatuses or methods.

SUMMARY

According to a first aspect there is provided a beam splitting apparatus for use within a lithographic system, comprising a plurality of static mirrors each arranged to receive a different part of a first radiation beam from a radiation source and to reflect a respective portion of radiation along one of a plurality of directions to form a plurality of branch radiation beams for provision to a plurality of tools.

The first aspect provides an efficient apparatus for splitting a single radiation beam into a plurality of radiation beams for provision to a plurality of tools, such as lithographic tools. By utilizing a plurality of static mirrors, the apparatus of the first aspect is easy to maintain.

The radiation source may comprise one or more free electron lasers.

Each of the plurality of directions may provide a respective branch optical path, each branch optical path being associated with a respective one of the plurality of tools. At least one branch optical path may be associated with a plurality of the static mirrors such that at least one branch radiation beam comprises a plurality the reflected portions. Each of the branch optical paths may be associated with a respective plurality of the static mirrors such that each branch radiation beam comprises a plurality of said reflected portions. The branch radiation beams may therefore be formed from different parts of the first radiation beam. For example, each branch radiation beam may be formed from portions corresponding to different parts of an intensity distribution of the first radiation beam.

Each static mirror may be arranged to extend partially across the first radiation beam.

At least some of the plurality of static mirrors are configured to reflect a solid area of the first radiation beam.

At least some of the plurality of static mirrors may be provided by a reflective grating. Each of a plurality faces of the grating may provide a respective one of the plurality of static mirrors.

Each reflective face of the grating that is associated with a same one of the plurality of directions may extend substantially parallel to a single silicon crystal plane. In this way, the grating may be particularly efficient to manufacture.

The grating may be a macro-scale grating. For example, a width of faces of the grating and/or a pitch between faces of the grating may be greater than 100 micrometres, for example 1 millimetre.

The reflective faces of the grating may be arranged such that expansion of each reflected portion causes partial overlap of at least two reflected portions associated with one branch optical path at the one of the plurality of tools associated with the one branch optical path. The reflective faces are arranged such that the overlapping reflected portions provide a branch radiation beam having an intensity profile substantially the same as an intensity profile of the first radiation beam. The expansion of each reflected portion may be caused, at least in part, by diffraction.

The grating may comprise a first plurality of faces associated with a first branch optical path to provide a first branch radiation beam. Each one of the first plurality of faces may be arranged to reflect a respective portion of the first radiation beam to form a respective sub-beam of the first branch radiation beam. The first plurality of faces may be arranged such that if a position of the first radiation beam changes in a plane perpendicular to a propagation direction of the first radiation beam, a power received by at least one of the first plurality of faces increases and a power received by at least one of the first plurality of faces decreases. In this way, the grating may be made insensitive to shifts in the position of the first radiation beam with respect to the grating.

The grating may be a micro-scale grating. For example, a width of the faces of the grating, and/or a pitch between faces of the grating may be of the order of micrometers, and may be less than 100 micrometers.

The reflective faces of the grating may be arranged such that portions of radiation reflected from the grating diffract to provide the plurality of branch radiation beams. For example, portions of the radiation reflected from the grating will spread out/expand. Those reflected portions will overlap as they propagate from the grating causing interference between the reflected portions. The interference (or diffraction) results in a plurality of positions of maximum intensity (or maxima). Each maxima may provide a respective branch radiation beam.

The reflective faces of the grating may be arranged such that each branch radiation beam has an intensity profile substantially similar to an intensity profile of the first radiation beam.

The reflective faces of the grating may have translational symmetry in at least one direction perpendicular to a direction of propagation of the first radiation beam. In this way, the grating may be made insensitive to variance in the pointing direction, and/or translation of, the first radiation beam.

The beam splitting apparatus may comprise expansion and/or flat-top forming optics and the reflective grating may be disposed upstream of said expansion and/or flat-top forming optics.

The reflective faces of the grating may be arranged to receive the radiation beam from a flat mirror disposed between the grating and the radiation source. This may help to protect the grating and other components from Bremsstrahlung radiation.

The grating may be formed from etched silicon. Grooves and/or faces of the grating may take any appropriate form. For example, the grooves may be symmetric, asymmetric, periodic or aperiodic.

The grating may comprise a reflective coating, the reflective coating comprising a material or composition selected for grazing incidence reflectivity of a desired wavelength.

The grating may also cause divergence or convergence of the radiation beam (e.g. to focus or defocus the reflected radiation). For example, the grating may be formed into a cylindrical, or other, shape suitable for focusing/defocusing the radiation beam. Gratings of such shapes may additionally or alternatively be used to compensate for variance in the amount of thermal expansion experienced in different parts of the grating caused by intensity gradients within the profile of the radiation beam.

The beam splitting apparatus may further comprise a further reflective grating arranged to further split at least one of the branch radiation beams provided by the grating.

At least one of the static mirrors may be provided with one or more apertures arranged to permit a portion of the first radiation beam not reflected by the at least one static mirror through the aperture towards a further one of the plurality of static mirrors.

At least one of said static mirrors may comprise a ring-shaped reflective surface arranged to reflect a portion of radiation along an associated branch optical path and to permit a portion of the first radiation beam through an aperture defined by the ring toward a further one of the plurality of static mirrors.

Said ring-shaped reflective surface may be arranged such that if a position of the first radiation beam changes in a plane perpendicular to a propagation direction of the first radiation beam, a power received by at least one part of the ring-based reflective surface increases and a power received by at least a further part of the ring-based reflective surface decreases.

At least one of the static mirrors may comprise a first surface and a second surface joined along an edge. The edge may be arranged for placement within a path of the first radiation beam, or within a path of a branch radiation beam provided by one or more of the other static mirrors.

At least one of the static mirrors may be provided with active cooling. For example, single and/or double phase coolants may be circulated "behind" (i.e. on a non-radiation receiving surface) one or more of the static mirrors. For example, water and/or liquefied gas (e.g. $N_2$, $CO_2$, etc.) may be used.

The beam splitting apparatus may further comprise at least one diverging optical element arranged to increase the divergence of a radiation beam.

The beam splitting apparatus may comprise a plurality of diverging optical elements, each arranged to increase the divergence of a respective one of the branch radiation beams.

According to a another aspect, there is provided a system comprising a radiation source operable to produce a first radiation beam; a plurality of tools arranged to receive respective branch radiation beams; and a beam splitting apparatus according to the first aspect, the beam splitting apparatus being arranged to split the first radiation beam into a plurality of branch radiation beams and to provide respective branch radiation beams to each of the plurality of tools.

The radiation source may comprise one or more free electron lasers.

The system may further comprise a respective diverging optical element for each of the plurality of tools. Where the beam splitting apparatus comprises a grating, each respective diverging optical element may be positioned downstream of the grating. The or each diverging optical element may comprise a convex, concave and/or saddle shaped grazing incidence mirror.

The system may further comprise optics configured to modify the cross-sectional shape of a branch radiation beam. The optics may comprises an array of mirrors arranged to split the branch radiation beam into a plurality of sub-beams and to combine the sub-beams together.

The first radiation beam may comprise EUV radiation.

The plurality of tools may comprise a lithographic apparatus and a mask inspection apparatus each arranged to receive a different one of the branch radiation beams.

According to another aspect, there is provided a method comprising: producing a first radiation beam in a radiation source; and directing the first radiation beam to a beam splitting apparatus according to the first aspect to produce a plurality of branch radiation beams.

The radiation source may comprise one or more free electron lasers.

The method may further comprise directing each branch radiation beam to a respective tool.

According to another aspect, there is provided a lithographic method comprising using a free electron laser to produce a main radiation beam, using a plurality of static mirrors to reflect different parts of the main radiation beam, each static mirror directing the reflected part of the main radiation beam along an associated branch optical path thereby forming a branch radiation beam, wherein a first branch radiation beam is directed towards a first lithographic apparatus and a second branch radiation beam is directed towards a second lithographic apparatus.

According to another aspect, there is provided a lithographic system comprising a free electron laser operable to produce a main radiation beam, a beam splitting apparatus comprising a plurality of static mirrors arranged to reflect different parts of the main radiation beam, each static mirror directing the reflected part of the main radiation beam along an associated branch optical path thereby forming a branch radiation beam, and a mask inspection apparatus and a lithographic apparatus, the mask inspection apparatus and the lithographic apparatus being arranged to receive a different branch radiation beam.

According to another aspect, there is provided a lithographic method comprising using a free electron laser to produce a main radiation beam, using a plurality of static mirrors to reflect different parts of the main radiation beam, each static mirror directing the reflected part of the main radiation beam along an associated branch optical path thereby forming a branch radiation beam, wherein a first branch radiation beam is directed towards a mask inspection apparatus and a second branch radiation beam is directed towards a lithographic apparatus.

According to another aspect, there is provided a system comprising a free electron laser operable to produce an EUV radiation beam and a mask inspection apparatus arranged to receive the EUV radiation beam.

According to another aspect, there is provided a method comprising generating an EUV radiation beam using a free electron laser, directing the EUV radiation beam to a mask inspection apparatus, and using the EUV radiation beam to inspect a mask.

According to another aspect, there is provided a beam splitting apparatus for use in a lithographic system, the beam splitting apparatus being operable to receive a main radiation beam and output at least one branch radiation beam, the beam splitting apparatus comprising: a first extraction optic arranged to direct a first part of the main radiation beam along a branch optical path to provide a first branch radiation beam; wherein the first extraction optic comprises a first plurality of portions, each one of the first plurality portions being arranged to reflect a respective part of the main radiation beam to form a respective sub-beam of the first branch radiation beam; and wherein the first plurality of portions is arranged such that if a position of the main radiation beam changes in a plane perpendicular to a propagation direction of the main radiation beam, a power received by at least one of the first plurality of portions increases and a power received by at least one of the first plurality of portions decreases.

Advantageously, the invention provides an arrangement that can extract at least a first branch radiation beam from a main radiation beam, wherein the power of the first branch radiation beam is less sensitive to pointing variations of the main radiation beam than, for example, an arrangement wherein the first extraction optic comprises a single rectangular mirror.

The first plurality of portions may be arranged such that a power of the first branch radiation beam is substantially invariant to changes in a position of the main radiation beam in a plane perpendicular to the propagation direction of the main radiation beam.

The first extraction optic may be shaped such that the power received by at least one of the first plurality of portions will increase and the power received by at least one of the plurality of portions will decrease, irrespective of the direction of the change in position of the main radiation beam in the plane perpendicular to its propagation direction.

Projections of each of the first plurality of portions onto the plane perpendicular to the propagation direction of the main radiation beam may be distributed generally evenly about a center of the main radiation beam.

Each of the first plurality of portions may be arranged such that projections of each of the first plurality of portions onto the plane perpendicular to the propagation direction of the main radiation beam are of substantially the same size and shape.

Each of the first plurality of portions may be arranged such that a projection of each of the first plurality of portions onto the plane perpendicular to the propagation direction of the main radiation beam is of square, triangular, rectangular, or hexagonal cross sectional area.

Each of the first plurality of portions may be arranged such that a projection of one of the first plurality of portions onto the plane perpendicular to the propagation direction of the main radiation beam has substantially no overlap with a projection of any other of the first plurality of portions onto the plane perpendicular to the propagation direction of the main radiation beam.

The orientation of each of the first plurality of portions may be such that the respective sub-beams are substantially adjacent.

The first plurality of portions may be arranged such that the respective sub-beams have substantially no overlap and such that any gaps between them are minimal.

The first plurality of portions may be arranged such that the respective sub-beams overlap substantially completely.

The first branch optical path may comprise a ripple plate arranged to condition a branch radiation beam propagating along it.

The first branch optical path may comprise a mechanism for adjusting the intensity of a branch radiation beam propagating along it.

The first branch radiation beam may propagate in a direction that is substantially perpendicular to the main radiation beam.

The beam splitting apparatus may further comprise one or more additional extraction optics each being arranged to direct a respective part of the main radiation beam along a respective branch optical path to provide a respective branch radiation beam; wherein each additional extraction optic comprises a respective plurality of portions, each one of each respective plurality of portions being arranged to reflect a respective part of the main radiation beam to form a respective sub-beam of the respective branch radiation beam; and wherein each plurality of portions is arranged such that if a position of the main radiation beam changes in a plane perpendicular to the propagation direction of the main radiation beam, a power received by at least one of the portions of the additional extraction optic will increase and a power received by at least one of the plurality of portions of the additional extraction optic will decrease.

The portions of the first extraction optic and the portions of each of the additional extraction optics may be arranged so that a projection of all of the portions of the first extraction optic and the additional extraction optics onto the plane perpendicular to the propagation direction of the main radiation beam substantially coincides with the cross sectional area of the main radiation beam.

According to another aspect there is provided a lithographic system comprising: a radiation source operable to produce a main radiation beam; a beam splitting apparatus according to one of the aspects described herein; and at least one lithographic apparatus, the at least one lithographic apparatus being arranged to a branch radiation beam from the beam splitting apparatus.

The main radiation beam may have an intensity distribution which is rotationally symmetric about its centre.

The main radiation beam may have a Gaussian-like intensity distribution.

The radiation source may comprise one or more free electron lasers.

The radiation source may comprise optics arranged to alter the size and/or shape of the cross section of the radiation beams received from the one or more free electron lasers.

The lithographic system may further comprise one or more mask inspection apparatus.

The main radiation beam may comprise EUV radiation.

According to another aspect there is a provided a beam splitting apparatus, comprising: a beam spot region for receiving a radiation beam; a periodic array formed by a plurality of discrete reflective elements; and a mechanism for moving the periodic array such that the plurality of reflective elements move through the beam spot region, wherein the reflective elements are arranged such that a first portion of the radiation beam forms a first branch radiation beam and a second portion of the radiation beam forms a second branch radiation beam.

Such an arrangement allows an incoming radiation beam to be split into outgoing first and second branch radiation beams.

In general, as the plurality of discrete reflective elements moves through the beam spot region, the relative intensities of the first and second branch radiation beams will vary with time. The variation is periodic, with a frequency determined by the speed and pitch of the periodic array. In turn, this will cause the dose of radiation delivered by each of the first and second branch radiation beams to vary with time. This variation in dose will average out to zero over a time period equal to an integer number of periods of the oscillation. It may be desirable for the frequency of the oscillation to be as high as possible so that a stable dose may be achieved in a small time period.

Since the periodic array comprises a plurality of discrete reflective elements, each of the reflective elements may be smaller and more closely spaced. This reduces the pitch of the periodic array and therefore increases the frequency at which the intensities of the first and second branch radiations beams oscillate for a given speed of the periodic array. Advantageously, this allows a stable dose to be achieved in a smaller time period for a given speed of the periodic array. Alternatively, it allows a stable dose to be achieved in a similar time period at a lower speed of the periodic array.

An advantage of an arrangement wherein the reflective elements move through the beam spot region is that the (time averaged) relative intensities of the first and second branch radiation beams are relatively insensitive to the direction and position of the incoming radiation beam, at least in the direction of motion of the periodic array. This is in contrast to an arrangement using static mirrors wherein relative movement of the incoming radiation beam and the static mirrors can result in a significant change in the relative intensities of the branch radiation beams, especially where the diameter of the incoming radiation beam is small. This is because, for an arrangement with static mirrors, for a given relative position of the radiation beam and the static mirrors, the relative intensities of the branch radiation beams are substantially time independent and are dependent upon the position of the radiation beam relative to the static mirrors. For a small beam spot region, a pointing a relatively small radiation beam, a relatively small change in the relative positions of the radiation beam and the static mirrors can result in a significant change in the relative intensities of the branch radiation beams. However, for an arrangement wherein the reflective elements move through the beam spot region, the relative intensities of the branch radiation beams will oscillate with time but over an integer number of periods of the oscillation this variation in dose will average out to zero. Therefore the time averaged (over an integer number of oscillation periods) relative intensities of the first and second branch radiation beams are relatively insensitive to the direction and position of the incoming radiation beam, at least in the direction of motion of the periodic array.

The beam splitting apparatus may comprise a generally disc-shaped body and the mechanism for moving the periodic array may be operable to rotate said body about a rotation axis.

Each of the plurality of discrete reflective elements may comprise a surface of a generally radially extending spoke.

A generally radially extending spoke is one that extends from an inner radial position to an outer radial position. A generally radially extending spoke may extend purely in a radial direction. Alternatively, a generally radially extending spoke may have a circumferential component such that it is arranged at an oblique angle to the radial direction.

The reflective elements may be arranged such that the first portion of the radiation beam is incident on, and reflected by, the reflective elements so as to form the first branch radiation beam and the second portion of the radiation beam passes through one or more gaps between the reflective elements so as to form the second branch radiation beam.

The one or more gaps between the reflective elements may each extend to an edge of a body of the beam splitting apparatus.

With such an arrangement the gaps between the reflective elements are open on one side. Advantageously, if the radiation beam propagates generally towards this open side, with such an arrangement a range of allowable grazing incidence angles is not limited by the thickness of the body. This is in contrast to an arrangement wherein the gaps do not extend to the edge of the body, i.e. they are of the form of apertures in the body and are closed on all sides. With such an arrangement the range of allowable grazing incidence angles is limited both by the size of the gaps in the direction of propagation of the radiation beam and the thickness of the body. The thickness of the body sets a lower limit on the grazing incidence angles.

An arrangement wherein the reflective elements each extend to an edge of a body of the beam splitting apparatus therefore allows smaller grazing incidence angles. This is beneficial for thermal reasons.

The beam splitting apparatus may further comprise an inclined ramp in at least one of the one or more gaps.

Advantageously such ramps can increase the stiffness and thermal conductivity of the beam splitting apparatus. Since the ramps are inclined, they may be arranged such that a surface of each ramp is generally parallel to the incoming radiation beam when its gap is in the beam spot region so that it does not interfere with the incoming radiation beam.

The beam spot region may be disposed on an axially facing surface of the body.

The plurality of discrete reflective elements may taper inwards in a direction of increasing radius.

Advantageously, with a sufficient amount of tapering of the reflective elements, a fraction of radiation that is lost from reflection from side walls of the reflective elements can be reduced to a negligible amount.

The plurality of discrete reflective elements may each taper inwards in an axial direction away from an axially facing upper surface of the reflective element.

This provides each of the reflective elements with an undercut. Advantageously, with a sufficient amount of tapering of the reflective elements, a fraction of radiation that is lost from reflection from side walls of the reflective elements can be reduced to a negligible amount.

Each of the plurality of reflective elements may extend in a direction that is at an oblique angle to a radial direction.

The propagation direction of the radiation beam is generally aligned with the direction in which reflective elements within the beam spot region extend. Therefore, the radiation beam direction is at an oblique angle to the radial direction. Advantageously, since the incoming radiation beam does not pass through the rotation axis, a body of the beam splitting apparatus can be supported for rotation on both of its opposed axial sides. This allows, for example, a shaft to extend out of the upper axial surface of the body without blocking the radiation beam.

The beam spot region may be disposed on a radially facing surface of the body.

Advantageously, for such embodiments each of the reflective elements can be generally rectangular in shape. Another advantage is that the incoming radiation beam does not cross, or pass close to, the rotation axis and therefore bearings and actuators may be placed on both sides of the beam splitting apparatus, allowing for a symmetric, more balanced design.

A radially facing surface of each of the plurality of reflective elements may be curved.

A radially facing surface of each of the plurality of reflective elements may be flat.

The plurality of discrete reflective elements may be tapered outwards in a direction of increasing radius.

This will provide an undercut for each reflective element. By providing a sufficient radial taper, a fraction of radiation incident upon side walls of the reflective elements may be reduced or eliminated.

The beam splitting apparatus may further comprise a cooling device and a mechanism for transferring heat from the reflective elements to the cooling device. The plurality of reflective elements move relative to said cooling device, which may be static.

The cooling device may be disposed close to a surface of a body of the beam splitting apparatus, separated therefrom by a gap.

Opposed surfaces of the body and the cooling device may be provided with coatings of a high emissivity material. This may promote radiation by the body and absorption of the emitted radiation by the cooling device.

The gap provided between the body and the cooling device may be filled with layer of liquid metal, which is kept in place by capillary forces. The metal may comprise a fusible alloy.

According to another aspect, there is provided a lithographic system comprising a beam splitting apparatus according one of the aspects described herein.

According to another aspect, there is provided a composite beam splitting apparatus comprising a plurality of beam splitting apparatus according one of the aspects described herein.

At least two of the plurality of beam splitting apparatuses may be arranged in series such that one of the branch radiation beams produced by a first one of the beam splitting apparatuses is received by a second one of the beam splitting apparatuses.

The composite beam splitting apparatus may further comprise an adjustment mechanism operable to control a relative phase of the movement of the periodic arrays of the at least two of the plurality of beam splitting apparatuses.

According to another aspect, there is provided a lithographic system comprising: two radiation sources, each operable to output a radiation beam; a plurality of lithographic apparatuses; two beam delivery systems, each beam delivery system arranged to receive a radiation beam and to distribute this to different set of the plurality of lithographic apparatuses; and at least one beam splitting apparatus according an aspect described herein, the at least one beam splitting apparatus being movable between an inactive position, wherein it is out of the path of both of the radiation beams output by the two radiation sources, and at least one deployed position, wherein it is disposed in the path of the radiation beam from one of the radiation beams, wherein when the at least one beam splitting apparatus is disposed in its inactive position, each of the two beam delivery systems receives a radiation beam from a different one of the two radiation sources and when the at least one beam splitting apparatus is disposed in its deployed position it is arranged to split the radiation beam output by one of the radiation sources into two branch radiation beams and each of the two beam delivery systems receives a different one of said branch radiation beams.

The radiation beam output by either or both of the two radiation sources may comprise EUV or x-ray radiation.

According to another aspect there is provided a lithographic system comprising: first and second radiation sources, each operable to output a radiation beam; a plurality of lithographic apparatuses; two beam delivery systems, each beam delivery system arranged to receive a radiation beam and to distribute this to a different set of the plurality of lithographic apparatuses; and first and second beam splitting apparatuses according to one of the aspects described herein, the first and second beam splitting apparatuses arranged such that: the radiation beam output by the first radiation source is received by the first beam splitting apparatus, a first portion of the radiation beam output by the first radiation source being incident on, and reflected by, the reflective elements of the first beam splitting apparatus so as to form first branch radiation beam, and a second portion of the radiation beam output by the first radiation source passing through gaps between the reflective elements of the first beam splitting apparatus so as to form a second branch radiation beam; and the radiation beam output by the second radiation source is received by the second beam splitting apparatus, a first portion of the radiation beam output by the second radiation source being incident on, and reflected by, the reflective elements of the second beam splitting apparatus so as to form a third branch radiation beam, and a second portion of the radiation beam output by the second radiation source passing through gaps between the reflective elements of the second beam splitting apparatus so as to form a fourth branch radiation beam; wherein the first and fourth branch radiation beams are generally adjacent and collinear and are directed towards a first one of the two beam delivery systems and wherein the second and third branch radiation beams are generally adjacent and collinear and are directed towards a second one of the two beam delivery systems.

Such an arrangement is advantageous because it is not required to move optical components in and out of the paths of the radiation beams output by the first and second radiation sources when one radiation source is not operating.

The radiation beam output by either or both of the two radiation sources may comprise EUV or x-ray radiation.

According to an aspect, there is a provided an undulator for a free electron laser, comprising: at least one undulator module operable to produce a periodic magnetic field and arranged so as to guide an electron beam along a periodic path such that electrons within the electron beam interact with radiation in the undulator to stimulate emission of coherent radiation to provide a radiation beam; a steering unit arranged to alter a trajectory of the electron beam within the at least one undulator module; and a control unit arranged to control to the steering unit.

In this way, the control unit can steer the electron beam, and therefore the radiation beam, within the at least one module of the undulator itself, thereby adjusting the radiation beam at the position in the path of the radiation beam where such adjustments have the greatest effect.

The steering unit may be positioned within the undulator at a location that is nearer to an exit of the undulator than an entrance of the undulator in relation to the direction of propagation of the electron beam.

The steering unit may be positioned between a final and a penultimate module of the undulator with respect to direction of propagation of the electron beam. That is, where a plurality of modules is provided, the electron beam moves between each module in turn. The final module that the electron beam passes through is the final module. The module through which the electron beam passes before entering the final module is the penultimate module.

The undulator may further comprise a sensor arrangement for providing a signal indicative of a trajectory of the electron beam to the control unit.

The sensor arrangement may comprise a first sensor positioned after a first one of the plurality of undulator modules and a second sensor positioned after a second one of the plurality of undulator modules.

The first sensor may be positioned after a penultimate module and the second sensor may be positioned after a final module.

The control unit may be arranged to determine a deviation of the trajectory of the electron beam from an ideal trajectory.

The control unit may be arranged to control the steering unit to reduce a difference between the trajectory of the electron beam and the ideal trajectory, or to substantially align the electron beam with a trajectory parallel to the ideal trajectory.

The control unit may be arranged to receive an indication of an intensity distribution within the radiation beam at a predetermined location. For example, the predetermined location may be a position at which optics for processing the radiation beam further are located. For example, the predetermined location may be at a position of a beam expander that is part of a lithographic system.

The undulator may be arranged to determine a difference between the intensity distribution within the radiation beam at the predetermined location and an ideal intensity distribution within the radiation beam at the predetermined location; and to control the steering unit to reduce the difference between the intensity distribution within the radiation beam at the predetermined location and an ideal intensity distribution within the radiation beam at the predetermined location.

The control unit may be arranged to control the steering unit to periodically vary the trajectory of the electron beam by a predetermined amount.

The control unit may be arranged to control steering unit to sequentially direct the electron beam at a plurality of discreet angles with respect to a longitudinal axis of the undulator.

The plurality of discreet angles may be selected so as to provide a plurality of spatially separate radiation beams.

The control unit may be arranged to control the steering unit to sweep the electron beam through a predetermined angular range with respect to a longitudinal axis of the undulator.

The control unit may be arranged to control the steering unit so as to provide a plurality of spatially overlapping radiation beams. In this way, averaged over time, a the plurality of overlapping beams may provide a substantially flat-top beam profile.

The control unit may be arranged to control the steering unit to sweep the electron beam through the predetermined angular range with a substantially constant angular speed.

The control unit may be arranged to control the steering unit to vary the trajectory up to an angle of 1000 µrad in a direction perpendicular to a longitudinal axis of the undulator. For example, the control unit may be arranged to control the steering unit to vary the trajectory up to angle of 1000 µrad within a planar undulator module when sweeping the electron beam in a plane perpendicular to magnetic field lines within the planar undulator module, and up to 100 µrad within a helical undulator module.

The steering unit may be a first steering unit and the undulator may further comprise a second steering unit placed after a final module of the undulator, the control unit being arranged to control the second steering unit to reduce a difference between a propagation trajectory of the electron beam before variation of the electron beam by the first steering unit and a propagation trajectory after variation of the electron beam by the first steering unit. For example, the second steering unit may be controlled by the control unit to restore the trajectory of the electron beam to a trajectory of the electron beam before the electron beam interacted with the first steering unit. In this way, the electron beam can be made to follow a desired path (that may be different to a desired path of the radiation beam), such as a path to a beam dump.

The undulator may further comprise a plurality of steering units controlled by the control unit to alter a direction of the electron beam.

According to another aspect, there is provided a free electron laser arranged to produce at least one radiation beam, the electron laser comprising an undulator according to one of the aspects described herein.

According to another aspect, there is provided a lithographic system comprising: a free electron laser arranged to produce at least one radiation beam according to an aspect described herein; and at least one lithographic apparatus, each of the at least one lithographic apparatus being arranged to receive at least one of the at least one radiation beams.

The lithographic system may further comprise optics arranged to alter the size and/or shape of the cross section of the at least one radiation beams received from the free electron laser. For example, the lithographic system may comprise beam expander optics.

The lithographic system may further comprise an intensity distribution sensor arranged to provide signals indicative of an intensity distribution within the at least one radiation beam to the control unit of the undulator. The intensity distribution sensor may be positioned, for example, in the vicinity of the beam expander optics.

The at least one lithographic apparatus may comprise one or more mask inspection apparatus.

The at least one radiation beam may comprise EUV radiation.

According to another aspect, there is provided a computer implemented method for varying a direction of an electron beam within an undulator operable to produce a periodic magnetic field and arranged so as to guide the electron beam along a periodic path such that electrons within the electron beam interact with radiation in the undulator to stimulate emission of coherent radiation to provide a radiation beam, the method comprising: receiving a signal indicative of a trajectory of the electron beam and/or receiving a signal indicative of an intensity distribution within the radiation beam at a predetermined location; determining a deviation of the trajectory of the electron beam from an ideal trajectory and/or determining a difference between the intensity distribution within the radiation beam at the predetermined location and an ideal intensity distribution within the radiation beam at the predetermined location; and controlling a steering unit within the undulator to steer the electron beam within a module of the undulator so as to reduce the determined deviation and/or so as to reduce the determined difference.

According to another aspect, there is provided an undulator for a free electron laser, comprising: a first undulator section arranged to provide a first radiation beam and a second undulator section arranged to provide a second radiation beam, each undulator section comprising at least one undulator module arranged to guide an electron beam along a periodic path so that the electron beam interacts with radiation in the first and second undulator sections so as to stimulate emission of coherent radiation and provide the first and second radiation beams respectively; and a first steering unit disposed between the first undulator section and the second undulator section and arranged to alter a trajectory of an electron beam exiting the first undulator section such that the electron beam is at least partially separated from the first radiation beam so that there is at least a first portion of the first radiation beam that is decoupled from the electron beam as it propagates through the second undulator section.

Such an arrangement allows for the production of two separate radiation beams: one from the first undulator section and one from the second undulator section. This allows a free electron laser using such an undulator to supply radiation beams to two different locations. The two separate radiation beams may, for example, be supplied to two different lithographic systems or sets of lithographic systems. This allows a single free electron laser to supply radiation to a plurality of lithographic apparatuses without the need to split a main radiation beam into a plurality of sub beams.

Free electron lasers can be used to produce radiation, which may be used, for example, for lithography. However, free electron lasers can be expensive to build and run. Therefore, in order for free electron lasers to be cost effective, especially for extreme ultraviolet (EUV) lithography, it may be desirable for a single free electron laser to provide radiation for a plurality of lithographic apparatuses. Free electron lasers typically produce a single radiation beam with a relatively small étendue. For example, an EUV free electron laser beam may have a diameter of the order of hundreds of microns and may have a divergence of the order of hundreds of micro-radians. Splitting a high power radiation beam with such a small étendue is challenging. The present invention simplifies such splitting of radiation and may even completely eliminate the need to split a single radiation beam.

The undulator may comprise more than two undulator sections and more than one steering unit, each steering unit being disposed between a different pair of adjacent undulator sections.

The first steering unit may bend the electron beam by an angle with respect to an axis of the first undulator section.

The angle through which the electron beam is bent in the first steering unit may exceed a divergence of the first radiation beam.

The electron beam may pass through a beam line pipe within the undulator and the angle through which the electron beam is bent in the first steering unit may be sufficiently small that the first and second radiation beams both fit within the electron beam line pipe. For embodiments wherein the undulator comprises more than two undulator sections and more than one steering unit, the angle through which the electron beam is bent in each steering unit may be sufficiently small that all of the radiation beams fit within the electron beam line pipe. For embodiments, wherein the undulator comprises more than two undulator sections and more than one steering unit and where the undulator is planar the steering units may be arranged such that a trajectory of the electron beam may remain substantially in one plane. Advantageously, this allows the beam line pipe to remain small in the direction perpendicular to said plane, which in turn allows a separation between magnets in the undulator to remain small. For embodiments, wherein the undulator comprises more than two undulator sections and more than one steering unit and where the undulator is helical, the steering units may be arranged such that the directions of the electron beam in each undulator section lie substantially on a cone. Advantageously, this allows a diameter of the beam line pipe to remain small while still accommodating the electron beam and all generated radiation beams.

The second undulator section may be arranged such that significant stimulated emission of coherent radiation within the second undulator section will only occur if the electron beam has an initial trajectory within a range of acceptable initial trajectories and the first steering unit may be arranged such that the electron beam enters the second undulator section with an initial trajectory within the range of acceptable initial trajectories.

The first and/or second undulator sections may comprise helical undulator modules.

A central axis of the second undulator section may not be aligned with a central axis of the first undulator section.

An angle between central axes of the first and second undulator sections may substantially match an angle through which the electron beam is bent in the first steering unit.

The first steering unit may be arranged to separate the electron beam from the first radiation beam in a direction substantially perpendicular to a central axis of the first undulator section.

The electron beam may be completely separated from the first radiation beam.

The or each steering unit may include magnets arranged to decrease aberrations due to the energy spread developed within the electron beam as it moves through the undulator.

A second portion of the first radiation beam may serve as seed radiation in the second undulator section.

The first or second radiation beam may serve as a seed radiation source.

The undulator may further comprise a phase adjusting unit between the first and second undulator sections, which may be arranged to provide optimal matching between seed radiation and the electron beam.

The first and second undulator sections may be tapered and the tapering of the first and second undulator sections may be independently controllable.

The undulator may further comprise an electron beam expander before the or each steering unit and an electron beam compressor after the or each steering unit.

The undulator may further comprise one or more electron beam shifting elements between the first and second undulator sections, which are operable to shift the electron beam in a direction substantially perpendicular to its propagation direction.

According to another aspect, there is provided a free electron laser arranged to produce at least one radiation beam comprising the undulator of any preceding claim.

According to another aspect, there is provided a lithographic system comprising: a free electron laser according to an aspect described herein, arranged to produce at least one radiation beam; and at least one lithographic apparatus, each of the at least one lithographic apparatus being arranged to receive at least a portion of one of the at least one radiation beams.

The lithographic system may further comprise optics arranged to alter the size and/or shape of the cross section of the at least one radiation beam received from the free electron laser.

The at least one lithographic apparatus may comprise one or more mask inspection apparatus.

The at least one radiation beam may comprise EUV radiation

According to another aspect, there is provided a method of generating radiation, comprising: producing a relativistic bunched electron beam; directing the electron beam through a first undulator section comprising at least one undulator module arranged to guide the electron beam along a periodic path such that it interacts with radiation in the undulator module stimulating emission of coherent radiation and producing a first radiation beam; altering a trajectory of an electron beam as it exits the first undulator section such that the electron beam is at least partially separated from the first radiation beam; and directing the electron beam through a second undulator section comprising at least one undulator module arranged to guide the electron beam along a periodic path such that it interacts with radiation in the undulator module stimulating emission of coherent radiation and producing a second radiation beam, wherein the at least partial separation between the electron beam and the first radiation beam ensures that at least a first portion of the first radiation beam is decoupled from the electron beam as it propagates through the second undulator section.

According to another aspect, there is a provided an optical element comprising: a body; a reflective surface provided on the body for receiving a radiation beam so as to form a beam spot region and a reflected radiation beam; and a movement mechanism operable to move the body such that the beam spot region moves over the reflective surface following a periodic path and a direction of the reflected radiation beam remains substantially constant.

A fraction of the power of the radiation beam is absorbed by the optical element, causing the reflective surface to heat up. Since the movement mechanism is operable to move the reflective surface such that the beam spot region moves over the reflective surface, the power absorbed by the optical element is spread over a larger area, decreasing the density of the heat load. This allows the optical element to receive radiation beams with higher power densities, unlike static optical elements.

Since the beam spot region follows a periodic path on the reflective surface, provided the beam spot region moves sufficiently quickly, the curvature of the reflective surface caused by the radiation beam heating the reflective surface in a direction along the period path is negligible. The maximum induced curvature is in a direction perpendicular to the periodic path. Such a curvature may be simpler to correct for.

The body may be generally disc-shaped and the movement mechanism may be operable to rotate the body about a rotation axis.

A direction along, or parallel to the rotation axis may be referred to as an axial direction. A direction running to or from the rotation axis and perpendicular to said rotation axis may be referred to as a radial direction.

The optical element may further comprise a distortion mechanism for altering a curvature of the reflective surface. The distortion mechanism may be arranged to alter the curvature of the reflective surface so as to at least partially correct for curvature of the reflective surface caused by the radiation beam incident upon the reflective surface.

The energy absorbed by the optical element will cause a temperature gradient away from the reflective surface. As a result of this temperature gradient, different parts of the optical element will expand differently, which will cause the reflective surface to distort. The distortion mechanism is arranged to alter the curvature of the reflective surface so as to at least partially correct for curvature of the reflective surface caused by this distortion.

The reflective surface may be disposed on an axially facing surface of the body.

With such an arrangement, the beam spot region will trace out an annular shaped region of the reflective surface.

The distortion mechanism may be operable to alter a radial curvature of the reflective surface.

The distortion mechanism may be operable to apply a generally axial force to a radially outer edge of the body.

The distortion mechanism may comprise one or more members extending away from the generally disc shaped body, said members being formed from a magnetic material, and one or more electrical coils, wherein the generally axial force may be applied to the radially outer edge of the body by a magnetic force from the one or more electrical coils acting on the one or more members.

Such an arrangement provides a simple mechanism for altering the curvature of the reflective surface. The amount of curvature can be adjusted by varying the current through the one or more electrical coils.

The distortion mechanism may comprise one or more masses extending axially away from the generally disc shaped body, rotation of the body may cause a centrifugal force to act on the plurality of masses in an outward radial direction, said centrifugal force may generate a moment that acts on a radially outer edge of the body, altering a radial curvature of the reflective surface.

Such an arrangement provides a simple mechanism for altering the curvature of the reflective surface. The amount of curvature can be adjusted by varying the speed of rotation of the body.

An axial thickness of the body may vary in a radial direction.

Such an arrangement allows a different curvature to be applied at different radial positions by the application of a single generally axial force.

The axial thickness of the body may generally match the thermal load applied by a radiation beam to the beam spot region such that the amount of curvature applied by the distortion mechanism to radial positions of the reflective surface that receive a relatively high thermal load is generally higher than the amount of curvature applied by the distortion mechanism to radial positions of the reflective surface that receive a relatively low thermal load.

The thermal load applied by a radiation beam to the beam spot region may be proportional to the projection of the intensity distribution of the radiation beam onto the reflective surface. For example, the axial thickness may be smallest at the centre of the beam spot region, where the thermal load may be highest.

The distortion mechanism may comprise one or more heating elements arranged to apply a thermal load to a surface of the body that is opposite to the reflective surface, in the vicinity of the beam spot region. Said thermal load may be generally complementary to the thermal load applied by the radiation beam to the beam spot region. Alternatively, said thermal load may be generally similar to the thermal load applied by the radiation beam to the beam spot region.

It is to be understood that a second thermal load is generally complementary to a first thermal load if in regions where the first thermal load is relatively low, the second thermal load is relatively high and vice versa.

The optical element may further comprise one or more channels in the body of the optical element for a flow of cooling fluid, wherein the one or more channels are at least partially disposed in a part of the body on which the reflective surface is disposed.

Such internal cooling can provide cooling very close to the reflective surface thus minimizing thermal deformation of the reflective surface.

The body may be shaped below the reflective surface so as to at least partially reduce a variation in a temperature of the reflective surface caused by a radiation beam incident upon the reflective surface.

For such embodiments, the reflective surface may be disposed on a radially facing surface of the body.

For such embodiments the incoming radiation beam does not cross, or pass close to, the rotation axis and therefore bearings and actuators may be placed on both sides of the optical element, allowing for a symmetric, more balanced design.

According to another aspect, there is provided a radiation system, comprising: a radiation source operable to produce a radiation beam; and an optical element according to an aspect described herein, arranged so that the radiation beam is incident upon the beam spot region of the reflective surface.

The radiation system may further comprise a radiation bunker in which the radiation source and the optical element are disposed.

The radiation source may comprise a free electron laser.

According to another aspect, there is provided a lithographic system comprising a radiation source according to an aspect described herein.

According to another aspect, there is provided an apparatus for receiving radiation from a radiation source and delivering the radiation to an output aperture of the apparatus for subsequent delivery to at least one lithographic apparatus, the apparatus comprising an input aperture for receiving the radiation, the output aperture, and a passage between the input aperture and the output aperture comprising a plurality of chambers, wherein each of at least some of the chambers include a respective pumping port for connection to at least one vacuum pump, and the apparatus further comprises a source of electrons or other ionizing particles, or ionizing radiation, for ionizing gas atoms or molecules in the passage between the input aperture and the output aperture.

By ionizing gas atoms or molecules between the input aperture and the output aperture, a trajectory of the gas atoms or molecules may subsequently be altered, for example by application of suitable electric or magnetic field, and in turn a probability of the gas atoms or molecules being pumped by one of the vacuum pumps may be increased.

The source of electrons or other ionizing particles, or ionizing radiation, may be configured to ionize gas atoms or molecules in at least one of the chambers and/or in an aperture between a pair of the chambers.

Optionally each chamber comprises a respective pumping port. Each chamber may be connected to at least one other of the chambers via a respective aperture.

The passage may include a line-of-sight path along which the radiation may pass from the input aperture to the output aperture.

The apparatus may further comprise at least one electric or magnetic field source for altering trajectories of the ionized gas atoms or molecules, for example for altering the trajectories in at least one of the chambers and/or in at least one of the apertures.

The electric or magnetic field source may be configured to disrupt ballistic trajectories of gas atoms or molecules that are subject to ionization.

The electric or magnetic field source may be configured to cause at least some of the ionized gas atoms or molecules to collide with a surface of a component of the apparatus. Thus, ballistic trajectories of said at least some ionized gas atoms or molecules may be broken.

The electric or magnetic field source may be configured to cause at least some of the ionized gas atoms or molecules to collide with a surface of at least one of the chambers or a surface of an aperture between a pair of the chambers. Said surface of at least one of the chambers or said surface of an aperture between a pair of the chambers may be configured such that in operation the ionized gas atoms or molecules bounce off the surface.

The apparatus may further comprise at least one electric or magnetic field source for altering trajectories of the electrons or other ionizing particles to increase a probability of collisions between the electrons or other ionizing particles and the gas atoms or molecules.

The at least one electric or magnetic field source for altering trajectories of the electrons or other ionizing particles may be configured to increase path lengths of the electrons or other ionizing particles.

The at least one electric or magnetic field source may be configured to increase path lengths of the electrons between a cathode that produces the electrons and an anode that is arranged to receive the electrons.

The at least one electric or magnetic field source for altering trajectories of the electrons or other ionizing particles may be configured to cause at least some of the electrons or other ionizing particles to follow at least partially helical trajectories.

The at least one electric or magnetic field source may be configured to concentrate electrons or other ionizing particles in a part of at least one of the chambers where gas atoms or molecules having a ballistic trajectory leading to the input aperture may be present.

The at least one electric or magnetic field source may comprise circuitry for applying an electric potential to a wall of at least one of the chambers.

The electrons may be produced by a cathode and the circuitry may be configured to hold said wall of at least one of the chambers at lower potential than said cathode in operation.

The at least one electric or magnetic field source for altering trajectories of ionized gas atoms or molecules and the at least one electric or magnetic field source for altering trajectories of electrons may comprise a common at least one electric or magnetic field source.

The electron source may comprise a cathode arrangement for producing electrons and an anode for collecting electrons produced by the cathode arrangement. The cathode arrangement and the anode may be arranged so that electrons produced by the cathode arrangement and collected by the anode pass through at least part of said at least one chamber.

The cathode arrangement may comprise a cathode and a further anode located between the cathode and the anode. The further anode may comprise an accelerating anode for accelerating electrons produced by the cathode. The further anode may be configured to apply an electric field to reduce acceleration of electrons after they pass the further anode. The use of a suitably arranged further anode may reduce variation in kinetic energy of at least some of the electrons during their passage between the further anode and the anode. The kinetic energy of at least some of the electrons may be maintained in a desired range of values during passage between the further anode and the anode.

The cathode arrangement may be configured to produce electrons by thermionic emission.

The electron source may be configured such that electrons produced by the electron source have a kinetic energy during at least part of their passage through said at least one chamber in the range 20 eV to 300 eV, optionally in the range 60 eV to 100 eV, further optionally substantially equal to 80 eV.

The cathode arrangement and anode may be configured such that at least some of the electrons produced by the cathode arrangement have kinetic energy in the range 20 eV to 300 eV, optionally in the range 60 eV to 100 eV, further optionally substantially equal to 80 eV, during substantially all of their passage between the cathode arrangement and the anode.

The cathode arrangement and anode may be configured such that at least some of the electrons produced by the cathode arrangement have kinetic energy in the range 20 eV to 300 eV, optionally in the range 60 eV to 100 eV, optionally substantially equal to 80 eV, during substantially all of their passage between the cathode arrangement and the anode in the absence of collisions, for example in the absence of collisions between the electrons and gas atoms or molecules.

The gas atoms or molecules may comprise hydrogen molecules. The gas atoms or molecules may comprise gas atoms or molecules resulting from outgassing.

The apparatus may be configured such that, in operation, with vacuum pumps connected to and pumping via the pumping ports, a pressure at the input aperture is maintained at less than $10^{-7}$ Pa, optionally around $10^{-8}$ Pa, and a pressure at the output aperture is maintained at greater than $10^{-1}$ Pa, optionally around 1 Pa.

The pressure at the input aperture may comprise a pressure outside the apparatus adjacent to the input aperture. The pressure at the output aperture may comprise a pressure outside the apparatus adjacent to the output aperture. The pressure at the input aperture may be less than or equal to $10^{-6}$ Pa optionally less than or equal to $10^{-6}$ Pa, further optionally less than or equal to $10^{-8}$ Pa. The pressure at the output aperture may be in a range 0.1 Pa to 5 Pa, optionally in a range 0.5 Pa to 3 Pa, optionally approximately equal to 1 Pa.

Optionally, the radiation source comprises a free electron laser radiation source, or a synchrotron radiation source. The radiation may have a wavelength in a range 4 nm to 25 nm. The radiation may comprise a beam of radiation. The radiation may comprise EUV radiation.

In a further aspect of the invention, which may be provided independently, there is provided a method of receiving a beam of radiation from a radiation source and delivering the beam of radiation via an apparatus to an output aperture of the apparatus for subsequent delivery to at least one lithographic apparatus, the apparatus comprising:—receiving the beam of radiation at an input aperture of the apparatus, pumping at least one chamber of the apparatus between the input aperture and the output aperture, wherein the at least one chamber forms part of a passage between the input aperture and the output aperture, and applying electrons or other ionizing particles, or ionizing radiation, to ionize gas atoms or molecules in the passage between the input aperture and the output aperture.

The method may further comprise applying at least one electric or magnetic field to alter trajectories of ionized gas atoms or molecules in the passage between the input aperture and the output aperture.

In a further aspect of the invention, which may be provided independently, there is provided a lithographic system comprising a radiation source, a lithographic apparatus arranged to project a pattern from a patterning device onto a substrate, and a system for delivering radiation from the radiation source to the lithographic apparatus, wherein the system for delivering the radiation comprises apparatus as claimed or described herein.

According to another aspect, there is provided an apparatus for adjusting an intensity of radiation used in a lithographic process, comprising: a first element for receiving a first radiation beam and arranged to reflect a portion of the first radiation beam in the form of a second radiation beam towards a second element, the second element being arranged to reflect a portion of the second radiation beam in the form of a third radiation beam away from the second element; and adjustment means adapted to adjust an incidence angle between at least one of the first radiation beam and the first element and second radiation beam and the second element so as to vary an intensity of the third radiation beam.

In this way, there is provided an apparatus for efficiently adjusting an attenuation of radiation entering the attenuation apparatus, thereby adjusting the intensity of the radiation beam output from the attenuation apparatus. A mechanism is provided which may be implemented in a mechanically efficient and straightforward manner, while allowing for rapid adjustments of the intensity of the third radiation beam.

The third radiation beam may be output from attenuation apparatus, for example, towards a lithographic apparatus. Alternatively, the third radiation beam may be directed towards a further attenuation apparatus.

The incidence angle of the first radiation beam at the first element may be the same as the incidence angle of the second radiation beam at the second element. The apparatus may be arranged to ensure that the incidence angle of the first radiation beam with respect to the first element is always substantially the same as the incidence angle of the second radiation beam with respect to the second element. In this way, the third radiation beam is reflected from the third element in substantially the same direction as the direction of propagation of the first radiation beam.

The adjustment means may be adapted to adjust the incidence angle of the first and second radiation beams between approximately 1 degree and approximately 10 degrees.

The first element may be arranged to rotate around a first point and/or the second element arranged to rotate around a second point. The adjustment means may be arranged to selectively rotate at least one of the first and second elements to adjust the incidence angles of the first or second radiation beams with the first and second elements. This provides a particularly effective and simple manner of implementing the apparatus for adjusting an intensity of radiation.

The first element may be arranged to be rotated around the first point and/or the second element is arranged to be rotated around the second point through an angle of approximately 9 degrees.

The attenuation apparatus may further comprise a third element for receiving the third radiation beam and for reflecting a portion of the third radiation beam in the form of a fourth radiation beam and a fourth element for receiving the fourth radiation beam and for reflecting a portion of the fourth radiation beam in the form of a fifth radiation beam away from the fourth element.

By provision of the third and fourth elements, an attenuation range of the attenuation apparatus may be increased. Alternatively, or additionally, provision of the third and fourth elements allows for an effect of reflection by the elements of the attenuation apparatus on a polarity of radiation to be reduced for a given attenuation.

The adjustment means may be adapted to adjust an incidence angle between at least one of the third radiation beam and the fourth element and the fourth radiation beam and the fourth element.

The adjustment means may be adapted to adjust the incidence angle of the first, second, third and fourth radiation beams with the respective first, second, third and fourth elements between approximately 1 degrees and approximately 5 degrees. In this way, an attenuation range of between approximately 8% and 20% may be achieved while better maintaining a polarity of the first radiation beam in the third radiation beam.

The first element may be arranged to rotate around a first point, the second element arranged to rotate around a second point, the third element arranged to rotate around a third point and the fourth element arranged to rotate around a fourth point. The adjustment means may be arranged to selectively rotate at least one of the first, second, third and fourth elements to adjust the incidence angles of the first, second, third or fourth radiation beams with the respective first, second, third or fourth elements.

Each of the first, second, third and fourth elements may be arranged to be rotated around the respective first, second, third or fourth point through an angle of approximately 4 degrees.

The apparatus may further comprise a controller arranged to control the adjustment means.

The controller may be arranged to receive indications of a radiation intensity from a sensor and to control the adjustment means in response to said indications. In this way, the attenuation provided by the first attenuation apparatus may be better controlled. The controller may, for example, comprise part of a control loop arranged to maintain an intensity of radiation provided at a predetermined location within a predetermined intensity range.

The apparatus may comprise a further attenuation apparatus. The further attenuation apparatus may comprise fixed attenuation apparatus. That is, the further attenuation apparatus may provide an attenuation that cannot be varied, or can be varied only by a small amount compared to the variation in attenuation achievable using the first and second elements, or using the first to fourth elements. The further attenuation apparatus may provide an attenuation factor larger than the attenuation of the variable attenuator. For example, the further attenuation apparatus may provide an attenuation factor of ten.

Alternatively, the further attenuation apparatus may comprise adjustable attenuation apparatus. The further attenuation apparatus may be adjustable through a larger range of attenuations than the first attenuation apparatus, but may be adjustable with a lower frequency than the frequency with which the first attenuation apparatus may be adjusted.

The further attenuation apparatus may comprise a chamber containing an EUV absorbing medium, the chamber being arranged in the path of a radiation beam.

The further attenuation apparatus may comprise a pressure sensor operable to monitor a pressure within the chamber.

The further attenuation apparatus may comprise a gas inlet and a gas outlet.

The apparatus may further comprise a second controller, wherein the second controller is in communication with the pressure monitor and is arranged to control the gas inlet and gas outlet to maintain a pressure within the chamber within a predetermined range.

The first and second controller may be the same controller.

The adjustment means may comprise respective adjustment means for each element to be adjusted.

The apparatus may further comprise a reflective membrane disposed at a non-normal angle with respect to the direction of propagation of one of the radiation beams, wherein the reflective membrane is arranged to transmit a portion of the one of the radiation beams and to reflect a portion of the one of the radiation beams.

The one of the radiation beams may be, for example, the first, second, third, or fourth radiation beams.

According to another aspect, there is provided a lithographic system comprising: a radiation source operable to produce a main radiation beam; an attenuation apparatus according an aspect described herein, arranged to receive at least a portion of the main radiation beam; and at least one lithographic apparatus, the at least one lithographic apparatus being arranged to receive an attenuated radiation beam from the attenuation apparatus.

For example, the main radiation beam, or a portion of the main radiation beam may provide the first radiation beam described above.

The lithographic system may comprise a beam splitting apparatus arranged to receive a main radiation beam and output at least one branch radiation beam. The attenuation apparatus may be arranged to receive the at least one branch radiation beam.

The beam splitting apparatus may be arranged to output a plurality of branch radiation beams. The lithographic system may comprise a respective attenuation apparatus for each of said plurality of branch radiation beams, each attenuation apparatus arranged to receive a respective one of said plurality of branch radiation beams.

Alternatively, the lithographic system may comprise one or more attenuation apparatus for some of the plurality of branch radiation beams. That is, some branch radiation beams may not pass through an attenuation apparatus in the lithographic system.

The radiation source may comprise one or more free electron lasers.

The at least one lithographic apparatus may comprise one or more mask inspection apparatus.

The main radiation beam may comprise EUV radiation.

According to another aspect, there is provided a radiation source for a lithographic system comprising: a free electron laser operable to produce a beam of radiation; an optical system provided with an adjustment mechanism and one or more movable optical elements arranged to receive the beam of radiation from the free electron laser, increase its cross sectional area, and provide an output beam; and a sensor apparatus for determining a direction of the output beam, wherein the adjustment mechanism is operable to move the one or more movable optical elements in response to the direction determined by the sensor apparatus to compensate for changes in the direction of the beam of radiation produced by the free electron laser.

The active feedback loop provided by the sensor apparatus and the adjustment mechanism allows the optical system to be separated from the free electron laser by a significant distance, whilst ensuring the direction of the radiation beam output by the optical system remains stable. Advantageously, this allows free electron lasers of increased power to be used for lithography. The feedback loop may also be configured to ensure that the position of the radiation beam output by the optical system remains stable. This may similarly allow free electron lasers of increased power to be used for lithography.

The beam of radiation produced by the free electron laser may comprise EUV radiation.

The beam of radiation produced by the free electron laser may have a divergence of 1000 μrad or less.

The output beam provided by the optical system has substantially zero divergence.

The one or more movable optical elements may comprise a first optical element and a second optical element, the first optical element comprising a convex mirror and the second optical element comprising a concave mirror.

The adjustment mechanism may be operable to move each of the one or more movable optical elements linearly. The adjustment mechanism may be operable to move each of the one or more movable optical elements linearly in two different directions.

The adjustment mechanism may be operable to rotate each of the one or more movable optical elements. The adjustment mechanism may be operable to rotate each of the one or more movable optical elements about two different axes.

The one or more movable optical elements comprise grazing incidence mirrors.

A distance between the free electron laser and a first optical element of the optical system may be greater than 10 metres.

The one or more movable optical elements may be shaped so as to alter the shape and/or intensity distribution of the radiation beam produced by the free electron laser.

The one or more movable optical elements may be spherical, astigmatic or a-spherical shaped.

The radiation source may further comprise a second free electron laser, operable to produce a second beam of radiation, wherein one or more movable optical elements are arranged to selectively receive a beam of radiation from one of the free electron lasers, increase its cross sectional area, and provide an output beam and the adjustment mechanism is operable to move the one or more movable optical elements in response to the direction determined by the sensor apparatus to compensate for changes in the direction of the beam of radiation produced by that free electron laser.

The beams of radiation produced by the two different free electron lasers may enter the optical system in different directions, and the direction of the beam of radiation output by the optical system may be independent of the free electron laser from which it originated.

According to another aspect, there is provided an apparatus comprising: an optical system provided with an adjustment mechanism and one or more movable optical elements arranged to receive the beam of radiation from a free electron laser, increase its cross sectional area, and provide an output beam; and a sensor apparatus for determining a direction of the output beam, wherein the adjustment mechanism is operable to move the one or more movable optical elements in response to the direction determined by the sensor apparatus to compensate for changes in the direction of the beam of radiation produced by the free electron laser.

According to another aspect, there is provided a lithographic system comprising: a radiation source as claimed in any one of claims 1 to 15; and one or more lithographic apparatuses.

The lithographic system may further comprise a mask inspection apparatus.

According to another aspect, there is provided a method of producing a beam of radiation, comprising the steps of: producing an initial beam of radiation with a free electron laser; allowing the radiation beam to propagate over a distance before entering an optical system comprising one or more movable optical elements; increasing the cross sectional area of the beam using the one or more movable optical elements to produce an output beam; determining a direction of the output beam leaving the one or more movable optical elements; and moving the one or more movable optical elements in response to the determined direction to compensate for changes in the direction of the initial beam of radiation.

The step of moving the one or more movable optical elements may involve moving two optical elements substantially simultaneously in order to ensure that the direction of the output beam remains substantially stable.

The step of moving the one or more movable optical elements may involve moving translating and/or rotating two optical elements in order to ensure that the direction of the output beam remains substantially stable.

According to a further aspect, there is provided a radiation source for a lithographic system comprising: two free electron lasers, each operable to produce a beam of radiation and switchable between an on state wherein it produces a beam of radiation and an off state wherein it does not; an optical system comprising a plurality of optical elements, arranged to receive a beam of radiation from each of the two free electron lasers and output an output radiation beam, wherein the optical system is arranged such that when both of the free electron lasers are in their respective on states, the output radiation beam comprises a composite radiation beam comprising radiation from each of the two free electron lasers and when only one of the free electron lasers is in its on state, the output radiation beam comprises radiation from that free electron laser.

The plurality of optical elements may be arranged to alter the size and/or shape of the cross section of the radiation beams received from the free electron lasers.

The plurality of optical elements may comprise a diverging optical element for each of the two free electron lasers, each diverging optical element arranged to increase the cross sectional area of the radiation beam received from a respective one of the free electron lasers.

The plurality of optical elements may further comprise a converging optical element for each of the two free electron lasers, each converging optical element arranged to reduce a divergence of the radiation beam received from a respective one of the free electron lasers to substantially zero after the cross sectional area of that radiation beam has been increased.

The plurality of optical elements may comprise one or more astigmatic or aspherical elements which are arranged to alter the cross sectional shape of the radiation beams received from the free electron lasers.

The optical elements may be shaped so that the radiation beams received from the free electron lasers are altered so as to be more rectangular in shape.

The optical system may be adjustable so that the size and/or shape of the cross section imparted to each of the radiation beams can be varied.

A divergence of at least one of the diverging optical elements may be able to be varied to vary the size and/or shape of the cross section imparted to a corresponding one of the radiation beams.

At least one of the diverging optical elements may comprise two reflective surfaces each having a different radius of curvature and is rotatable about an axis so as to selectively place each of the two reflective surfaces in a path of the radiation beam received from the respective one of the free electron lasers.

For each of the two free electron lasers, the plurality of optical elements may comprise a plurality of diverging optical elements having different radii of curvature; wherein each optical element within each plurality of diverging optical elements may be movably mounted within the optical system so that each can be selectively moved in and out of a path of the radiation beam received from the respective one of the free electron lasers.

The radiation source may further comprise a controller which is operable to adjust the size and/or shape of a cross section imparted to each of the radiation beams, in dependence on the states of the two free electron lasers.

The controller may be operable adjust the optical system such that: when both of the free electron lasers are in their respective on states, the optical system alters beams of radiation from each of the free electron lasers to a first cross section, and the beams of radiation from the two free electron lasers combine to form a composite radiation beam with a second cross section, and when only one of the two free electron lasers is in its on state, the optical system alters the beam of radiation from that free electron laser to a third cross section. The third cross section may be more similar to the second cross section than the first cross section is to the second cross section.

The third cross section may be substantially the same as the second cross section.

The optical system may be arrangable so as to direct the radiation beams received from the free electron lasers so that they are adjacent and substantially mutually parallel.

The radiation source may further comprise: a sensor apparatus for determining a direction of the output radiation beam; and an adjustment mechanism which is operable to move optical elements of the optical system in response to the direction determined by the sensor apparatus to compensate for changes in the direction of the beams of radiation produced by the two free electron lasers.

The adjustment mechanism may be operable to rotate one or more of the plurality of optical elements about two different axes.

The adjustment mechanism may be operable to move one or more of the plurality of optical elements linearly in two different directions.

The beams of radiation produced by the two free electron lasers may comprise EUV radiation.

According to a further aspect, there is provided a beam delivery system for use with a radiation source of an aspect described herein, comprising: an optical system comprising a plurality of optical elements, arranged to receive one or two beams of radiation and output an output radiation beam, wherein the optical system is arranged such that when two beams of radiation are received, the output radiation beam comprises a composite radiation beam comprising radiation from each of the two beams and when only one beam of radiation is received, the output radiation beam comprises radiation from that radiation beam.

According to a further aspect, there is provided a lithographic system comprising: a radiation source according to an aspect described herein; one or more lithographic apparatuses; and a beam splitting apparatus operable to direct a portion of a radiation beam output by the radiation source to each of the one or more lithographic apparatuses.

The beam splitting apparatus may comprise a plurality of static mirrors arranged to reflect different parts of the radiation beam output by the radiation source, each static mirror directing the reflected part of the main radiation beam along an associated branch optical path thereby forming a branch radiation beam.

Each static mirror may be arranged to extend partially across the main radiation beam and is configured to reflect a solid area of the main radiation beam.

The static mirrors may be substantially identical.

According to a further aspect, there is provided a method of producing a beam of radiation, comprising the steps of: providing two free electron lasers, each operable to produce a beam of radiation and switchable between an on state wherein it produces a beam of radiation and an off state wherein it does not; using one or two of the free electron lasers to produce radiation; determining whether or not each of the two free electron lasers is producing radiation; and if both of the free electron lasers are in their respective on states forming a composite radiation beam comprising radiation from both of the two free electron lasers and outputting it; or if only one of the free electron lasers is in its on state, outputting a radiation beam comprising radiation from that free electron laser.

According to another aspect, there is a provided a lithographic apparatus comprising: an optical system operable to receive radiation, impart the radiation with a pattern in its cross-section to form a patterned radiation beam and project the patterned radiation onto a substrate; and a plurality of focusing elements, wherein each of the plurality of focusing elements is arranged to receive a different radiation beam, focus it at a different intermediate focus and direct it to a first optical element of the optical system, such that at the first optical element the radiation from each of the different radiation beams at least partially overlaps.

Such an arrangement allows the lithographic apparatus receive radiation from a plurality of radiation sources operable to produce a radiation beam, each radiation beam being received by a different one of the plurality of focusing elements. Further, the at least partial overlap between the radiation beams at the first optical element limits the effect on the operation of the lithographic apparatus when one of the radiation sources is not producing radiation.

Each of the plurality of focusing elements may be arranged such that substantially the entire field of the first optical element is illuminated by each of the different radiation beams.

It will be appreciated that "the entire field of the first optical element" comprises all those parts of the first optical element that project onto the substrate regardless of any pattern imparted to the radiation beam by the lithographic apparatus. That is, when those parts of the first optical element receive radiation, and no pattern is imparted to the radiation beam, that radiation will propagate through the optical system to the substrate.

With such an arrangement, the operation of the lithographic apparatus is substantially independent of the number of focusing elements that receive radiation. When a radiation source is not producing radiation, and therefore not supplying radiation to one of m focusing elements, the lithographic apparatus will continue to operate in the same manner as it would when all m of the focusing elements receive radiation. No adjustments are necessary. When one of m focusing elements does not receive radiation, the lithographic apparatus will only receive a fraction (m−1)/m of the radiation that would be received when all m of the focusing elements receive radiation (assuming that the radiation sources supplying the plurality of focusing elements are of substantially equal output power).

The intermediate foci of the plurality of focusing elements may be distributed around an optical axis of the first optical element.

Each of the plurality of focusing elements may comprise a Wolter collector.

The first optical element may comprise a multifaceted mirror.

Each of the plurality of focusing elements may be arranged to receive a generally parallel beam and to focus it with a numerical aperture substantially matching that of the first optical element.

According to another aspect, there is provided a lithographic system comprising: a plurality of radiation sources, each operable to produce a main radiation beam; a plurality of lithographic apparatuses; and a beam delivery system arranged to receive the main radiation beams produced by each of the plurality of radiation sources and direct a portion of each main radiation beam to the or each lithographic apparatus.

Each of the plurality of lithographic apparatuses may comprise a lithographic apparatus according to an aspect described herein. The portion of each main radiation beam that is directed to each of the plurality of lithographic apparatuses may be received by a different one of its plurality of focusing elements.

Each of the plurality of radiation sources may comprise a free electron laser.

A numerical aperture of each of the plurality of lithographic apparatuses may be greater than that of each of the plurality of radiation sources.

The beam delivery system may comprise beam combining optics arranged to receive a main radiation beam from each of the radiation sources and to output a composite radiation beam. The beam delivery system may further comprise beam splitting optics arranged to receive the composite radiation beam and output a plurality of branch radiation beams, such that each of the plurality of branch radiation beams is received by a different one of the plurality of lithographic apparatuses.

Alternatively, the beam delivery system may comprise separate beam splitting optics for each of the plurality of radiation sources, each beam splitting optic arranged to receive a single main radiation beam and output a plurality of branch radiation beams, such that each of the plurality of branch radiation beams is received by a different one of the plurality of lithographic apparatuses.

The beam delivery system may comprise beam expanding optics, arranged to increase a diameter of the main radiation beams.

The beam delivery system may comprise beam shaping optics, arranged to alter a cross sectional shape and/or intensity profile of the main radiation beams.

The main radiation beams may comprise EUV radiation.

According to another aspect, there is provided a method of providing radiation to a lithographic apparatus comprising an optical system configured to receive radiation, impart the radiation with a pattern in its cross-section to form a patterned radiation beam and project the patterned radiation onto a substrate, the method comprising: producing a plurality of adjacent radiation beams; focusing each of the plurality of adjacent radiation beams at a different intermediate focus and directing it to a first optical element of the optical system, such that at the first optical element the radiation from each of the plurality of adjacent radiation beams at least partially overlaps.

The focusing of each of the plurality of adjacent radiation beams may be such that substantially the entire field of the first optical element is illuminated by each of the plurality of adjacent radiation beams.

Each of the plurality of adjacent radiation beams may be produced by a free electron laser.

Each of the plurality of adjacent radiation beams may comprise EUV radiation.

Focusing of each of the plurality of adjacent radiation beams elements may use a Wolter collector.

According to another aspect, there is provided a mirror for use in a beam delivery system, comprising: a reflective surface arranged to receive a radiation beam, to reflect the radiation beam in a first direction and to clip the radiation beam such that an intensity profile of the reflected radiation beam is gradually reduced towards a clipped edge of the intensity profile.

The mirror may be provided with soft-clipping means, the soft-clipping means being arranged to absorb an increasing amount of radiation in a direction extending radially outward from a central portion of the reflective surface.

The soft-clipping means may comprise a radiation-absorbing material having a depth perpendicular to the reflective surface that increases in direction extending radially outward from the central portion of the reflective surface.

The soft-clipping means may comprise a radiation-absorbing material that covers an increasing portion of the reflective surface in a direction extending radially outward from the central portion of the reflective surface.

The radiation-absorbing material may comprise a material having a refractive index for EUV radiation substantially similar to that of a vacuum.

The radiation-absorbing material may comprise a coating comprising at least one of aluminium, gold, nickel or rhenium.

The mirror may be provided with soft-clipping means, the soft-clipping means being arranged to reflect a portion of the radiation beam in a second direction different to the first direction.

The portion of the radiation beam reflected in a second direction increases in a direction extending radially outward from a central portion of the reflective surface.

The soft-clipping means may comprise a plurality of wells in the reflective surface. The wells may be coated with a reflective coating.

The mirror may further comprise an insulation portion arranged to insulate an edge portion of the mirror comprising said soft-clipping means from an inner portion of the mirror not comprising said soft-clipping means.

According to another aspect, there is provided a beam delivery system for a lithographic system comprising one or more mirrors according to one of the aspects described herein.

The beam delivery system may comprise a first mirror according to one of the aspects described herein, and a second mirror according to one of the aspects above. The first and second mirrors may be cooperatively arranged to soft-clip a radiation beam received by the beam delivery system.

Soft-clipping means may be provided along a first edge portion of a reflective surface of the first mirror but not along a second edge portion of the reflective surface of the first mirror and soft-clipping means may be provided along a second edge portion of a reflective surface of the second mirror but not along a first edge portion of the reflective surface of the second mirror.

According to another aspect, there is provided a lithographic system comprising: a radiation source operable to produce a radiation beam; at least one lithographic apparatus; and a beam delivery system according to one of the aspects described herein, arranged to receive the radiation beam and direct the radiation beam to the at least one lithographic apparatus.

According to another aspect, there is provided a lithographic system comprising: a radiation source comprising a free electron laser, wherein the radiation source is configured to emit a first radiation beam having a first polarization state; and a beam delivery system comprising a plurality of reflective elements arranged to receive the radiation beam from the radiation source and direct at least some of the radiation beam to a lithographic tool so as to provide the lithographic tool with a second radiation beam having a second polarization state, wherein the reflective elements are configured to alter the polarization of radiation which is directed by the reflective elements such that polarization contrast of the second polarization state is less than a polarization contrast of the first polarization state.

The beam delivery system may be configured to split the first radiation beam into a plurality of branch radiation beams and wherein the second radiation beam is one of the branch radiation beams.

The beam delivery system may be configured to change the polarization of the branch radiation beams so as to output a plurality of branch radiation beams which have substantially the second polarization state.

The second polarization state may be a substantially circular polarization state.

The radiation source may comprise a plurality of free electron lasers and an optical system configured to combine radiation output from each of the free electron lasers to form the first radiation beam.

The reflective elements of the beam delivery system are configured such that radiation which is incident on each of the reflective elements comprises an s-polarized component and a p-polarized component which have substantially the same magnitude.

The reflective elements of the beam delivery system may be configured to cause a phase retardance between the s-polarized component and the p-polarized component at each reflective element.

The radiation source may be configured to emit a first radiation beam which is substantially linearly polarized in a polarization plane.

The beam delivery system may comprise a plurality of reflective elements which are orientated such that a plane of incidence at each of the reflective elements forms an angle of approximately 45° with the polarization plane.

The plurality of reflective elements may comprise a first group of reflective elements which are orientated such that a plane of incidence at each of the reflective elements forms an angle of approximately +45° with the polarization plane and a second group of reflective elements which are orientated such that a plane of incidence at each of the reflective elements forms an angle of approximately −45° with the polarization plane.

The difference between the total phase retardance which is caused by reflection at the first group of reflective elements and the total phase retardance which is caused by reflection at the second group of reflective elements may be approximately 90°.

The radiation source may be configured to emit a first radiation beam which is substantially elliptically polarized.

A free electron laser of the radiation source may comprise an undulator comprising a plurality of undulator sections, wherein at least one of the undulator sections is a helical undulator section and wherein at least one of the undulator sections is a planar undulator section.

The polarization contrast of the second polarization state may be less than approximately 0.1.

The lithographic tool may comprise a lithographic apparatus.

The first radiation beam may be an EUV radiation beam.

According to another aspect, there is provided a method of configuring a lithographic system comprising a free electron laser and a beam delivery system comprising a plurality of reflective elements, the method comprising: determining an output polarization state, wherein the output polarization state is a desired polarization state of a radiation beam which is output by the beam delivery system; determining an input polarization state of a radiation beam which is emitted from the free electron laser and input to the beam delivery system; determining a change in polarization which when applied to the input polarization state results in the output polarization state; and configuring reflective elements of the beam delivery system such that reflection of radiation at the reflective elements of the beam delivery system results in the determined change in polarization.

The output polarization state may be a substantially circular polarization state.

The input polarization state may be a substantially linear polarization state.

Determining the change in polarization may comprise determining a phase retardance which when applied to the input polarization state results in the output polarization state.

Configuring the reflective elements of the beam delivery system may comprise orientating the reflective elements such that radiation which is incident on each of the reflective elements comprises an s-polarized component and a p-polarized component which have substantially the same magnitude.

Configuring the reflective elements of the beam delivery system may comprise orientating the reflective elements of the beam delivery system so as to cause a phase retardance between the s-polarized component and the p-polarized component at each reflective element.

The total phase retardance which is caused by the reflective elements may be the determined phase retardance.

According to another embodiment of the invention, a method of configuring a lithographic system comprising a free electron laser and a beam delivery system comprising a plurality of reflective elements, the method comprising: determining an output polarization state, wherein the output polarization state is a desired polarization state of a radiation beam which is output by the beam delivery system; determining a change in polarization which is caused by reflection of radiation at the reflective elements of the beam delivery system; determining an input polarization state, which when the determined change in polarization is applied to the input polarization state results in the output polarization state; and configuring the free electron laser such that the free electron laser outputs a radiation beam having the input polarization state.

The output polarization state may be a substantially circular polarization state.

Determining the change in polarization may comprise determining a phase retardance which is caused by reflection of radiation at the reflective elements of the beam delivery system.

Determining the change in polarization may comprise determining a Jones matrix of the beam delivery system.

Determining the input polarization state may comprises inverting the Jones matrix.

Determining the input polarization state may further comprise multiplying the inverted Jones matrix by a Jones vector which represents the output polarization state.

Configuring the free electron laser may comprise providing an undulator comprising a plurality of undulator sections, wherein at least one of the undulator sections is a helical undulator section and wherein at least one of the undulator sections is a planar undulator section.

Configuring the free electron laser may further comprise configuring the length of the at least one helical undulator section relative to the length of the at least one planar undulator section such that the free electron laser outputs a radiation beam having the input polarization state.

Features of one or more aspects described above may be combined with features of others of the aspects described above.

BRIEF DESCRIPTION OF THE DRAWINGS

Embodiments of the invention will now be described, by way of example only, with reference to the accompanying schematic drawings, in which:

FIG. 58 is a thermal map for a first geometry of the body of the optical element of FIG. 56;

FIG. 59 is a thermal map for a second geometry of the body of the optical element of FIG. 56;

FIGS. 78A and 78B schematically illustrate a cross section of a beam output by the radiation source shown in FIG. 77 when both free electron lasers are on;

FIG. 82 shows the cross section of the beam output by the radiation source shown in FIG. 79 when only one free electron laser is on;

FIGS. 85A and 85B show the cross section of the beam output by the radiation source shown in FIG. 83 when both free electron lasers are on;

DETAILED DESCRIPTION

The term "beam delivery system" as used herein may be used to refer to any combination of optical elements used to provide a beam produced by a source to a tool, such as a lithographic apparatus.

Figure 1:
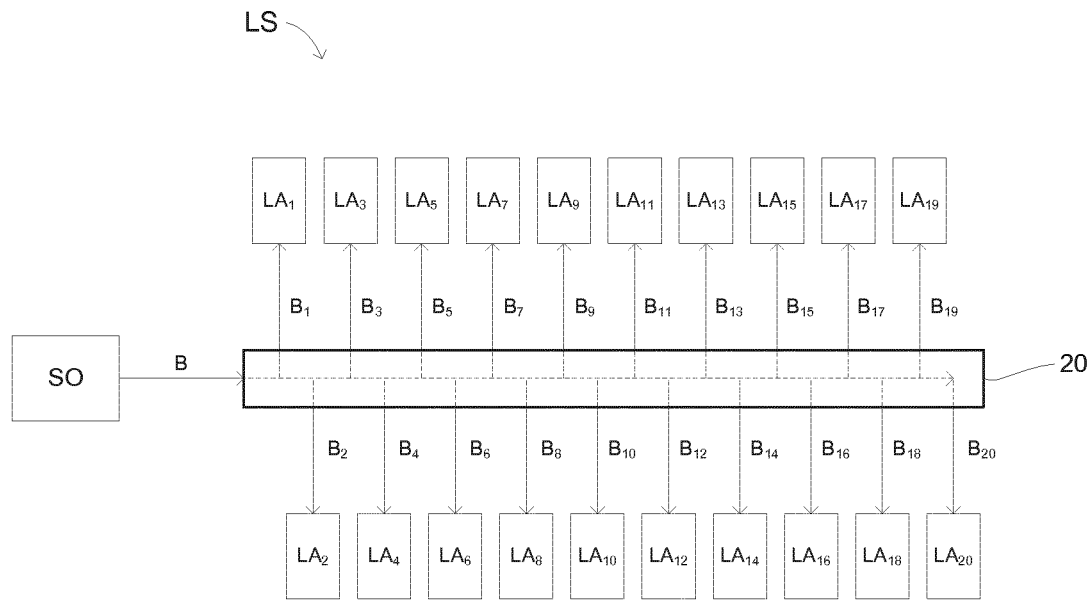
FIG. 1 is a schematic illustration of a lithographic system comprising a radiation source and a plurality of lithographic apparatus.

FIG. 1 shows a lithographic system LS, comprising: a radiation source SO, a beam splitting apparatus 20 and a plurality of tools. In FIG. 1 twenty tools $LA_1$-$LA_{20}$ are provided. Each of the tools may be any tool which receives a radiation beam. The tools $LA_1$-$LA_{20}$ are generally referred to herein as lithographic apparatuses, although it will be appreciated that the tools are not so limited. For example, the tools may comprise lithographic apparatuses, mask inspection apparatuses, Arial Image Measurement Systems (AIMS).

The radiation source SO comprises at least one free electron laser and is configured to generate an extreme ultraviolet (EUV) radiation beam B (which may be referred to as a main beam). The main radiation beam B is split into a plurality of radiation beams $B_1$-$B_{20}$ (which may be referred to as branch beams), each of which is directed to a different one of the lithographic apparatus $LA_1$-$LA_{20}$, by the beam splitting apparatus 20. The branch radiation beams $B_1$-$B_{20}$ may be split off from the main radiation beam B in series, with each branch radiation beam being split off from the main radiation beam B downstream from the preceding branch radiation beam. The beam splitting apparatus may, for example, comprise a series of mirrors (not shown) which are each configured to split off a portion of the main radiation beam B into a branch radiation beam $B_1$-$B_{20}$.

Figure 2:
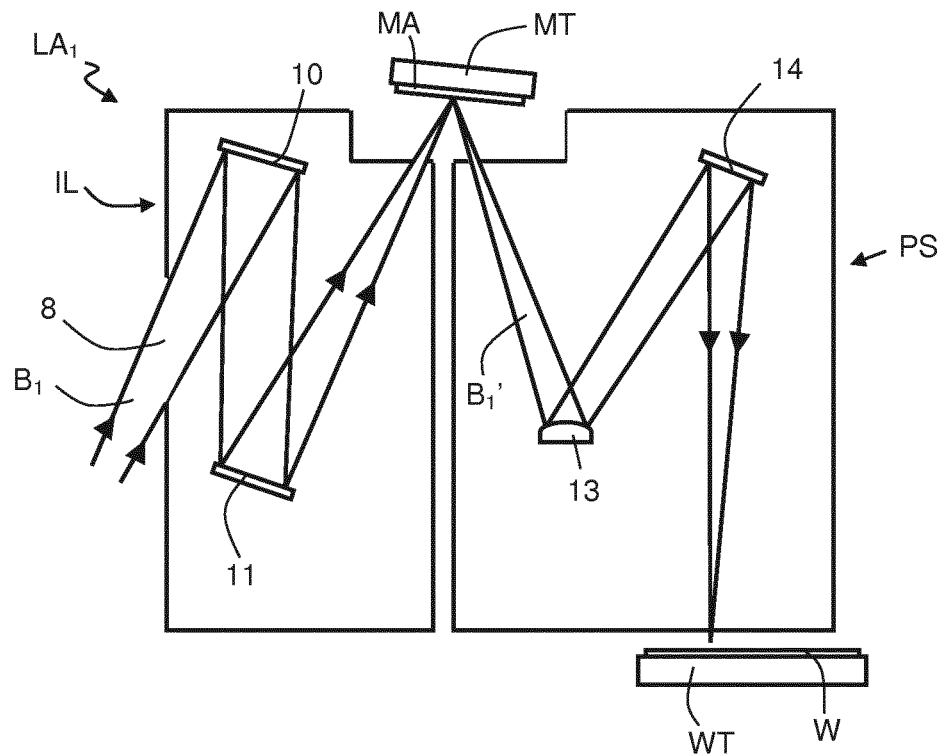
FIG. 2 is a schematic illustration of a lithographic apparatus that may form part of a lithographic system described herein.

The branch radiation beams $B_1$-$B_{20}$ are depicted in FIG. 1 as being split off from the main radiation beam B such that the branch radiation beams $B_1$-$B_{20}$ propagate in directions which are approximately perpendicular to the direction of propagation of the main radiation beam B. However, in some embodiments the branch radiation beams $B_1$-$B_{20}$ may instead be split off from the main radiation beam B such that an angle between the direction of propagation of each branch radiation beam $B_1$-$B_{20}$ and the direction of propagation of the main radiation beam is substantially less than 90 degrees. This may allow mirrors of the beam splitting apparatus to be arranged such that the main radiation beam B is incident on the mirrors at an angle of incidence which is less than normal. This may advantageously decrease the amount of radiation which is absorbed by the mirrors and therefore increase the amount of radiation which is reflected from the mirrors and which is provided to the lithographic apparatus $LA_1$-$LA_{20}$ via the branch radiation beams $B_1$-$B_{20}$. Additionally, it may be desirable to direct one or more branch radiation beams at an angle with respect to the entrance of the illuminator (as illustrated in FIG. 2). This may allow for the branch radiation beam to be supplied to the illuminator with fewer mirrors and hence less power loss/higher transmission.

As will be apparent from the description below, although in FIG. 1 the branch beams $B_1$-$B_{20}$ are shown to originate directly from the main radiation beam B it will be appreciated that the main radiation beam B may be split into one or more sub-beams and one or more of the sub-beams may then be further split, at least one more time, to produce the branch radiation beams $B_1$-$B_{20}$.

The lithographic apparatus $LA_1$-$LA_{20}$ may all be positioned on the same vertical level. The vertical level on which the lithographic apparatus $LA_1$-$LA_{20}$ are positioned may be substantially the same vertical level as the vertical level on which the beam splitting apparatus 20 is positioned and on which the main beam B is received from the radiation source SO. Alternatively, the beam splitting apparatus 20 may direct at least some of the branch radiation beams $B_1$-$B_{20}$ to one or more different vertical levels on which at least some of the lithographic apparatus $LA_1$-$LA_{20}$ are positioned. For example, the main radiation beam B may be received by the beam splitting apparatus on a basement or ground floor vertical level. The beam splitting apparatus 20 may direct at least some branch radiation beams $B_1$-$B_{20}$ to a vertical level which is positioned above the beam splitting apparatus and on which at least some of the lithographic apparatus $LA_1$-$LA_{20}$ are positioned. The lithographic apparatus $LA_1$-$LA_{20}$ may be positioned on multiple vertical levels and as such the beam splitting apparatus 20 may direct the branch radiation beams $B_1$-$B_{20}$ to different vertical levels in order to be received by the lithographic apparatus $LA_1$-$LA_{20}$.

The radiation source SO, beam splitting apparatus 20 and lithographic apparatus $LA_1$-$LA_{20}$ may all be constructed and arranged such that they can be isolated from the external environment. A vacuum may be provided in at least part of the radiation source SO, beam splitting apparatus 20 and lithographic apparatus $LA_1$-$LA_{20}$ so as to minimise the absorption of EUV radiation. Different parts of the lithographic system LS may be provided with vacuums at different pressures (i.e. held at different pressures which are below atmospheric pressure) and different gas compositions (in which different gas mixtures are supplied to different locations within SO and beam splitting apparatus 20).

FIG. 2 is a schematic depiction of a lithographic apparatus $LA_1$, of the lithographic system LS shown in FIG. 1. The lithographic apparatus $LA_1$, comprises an illumination system IL, a support structure MT configured to support a patterning device MA (e.g. a mask), a projection system PS and a substrate table WT configured to support a substrate W. The illumination system IL is configured to condition the branch radiation beam $B_1$ that is received by the lithographic apparatus $LA_1$, before it is incident upon the patterning device MA. The projection system PS is configured to project the branch radiation beam $B_1$ (now patterned by the mask MA) onto the substrate W. The substrate W may include previously formed patterns. Where this is the case, the lithographic apparatus aligns the patterned radiation beam $B_1$ with a pattern previously formed on the substrate W.

The branch radiation beam $B_1$ that is received by the lithographic apparatus $LA_1$ passes into the illumination system IL from the beam splitting apparatus 20 through an opening 8 in an enclosing structure of the illumination system IL. Optionally, the branch radiation beam $B_1$ may be focused to form an intermediate focus at or near to the opening 8.

The illumination system IL may include a facetted field mirror device 10 and a facetted pupil mirror device 11. The faceted field mirror device 10 and faceted pupil mirror device 11 together provide the radiation beam $B_1$ with a desired cross-sectional shape and a desired angular distribution. The radiation beam $B_1$ passes from the illumination system IL and is incident upon the patterning device MA held by the support structure MT. The patterning device MA reflects and patterns the radiation beam to form a patterned beam $B_1'$. The illumination system IL may include other mirrors or devices in addition to or instead of the faceted field mirror device 10 and faceted pupil mirror device 11. The illumination system IL may for example include an array of independently moveable mirrors. The independently moveable mirrors may for example measure less than 1 mm across. The independently moveable mirrors may for example be MEMS devices.

Following reflection from the patterning device MA the patterned radiation beam $B_{11}$ enters the projection system PS. The projection system comprises a plurality of mirrors 13, 14 which are configured to project the radiation beam $B_{11}$ onto a substrate W held by the substrate table WT. The projection system PS may apply a reduction factor to the radiation beam, forming an image with features that are smaller than corresponding features on the patterning device MA. A reduction factor of 4 may for example be applied.

Although the projection system PS has two mirrors 13, 14 in FIG. 2, the projection system may include any number of mirrors (e.g. six mirrors).

In some embodiments a lithographic system LS may include one or more mask inspection apparatus (not shown). A mask inspection apparatus may include optics (e.g. mirrors) configured to receive a branch radiation beam $B_1$-$B_{20}$ from the beam splitting apparatus 20 and direct the branch radiation beam at a mask MA. The mask inspection apparatus may further include optics (e.g. mirrors) configured to collect radiation reflected from the mask and form an image of the mask at an imaging sensor. The image received at the imaging sensor may be used to determine one or more properties of the mask MA. The mask inspection apparatus may, for example, be similar to the lithographic apparatus LA1 shown in FIG. 2, with the substrate table WT replaced with an imaging sensor.

In some embodiments a lithographic system LS may include one or more Aerial Image Measurement System (AIMS) which may be used to measure one or more properties of a mask MA. An AIMS may, for example, be configured to receive a branch radiation beam $B_1$-$B_{20}$ from the beam splitting apparatus 20 and use the branch radiation beam $B_1$-$B_{20}$ to determine one or more properties of a mask MA.

The radiation source SO comprises a free electron laser FEL which is operable to produce a beam of EUV radiation. Optionally, the radiation source SO may comprise more than one free electron laser FEL as described with reference to the example embodiments below. It will be appreciated however that in other embodiments, the radiation source SO may comprise other means of generating radiation. For example, the radiation source SO may comprise one or more "laser produced plasma" (LPP) sources. Indeed, it is to be understood that in some embodiments, the radiation source SO may utilise any means operable to provide a suitably powerful radiation beam.

A free electron laser comprises an electron source, which is operable to produce a bunched relativistic electron beam, and a periodic magnetic field through which the bunches of relativistic electrons are directed. The periodic magnetic field is produced by an undulator and causes the electrons to follow an oscillating path about a central axis. As a result of the acceleration caused by the magnetic fields the electrons spontaneously radiate electromagnetic radiation generally in the direction of the central axis. The relativistic electrons interact with radiation within the undulator. Under certain conditions, this interaction causes the electrons to bunch together into microbunches, modulated at the wavelength of radiation within the undulator, and coherent emission of radiation along the central axis is stimulated.

Figure 3:
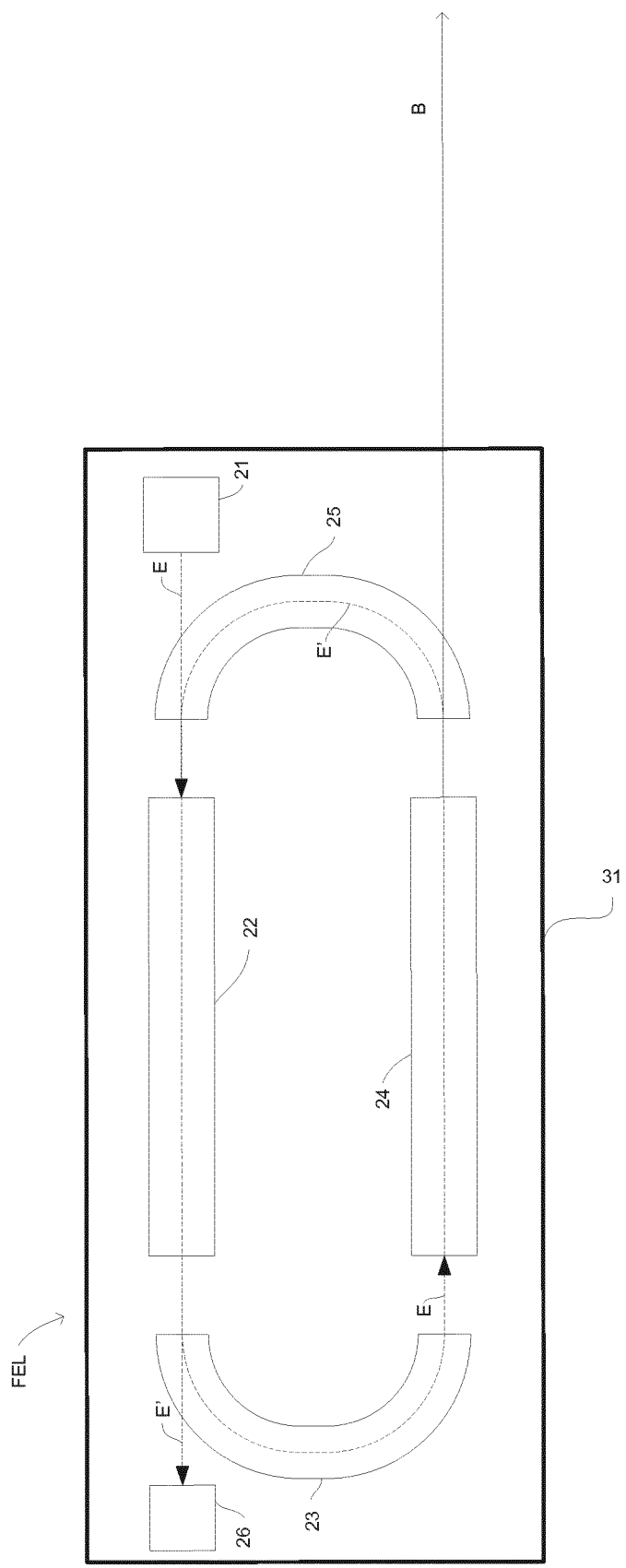
FIG. 3 is a schematic illustration of a free electron laser.

FIG. 3 is a schematic depiction of a free electron laser FEL comprising an electron source 21, a linear accelerator 22, a steering unit 23 and an undulator 24. The electron source 21 may alternatively be referred to as an injector and the undulator 24 may alternatively be referred to as a wiggler.

The electron source 21 is operable to produce a beam of electrons E. The electron source 21 may, for example, comprise a photo-cathode or a thermionic cathode and an accelerating electric field. The electron beam E is a bunched electron beam E which comprises a series of bunches of electrons. Electrons in the beam E are further accelerated by the linear accelerator 22. In an example, the linear accelerator 22 may comprise a plurality of radio frequency cavities, which are axially spaced along a common axis, and one or more radio frequency power sources, which are operable to control the electromagnetic fields along the common axis as bunches of electrons pass between them so as to accelerate each bunch of electrons. The cavities may be superconducting radio frequency cavities. Advantageously, this allows: relatively large electromagnetic fields to be applied at high duty cycles; larger beam apertures, resulting in fewer losses due to wakefields; and for the fraction of radio frequency energy that is transmitted to the beam (as opposed to dissipated through the cavity walls) to be increased. Alternatively, the cavities may be conventionally conducting (i.e. not superconducting), and may be formed from, for example, copper.

The final energy of the beam E can be reached over several acceleration steps. For example, the beam E may be sent through a plurality of linear accelerator modules, which are separated by beam transport elements (bends, drift spaces, etc.). Alternatively, or additionally, the beam E may be sent through the same linear accelerator module repeatedly, with gains and/or losses of energy in the beam E corresponding to the number of repetitions. Other types of linear accelerators may also be used. For example, laser wake-field accelerators or inverse free electron laser accelerators may be used.

The relativistic electron beam E which exits the linear accelerator 22 enters the steering unit 23. The steering unit 23 is operable to alter the trajectory of the relativistic electron beam E so as to direct the electron beam E from the linear accelerator 22 to the undulator 24. The steering unit 23 may, for example, comprise one or more electromagnets and/or permanent magnets configured to generate a magnetic field in the steering unit 23. The magnetic field exerts a force on the electron beam E which acts to alter the trajectory of the electron beam E. The trajectory of the electron beam E upon leaving the linear accelerator 22 is altered by the steering unit 23 so as to direct the electrons to the undulator 24.

In embodiments in which the steering unit 23 comprises one or more electromagnets and/or permanent magnets, the magnets may be arranged to form one or more of a magnetic dipole, a magnetic quadrupole, a magnetic sextupole and/or any other kind of multipole magnetic field arrangement configured to apply a force to the electron beam E. The steering unit 23 may additionally or alternatively comprise one or more electrically charged plates, configured to create an electric field in the steering unit 23 such that a force is applied to the electron beam E. In general the steering unit 23 may comprise any apparatus which is operable to apply a force to the electron beam E to alter its trajectory.

The steering unit 23 directs the relativistic electron beam E to the undulator 24. The undulator 24 is operable to guide the relativistic electrons along a periodic path so that the electron beam E interacts with radiation within the undulator 24 so as to stimulate emission of coherent radiation. Generally the undulator 24 comprises a plurality of magnets, which are operable to produce a periodic magnetic field which causes the electron beam E to follow a periodic path. As a result the electrons emit electromagnetic radiation generally in the direction of a central axis of the undulator 24. The undulator 24 may comprise a plurality of sections (not shown), each section comprising a periodic magnet structure. The undulator 24 may further comprise a mechanism for refocusing the electron beam E such as, for example, a quadrupole magnet in between one or more pairs of adjacent sections. The mechanism for refocusing the electron beam E may reduce the size of the electron bunches, which may improve the coupling between the electrons and the radiation within the undulator 24, increasing the stimulation of emission of radiation.

As electrons move through the undulator 24, they interact with the electric field of the electromagnetic radiation in the undulator 24, exchanging energy with the radiation. In general the amount of energy exchanged between the electrons and the radiation will oscillate rapidly unless conditions are close to a resonance condition, given by:

$$\lambda_{em} = \frac{\lambda_u}{2\gamma^2}\left(1 + \frac{K^2}{A}\right), \tag{1}$$

where $\lambda_{em}$ is the wavelength of the radiation, $\lambda_u$ is the undulator period, y is the Lorentz factor of the electrons and K is the undulator parameter. A is dependent upon the geometry of the undulator 24: for a helical undulator A=1, whereas for a planar undulator A=2. For a helical undulator which produces a light which is not circularly polarized, but elliptically polarized A will be in the range of 1 to 2. In practice, each bunch of electrons will have a spread of energies although this spread may be minimised as far as possible (by producing an electron beam E with low emittance). The undulator parameter K is typically approximately 1 and is given by:

$$K = \frac{q\lambda_u B_0}{2\pi mc}, \tag{2}$$

where q and m are, respectively, the electric charge and mass of the electrons, $B_0$ is the amplitude of the periodic magnetic field, and c is the speed of light.

The resonant wavelength $\lambda_{em}$ is equal to the first harmonic wavelength spontaneously radiated by electrons moving through the undulator 24. The free electron laser FEL may operate in self-amplified spontaneous emission (SASE) mode. Operation in SASE mode may require a low energy spread of the electron bunches in the electron beam E before it enters the undulator 24. Alternatively, the free electron laser FEL may comprise a seed radiation source, which may be amplified by stimulated emission within the undulator 24. The free electron laser FEL may operate as a recirculating amplifier free electron laser (RAFEL), wherein a portion of the radiation generated by the free electron laser FEL is used to seed further generation of radiation.

Electrons moving through the undulator 24 may cause the amplitude of radiation to increase, i.e. the free electron laser FEL may have a non-zero gain. Maximum gain may be achieved when the resonance condition is met or when conditions are close to but slightly off resonance.

An electron which meets the resonance condition as it enters the undulator 24 will lose (or gain) energy as it emits (or absorbs) radiation, so that the resonance condition is no longer satisfied. Therefore, in some embodiments the undulator 24 may be tapered. That is, the amplitude of the periodic magnetic field and/or the undulator period $\lambda_u$ may vary along the length of the undulator 24 in order to keep bunches of electrons at or close to resonance as they are guided though the undulator 24. Note that the interaction between the electrons and radiation within the undulator 24 produces a spread of energies within the electron bunches. The tapering of the undulator 24 may be arranged to maximise the number of electrons at or close to resonance. For example, the electron bunches may have an energy distribution which peaks at a peak energy and the tapering maybe arranged to keep electrons with this peak energy at or close to resonance as they are guided though the undulator 24. Advantageously, tapering of the undulator has the capacity to significantly increase conversion efficiency. The use of a tapered undulator may increase the conversion efficiency (i.e. the portion of the energy of the electron beam E which is converted to radiation in the radiation beam B) by more than a factor of 2. The tapering of the undulator may be achieved by reducing the undulator parameter K along its length. This may be achieved by matching the undulator period $\lambda_u$ and/or the magnetic field strength $B_0$ along the axis of the undulator to the electron bunch energy to ensure that they are at or close to the resonance condition. Meeting the resonance condition in this manner increases the bandwidth of the emitted radiation.

After leaving the undulator 24, the electromagnetic radiation is emitted as a radiation beam B'. The radiation beam B' comprises EUV radiation and may form all or part of the radiation beam B which is provided to the beam splitting apparatus 20 (depicted in FIG. 1) and which forms the branch radiation beams $B_{1-20}$ which are provided to the lithographic apparatus $LA_{1-20}$.

In the embodiment of a free electron laser which is depicted in FIG. 3, the electron beam E' which leaves the undulator 24 enters a second steering unit 25. The second steering unit 25 alters the trajectory of the electron beam E' which leaves the undulator 24 so as to direct the electron beam E' back through the linear accelerator 22. The second steering unit 25 may be similar to the steering unit 23 and may, for example, comprise one or more electromagnets and/or permanent magnets. The second steering unit 25 does not affect the trajectory of the radiation beam B' which leaves the undulator 24. The steering unit 25 therefore decouples the trajectory of the electron beam E' from the radiation beam B'. In some embodiments, the trajectory of the electron beam E' may be decoupled from the trajectory of the radiation beam B' (e.g. using one or more magnets) before reaching the second steering unit 25.

The second steering unit 25 directs the electron beam E' to the linear accelerator 22 after leaving the undulator 24. Electron bunches which have passed through the undulator 24 may enter the linear accelerator 22 with a phase difference of approximately 180 degrees relative to accelerating fields in the linear accelerator 22 (e.g. radio frequency fields). The phase difference between the electron bunches and the accelerating fields in the linear accelerator 22 causes the electrons to be decelerated by the fields. The decelerating electrons E' pass some of their energy back to the fields in the linear accelerator 22 thereby increasing the strength of the fields which accelerate the electron beam E arriving from the electron source 21. This arrangement therefore recovers some of the energy which was given to electron bunches in the linear accelerator 22 (when they were accelerated by the linear accelerator) in order to accelerate subsequent electron bunches which arrive from the electron source 21. Such an arrangement may be known as an energy recovering LINAC.

Electrons E' which are decelerated by the linear accelerator 22 are absorbed by a beam dump 26. The steering unit 23 may be operable to decouple the trajectory of the electron beam E' which has been decelerated by the linear accelerator 22 from the trajectory of the electron beam E which has been accelerated by the linear accelerator 22. This may allow the decelerated electron beam E' to be absorbed by the beam dump 26 whilst the accelerated electron beam E is directed to the undulator 24.

The free electron laser FEL may comprise a beam merging unit (not shown) which substantially overlaps the trajectories of the beam E coming from the source 21 and the beam E' coming from the steering unit 25. The merging is possible due to the fact that prior to acceleration by the accelerator 22, the energy of the beam E is significantly smaller than the energy of the beam E'. The trajectory of the accelerated electron beam E may be decoupled from the trajectory of the decelerated electron beam E' by generating a substantially constant magnetic field. The difference in energies between the accelerated electron beam E and the decelerated electron beam E' causes the trajectories of the two electron beams to be altered by different amounts by the constant magnetic field. The trajectories of the two electron beams will therefore become decoupled from each other.

Alternatively, the steering unit 23 may, for example, be operable to generate a periodic magnetic field which has a substantially constant phase relationship with the electron bunches which form the accelerated electron beam E and the decelerated electron beam E'. For example at times at which electron bunches from the accelerated electron beam E enter the steering unit 23, the steering unit 23 may generate a magnetic field which acts to direct the electrons to the undulator 24. At times at which electron bunches from the decelerated electron beam E' enter the steering unit 23, the steering unit 23 may generate a magnetic field which acts to direct the electrons to the beam dump 26. Alternatively, at times at which electron bunches from the decelerated electron beam E' enter the steering unit 23, the steering unit 23 may generate little or no magnetic field such that the electrons pass out of the steering unit 23 and to the beam dump 26.

Alternatively the free electron laser FEL may comprise a beam splitting unit (not shown) which is separate from the steering unit 23 and which is configured to decouple the trajectory of the accelerated electron beam E from the trajectory of the decelerated electron beam E' upstream of the steering unit 23. The beam splitting unit may, for example, be operable to generate a periodic magnetic field which has a substantially constant phase relationship with the electron bunches which form the accelerated electron beam E and the decelerated electron beam E'.

The beam dump 26 may, for example, include a large amount of water or a material with a high threshold for radioactive isotope generation by high energy electron impact. For example, the beam dump 26 may include aluminium with a threshold for radioactive isotope generation of approximately 15 MeV. By decelerating the electron beam E' in the linear accelerator 22 before it is incident on the beam dump 26, the amount of energy the electrons have when they are absorbed by the beam dump 26 is reduced. This reduces the levels of induced radiation and secondary particles produced in the beam dump 26. This removes, or at least reduces, the need to remove and dispose of radioactive waste from the beam dump 26. This is advantageous since the removal of radioactive waste requires the free electron laser FEL to be shut down periodically and the disposal of radioactive waste can be costly and can have serious environmental implications.

When operating as a decelerator, the linear accelerator 22 may be operable to reduce the energy of the electrons E' to below a threshold energy. Electrons below this threshold energy may not induce any significant level of radioactivity in the beam dump 26.

In some embodiments a decelerator (not shown) which is separate to the linear accelerator 22 may be used to decelerate the electron beam E' which has passed through the undulator 24. The electron beam E' may be decelerated by the decelerator in addition to being decelerated by the linear accelerator 22 or instead of being decelerated by the linear accelerator 22. For example, the second steering unit 25 may direct the electron beam E' through a decelerator prior to the electron beam E' being decelerated by the linear accelerator 22. Additionally or alternatively the electron beam E' may pass through a decelerator after having been decelerated by the linear accelerator 22 and before being absorbed by the beam dump 26. Alternatively the electron beam E' may not pass through the linear accelerator 22 after leaving the undulator 24 and may be decelerated by one or more decelerators before being absorbed by the beam dump 26.

Optionally, the free electron laser FEL may comprise one or more bunch compressors. Bunch compressors may be disposed downstream or upstream of the linear accelerator 22. A bunch compressor is configured to bunch electrons in the electron beams E, E' and spatially compress or stretch existing bunches of electrons in the electron beams E, E'. Compression may be used to increase the conversion efficiency in the undulator 24 by providing a high peak current. Stretching of the bunches may be used to enable transport bunches with low peak current.

One type of bunch compressor comprises a radiation field directed transverse to the electron beam E. An electron in the electron beam E interacts with the radiation and bunches with other electrons nearby. Another type of bunch compressor comprises a magnetic chicane, wherein the length of a path followed by an electron as it passes through the chicane is dependent upon its energy. This type of bunch compressor may be used to compress a bunch of electrons which have been accelerated in a linear accelerator 22 by a plurality of conductors whose potentials oscillate at, for example, radio frequencies.

It may be desirable for electron bunches entering the undulator 24 to be tightly bunched and therefore have a higher peak current than in other locations within the accelerator. It may therefore be desirable to compress the electron bunches before they pass into the undulator 24 using one or more bunch compressors. A separate bunch compressor (not shown) may therefore be disposed between the steering unit 23 and the undulator 24. Alternatively, or additionally, the steering unit 23 itself may act to bunch the electrons in the electron beam E. An electron bunch which is accelerated by the linear accelerator 22 may have a correlated spread of energies which is a gradient of mean energy along the length of the bunch. For example, some electrons in an electron bunch may have energies which are higher than an average energy of the electron bunch and some electrons in the bunch may have energies which are lower than the average energy. The alteration of the trajectory of an electron which is caused by the steering unit 23 may be dependent on the energy of the electrons (e.g. when the trajectory is altered by a magnetic field). Electrons of different energies may therefore have their trajectories altered by different amounts by the steering unit 23, which may be difference in trajectories may be controlled to result in a compression of an electron bunch.

The free electron laser FEL shown in FIG. 3 is housed within a building 31. The building 31 may comprise walls which do not substantially transmit radiation which is generated in the free electron laser FEL whilst the free electron laser FEL is in operation. For example, the building 31 may comprise thick concrete walls (e.g. walls which are approximately 4 metres thick). The walls of the building 31 may be further provided with radiation shielding materials such as, for example, lead and/or other materials which are configured to absorb neutrons and/or other radiation types. Radiation shielding may comprise both materials with high density and high content of heavy elements (e.g. materials having a high Z value) in order to intercept electrons and gamma-photons and in materials with high content of light elements (e.g. materials having a low Z value, such as Hydrogen or Boron) to intercept neutrons. Providing walls of a building 31 with radiation absorbing materials may advantageously allow the thickness of the walls of the building 31 to be reduced. However adding radiation absorbing materials to a wall may increase the cost of constructing the building 31. A relatively cheap material which may be added to a wall of the building 31 in order to absorb radiation may, for example, be a layer of earth or sand.

In addition to providing walls of the building 31 which have radiation shielding properties. The building 31 may also be configured to prevent radiation generated by the free electron laser FEL from contaminating ground water below the building 31. For example, the base and/or foundations of the building 31 may be provided with radiation shielding materials or may be sufficiently thick to prevent radiation from contaminating ground water below the building 31. In an embodiment the building 31 may be positioned at least partly underground. In such an embodiment ground water may surround portions of the exterior of the building 31 as well as being below the building 31. Radiation shielding may therefore be provided around the exterior of the building 31 in order to prevent radiation from contaminating ground water which surrounds the building 31.

In addition to or as an alternative to shielding radiation at the exterior of the building 31, radiation shielding may also be provided inside of the building 31. For example, radiation shielding may be provided inside the building 31 at locations proximate to portions of the free electron laser FEL which emit large amounts of radiation.

It will be appreciated that while an FEL having a particular layout is shown in FIG. 3, the FEL may be otherwise arranged. For example, in other embodiments, the accelerator 22 and the undulator 24 may be arranged in-line. In other embodiments the electron beam which exits the undulator may not be directed back to the accelerator. Generally, therefore, it is to be understood that the FEL may be arranged in any appropriate way.

The source SO may comprise a single free electron laser FEL. The free electron laser FEL may supply an EUV radiation beam to the beam splitting apparatus 20 which provides branch radiation beams to the lithographic apparatus $LA_1$-$LA_{20}$. The radiation source SO may comprise an optical system which includes dedicated optical components configured to direct a radiation beam B output from a free electron laser FEL to the beam splitting apparatus 20 of a lithographic system LS. Since EUV radiation is generally well absorbed by all matter, reflective optical components are generally used (rather than transmissive components) so as to minimise losses. The dedicated optical components of the optical system may adapt the properties of the radiation beam produced by the free electron laser FEL so that it is suitable for acceptance by the tools (e.g. the illumination systems IL of the lithographic apparatus $LA_1$-$LA_{20}$ and/or a mask inspection apparatuses).

Alternatively a radiation source SO may comprise a plurality of free electron lasers (e.g. two free electron lasers) which may each provide an EUV radiation beam, B', B" to an optical system. The optical system may be considered to form part of the radiation source SO, or may be considered to be separate to the radiation source SO. The optical system may receive a radiation beam from each of the plurality of free electron lasers and may combine the radiation beams into a composite radiation beam which is provided to the beam splitting apparatus 20 in order to provide the branch radiation beams $B_1$-$B_{20}$ to the lithographic apparatus $LA_1$-$LA_{20}$.

Figure 4:
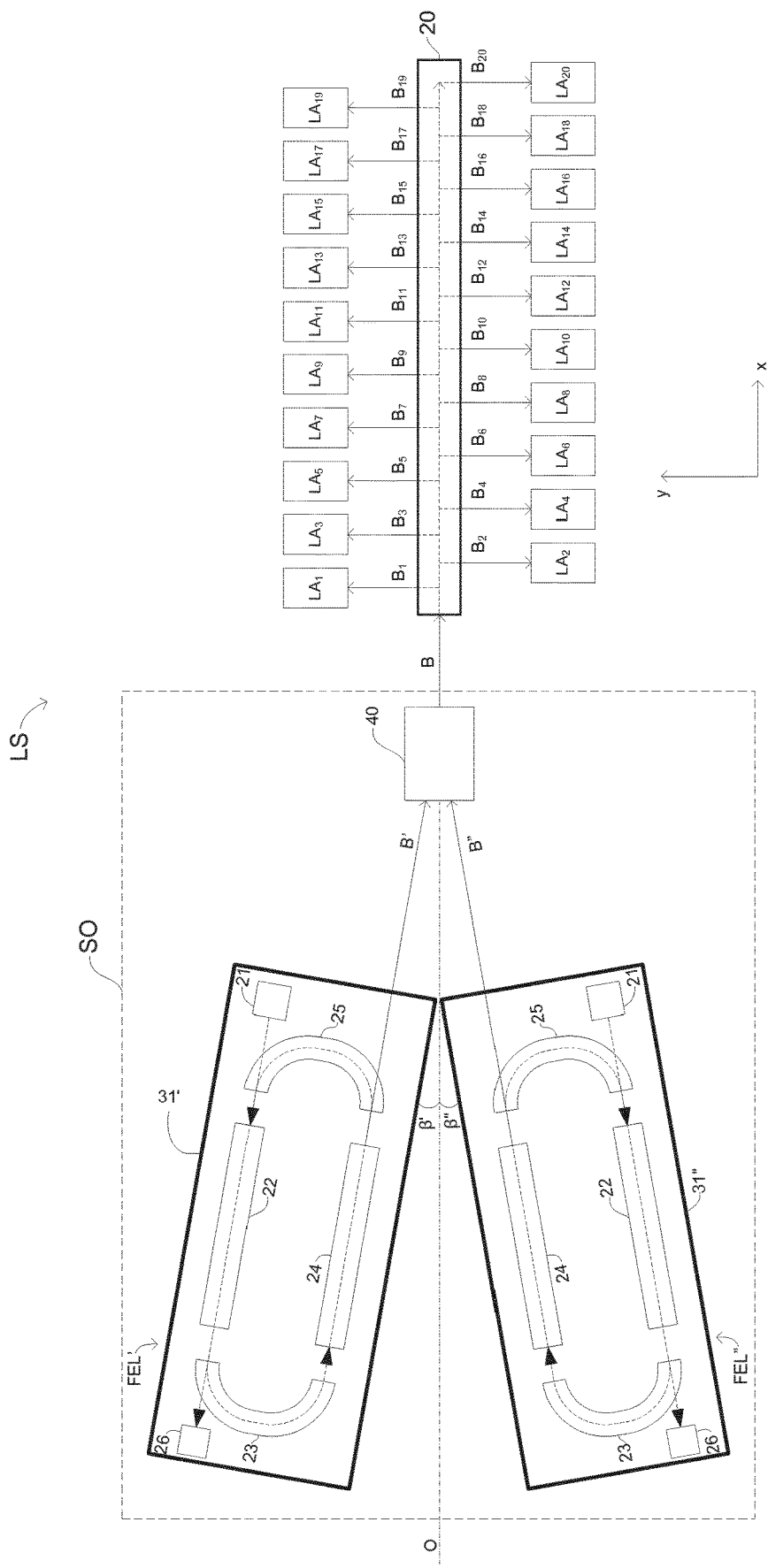
FIG. 4 is a schematic illustration of a lithographic system including a radiation source comprising two free electron lasers.

FIG. 4 is a schematic depiction of a lithographic system LS which includes a radiation source SO comprising a first free electron laser FEL' and a second free electron laser FEL". The first free electron laser FEL' outputs a first EUV radiation beam B' and the second free electron laser FEL" outputs a second EUV radiation beam B". The first free electron laser FEL' is housed within a first building 31'. The second free electron laser FEL" is housed within a second building 31".

The first and second radiation beams B', B" are received by an optical system 40. The optical system 40 comprises a plurality of optical elements (e.g. mirrors) which are arranged to receive the first radiation beam B' and the second radiation beam B" and output a main radiation beam B. At times at which both the first and second free electron lasers are operating, the main radiation beam B is a composite radiation beam which comprises radiation from both the first and second radiation beams B', B". The composite radiation beam B is provided to the beam splitting apparatus 20 which provides branch radiation beams $B_1$-$B_{20}$ to lithographic apparatus $LA_1$-$LA_{20}$.

The arrangement which is depicted in FIG. 4 in which two free electron lasers are arranged to provide radiation beams B', B" to form a main radiation beam B, may allow one of the free electron lasers to be turned off whilst radiation is continuously provided to the lithographic apparatus $LA_1$-$LA_{20}$. For example, one of the free electron lasers may be taken out of operation in order to, for example, allow the free electron laser to be repaired or to undergo maintenance. In this event the other free electron laser may continue to provide a radiation beam which is received by the optical system 40. In the event that only one of the free electron lasers provides radiation to the optical system 40, the optical system 40 is operable to form a main radiation beam B which comprises radiation from the free electron laser which is providing radiation to the optical system 40. This allows for continuous operation of the lithographic apparatus $LA_1$-$LA_{20}$ even when one of the free electron lasers is taken out of operation.

Figure 5:
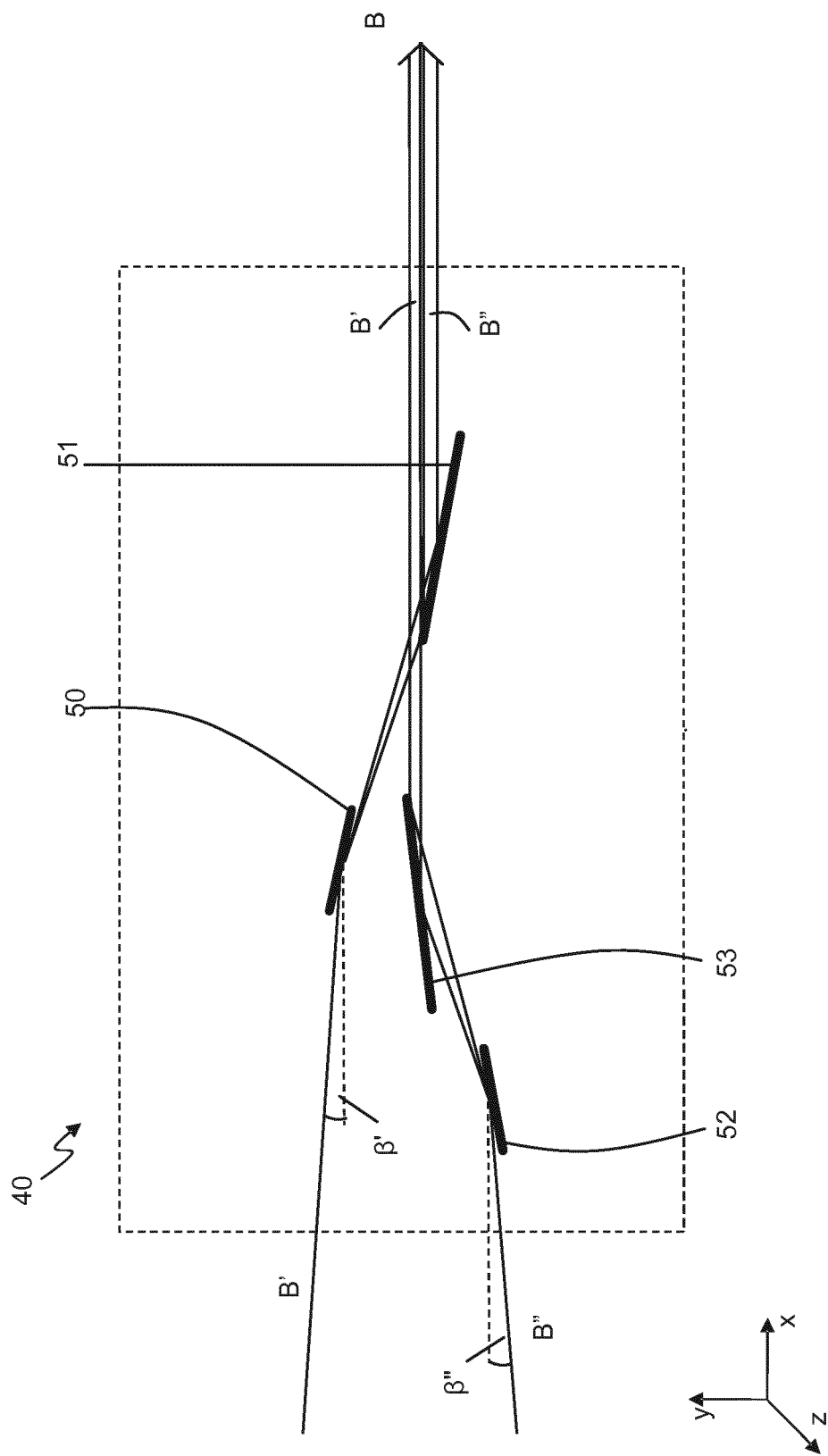
FIG. 5 is a schematic illustration of an optical system for a source comprising two free electron lasers.

FIG. 5 is a schematic depiction of an embodiment of an optical system 40 according to an embodiment of the invention which is arranged to receive a beam of radiation B', B" from each of the free electron lasers FEL', FEL" and to output an output radiation beam B. The radiation beam B that is output by the optical system 40 is received by the beam splitting apparatus 20 (see FIG. 1).

The optical system 40 comprises four optical elements: first and second optical elements 50, 51 associated with the free electron laser FEL'; and first and second optical elements 52, 53 associated with the free electron laser FEL". The optical elements 50, 51, 52, 53 are arranged to alter the size and shape of the cross section of the radiation beams B', B" from the free electron lasers FEL', FEL".

In particular, the first optical elements 50, 52 are convex mirrors, which act to increase the cross sectional area of the radiation beams B', B" from the free electron lasers FEL', FEL". Although in FIG. 5 the first optical elements 50, 52 appear to be substantially flat in the x-y plane they may be convex both in this plane and in the z direction. Since the first optical elements 50, 52 are convex, they will increase the divergence of the EUV radiation beams B', B", thereby decreasing the heat load on mirrors downstream of them. The first optical element 50 is therefore a diverging optical element arranged to increase the cross sectional area of the radiation beam B' received from the first free electron laser FEL'. The first optical element 52 is a diverging optical element arranged to increase the cross sectional area of the radiation beam B" received from the second free electron laser FEL". This may allow mirrors downstream to be of a lower specification, with less cooling, and therefore less complex and expensive. Additionally or alternatively, it may allow the downstream mirrors to be nearer to normal incidence. In practice, as described below, the radiation beam B output by the radiation source SO may be split by a plurality of consecutive, static, edge-forming mirrors arranged in series in the path of the beam B. Increasing the size of the beam B (by, for example, using convex mirrors as the first optical elements 50,52) may reduce the accuracy with which such static mirrors need be located in the beam B path. Therefore, this allows for more accurate splitting of the output beam B by the splitting apparatus 20.

The second optical elements 51, 53 are concave and are complementary in shape to the first optical elements such that the beams leaving the second optical elements 51, 53 have substantially zero divergence. Therefore, downstream of the second optical elements 51, 53 the beams are substantially collimated. Again, although in FIG. 5 the second optical elements 51, 53 appear to be substantially flat in the x-y plane they are in fact concave both in this plane and in the z direction. Alternatively, any of the mirrors 50, 51, 52, 53 may be hyperbolic-parabola-like in shape, so as to have both positive and negative curvatures. Alternatively, the mirrors 50 to 53 may be flat and used solely to control shift and tilt of the beam. Additionally, radiation absorbers may be provided behind the mirrors 50, 52, in order to intercept gamma photons, and neutrons co-propagating with beams B' and B" and originating in the undulators 24 due to Bremsstrahlung radiation. Again, radiation shielding may, for example, be provided by high density, high Z value materials, possibly in combination with low density, low Z value materials).

It may be preferable for the output beam B, which is received by the beam splitting apparatus 20, to have a different shape and/or intensity distribution to that output by the free electron lasers FEL', FEL". For example, a rectangular shape may be preferable to a circular beam for consecutive edge-forming extraction mirrors within the beam splitting apparatus 20. Therefore, in addition to increasing the cross sectional area of the radiation beams B', B", the optical elements 50, 51, 52, 53 may act to alter the cross sectional shape of the radiation beams B', B". In particular, the optical elements 50, 51, 52, 53 may be astigmatic or aspherical and may be shaped so as to ensure that the radiation beams B', B" leaving the second optical elements 51, 53 are more rectangular in shape than the radiation beams B', B" produced by the free electron lasers FEL', FEL". For example, the optical elements may be shaped so that the beams B', B" leaving the second optical elements 51, 53 are generally rectangular but with rounded corners, although other shapes are also possible. The two dimensions of such a rectangular shape may be related to radii of curvature of the optical elements in two perpendicular directions such as, for example, in the x-y plane and in the z direction. Advantageously, this allows the mirrors that are used to split the output radiation beam B into branch radiation beams $B_1$-$B_{20}$ (see FIG. 1) before they enter the lithographic apparatuses $LA_1$-$LA_{20}$, to be identical or at least very similar. This is especially beneficial from a manufacturing point of view.

In addition to the shape of the cross section of the beam leaving optical system 40, the optical system 40 may be operable to modify an intensity profile over the cross section of the radiation beam B in comparison to the intensity profiles of the beams B' and B". For example, the intensity profile may be modified from a Gaussian to a more flat "top hat" profile. Such modifications may allow for more straightforward extraction of portions of the beam B by the beam splitting apparatus 20, as is described in further detail below. When both of the free electron lasers FEL', FEL" are on, the optical system 40 is operable to combine their radiation beams B', B" to form a composite radiation beam B. In this embodiment, this is achieved by offsetting the first and second optical elements 50, 51 of the first free electron laser FEL' from those 52, 53 of the second free electron laser FEL" in the x-direction so that the beams B', B" leaving the second optical elements 51, 53 are both adjacent to each other and mutually parallel. In particular, the first and second optical elements 50, 51 of the first free electron laser FEL' are disposed "downstream" (with respect to the direction of propagation of the laser beams B', B") of those 52, 53 of the second free electron laser FEL".

In such an arrangement, the optical system 40 is operable to combine the two radiation beams B', B" to form a composite radiation beam. The composite beam is the output radiation beam B output by the optical system 40.

It will be appreciated that FIG. 5 is merely exemplary and that the optical system 40 may be implemented other than as shown in FIG. 5.

Although embodiments of a free electron laser have been described above as comprising a linear accelerator 22, it should be appreciated that a linear accelerator 22 is merely an example of a type of particle accelerator which may be used to accelerate electrons in a free electron laser. A linear accelerator 22 may be particularly advantageous since it allows electrons having different energies to be accelerated along the same trajectory. However in alternative embodiments of a free electron laser other types of particle accelerators may be used to accelerate electrons to relativistic energies.

Embodiments of a free electron laser have been described in which an electron beam propagates along a first path and substantially in a first direction and along a second path and substantially in a second direction, wherein the first path and the second path are vertically separated from one another. Whilst embodiments have been described and depicted in which the first and second paths are substantially parallel with each other and are substantially parallel with a horizontal direction, other arrangements may instead be used. For example, in some embodiments the first path and/or the second path may be disposed at a non-zero angle with respect to the horizontal whilst remaining vertically separated from each other. In some embodiments the first and second paths may form different angles with respect to the horizontal and may therefore be disposed at a non-zero angle with respect to each other.

Whilst embodiments of a radiation source SO have been described and depicted as comprising two free electron lasers FEL, it should be appreciated that a radiation source may comprise any number of free electron lasers FEL. For example, a radiation source may comprise a single free electron laser FEL or may comprise a number of free electron lasers which is greater than two.

Whilst embodiments of a radiation source SO have been described and depicted as comprising an optical system 40, it should be appreciated that some embodiments of a radiation source SO may not include an optical system 40. For example, a free electron laser may provide a radiation beam B' directly to a beam splitting apparatus 20 of a lithographic system LS without first being directed to an optical system 40.

As described above, the radiation beam B produced by the source SO may be split into a plurality of branch radiation beams for provision to a plurality of tools, such as lithographic apparatus and mask inspection apparatus. Beam splitting arrangements suitable for splitting the radiation beam B into branch radiation beams using a plurality of static mirrors are now described. By static it is to be understood that the mirrors do not move during normal operation, or put another way, that splitting is not achieved through movement of the mirrors. Therefore the relative fraction of the main radiation beam that is incident upon each static mirror remains substantially constant during normal operation. Although the mirrors described below are static, they may be adjustable, to allow, for example, for adjustment of overlap of the mirrors with the main radiation beam B and/or alignment of branch radiation beams B (e.g. during installation of the lithographic system or installation of new tools to an existing lithographic system).

Figure 6:
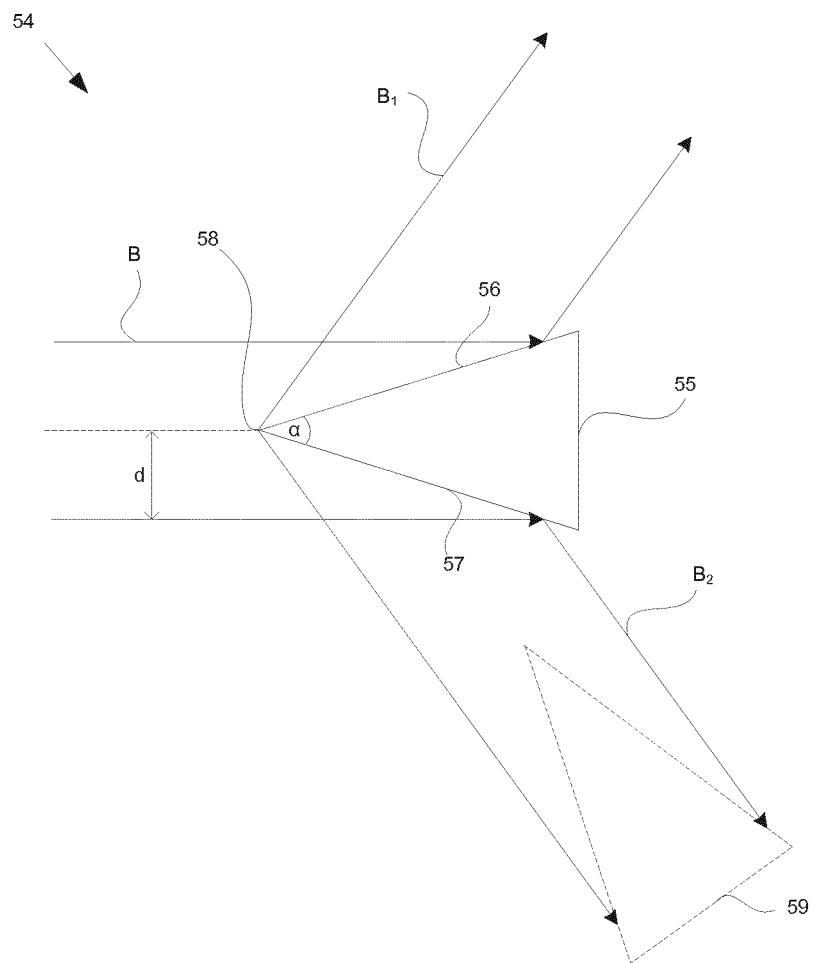
FIGS. 6 to 11 are schematic illustrations of beam splitting apparatus comprising a plurality of static mirrors.

FIG. 6 is a schematic depiction a beam splitting apparatus 54 which is suitable for splitting the radiation beam B to provide two or more branch radiation beams. In the arrangement 54, the radiation beam B is directed at a splitting element 55 having a first reflective surface 56 arranged to reflect a first portion of the radiation beam B, and a second reflective surface 57 arranged to reflect a second portion of the radiation beam B. The first reflective surface 56 and the second reflective surface 57 meet to form an edge 58 that is disposed in the path of the radiation beam B. The splitting element 55 may be considered to provide two static mirrors. The splitting element 55 may be formed, for example, as a triangular prism, although it is to be appreciated that any construction may be used.

Reflection of a first portion of the beam B that is incident on the first reflective surface 56 provides a first branch radiation beam $B_1$, while reflection of a second portion of the radiation beam B from the second reflective surface 57 provides a second branch radiation beam $B_2$.

The branch radiation beams $B_1$, $B_2$ may be directed to tools such as, for example, a lithographic apparatus or mask inspection apparatus, without further splitting. Alternatively, either or both of the branch radiation beams $B_1$, $B_2$ may be provided to further splitting means, such as, for example, further edge-forming splitting elements. This possibility is illustrated by a further edge-forming splitting element 59, depicted in dashed outline, disposed in the path of the branch radiation beam $B_2$. While not shown in FIG. 6, it will be appreciated that branch radiation beams provided by splitting the branch radiation beam $B_2$ using the splitting element 59 may themselves be provided to further splitting elements.

An angle α between the first surface 56 and the second surface 57 together with the angle $α_1$ (not shown) between the knife edge of the prism (intersection of surface 56 and 57) and the beam B determine the angle of incidence of the portions of the radiation beam on the first and second surfaces 56, 57. The angle α and/or $α_1$ may be made sufficiently small that the radiation beam B is at a grazing incidence angle with respect to each of the surfaces 56, 57 so as to reduce absorption and increase reflectance of EUV radiation. For example, the angle α and/or $α_1$ may be 10 degrees or less.

Reducing absorption by the splitting element 55 is also desirable to reduce heating, hence thermal stress, within the splitting element 55, and in particular heating of the edge 58, which may have a small cross sectional area. In order to reduce heating of the splitting element 55 further, the splitting element 55 may be cooled by active cooling means (not shown). For example, a liquid coolant may be circulated within the splitting element 55 to transport heat away. For example, channels may be provided on a reverse side of the reflective surfaces 56, 57 and along the edge 58. Other cooling means may alternatively be used.

The splitting element 55 may be constructed from any appropriate material. For example, the splitting element 55 may be constructed from copper. Constructing the splitting element 55 from copper may be advantageous given copper's high thermal conductivity. In order to increase reflectivity, a material having a high reflectivity at a desired wavelength of radiation may be deposited on the reflective surfaces 56, 57 of the splitting element 55. For example, molybdenum (Mo) or ruthenium (Ru) which have a high grazing incidence reflectivity for radiation having wavelengths of 13.5 nm may be used. Coatings of other materials may be used for other high grazing incidence reflectivity of radiation having other wavelengths, such as Nb, Zr, Ca, Eu, Pd, Ru, Rh, Te, La, Be, B, C, Ti, Sc, Au and Pt.

A distance d between the edge 58 of the splitting element 55 and a bottom edge of the radiation beam B may be controlled in order to vary the amount of radiation that is provided to the branch radiation beams $B_1$, $B_2$. In FIG. 6 the edge 58 is shown disposed at a central point of the radiation beam B such that the ratio between the branch radiation beams $B_1$, $B_2$ is substantially 50:50. By reducing the distance d, however, the amount of the radiation beam B that contributes to the branch radiation beam $B_1$ is increased while the amount of the radiation beam B that contributes to the branch radiation beam $B_2$ is decreased. Increasing the distance d will have the opposite effect.

While depicted as substantially planar in FIG. 6, the reflective surfaces 56, 57 may be curved in order to increase divergence of the branch radiation beams $B_1$, $B_2$. For example, each of the surfaces 56, 57 may be concave or convex. Alternatively or additionally, optics placed in the path of the branch radiation beams $B_1$, $B_2$ may be provided to condition the branch radiation beams for provision to particular tools or to further splitting arrangements.

Advantageously, the splitting element 55 provides for a large degree of separation between the branch radiation beams $B_1$, $B_2$ within a small distance. For example, it will be appreciated that a 10 degree angle α provides 10 degree deflection angles of the branch radiation beams $B_1$, $B_2$ with respect to the radiation beam B.

Figure 7:
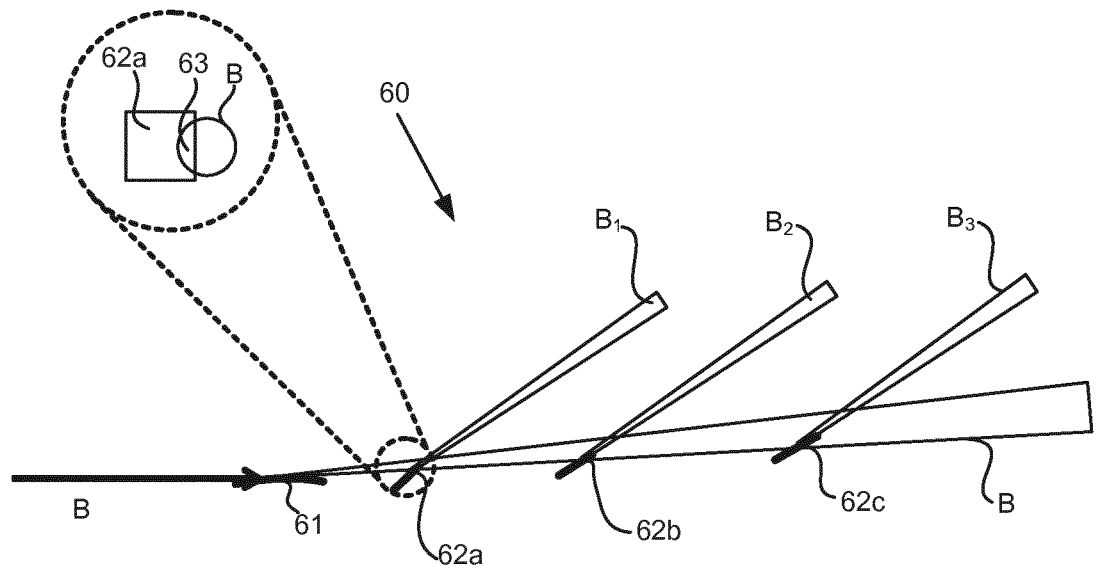

FIG. 7 schematically illustrates an alternative arrangement for splitting a radiation beam B into a plurality of branch radiation beams. In the example arrangement of FIG. 7, a beam splitting apparatus 60 is operable to receive the radiation beam B from the source SO (not shown) and split it into branch radiation beams. Three branch radiation beams, $B_{1-3}$ are depicted in FIG. 7, though it will be readily appreciated that more or fewer branch radiation beams may be created using the general arrangement of FIG. 7.

The beam splitting apparatus 60 includes a convex mirror 61 which is a grazing incidence mirror. The radiation beam B received by the beam splitting apparatus 60 is incident upon the convex mirror 61, which acts to increase the divergence of the main radiation beam B. The convex mirror 61 is an example of a diverging optical element (i.e. an optical element which acts to cause divergence of a radiation beam). One or more additional diverging optical elements may be provided in the path of the radiation beam B.

The beam splitting apparatus 60 further comprises three mirrors 62a-c, each of which is disposed in the path of the main radiation beam B. Each of the mirrors 62a-c extends partially across the radiation beam B and reflects the part of the main radiation beam with which it intersects. Each of the mirrors 62a-c deflects a respective portion $B_{1-3}$ of the main radiation beam B along a different branch optical path.

One or more of the branch radiation beams $B_{1-3}$ may be directed to respective tools, such as a lithographic or mask inspection apparatus. Additionally or alternatively, one or more of the branch radiation beams may be directed to further splitting means in order to split each of the branch radiation beams $B_{1-3}$ into further branch radiation beams.

A front view of the first mirror 62a is shown in FIG. 7 to illustrate schematically the intersection of the main radiation beam B with that mirror. The first mirror 62a intersects with a solid area 63 of the main radiation beam B, and reflects this area of the main radiation beam B. Thus, the first branch radiation beam $B_1$ has the cross-sectional shape of a section taken from a disk.

As described above, although the mirrors 62a-c are static, they may be provided on adjustable mounts, to allow, for example, for adjustment of the overlap of the mirrors 62a-c with the main radiation beam B and/or alignment of branch radiation beams $B_{1-3}$.

As with the splitting element 55 described above, the mirrors 62a-c may be constructed in any appropriate way and may, for example, be formed from metal. The mirrors 62a-c may be grazing incidence mirrors. As described above, the use of grazing incidence mirrors is advantageous because a reflection from a grazing incidence mirror gives rise to a relatively low loss of EUV radiation (e.g. a loss of around 10%). Other optics of the beam splitting apparatus may also be formed from grazing incidence mirrors, which may for example be metal or coated Si.

The convex mirror 61 increases the cross-sectional area of the main radiation beam B at the location of each of the mirrors 62a-c. Such optics may be referred to as diverging optics herein. It is to be understood that similar diverging optics may be used in combination with others of the beam splitting apparatus described herein, such as the beam splitting element 55 described above, and with beam splitting apparatus described in FIGS. 8, 9 and 10 below.

Since the main radiation beam B is produced by one or more free electron lasers, it may have a relatively small divergence and therefore a small diameter at the splitting apparatus 60 (depending upon the distance of the splitting apparatus from the free electron laser that produces the radiation beam B. The smaller the dimensions of the main radiation beam B, the more accurately the mirrors 62a-c must be placed to ensure a desired fraction of the beam B is diverted from the main radiation beam B.

The convex mirror 61 increases the dimensions of the main radiation beam B, allowing the mirrors 62a-c to be accurately positioned more easily so as to divert a desired fraction of the main radiation beam B along each of the branch optical paths $B_{1-3}$. Furthermore, by increasing the divergence of the main beam B, the intensity of radiation incident upon optical elements downstream of the convex mirror 61, such as mirrors 62a-c, is reduced. This reduces the concentration of heat on the mirrors caused by the main beam B. This is advantageous because the amount of heat in the main radiation beam B is substantial, and active cooling of the mirrors may be needed. The dimensions of the main radiation beam B will be relatively small upstream of the convex mirror 61. Therefore the convex mirror 61 may be provided with active cooling. The active cooling may be achieved by supplying a cooling fluid, for example a liquid such as water.

Since the mirrors 62*a-c* only extend partially across the main radiation beam B, the radiation beams propagating along the branch optical paths may have non-standard beam profiles. For example, referring to FIG. 7, the first branch radiation beam $B_1$ has the general cross-sectional shape 63 of a segment of a circle. This beam shape may not desirable when projecting a pattern from a mask MA to a substrate W using a lithographic apparatus. Optics placed in the path of the branch radiation beams may be arranged to modify the beam shape of the branch optical beam to provide a desired beam shape.

For example, referring to FIG. 2, the illumination system IL of the lithographic apparatus may be configured to modify the beam shape to provide a desired beam shape. This may be achieved for example by using an array of mirrors (e.g. the field facet mirror 10) to separate the beam into a plurality of sub-beams, each sub-beam being a different part of the area 63 of the branch radiation beam $B_1$. The field facet mirror directs the plurality of sub-beams onto the same location on a mirror such that the sub-beams are incident on top of one another. In this way the sub-beams are combined together. Different edge features of different sub-beams overlap one another and are thereby smoothed away to form a beam having a more useful cross-sectional shape. The cross-sectional shape may correspond with the shape of facets of the field facet mirror. The initial undesirable shape of the branch radiation beam $B_1$ is thus removed and replaced with a desired radiation beam shape.

In general, any suitable optics for obtaining a desired beam shape may be used. This may comprise separating an incident beam into a plurality of sub-beams which are then directed such that they are incident on top of one another.

In comparison with the arrangement of FIG. 6 the arrangement of FIG. 7 does not comprise sections of particularly small cross-sectional area (such as the edge 58 of the splitting element 55 of FIG. 6). This allows the mirrors 62*a-62c* of FIG. 7 to better withstand heat absorbed from the radiation beam B.

Figure 8:
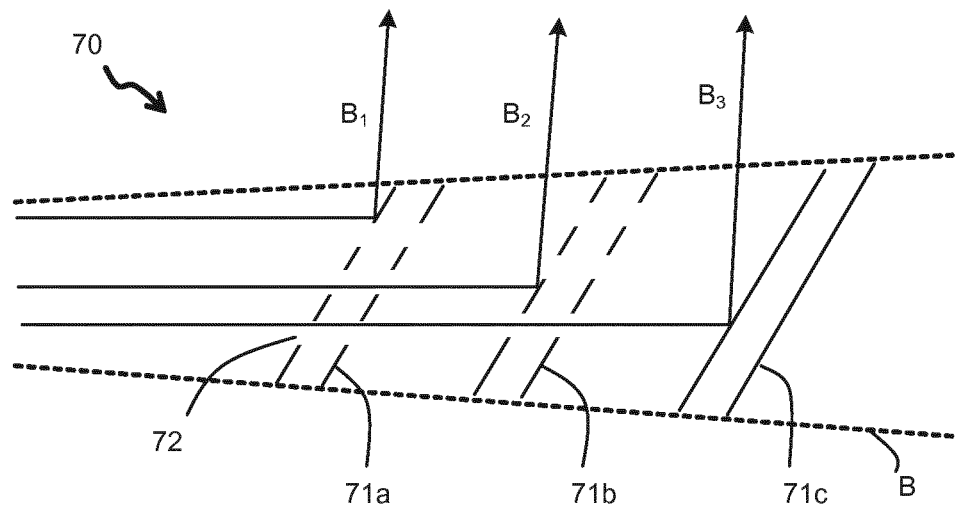

Referring to FIG. 8, an alternative beam splitting apparatus 70 is depicted. The beam splitting apparatus 70 comprises a series of static mirrors 71*a-b*, each of which is provided with a plurality of apertures 72, and each of which extends across the entire main radiation beam B. A third (and final) static mirror 71*c* does not comprise apertures. A portion of the main beam B which is incident on reflective areas of the first mirror 71*a* is directed along a branch optical path as first branch radiation beam $B_1$. A portion of the main beam B which is incident on the apertures 72 of the first mirror 71*a* passes through the apertures and is undeflected. The second mirror 71*b* reflects a portion of the main radiation beam B along a second branch optical path as a second branch radiation beam $B_2$ while allowing some of the main beam to pass undeflected through the apertures 72 in the mirror 71*b*. The third mirror 71*c* reflects the remainder of the main radiation beam B along a third branch optical path as a third branch radiation beam $B_3$.

The embodiment of FIG. 8 will form branch radiation beams $B_{1-3}$ which have arrays of holes in them and which may therefore not be suitable for pattern projection by a lithographic apparatus. As explained above in relation to FIG. 7, optics may be arranged in the path the branch radiation beams for modifying the branch radiation beam to obtain a desired branch radiation beam shape. This may comprise separating a branch radiation beam into a plurality of sub-beams which are then directed such that they are incident on top of one another.

It will be appreciated that while only three mirrors 71*a-*71*c* are shown in FIG. 8, additional (or fewer) mirrors may be provided in such an arrangement. While the reflective surfaces of the mirrors 71*a-*71*c* are shown as substantially planar in FIG. 8, one or more of the mirrors 71*a-*71*c* may be curved in order to increase divergence of the branch radiation beams.

Figure 9:
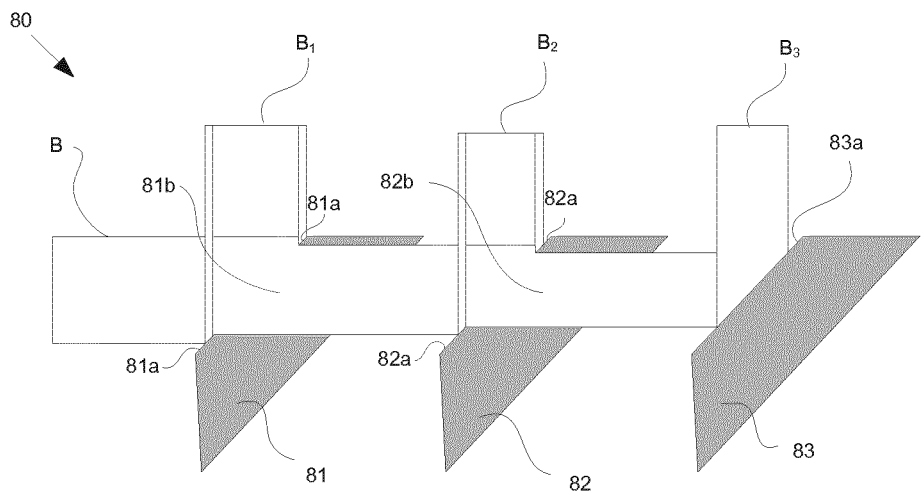

FIG. 9 illustrates, in side-profile, a beam splitting apparatus 80 for splitting the main radiation beam B into a plurality of branch radiation beams. In the arrangement 80, three static mirrors 81, 82, 83 are arranged in the path of the radiation beam B. Each mirror 81, 82, 83 is arranged at an angle with respect to the path of propagation of the radiation beam B to reflect a portion of the radiation beam B along a respective branch optical path. The first mirror 81 is a ring mirror having an outer ring-shaped reflective portion 81*a* arranged to reflect a portion of the radiation beam B. The ring-shaped reflective surface 81*a* defines an aperture 81*b* through which a remaining portion of the radiation beam B passes in the direction of the second mirror 82. Reflection by the first mirror 81 provides a ring shaped branch radiation beam $B_1$. The branch radiation $B_1$ is depicted in cross section as viewed along a longitudinal axis of the branch radiation beam $B_1$ above the first mirror 81 in FIG. 9.

The second mirror 82 is also a ring mirror having a reflective outer ring 82*a* arranged to reflect a second portion of the radiation beam B to provide a second branch radiation beam $B_2$. The outer ring 82*a* defines an aperture 82*b*, which is smaller than the aperture 81*b*. A third portion of the radiation beam B passes through the aperture 82*b* in the second mirror 82 in the direction of the third mirror 83. In the depiction of FIG. 9, the third mirror is a solid mirror having an unbroken reflective surface 83*a* (i.e. without an aperture) arranged to reflect the remaining portion of the radiation beam B to provide a third branch radiation beam $B_3$. It will of course be appreciated, however, that additional ring mirrors, with increasingly smaller apertures may be provided in the path of the radiation beam B.

As described above, with respect to other beam splitting apparatus, the mirrors 81, 82, 83 may constructed from any appropriate material, such as metal.

As in the examples described above with respect to FIGS. 6, 7 and 8, the branch radiation beams produced by the arrangement 80 may be provided to tools such as lithographic tools or mask inspection apparatus. Alternatively, or additionally, one or more of the branch radiation beams may be provided to further splitting apparatus to provide additional branch radiation beams.

Ring mirrors of the type illustrated in FIG. 9 may advantageously be constructed so as to provide sufficient material around the aperture that heat is conducted away from portion of the mirrors on which the radiation beam B is incident.

Additionally, the arrangement of FIG. 9 is such that variations of the position of the radiation beam B, or variations in the intensity distribution of the beam B, cause less variation in the intensity of the respective branch radiation beams $B_{1-3}$. That is, for each of the ring mirrors 81, 82, a decrease in the intensity of radiation received at one part of the ring-shaped reflective surface is generally compensated for by an increase in the intensity of radiation received at a different part of the ring-shaped reflective surface. An intensity distribution of the branch radiation beams $B_1$, $B_2$, $B_3$ produced by the apparatus 80 may therefore be substantially invariant to shifts in the position of the main radiation beam B, such shifts being caused by operation of the one or more FELs within the source SO.

There are now described embodiments in which a splitting apparatus is provided by a mirror comprising grooves to divide a reflective surface of the mirror into a plurality of groups of faces. The faces within a particular group each have a particular orientation which is different to faces in other groups. Generally, the faces of the mirrors may be micro-scale or macro-scale. For example, faces of the mirrors and a pitch between faces may be of the order of micrometres (micro-scale) or larger (macro-scale—for example, of the order of millimetres). In either case, radiation incident on the mirror is reflected from each face of the mirror, causing a plurality of reflective portions or "sub-beams".

In both cases, also, radiation reflected from the faces is subject to diffraction. That is, interaction with the faces of the mirror will cause each of the sub-beams to spread out (diverge). The amount of divergence of the sub-beams will depend upon the size and pitch of the faces, with a greater divergence of the sub-beams occurring in the case of micro-scale mirrors. Both micro-scale mirrors and macro-scale mirrors are referred to herein as gratings. For both micro-scale and macro-scale gratings, as the grating comprises a plurality of reflective faces, the gratings may be considered to provide a plurality of static mirrors.

As is described in more detail below, both micro-scale gratings and macro-scale gratings may be used as a splitting apparatus to provide a plurality of branch radiation beams from a single incident radiation beam. In each case, however, the way in which splitting occurs may be different. For macro-scale gratings, reflection of sub-beams in different directions may be the dominant process of splitting an incident radiation beam into a plurality of branch radiation beams (e.g. a different branch beam may be provided for each direction of reflection). Diffraction of the sub-beams from a macro-scale grating may be sufficient to cause, in a far-field (for example at the entrance to an illuminator), a small overlap between sub-beams travelling in the same direction. This overlap may cause a smoothing of the intensity profile of each branch radiation beams.

For micro-scale gratings, where diffraction is much greater, the sub-beams from multiple faces overlap significantly, resulting in an interference pattern in the far-field. Each maxima within the interference pattern may provide a respective branch radiation beam. For example, a grating causing diffraction with $0^{th}$ order, $1^{st}$ order and $-1^{st}$ order beams may be used to provide three branch radiation beams.

Figure 10A:
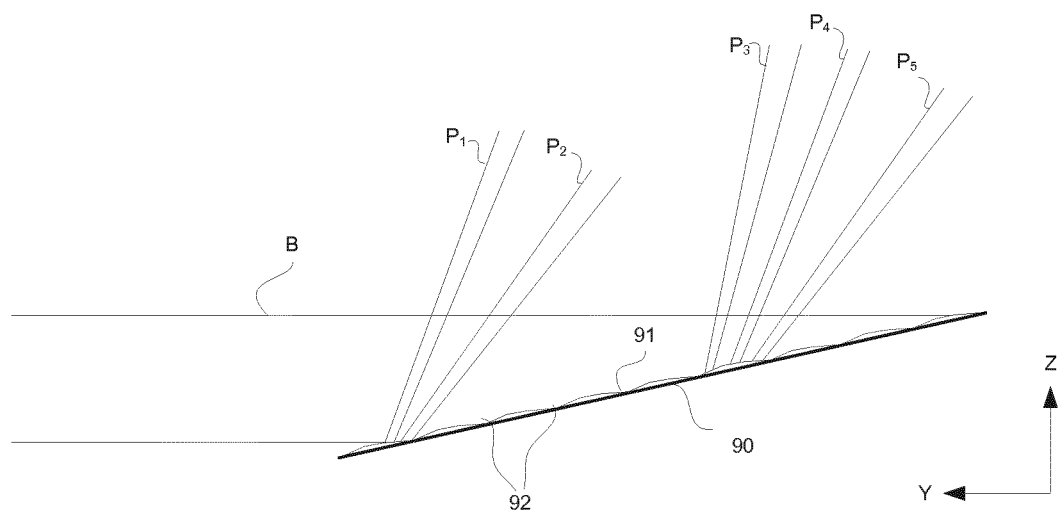
Figure 10B:
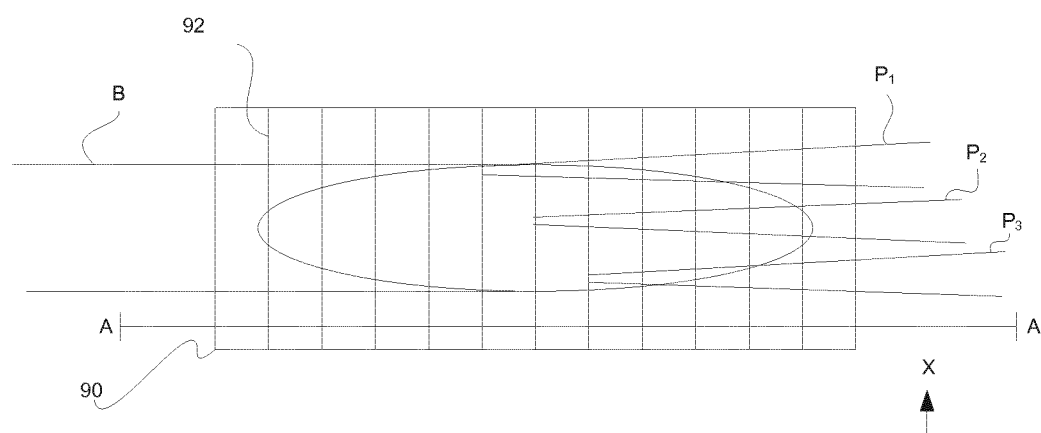
Figure 10C:
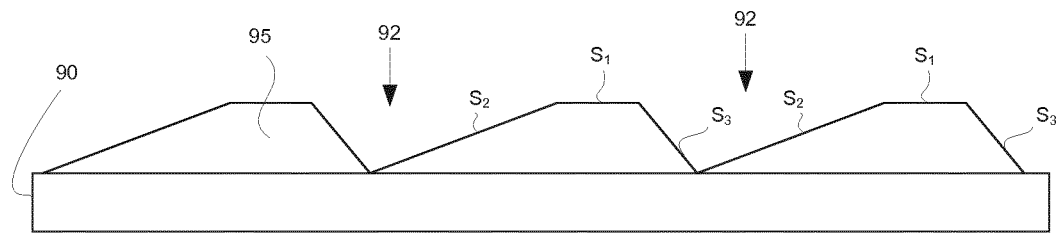

Referring to FIG. 10 a mirror 90 is provided in the path of the main radiation beam B. FIG. 10A presents a side-profile view of the mirror 90, FIG. 10B presents a top-down view, and FIG. 10C presents a cross-section of the mirror 90. It is to be understood, however, that the depictions in FIG. 10 are merely schematic.

The mirror 90 may be a grazing incidence mirror. The mirror 90 comprises a reflective surface 91. A plurality of regularly spaced grooves 92 extend across the reflective surface 91 in a direction substantially perpendicular to the direction of propagation of the radiation beam B to provide a grating. The grooves 92 may be formed by any suitable process such as, for example, etching, stamping or electro-forming. The grooves 92 divide the reflective surface 91 into a plurality of groups of reflective faces, wherein the faces within each group are substantially parallel, but at different angles with respect to the faces of each other group. Each group of faces therefore acts to reflect portions of the radiation beam B in a respective direction. In this way, each of the faces may be considered to be a respective static mirror, the plurality of faces providing a plurality of static mirrors.

Referring to FIG. 10C, the mirror 90 is shown in cross-section along the line A-A in FIG. 10B. It can be seen that in the example arrangement the grooves 92 of the mirror 90 are asymmetrical so as to provide a substantially grazing incidence angle with respect to the radiation beam B on at least two of the three groups of faces. That is, when viewed in cross section, a right-hand side of each groove 92 is a different length and orientation to a left-hand side of each groove 92.

The grooves 92 form a plurality of ridges 95, dividing the reflective surface 91 into three groups of reflective faces. Top faces of each ridge 95 form a first group of faces $S_1$, left-hand sides of each ridge 95 form a second group of faces $S_2$ and right-hand sides of each ridge 95 form the third group of faces $S_3$. The mirror 90 may comprise any suitable number of reflective faces in each group, and may, in one example embodiment, comprise of the order of 1000 reflective faces in each group.

In the case of macroscopic grooves, portions of the radiation beam B which are incident on faces of the first group $S_1$ are each directed in a first direction, portions of the radiation beam B which are incident on faces of a second group $S_2$ are each directed in a second direction, and portions of the radiation beam B which are incident on faces of a third group $S_3$ are each directed in a third direction. In the case of microscopic grooves diffraction of the radiation beam B on the faces of all groups $S_1$, $S_2$, $S_3$, or on edges between faces of all groups $S_1$, $S_2$, $S_3$, will produce several branches, which can be for example two or three branches with approximately even power distribution between the branches.

Referring to FIG. 10A it may be considered that portions $P_1$, $P_4$ are reflected from faces of the first group $S_1$, portion $P_3$ is reflected from faces of the second group $S_2$, and portions $P_2$, $P_5$ are reflected from faces of the third group $S_3$. It will be appreciated, however, that depiction of the portions of branch radiation beams is merely schematic. As described above, interaction between the reflected portions $P_1$-$P_5$ to create branch radiation beams will differ depending upon the scale of the grating. Where the grating 90 is a macro-scale grating, only radiation from a single group of faces contributes to each respective branch radiation beam. As such, for a macro-scale grating, the portions $P_1$ and $P_4$ (together with other sub-beams reflected from $S_1$ faces) will form one branch radiation beam, the portion $P_3$ (together with other sub-beams reflected from $S_2$ faces) will from a second branch radiation beam, and the portions $P_2$ and $P_5$ (together with other sub-beams reflected from $S_3$ faces) will form a third branch radiation beam.

Where the grating is a micro-scale grating, a plurality of branch radiation beams is generated due to diffraction of all sub-beams of radiation reflected from the grating 90, such that sub-beams reflected from different groups of faces will contribute to the final interference pattern, and therefore the respective branch radiation beams.

In the example embodiment of FIG. 10 the grooves 92 extend generally perpendicular to the direction of propagation of the radiation beam B. In an alternative embodiment, illustrated in FIG. 11, a mirror 100 is provided having grooves 101 extending generally parallel to the direction of propagation of the radiation beam B to provide a grating with three groups of reflective faces, each group of faces reflecting portions of the radiation beam B in a different respective direction.

Figure 11A:
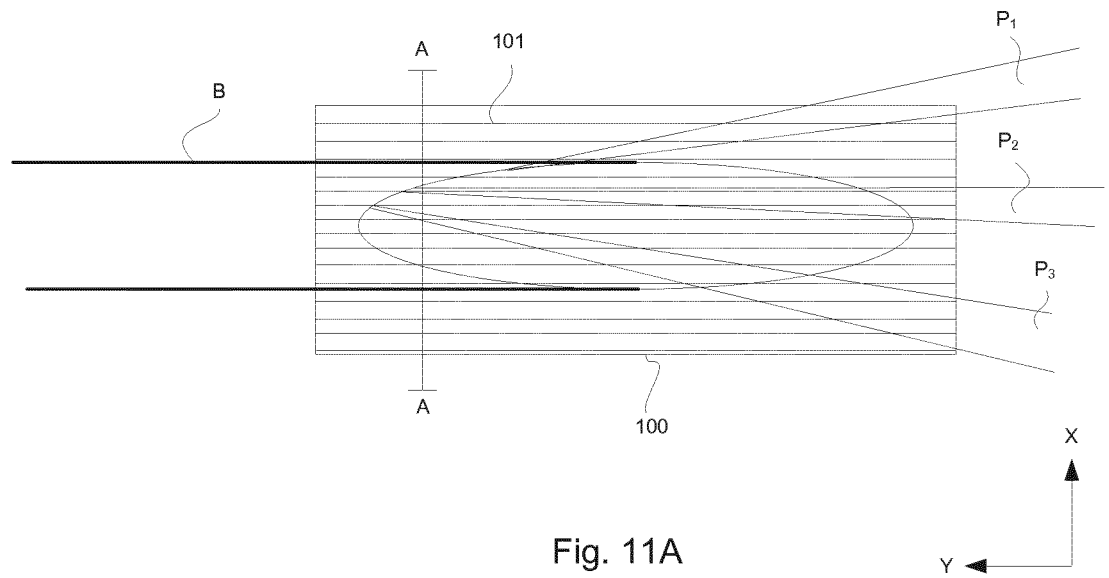
Figure 11B:
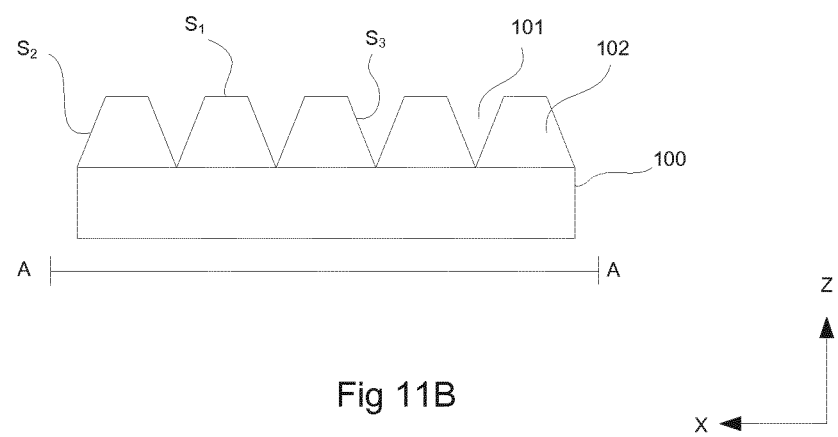

FIG. 11A schematically depicts the mirror 100 in a top-down view, while FIG. 11B schematically depicts a cross section of the mirror 100 along the line A-A shown in FIG. 11A. Referring to FIG. 11B, it can be seen that the grooves 101 form a plurality of parallel ridges 102. Top faces of each ridge 102 form a first group of faces $S_1$, left-hand sides of each ridge 102 form a second group of faces $S_2$ and right-hand sides of each ridge 102 form the third group of faces $S_3$. The mirror 100 may comprise any suitable number of reflective faces in each group, and may, in one example embodiment, comprise of the order of 1000 reflective faces in each group.

As described above, for macro-scale gratings, each branch radiation beam comprises a plurality of sub-beams, each sub-beam comprising a portion of the radiation beam B reflected from a different face within a single group. Since each of the faces within a given group of faces is substantially parallel, each of the sub beams is substantially parallel, at least in the near field of the mirror 90, 100. As such, in the near field (on or very close to the mirror 90, 100), the power distribution of each branch radiation beam will be similar in shape to that of the radiation beam B except for a plurality of strips throughout the power distribution of each branch radiation beam, corresponding to locations of the faces of other groups, where the power is substantially zero.

Figure 12A:
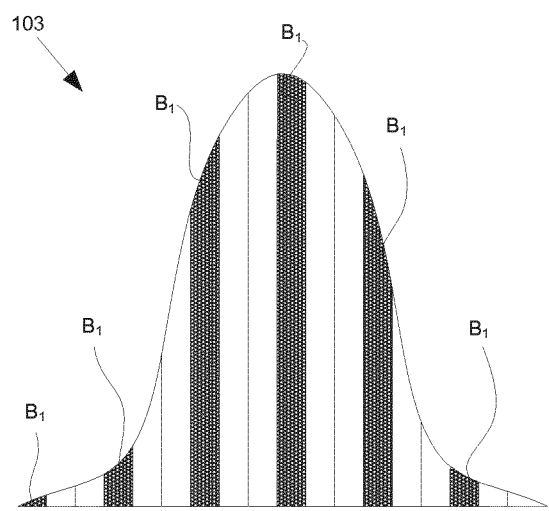
FIGS. 12a, 12b are schematic illustrations of an intensity distribution of a branch radiation beam produced by a reflective grating in the near-field and in the far-field respectively.

This is depicted in FIG. 12A which shows an intensity distribution 103 of the radiation beam B. An intensity distribution of a branch radiation beam $B_1$ in the near field (i.e. on or very close to the mirror 90, 100) is depicted by a plurality of shaded sub-sections of the intensity distribution 103. That is, each of the shaded sections of the intensity distribution 103 corresponds to a portion of the radiation beam B that is incident upon faces of the mirror 90, 100 belonging to a single group of faces. For example, each of the shaded subsections labelled $B_1$ in FIG. 12A may correspond to a respective portion of radiation reflected from the $S_1$ faces of the mirror 90, 100. Gaps between the shaded sub-sections represent parts of the radiation beam B which are incident upon faces of different groups.

Figure 12B:
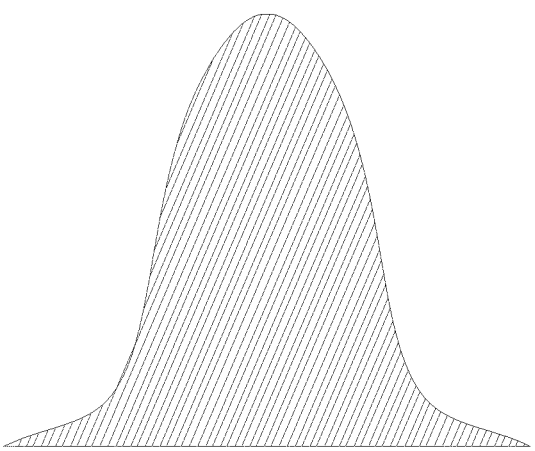

Due to the non-zero divergence of the branch radiation beams $B_1$, $B_2$, $B_3$ (caused to some extent by diffraction), the plurality of sub beams of each branch radiation beam will overlap in the far field and will combine to form a power distribution that is substantially similar in shape to the radiation beam B as depicted in FIG. 12B. The far field may be, for example, the entrance to a lithographic tool, such as the lithographic tool $LA_1$, shown in FIG. 2. It will be appreciated that the distance over which the intensity distribution of the branch radiation beams becomes substantially homogenous will vary in dependence upon the particular pattern of grooves disposed on the particular mirror. In some embodiments, however, the far field may be, for example, of the order of 50 meters away from the mirror.

In the case of micro-scale gratings, the interference between the sub-beams reflected from the faces of the grating also results in branch radiation beams having, in the far field, substantially the same intensity distribution as the radiation beam B.

The mirrors 90, 100 can be formed from silicon by, for example, anisotropic etching along crystal planes of a silicon wafer. Referring again to FIG. 11B, and assuming that the mirror 100 is formed from silicon, for example, the top faces $S_1$ may be formed along the (100) crystallographic plane and the faces $S_2$, $S_3$ formed along the (111) and (−111) crystallographic planes. In this case, the angle at the bottom of the grooves will be approximately 70.5 degrees (or the supplementary angle of approximately 110 degrees) and the grooves 101 and ridges 102 will extend along the <01-1> direction. The direction of the incoming radiation beam B may be disposed at a small (grazing incidence) angle to the <01-1> direction. It will be appreciated that various layouts are possible depending on the <h k l> direction of top the surface.

A grating in which the top faces $S_1$ are formed along the (100) crystallographic plane and the faces $S_2$, $S_3$ are formed along the (111) and (−111) crystallographic planes would form three branch radiation beams, with the ratios of intensities of the branch radiation beams being dependent on the ratio of the width of the $S_1$ faces to the pitch of the grating, as well as upon angle of incidence of the beam B upon the grating and the angle the grooves make with respect to the plane of incidence of beam B (which can be 0 degrees—grooves parallel to the beam B; 90 degrees—grooves perpendicular to the beam B; or any other angle). It may be desirable to provide branch radiation beams of equal power. In this case, the parameters above can be optimized to tune the grating for a particular angle of incidence of beam B.

Additional examples of possible micro-grating constructions are provided in Table 1 below, showing a percentage of energy in each order of diffraction.

TABLE 1

| Crystal orientation | Lines Per mm | θ [°] | φ [°] | Duty cycle % non-etched surf. | % energy in order | | | | |
|---|---|---|---|---|---|---|---|---|---|
| | | | | | 0 | 1 | −1 | 2 | −2 |
| <101> | 450 | 89.5 | 23.0 | 40 | 56 | 42 | | | |
| <101> | 450 | 89.5 | 22.9 | 37 | 49 | 49 | | | |
| <101> | 900 | 89.0 | 22.9 | 37 | 49 | 49 | | | |
| <101> | 1800 | 88.0 | 22.9 | 37 | 49 | 49 | | | |
| <101> | 666 | 89.0 | 0 | 49 | 23 | 37 | 37 | | |
| <101> | 700 | 89.0 | 0 | 44 | 17 | 40 | 40 | | |
| <100> | 1000 | 88.7 | 0 | 38 | 27 | 36 | 36 | | |
| <100> | 1000 | 88.9 | 0 | 26 | 32 | 32 | 32 | | |
| <101> | 400 | 89.1 | 0 | 45 | 37 | 18 | 18 | 13 | 13 |
| <101> | 450 | 89.0 | 0 | 44 | 38 | 15 | 15 | 15 | 15 |
| <101> | 900 | 88.0 | 0 | 44 | 38 | 15 | 15 | 15 | 15 |
| <100> | 400 | 89.1 | 0 | 65 | 38 | 21 | 21 | 9 | 9 |
| <100> | 800 | 88.7 | 0 | 51 | 30 | 30 | 30 | 4 | 4 |

Figure 11C:
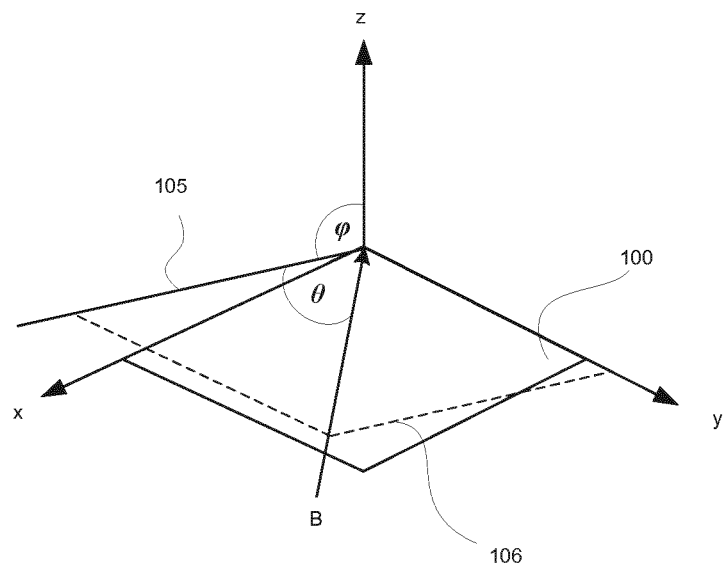

In Table 1, the crystal orientation column refers to the crystal orientation of the top faces of the grating (e.g. the faces in group $S_1$ in FIG. 11B). The lines per mm column indicates a number of grooves per mm of the grating. A first angle θ and a second angle φ indicate an orientation of the grating with respect to an incoming radiation beam. The angles θ and φ are illustrated in FIG. 11C. In FIG. 11C, top faces of the grating 100 define an x-y plane, with each of the grooves 101 extending along the y-direction. A line 105 represents an orthogonal projection of the incident radiation beam B onto the x-z plane. The angle φ is the angle between the orthogonal projection 105 and the z axis. Put another way, the incident radiation beam B together with the y-axis defines a plane 106. The angle φ is the angle that the plane 106 makes with the z axis. The angle θ is the angle between the incident radiation beam B and its orthogonal projection 105.

The "duty cycle" column indicates the percentage of the top surface of the grating that is "flat" (i.e. non-etched). For example, a value of 40% in the duty cycle column indicates that 40% of the surface of the grating has not been etched, while 60% of the top surface has been etched to form the grooves.

The mirror 90, 100 may be provided with a coating of a more reflective (less absorbing) material (for EUV radiation). For example, the mirror may be provided with a coating of ruthenium (Ru) or molybdenum (Mo). This may, for example, have a thickness of around 50 nm.

An advantage of using silicon for mirrors (such as the mirrors 90, 100, and the mirrors described above with reference to other splitting apparatus) is that thermal expansion during operation may be limited by operating at approximately 123 K. At this temperature the heat conductivity of silicon is of the order of 600 W/m/K or more, which is a factor of 4 better than its heat conductivity at room temperature and around 50% better than the heat conductivity of copper (Cu). Therefore, even a relatively large heat load can be withstood, while keeping the temperature of the mirror 90, 100 in the range where expansion of the mirror 90, 100 is low and the mirror 90, 100 maintains its designed structural dimensions.

Advantageously, the use of mirrors such as those described with reference to FIGS. 10 and 11 can provide branch radiation beams with substantially equal power, and with an intensity distribution in the far field (e.g. at a lithographic tool) that is substantially similar to the intensity distribution of the radiation beam B before splitting.

Additionally, gratings such as the mirrors 90, 100 may be used to split the radiation beam B without first expanding the radiation beam B with dedicated expansion optics, or without first forming the intensity distribution of the radiation beam B into a flat-top intensity distribution. Generally, it may be necessary to place such expansion/flat-top forming optics at a significant distance (for example 50 meters) from the exit of the FEL, creating a very low tolerance to pointing and divergence instability. Pointing and divergence instability will cause the radiation beam B to shift with respect to the expansion/flat-top forming optics, potentially causing distortion of the expanded beam. Such distortion of the radiation beam B before splitting can lead to variations in the power within the respective branch radiation beams, and therefore variations in the power that is provided to, for example, each lithographic apparatus, or mask inspection tool.

It may additionally be difficult to consistently achieve a flat-top intensity distribution from the flat-top forming optics. While the power distribution of the radiation beam B may be substantially Gaussian, the power distribution will not be exactly Gaussian and may vary significantly as a result of parameters and settings of the FEL which may vary during operation. Also the angle of trajectory of the radiation beam B (beam pointing) may vary in time, leading to significant deviations of the flat-top intensity profile generated by flat-top forming optics.

By providing a splitting grating which is invariant to shifts of the radiation beam B, before expanding the beam using expansion optics (where desired), the disadvantages associated with expanding the radiation beam or conditioning the intensity distribution to provide a flat-top intensity distribution before splitting, may be avoided. Indeed, as described above, the process of splitting the radiation beam B with a grating of the type described herein, scaled copies of the beam B may be provided, and is insensitive to pointing errors and to the shape of the intensity profile of the radiation beam B.

While the grating (or one or more of the gratings where a plurality are provided) may be positioned before (upstream of) beam expanding and/or flat-top forming optics, the grating (or one or more gratings) may be positioned after (downstream of) one or more flat mirrors. Reflection of the radiation beam B by one or more flat mirrors may be used to protect the grating from Bremsstrahlung radiation, while avoiding amplification in variation of beam angle or position which may result from reflection by curved mirrors.

It will be appreciated that while the mirrors 90, 100 each provide a grating for splitting a radiation beam into three branch radiation beams, gratings may be provided which split a radiation beam into a different number of branch radiation beams. Generally, a grating may be provided which splits a radiation beam into two or more branch radiation beams.

As described above, it may be desirable to orient the mirror 90, 100 at a grazing angle of incidence. In some embodiments, however, configurations such as that depicted in FIG. 11 may limit the useable angles of incidence. In particular, for some angles of incidence of the radiation beam B with respect to the mirror 100, portions of radiation reflected from the faces $S_3$ or $S_4$ may be at least partially incident upon an opposing $S_2$ or $S_3$ face of an adjacent ridge. Accurate splitting of the radiation beam B into a desired number of branch radiation beams may therefore be difficult for some angles of incidence.

Figure 13:
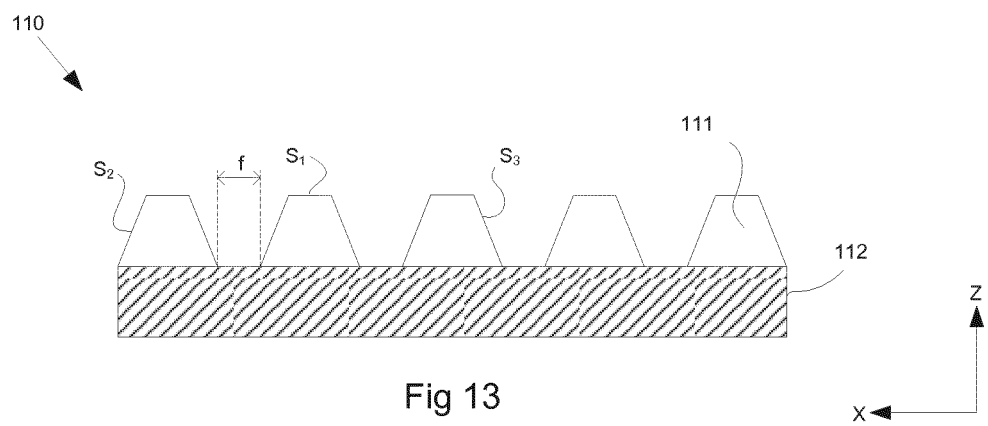
FIG. 13 is a schematic illustration of an alternative grating for splitting a radiation beam.

FIG. 13 illustrates an alternative embodiment of a mirror 110 which provides a reflective grating. Like the mirror 100, the mirror 110 comprises a plurality of ridges 111 and the ridges 111 provide three groups of face features; a first group of face features $S_1$, a second group of face features $S_2$ and a third group of face features $S_3$. In the embodiment of FIG. 13, however, the $S_2$ face of each ridge is separated from the $S_3$ face of an adjacent ridge by a distance f at the closest points of each face.

The distance f can be selected so as to ensure that radiation reflected from an $S_2$ or an $S_3$ face is not subsequently incident on an $S_2$ or $S_3$ face of an adjacent ridge.

The mirror 110 may be constructed, for example, by providing a base portion 112 of a material that is etch resistant with respect to the etching process used to etch a top layer of silicon to provide the ridges 111. For example, the based portion may be made from silicon dioxide (SiO2) or silicon nitride (Si3N4). It will be appreciated that an arbitrary distance f may therefore be provided between ridges 111.

In an alternative embodiment to prevent re-reflection, ridges may, for example, be formed by etching along the (110) and (111) planes of a silicon grating.

From the above, it will be apparent that mirrors which provide a reflective grating may be manufactured in any of a plurality of suitable ways. In one embodiment, gratings may be produced by processing a silicon wafer using a plurality of etchants in order to provide ridges with surfaces that are substantially atomically flat. Etchants such as potassium hydroxide (KOH), sodium dydroxide (NaOH) and ammonium fluoride (NH4F), for example, may be used.

A coating may be deposited on the etched mirror so as to increase grazing incidence reflection and decrease absorption of radiation having a desired wavelength (for example EUV radiation). For example, molybdenum (Mo) or ruthenium (Ru) which have a high grazing incidence reflectivity for radiation having wavelengths of 13.5 nm may be used. Other coatings may be selected for other wavelengths of radiation. Generally, however, transparent materials with a sufficiently high electron density provide good grazing incidence reflection. Heavy element metals are examples of such materials. Additionally, materials may be selected for resistance to conditions likely to be present within the beam splitting apparatus, such as the generation of EUV radiation-induced plasma.

In some embodiments, an amorphous metal (or metal glass), such as a mix of Mo and Ru, may be deposited on the etched layer to provide a reflective coating. The amorphous structure of the metal glass may be used to provide smooth surfaces with high reflectivity for a desired wavelength.

It will be appreciated that any other appropriate materials such as zirconium (Zr), platinum (Pt), nickel (Nt), copper (Cu), silver (Ag) gold (Au) may be used. Different coating materials or compositions may be applied to different parts of the etched surface. For example, with reference to FIGS. 11 and 13, different coatings may be applied to the $S_1$, $S_2$ and $S_3$ faces. By applying different coatings to different portions of the etched surface, expected thermal expansion of the faces may be compensated.

Where a reflective coating is provided, a further coating may be applied to the reflective coating. For example, oxides, nitrides, carbides, etc, may be applied in order to increase the stability and resistance of the reflective coating to conditions likely to be present.

Where a reflective coating is provided, one or more interface layers may be provided between the etched material (e.g. Si) and the reflective coating to reduce surface roughness and increase thermal conductivity. For example, an interface layer of graphene may be provided.

While not depicted in FIGS. 10 to 13, cooling channels may be provided on a reverse side of the mirrors (i.e. a side which does not receive the radiation beam B). Such cooling channels may be arranged to receive a liquid coolant such as water, or a two-phase liquid/gas coolant. Coatings may also be applied to one or more of the cooling channels in order to increase heat conduction, such as, for example, graphene.

While it is described above that the etched surface may be silicon, it is to be understood that other materials may be used. Examples of other materials which may be anisotropically etched to provide a grating include germanium (Ge), gallium arsenide (GaAs), silicon-germanium (SiGe), indium phosphide (InP) and indium arsenide (InAs). Generally, however, any suitable material may be used.

A suitable grating may be manufactured as described above. The grating may then be copied using a process such as thermoplastic molding in a metal glass, or by stamping, for example.

One or more of the arrangements for splitting a radiation beam described above may be used in combination with other arrangements for splitting a radiation beam. For example, in one embodiment, the radiation beam B provided from the source may initially be split into, for example, three branch radiation beams using an mirror providing a grating of the type described with reference to FIGS. 10 to 13. Each of the three branch radiation beams may be provided to a respective edge-forming mirror such as those described with reference to FIG. 7, to split each branch radiation beam into two further branch radiation beams, thereby providing six branch radiation beams. The six branch radiation beams may be directed to respective tools, such as lithographic apparatus, mask inspection apparatus, or otherwise. More generally, any arrangement and combination of beam splitting apparatus as described herein may be provided to split a radiation beam provided by the source SO in order to provide a desired number of branch radiation beams.

Figure 14:
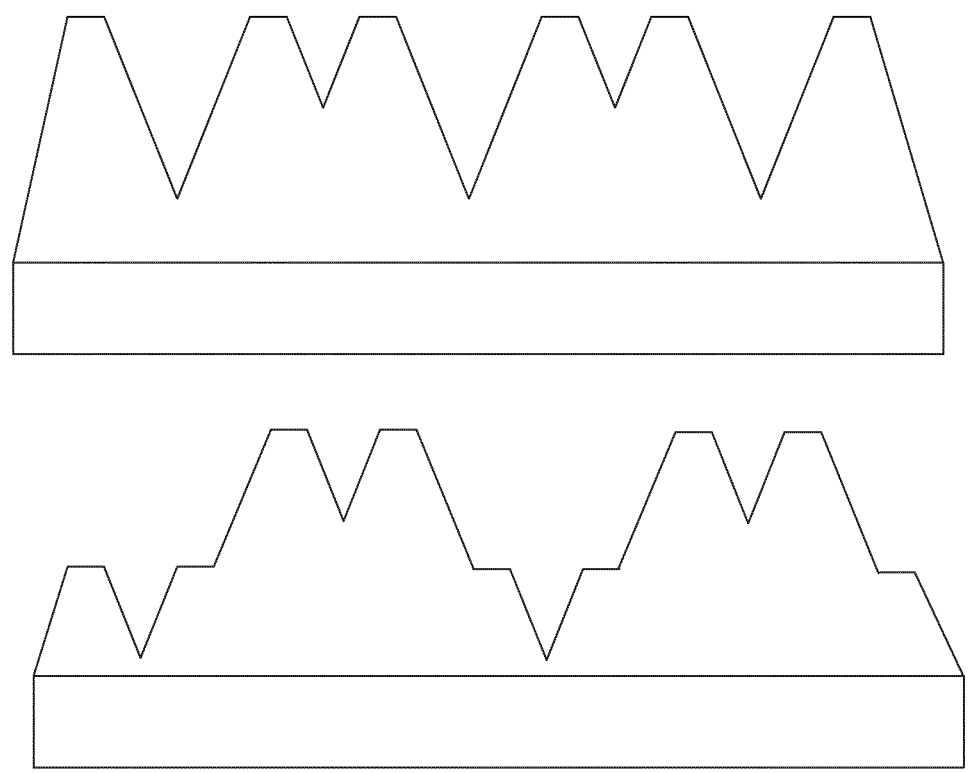
FIG. 14 is a schematic illustration of alternative gratings for splitting a radiation beam.

Generally, it will be appreciated that gratings may be provided in which the grooves are disposed at any angle to the radiation beam B. Further, although the described examples show gratings in which each groove is a translated copy of each adjacent groove, other structures of grooves may be provided. For example, alternative groove structures are illustrated, in cross-section, in FIG. 14. In both examples shown in FIG. 14, each groove is different to an adjacent groove, although still periodic. Additionally, the groove structure may not be periodic, such that there are no repeating patterns of grooves. Generally, structures such as those illustrated in FIG. 14 may be used, for example, for the provision of more than three branch radiation beams, or to compensate for thermal expansion of the grating with modulated absorption. For example, the radiation beam B may have generally radial intensity profile (having a higher intensity in a center portion, and a lower intensity in an outside portion), such that, if a mirror has a constant absorption coefficient across its reflective surface, energy dissipation from the radiation beam B will depend on the position within the radiation beam. As such, a temperature of different portions of a mirror will increase by different amounts depending upon which part of the radiation beam B is incident on those parts, leading to variations in thermal expansion across the mirror.

In order to compensate for thermal expansion, absorbing material may be provided at an outer edge of a mirror so as to reduce temperature gradients along the mirror, and additionally, reduce gradients in the branch radiation beams that are reflected from the mirror, which may be beneficial for imaging purposes. For example, a particular mirror geometry may result in an intensity profile of a radiation beam being "clipped" at, for example, 2-3 sigma. In this case, there will be a sharp transition between "power" and "no power" in the reflected radiation beams. By providing absorbing material at outer edges of the mirror, such transitions can be smoothed.

Figure 15:
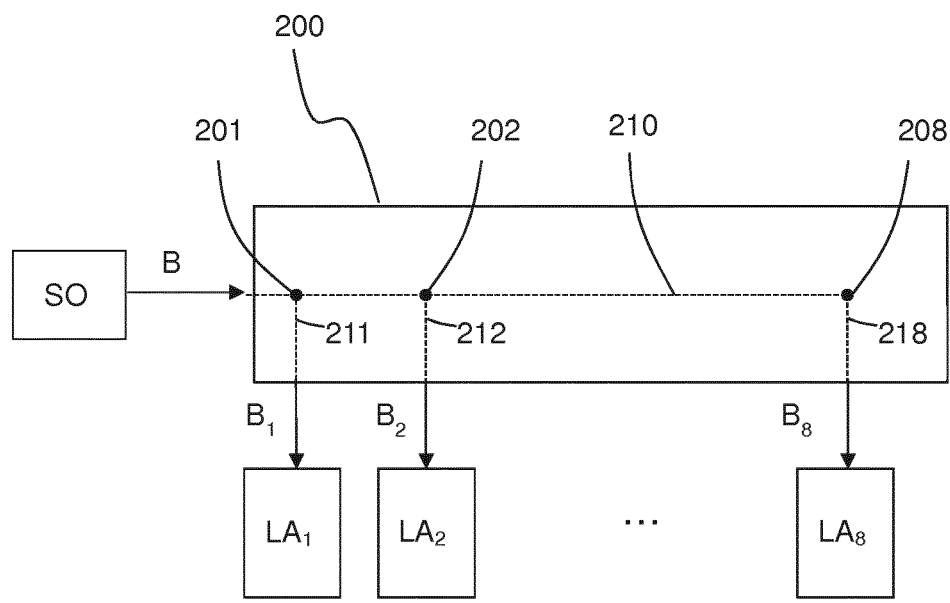
FIG. 15 depicts a lithographic system comprising a beam splitting apparatus according to an embodiment described herein.

FIG. 15 schematically illustrates a further embodiment of a beam splitting apparatus 200 suitable for splitting the main radiation beam B into a plurality of branch radiation beams.

The beam splitting apparatus 200 is arranged to receive the main radiation beam B from the radiation source SO and output a plurality of radiation beams $B_1$-$B_8$. The beam splitting apparatus 200 comprises eight extraction optics 201 to 208 (of which only extraction optics 201, 202 and 208 are depicted in FIG. 15 for clarity). With reference to FIG. 1, in which it is shown that the main radiation beam B is split into twenty branch radiation beams, it will be appreciated that the beam splitting apparatus 200 may comprise more or fewer extraction optics and that the beam splitting apparatus 200 may be a part of the beam splitting apparatus 20.

Each extraction optic 201-208 extends partially across a trajectory 210 of the main radiation beam B and is arranged to reflect part of the main radiation beam B so as to direct it along an associated branch optical path 211-218 thereby forming a branch radiation beam B1-B20.

Figure 16A:
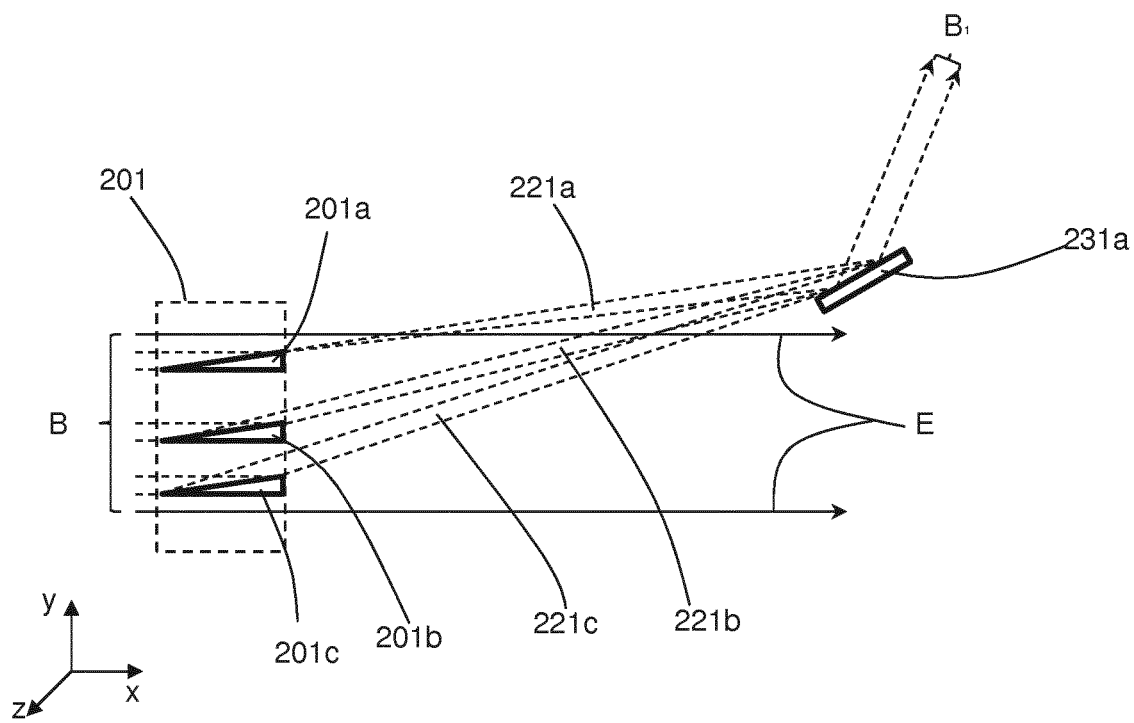
FIG. 16a is a cross sectional side view of a main radiation beam within the beam splitting apparatus illustrated in FIG. 15, showing a first portion of an extraction optic of the beam splitting apparatus in greater detail.
Figure 16B:
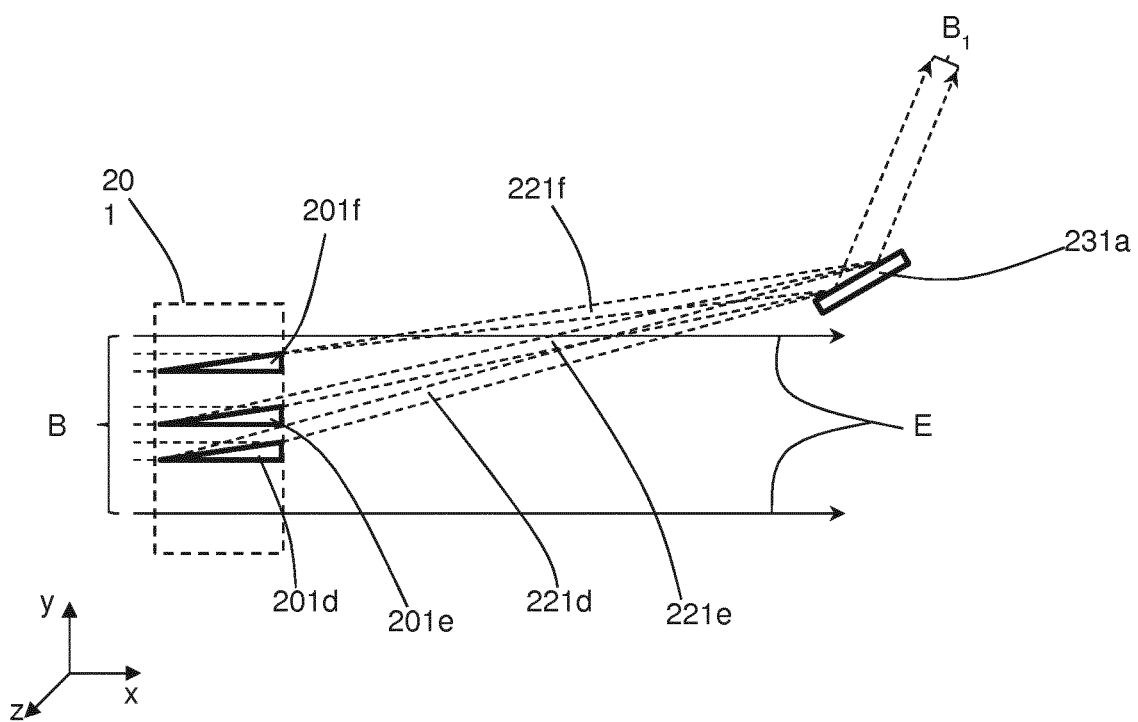
FIG. 16b is a cross sectional side view of a main radiation beam within the beam splitting apparatus illustrated in FIG. 15, showing a second portion of an extraction optic of the beam splitting apparatus in greater detail.
Figure 17:
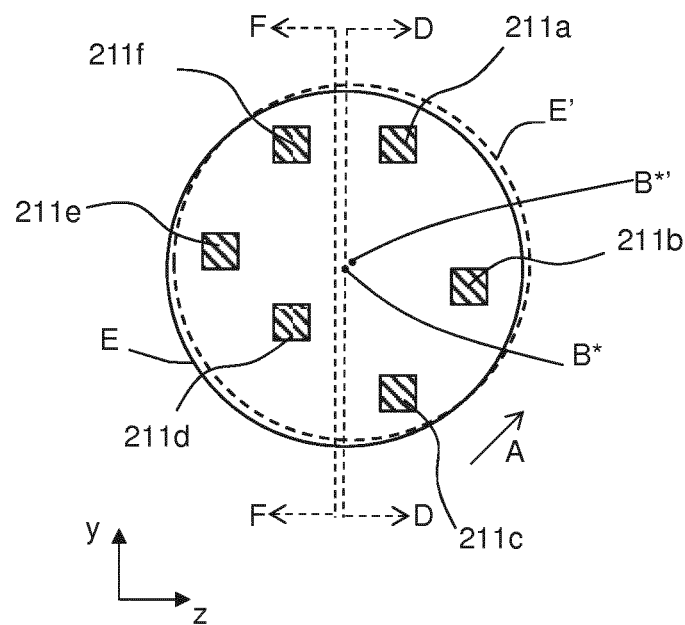
FIG. 17 shows the projection of the extraction optic of FIGS. 16a and 16b onto the cross section of a main radiation beam.

Each extraction optic 201-208 comprises a plurality of portions. In particular, in the depicted example, the portions take the form of a plurality of mirrors. Referring to FIGS. 16a, 16b and 17, one of the extraction optics 201 is described in greater detail below.

The extraction optic 201 comprises six mirrors 201a-201f. Each mirror 201a-201f is a wedge shaped grazing incidence mirror, which is provided with a reflective surface that is arranged to reflect part of the main radiation beam B. The projection of the reflective surface of each mirror 201a-201f onto a plane perpendicular to the propagation direction of the main radiation beam B forms a square area 211a-211f (FIG. 17). The part of the main radiation beam B reflected by each of the mirrors 201a-201f may be referred to as a sub-beam 221a-221f. Therefore the extraction optic 201 is arranged to reflect a plurality of disconnected solid square areas (corresponding to the areas 211a-211f) distributed over the cross section of the main radiation beam B.

The edge of the main radiation beam B is represented in FIGS. 16a, 16b by two parallel arrows E and in FIG. 17 by a circle E. As used in this context, the edge of the main radiation beam B may be defined as the point where the intensity has dropped below a pre-set threshold. The pre-set threshold may for example be a percentage of the maximum intensity. FIG. 17 shows the projection of the extraction optic 201 onto the plane perpendicular to the propagation direction of the main radiation beam B.

FIG. 16a is a cross sectional side view of the main radiation beam B along the line D-D in FIG. 17. Therefore, only the mirrors 201a-201c are shown in FIG. 16a. FIG. 16b is a cross sectional side view of the main radiation beam B along the line F-F in FIG. 17. Therefore, only the mirrors 201d-201f are shown in FIG. 16b.

Each mirror 201a-201f may be provided with an active cooling mechanism (not shown) such as, for example, a supply of cooling fluid such as, for example, water or carbon dioxide ($CO_2$). The mirrors 201a-201f may be formed from a material which is a good conductor of heat such as, for example, copper, with a coating that maximizes reflectivity and minimizes absorption such as, for example, ruthenium (Ru).

In general, the surfaces of each mirror 201a-201f may be inclined at different angles to the trajectory 210 of the main radiation beam B. The surface of each mirror 201a-201f may be inclined at an angle of around 10 degrees to the trajectory 210 of the main radiation beam B.

The beam splitting apparatus 200 further comprises one or more branch mirrors associated with each of the extraction optics 201-208. In particular, the beam splitting apparatus comprises a first branch mirror 231a associated with the extraction optic 201. The extracted sub-beams 221a-221f are incident upon the first branch mirror 231a. The orientation of the plurality of mirrors 201a-201f and/or the first branch mirror 231a is such that after reflection from the first branch mirror 231a the extracted sub beams 221a-221f combine to form a single composite branch radiation beam $B_a$.

In this embodiment, the first extraction mirror 231a is a multi-facet mirror, comprising six facets (not shown), each facet being a flat mirror. The part of the main radiation beam B that is reflected by each of the plurality of mirrors 201a-201f is incident upon a different one of the facets of the first extraction mirror 231a. The facets are disposed at different angles to take into account the different paths of the extracted sub beams 221a-221f and ensure that, after reflection from the first branch mirror 231a, the extracted sub beams 221a-221f all propagate in substantially the same direction to form a single composite branch radiation beam $B_1$.

In an alternative embodiment, the first extraction mirror 231a is not a multi-facet mirror. In order to ensure that after reflection from the first branch mirror 231a the extracted sub beams 221a-221f form a single composite branch radiation beam $B_1$, the plurality of mirrors 201a-201f may be disposed at different positions along the propagation direction of the main radiation beam B. The positions and angles of the plurality of mirrors 201a-201f are arranged such that the extracted sub beams 221a-221f all propagate in substantially the same direction. For example, referring to FIG. 16a, in such an embodiment, mirror 201a may be displaced to the right with respect to mirror 201b, and mirror 201c may be displaced to the left with respect to mirror 201b. By suitable choice of these displacements, the extracted sub beams 221a-221f from these mirrors 201a-201c can propagate in substantially the same direction.

Figure 19:
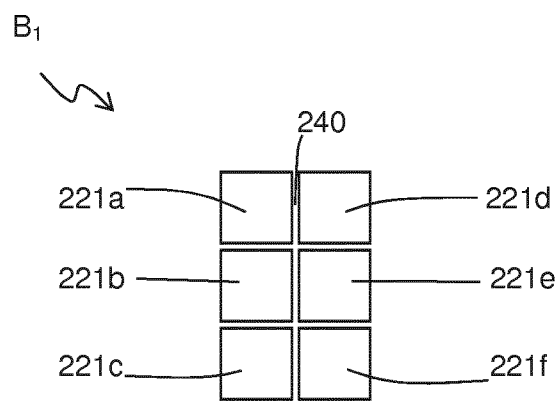
FIG. 19 shows the cross section of a branch radiation beam formed by the beam splitting apparatus illustrated in FIG. 15.

In one embodiment, as shown in FIG. 19, the orientation of the plurality of mirrors 201a-201f is such that within the composite branch radiation beam $B_1$ the extracted sub-beams 221a-221f are adjacent. Preferably, the orientation of the plurality of mirrors 201a-201f is chosen so that the extracted sub-beams 221a-221f have substantially no overlap but such that any gaps 240 between each adjacent sub-beam 221a-221f is minimised. For such embodiments, a ripple plate (not shown) may be provided for further conditioning of each branch radiation beam B1-B20. A ripple plate comprises a reflecting surface which is generally flat, with an average normal direction, with random local variations to the average normal direction. This acts to smooth out the intensity distribution of the branch radiation beams B1-B20 reducing the effects of overlaps or gaps 240 between the extracted sub-beams 221a-221f. The size of the overlap and/or gaps 240 between the sub-beams 221a-221f may be less than, for example, 1% of the size of the composite branch radiation beam $B_a$. Additionally or alternatively, the size of the overlap and/or gaps 240 between the sub-beams 221a-221f may be of the same order of magnitude as the smearing effect of the ripple plate or less. The smearing effect of the ripple plate may be, for example, less than around 1 mm or even less than around 10 μm.

Alternatively, in another embodiment, the orientation of the plurality of mirrors 201a-201f is such that within the composite branch radiation beam $B_1$ the extracted sub beams 221a-221f overlap substantially completely. In this way, the composite branch radiation beam $B_1$ comprises an area of substantially similar dimensions to the areas 211a-211f.

Each branch optical path 211-218 may comprise a mechanism (not shown) for adjusting the intensity of the branch radiation beam $B_1$-$B_8$ propagating along it before the branch radiation beam $B_1$-$B_8$ passes into the illumination system IL of its corresponding lithographic apparatus LA1-LAB. The mechanism for adjusting the intensity of the branch radiation beam $B_1$-$B_8$ may comprise a coarse adjustment mechanism and a fine adjustment mechanism. The coarse adjustment mechanism may be operable to provide intensity adjustments of up to a factor of 10 and the fine adjustment mechanism may be operable to provide intensity adjustments of around 10%.

The branch radiation beams $B_1$-$B_8$ may propagate in any direction as desired or required. The direction of each branch radiation beam $B_1$-$B_8$ will depend on the orientation of the associated extracting optic 201-208 and branch mirrors. In FIGS. 16a and 16b only one branch mirror 231a is shown. However, a plurality of branch mirrors may be provided. In one embodiment, the branch radiation beams $B_1$-$B_8$ propagate in a direction that is substantially perpendicular to the main radiation beam B. For example, the main radiation beam B produced by the radiation source SO may propagate in a substantially horizontal direction and the branch radiation beams $B_1$-$B_8$ may propagate in a substantially vertical direction. Such an arrangement allows the plurality of lithographic apparatuses LA1-LA8 within the lithographic system LS to be disposed at different vertical positions. For example, the plurality of lithographic apparatuses LA1-LA8 within the lithographic system LS may be on different floors of the same building. The transmission and the polarization of the branch radiation beams $B_1$-$B_8$ will depend on the number of mirrors used to rotate the radiation from the main radiation beam B through 90 degrees. The greater the number of mirrors used, the smaller the angle between the radiation and the surface of each mirror can be. As the angle between a radiation beam and the surface of a mirror it hits decreases, the transmission will increase and the effect of the reflection on the polarization of the radiation beam will decrease. Therefore, the greater the number of mirrors used to rotate the radiation from the main beam B through 90 degrees, the greater the transmission will be and the smaller the effect of the mirrors on the polarization of the radiation beam will be. However, each additional mirror increases the cost and complexity of the lithographic system LS. In an embodiment, each branch optical path 211-218 may comprise, for example, two to eight branch mirrors.

The power P received by each of the mirrors 201a-201f is given by:

$$P = \int_A I_B(y, z) dS, \quad (3)$$

where $I_B(y,z)$ is the intensity profile of the main radiation beam B and the area A over which the surface integral is performed is the square area 211a-211f formed by projecting the reflective surface of that mirror onto a plane perpendicular to the propagation of the main radiation beam B (the y-z plane in FIGS. 16a, 16b & 17).

The mirrors 201a-201f may be substantially static. However, if the main radiation beam B moves in the plane perpendicular to its propagation (the y-z plane in FIGS. 16a, 16b & 17) the power received by each of the plurality of mirrors 201a-201f will change if either: (a) the intensity distribution $I_B(y,z)$ is non-uniform; or (b) the main radiation beam B moves so that it no longer illuminates the entire reflective surface of one or more of the mirrors 201a-201f. Movement of the main radiation beam B in the y-z plane will result in the circle E in FIG. 17 moving relative to the square areas 211a-211f. For example, if the position of the main radiation beam B in the y-z plane shifts in the direction indicated by arrow A, the circle E will shift in position to circle E' and a center B* of the main radiation beam B will shift to B*'.

The intensity profile of the main radiation beam B may be Gaussian-like and the circle E in FIG. 17 may indicate the 3-sigma width of the Gaussian intensity profile. For such embodiments, a shift of the main radiation beam B in the y-z plane will change the power received by each of the plurality of mirrors 201a-201f. Some of the plurality of mirrors 201a-201f will receive more power and some of the plurality of mirrors 201a-201f will receive less power. Therefore, the increase in power received by some of the mirrors 201a-201f will at least partially cancel the decrease in power received by the others. Advantageously, the radiation beams $B_1$-$B_8$ produced by such an arrangement are less sensitive to pointing variations of the main radiation beam B produced by the radiation source SO than, for example, an arrangement wherein each extraction optic comprises a single rectangular mirror.

The square areas 211a-211f are distributed over the cross section of the main radiation beam B so as to maximize the cancellation between the increase in power received by some of the mirrors 201a-201f and the decrease in power received by the others when the main radiation beam B moves. That is, the distribution of square areas 211a-211f is chosen to minimise the sensitivity of the power of the branch radiation beams $B_1$-$B_8$ to pointing variations of the main radiation beam B. To achieve this, since the intensity profile of the main radiation beam B is Gaussian-like, the square areas 211a-211f are distributed generally evenly about the center B* of the main radiation beam B. With such as arrangement, when the position of the main radiation beam B in a plane perpendicular to its propagation changes, the power received by at least a first of the mirrors 201a-201f will increase and the power received by at least a second of the plurality of mirrors 201a-201f will decrease, irrespective of the direction of movement of the main radiation beam B in the y-z plane.

A more even distribution of the square areas 211a-211f about the center B* of the main radiation beam B may be achieved by a greater number of mirrors in the extraction optic 201. This may provide a better cancellation and therefore a more stable branch radiation beam $B_1$. However, it will increase the cost and complexity of the beam splitting apparatus 200.

The other extraction optics 202-208 may be substantially the same as the extraction optic 201 described above but with a different spatial distribution of the areas formed by projecting the reflective surface of that mirror onto a plane perpendicular to the propagation of the main radiation beam B.

Figure 18:
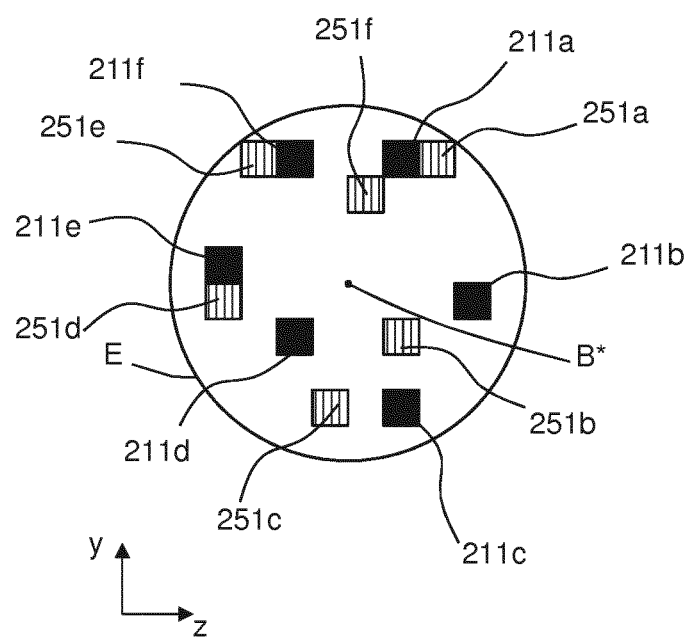
FIG. 18 shows projections onto the cross section of a main radiation beam of: the extraction optic of FIGS. 16a and 16b; and a second extraction optic of the beam splitting apparatus.

For example, the second extraction optic 202 may also comprise six wedge shaped grazing incidence mirrors. The projection of a reflective surface of each of the six mirrors of the second extraction optic 202 onto a plane perpendicular to the propagation direction of the main radiation beam B comprises a respective square area 251a-251f. FIG. 18 shows the distribution of the square areas 251a-251f onto a plane perpendicular to the propagation direction of the main radiation beam B. The square areas 211a-211f that represent the projection of the reflective surfaces of the mirrors 201a-201f of the first extraction optic 201 are also shown in FIG. 18, in black, to indicate that these parts of the main radiation beam B have already been extracted by the first extraction optic 201.

The mirrors in each extraction optic 201-208 may be substantially identical, which is particularly advantageous for manufacturing the mirrors. The plurality of mirrors in the plurality of extraction optics 201-208 may be shaped and positioned so that their projection onto a plane perpendicular to the propagation direction of the main radiation beam B substantially coincides with the cross sectional area of the main radiation beam B, without overlap and with minimal gaps.

In the above embodiment, each extraction optic 201-208 comprises a plurality of mirrors, each mirror forming a portion of the extraction optic 201-208. However, in alternative embodiments each extraction optic may comprise a single mirror comprising a plurality of different portions shaped such that when the position of the main radiation beam in a plane perpendicular to its propagation changes, the power received by at least a first of the plurality of portions will increase and the power received by at least a second of the plurality of portions will decrease. For example, each extraction optic may comprise a generally annular mirror, concentric with the main radiation beam B.

In the above embodiment, the specific example of a main radiation beam B with a Gaussian-like intensity profile has been discussed. However, embodiments of the present invention may be adapted for use with main radiation beams B with different intensity profiles. For an intensity distribution which is rotationally symmetric about its centre (i.e. it is only a function of the distance from the centre), a plurality of portions of each extraction optic 201-208 may be arranged evenly around the centre. For an intensity distribution which is not rotationally symmetric about its centre, a different distribution of the plurality of portions of each extraction optic 201-208 may be used.

In the above embodiment, each extraction optic 201-208 comprises six mirrors. However, other numbers of mirrors may alternatively be used. Different extraction optics 201-208 may be provided with different numbers of mirrors.

Preferably the projection of all of the mirrors onto a plane perpendicular to the propagation direction of the main radiation beam B substantially coincides with the cross sectional area of the main radiation beam B, without overlap and with minimal gaps. In the above embodiment, this is achieved by using mirrors shaped and orientated so that their projection onto a plane perpendicular to the propagation direction of the main radiation beam B is a square area. However, in other embodiments these areas may have of different shapes. For example, the mirrors may be shaped so that the areas are triangular, rectangular, or hexagonal.

It is described above that a main radiation beam B may be split by a beam splitting apparatus comprising one or more of static mirrors, which during normal operation, do not move. That is, in the embodiments described above, splitting of the main radiation beam B is not achieved through movement of the mirrors of the beam splitting apparatus. There are now described embodiments in which splitting is achieved by other means.

Figure 20:
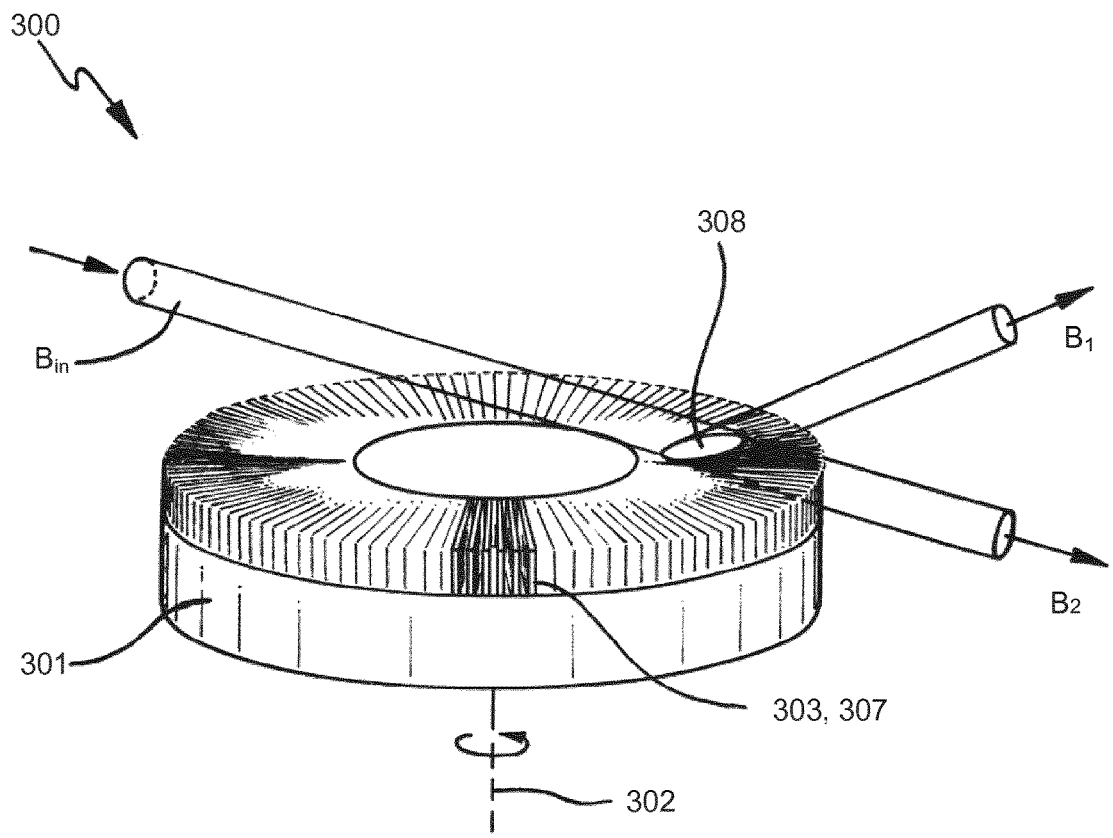
FIG. 20 is a perspective view of an embodiment of a beam splitting apparatus according an embodiment described herein, which may form part of a lithographic system described herein.
Figure 21:
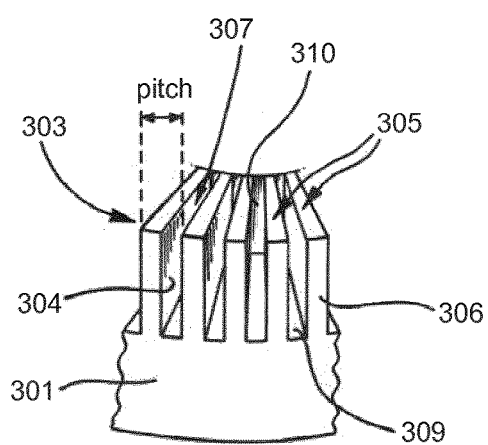
FIG. 21 is a perspective view of a section of the beam splitting apparatus of FIG. 20.

Referring to FIGS. 20 and 21, a beam splitting apparatus 300 is shown. The beam splitting apparatus may be, or may form part of, the beam splitting optics 35 shown in FIG. 1.

The beam splitting apparatus 300 comprises a generally disc-shaped body 301 and a mechanism (not shown) operable to rotate said body 301 about a rotation axis 302. For example, the disc-shaped body 301 may comprise a shaft extending along the rotation axis 302. The shaft may be supported by one or more bearings, for example two bearings. The bearings may be passive bearings such as, for example, rolling element bearings or aerostatic bearings. Alternatively, the bearings may be active bearings such as, for example, magnetic bearings. The shaft may be driven to rotate by any suitable mechanism such as a motor or engine.

A direction along, or parallel to the rotation axis 302 may be referred to as an axial direction. A direction running to or from the rotation axis 302 and perpendicular to said rotation axis 302 may be referred to as a radial direction.

The beam splitting apparatus 300 further comprises a plurality of radially extending spokes 303. Each of the spokes 303 comprises two radially extending side walls 304, an axially facing upper surface 305 and a radially facing end wall 306. The shape of the upper surface 305 of each spoke is therefore an annular sector. The upper surface 305 of each spoke is formed from a reflective material. The spokes 303 are separated from each other by respective gaps 307. As such the axially facing upper surfaces 305 of the plurality of spokes 303 form a plurality of discrete reflective elements. Each of the spokes 303 is substantially the same size and shape and each of the gaps 307 is substantially the same size and shape. Therefore, the axially facing upper surfaces 305 of the plurality of spokes 303 form a periodic array of discrete reflective elements. A pitch of the periodic array at a given radial point is given by the angular extent of one axially facing upper surface 305 and one gap 307.

The beam splitting apparatus 300 comprises a beam spot region 308 arranged to receive a radiation beam $B_{in}$. The beam spot region 308 is disposed on an axially facing surface of the body 301, which is formed from the upper axial surfaces 305 of the spokes 303.

The radiation beam $B_{in}$ may be produced by a free electron laser FEL. For example, the radiation beam $B_{in}$ may be the main radiation beam B, or may be a branch radiation beam. A radiation beam output by an undulator of a free electron laser may, for example, have a diameter of the order of 100 µm and a divergence of the order of 100 µrad. Further, if the free electron laser is to provide radiation for of the order of ten lithographic apparatuses, then the radiation beam output by the undulator may have a power of the order of tens of kilowatts. For thermal reasons therefore, the beam splitting apparatus 300 may be separated from the undulator 24 by a distance of the order of tens to hundreds of metres. For example, at the beam splitting apparatus 300, the radiation beam $B_{in}$ may have a diameter of the order of 5 mm. Again for thermal reasons, the radiation beam $B_{in}$ may approach the beam spot region 308 at a small grazing incidence angle. This will spread the power over a greater area of the beam spot region and may also increase the reflectivity of the upper axial surfaces 305 of the spokes 303. For example, the grazing incidence angle may be around 1.4 degrees. At this angle, an incoming radiation beam $B_{in}$ with a diameter of 5 mm will spread out over an ellipse shaped beam spot region 308 with major and minor axes of approximately 210 mm by 5 mm.

Figure 22:
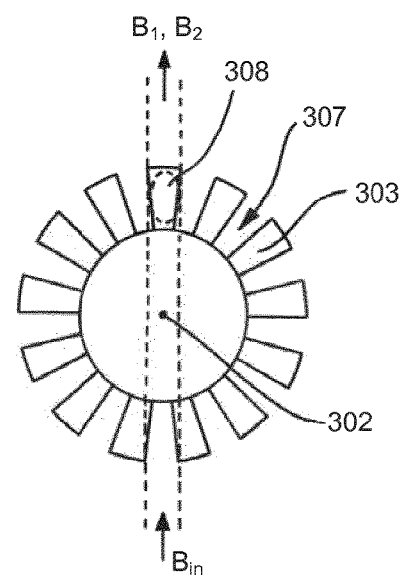
FIG. 22 is a plan view of the beam splitting apparatus of FIG. 20.

Referring to FIG. 22, the incoming radiation beam $B_{in}$ passes over one side of the axially facing surface of the body 301, over the rotation axis 302, and approaches the beam spot region 308. As the radiation beam $B_{in}$ is incident upon the beam spot region 308, its propagation direction is generally in a (local) radial direction (i.e. perpendicular to the rotation axis 302), with a small axial component (i.e. parallel to the rotation axis 302). The size of the axial component is determined by the grazing incidence angle of the radiation beam $B_{in}$.

As the body 301 rotates about the rotation axis 302, the periodic array moves such that the plurality of reflective elements (formed by the upper surface 305 of the spokes 303) move through the beam spot region 308. A first portion of the radiation beam is incident on, and reflected by, the upper surface 305 of the spokes 303 so as to form a first branch radiation beam $B_1$. A second portion of the radiation beam passes through the gaps 307 between the reflective elements so as to form a second branch radiation beam $B_2$. The beam splitting apparatus 300 therefore allows an incoming radiation beam $B_{in}$ to be split into outgoing first and second branch radiation beams $B_1$, $B_2$. While in the present description, the beam splitting apparatus 300 is described as producing the branch radiation beams $B_1$, $B_2$, this is merely exemplary. The beam splitting apparatus 300 may, for example, be used to provide others of the branch radiation beams $B_1$-$B_{20}$.

In general, as the upper surfaces 305 of the plurality of spokes 303 move through the beam spot region 308, the intensities of the first and second branch radiation beams $B_1$, $B_2$ will vary with time as a greater or lesser amount or the incoming radiation is reflected or transmitted at different times. The variation in intensities is a periodic oscillation. Where the reflective elements are substantially equally reflective, the frequency of the oscillation is determined by the speed and pitch of the periodic array. In turn, this will cause the dose of radiation delivered by each of the first and second branch radiation beams $B_1$, $B_2$ to vary with time.

This variation in dose will average out over a time period equal to an integer number of periods of the oscillation. Therefore, in order to ensure that a dose of radiation delivered by the first and second branch radiation beams $B_1$, $B_2$ for a given exposure time remains constant, the exposure time should be equal to an integer number of periods of the oscillation. In practice, it may not be possible to meet this criterion. If the exposure time is not equal to an integer number of periods of the oscillation, then the dose of radiation delivered by the first and second branch radiation beams $B_1$, $B_2$ for a given exposure time will vary periodically with time. As the (non-integer) number periods of the oscillation that occur during the exposure time increases, the ratio of the amplitude of this variation in dose to the average dose received during an exposure time decreases. Therefore, it may be desirable for the frequency of the oscillation to be as high as possible so that a more stable dose may be achieved in a given exposure time period.

The first and second branch radiation beams $B_1$, $B_2$ may be supplied to one or more of the lithographic apparatuses $LA_1$-$LA_{20}$ of the lithographic system LS shown in FIG. 1. For such an arrangement, it may be desirable for the frequency of the oscillation in the intensities of the first and second branch radiation beams $B_1$, $B_2$ to be sufficiently high that a stable dose may be achieved in a typical exposure time of the lithographic apparatuses LA1-LAB. This exposure time may be of the order of 1 ms and it may therefore be desirable for the frequency of the oscillation in the intensities to be greater than 1 kHz. As explained above, it may be desirable for the frequency of the oscillation in the intensities to be sufficiently high so that several periods of the oscillation occur during the exposure time. For example, the frequency of the oscillation in the intensities may be of the order of 16 kHz or above, resulting in 16 or more periods of the oscillation during the exposure time, or of the order of 30 kHz or above, resulting in 30 or more periods of the oscillation during the exposure time.

The frequency of the oscillation in the intensities of the first and second branch radiation beams $B_1$, $B_2$ is given by the frequency of rotation of the body 301 multiplied by the number of periods of the periodic array disposed on the body 301 (i.e. the number of spokes 303 disposed on the body 301). For example, if there are 300 spokes 303 (and 300 gaps 307) disposed on the body 301 and the body 301 rotates at a frequency of 160 Hz then the frequency of the oscillation in the intensities of the first and second branch radiation beams $B_1$, $B_2$ is 16 kHz.

Since the periodic array comprises a plurality of discrete reflective elements, each of the spokes 303 may be smaller and more closely spaced. This reduces the pitch of the periodic array and therefore increases the frequency at which the intensities of the first and second branch radiations $B_1$, $B_2$ beams oscillate for a given speed of the periodic array. Advantageously, this allows a stable dose to be achieved in a smaller time period for a given speed of the periodic array. Alternatively, it allows a stable dose to be achieved in a similar time period at a lower speed of the periodic array.

An advantage of an arrangement wherein the reflective elements move through the beam spot region is that the relative intensities of the first and second branch radiation beams $B_1$, $B_2$ (time averaged over an integer number of periods of the oscillation) are relatively insensitive to the direction and position of the incoming radiation beam $B_{in}$, at least in the direction of motion of the periodic array. This is in contrast to a beam splitting arrangement which uses static mirrors to provide two or more branch radiation beams wherein relative movement of the incoming radiation beam $B_{in}$ and the static mirrors can result in a significant change in the relative intensities of the branch radiation beams. This is especially so where the diameter of the incoming radiation beam $B_{in}$ is small, which is generally the case for radiation beams produced by a free electron laser, which, as described above, may have a diameter of the order of 100 µm and a divergence of the order of 100 µrad.

The plurality of spokes 303 and gaps 307 each extend to an edge of the body 301 of the beam splitting apparatus 300. Therefore each gap 307 is defined by two of the radially extending side walls 304, each from a different one of a pair of adjacent spokes 303, an axially facing lower surface 309 and a radially facing wall 310. The shape of each gap 307 as viewed from above (in an axial direction) is therefore an annular sector. Since each of the gaps 307 extends to an edge of the body 301 of the beam splitting apparatus 300, the gaps 307 are open on one (radially outer) side. The incoming radiation beam $B_{in}$ propagates to and from the beam spot region 308 in a generally radially increasing direction. For example, for a gap 307 within the beam spot region 308, the radiation beam $B_{in}$ propagates generally from the radially facing wall 310 towards the open side of the gap 307. Advantageously, with such an arrangement a range of allowable grazing incidence angles is not limited by the thickness of the body 301.

This is in contrast to an arrangement wherein the gaps 307 do not extend to the edge of the body 301, such as gaps of the form of apertures in the body 301 which are closed on all sides. With such an arrangement, the range of allowable grazing incidence angles is limited both by the size of the gaps in the direction of propagation of the radiation beam and the thickness of the body, the thickness of the body setting a lower limit on the possible grazing incidence angles.

Since the plurality of gaps 307 each extend to an edge of the body 301, the beam splitting apparatus 300 therefore allows the incoming radiation beam $B_{in}$ to approach with smaller grazing incidence angles. This is beneficial both for thermal reasons and for reflectivity.

The spokes 303 and the gaps 307 may be substantially the same size. With such an arrangement, the first and second branch radiation beams $B_1$, $B_2$ will have substantially the same intensity. Alternatively, the spokes 303 and the gaps 307 may have different sizes. By varying the ratio of the sizes of the spokes 303 to the gaps 307, the ratio of the intensities of the first and second branch radiation beams $B_1$, $B_2$ may be varied.

The pitch of the periodic array may be smaller than, equal to or larger than the diameter of the incoming radiation beam $B_{in}$. A non-zero fraction of the radiation beam will be incident on, and reflected by, the radially extending side walls 304 of the spokes 303. This fraction of the incoming radiation beam does not form part of the first or second radiation branch beams $B_1$, $B_2$, and is therefore lost. The fraction of radiation that is lost in this way will be small provided that the radius of the body 301 of the beam splitting apparatus 300 is sufficiently large that the individual spokes 303 are substantially parallel.

Figure 23:
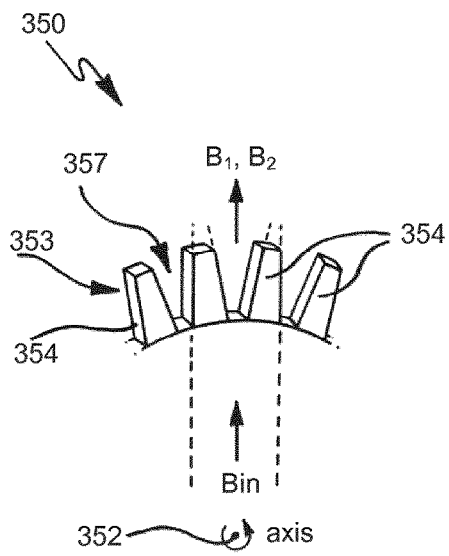
FIG. 23 is a plan view of a section of another embodiment of a beam splitting apparatus, which may form part of a lithographic system described herein.
Figure 24:
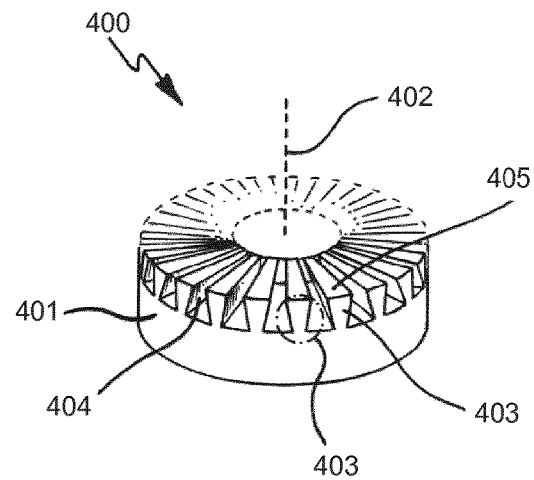
FIG. 24 is a perspective view of another embodiment of a beam splitting apparatus, which may form part of a lithographic system described herein.

Two alternative embodiments of beam splitting apparatuses, which are arranged so as to eliminate, or at least reduce, losses caused by reflection from the radially extending side walls 304 of the spokes 303, are illustrated in FIGS. 23 and 24.

Referring to FIG. 23, an alternative beam splitting apparatus 350 is illustrated. Beam splitting apparatus 350 differs from beam splitting apparatus 300 of FIGS. 20 to 22 in that a plurality of spokes 353 taper inwards in a direction of increasing radius (i.e. away from a rotation axis 352). In corollary, gaps 357 taper outwards in a direction of increasing radius. Therefore, side walls 354 of the spokes 253 do not extend in a purely radial direction. In all other aspects, beam splitting apparatus 350 may be generally similar to beam splitting apparatus 300. With a sufficient amount of tapering of the spokes 253, a fraction of radiation that is lost from reflection from the side walls 354 of the spokes 353 can be reduced to a negligible amount, and may for example be zero.

The tapering of the spokes 353 will introduce an intensity gradient across the cross section of the first and second branch radiation beams $B_1$, $B_2$. The impact of such an intensity gradient on the performance of the lithographic apparatuses LA1-LA20 may be limited by mixing performed by the faceted field mirror device 10 and the faceted pupil mirror device 11 (see FIG. 2) within the illumination system IL of each lithographic apparatus LA1-LA20. The impact of such an intensity gradient on the performance of the lithographic apparatuses LA1-LA20 is lowest when the direction of the intensity gradient is in a scan direction of the lithographic apparatus LA1-LA20.

Referring to FIG. 24, an alternative beam splitting apparatus 400 is illustrated. Beam splitting apparatus 400 comprises a generally disc-shaped body 401 and a mechanism (not shown) operable to rotate said body 401 about a rotation axis 402. Beam splitting apparatus 400 differs from the beam splitting apparatus 300 of FIGS. 20 to 22 in that a plurality of spokes 403 taper inwards in an axial direction away from axially facing upper surfaces 405 of the spokes 403 so as to provide each of the spokes with an undercut. Therefore, side walls 404 of the spokes 403 do not extend in a purely radial direction. In all other aspects, beam splitting apparatus 400 may be generally similar to beam splitting apparatus 300. With a sufficient amount of tapering, the fraction of radiation that is lost from reflection from the side walls of the spokes 403 can be reduced to negligible amount.

Advantageously, in comparison with the beam splitting apparatus 300 the beam splitting apparatus 400 eliminates, or at least reduces, losses that may result from reflection from the side walls of the spokes 403 without introducing an intensity gradient in the branch radiation beams $B_1$, $B_2$.

Figure 25:
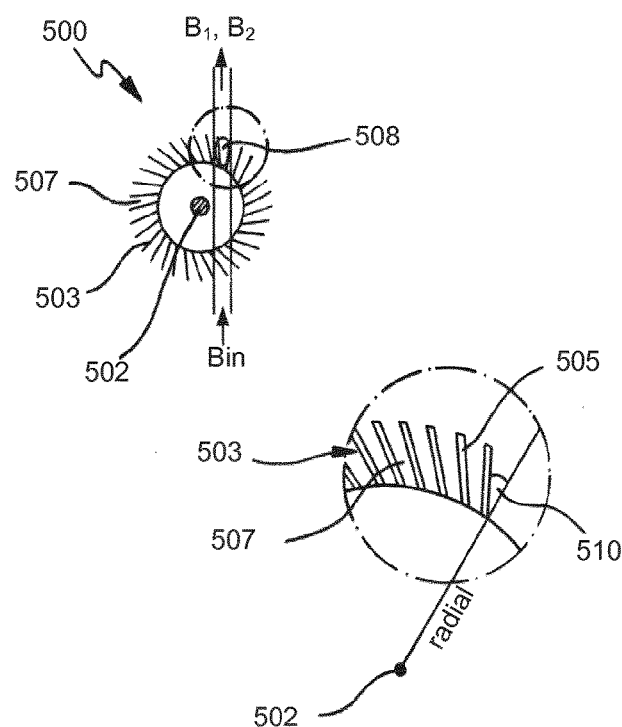
FIG. 25 is a plan view of another embodiment of a beam splitting apparatus, which may form part of a lithographic system described herein.
Figure 26:
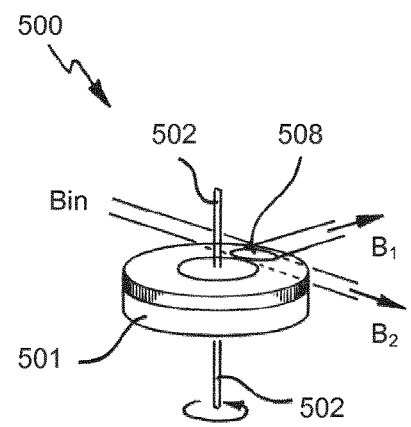
FIG. 26 is a perspective view of the beam splitting apparatus of FIG. 25.

A further embodiment of a beam splitting apparatus 500 is illustrated in FIGS. 25 and 26. Beam splitting apparatus 500 further comprises a plurality of spokes 503, which are separated from each other by respective gaps 507. Beam splitting apparatus 500 differs from the beam splitting apparatus 300 of FIGS. 20 to 22 in that although each of a plurality of spokes 503 extends in a generally radial direction (i.e. they extend between a radially inner and a radially outer point, they do not extend in a purely radial direction. Rather, the side walls of each of the plurality of spokes 503 extend in a direction that is at an oblique angle 510 to the radial direction. The shape of the upper surface 505 of each spoke 503 may be generally rectangular. Alternatively, the upper surface 505 of each spoke 503 may taper outwards in the direction of increasing radius.

In all other aspects, beam splitting apparatus 500 may be generally similar to beam splitting apparatus 300.

In the embodiment of FIGS. 25 and 26, the incoming radiation beam $B_{in}$ no longer passes through A rotation axis 502 as it approaches A beam spot region 508. Rather, as can be see most clearly in FIG. 25, the propagation direction of the radiation beam $B_{in}$ is generally aligned with the direction in which axially facing upper surfaces 505 of the spokes 503 that are within the beam spot region 508 extent. Therefore, the radiation beam direction is at an oblique angle to the radial direction.

Advantageously, since the incoming radiation beam does not pass through the rotation axis 502, a body 501 of the beam splitting apparatus can be supported for rotation on both of its opposed axial sides. This allows, for example, a shaft to extend out of the upper axial surface of the body without blocking the radiation beam $B_{in}$. This may allow, for example, the shaft to be supported by bearings on either side of the body, allowing for easier and more stable implementation, than provided by a single-side axle mounting.

Features of the above described embodiments of beam splitting apparatuses 300, 350, 400, 500 may be combined. For example, the embodiment 500 of FIGS. 25 and 26 may be provided with a taper as described in relation to the embodiment 350 of FIG. 23 or a taper as described in relation to the embodiment 400 of FIG. 24.

Figure 27:
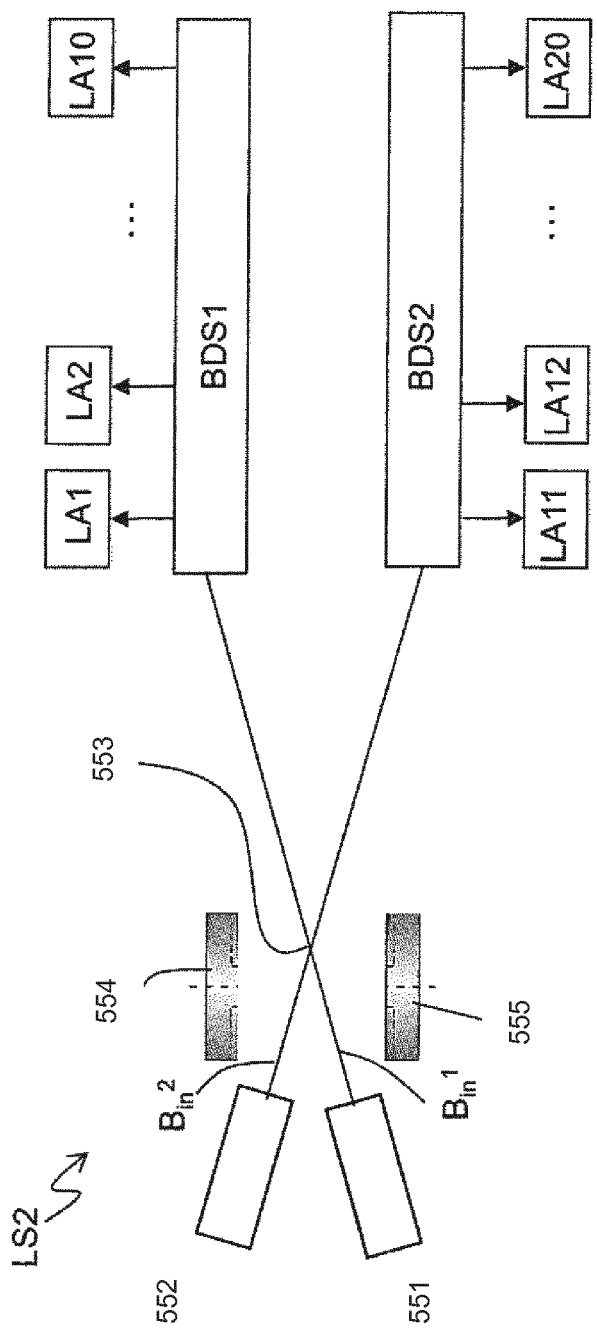
FIG. 27 is a schematic illustration of another embodiment of a lithographic system comprising two beam splitting apparatus, the lithographic system disposed in a first configuration.
Figure 28:
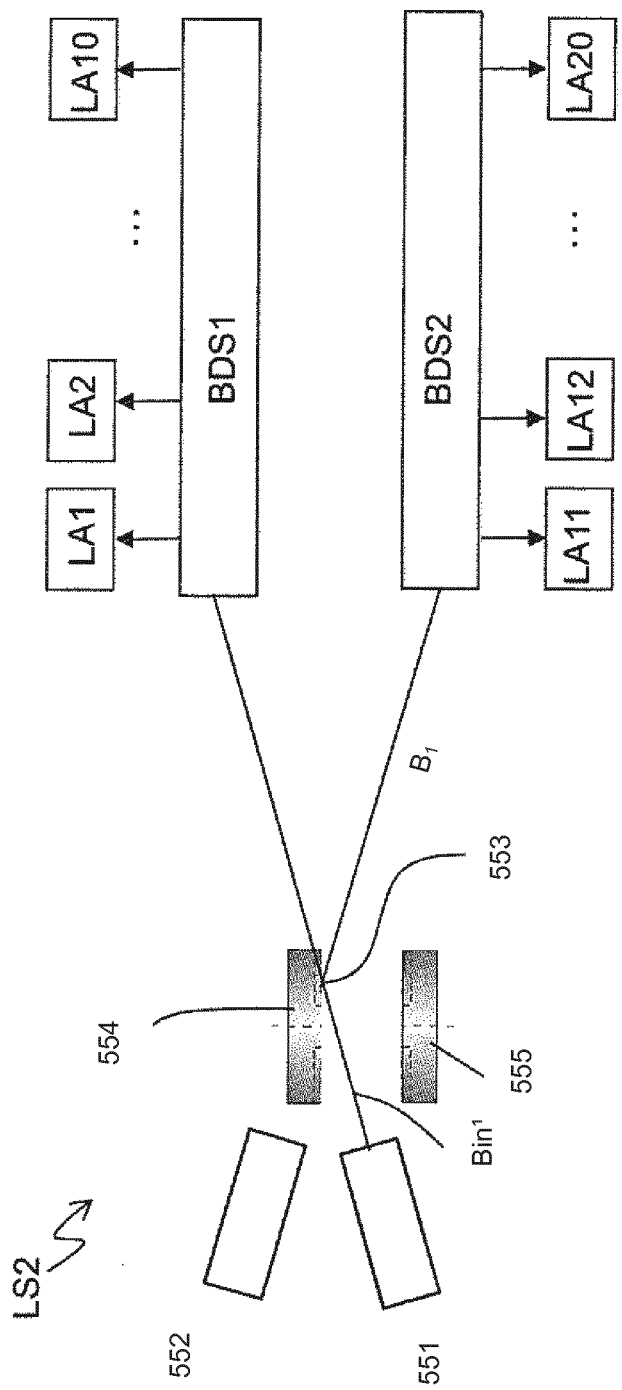
FIG. 28 is a schematic illustration of the lithographic system of FIG. 27 disposed in a second configuration.

Referring FIGS. 27 and 28, an alternative embodiment of a lithographic system LS2 is shown. The lithographic system LS2 comprises two radiation sources 551, 552. Each radiation source 551, 552 may, for example, comprise a free electron laser. Each of the radiation sources 551, 552 is provided with a corresponding beam delivery system BDS1, BDS2. Each beam delivery system BDS1, BDS2 is arranged to receive a radiation beam $B_{in}^1$, $B_{in}^2$ from its corresponding radiation sources 551, 552 and to distribute this to a plurality of lithographic apparatuses LA1-LA10, LA11-LA20 respectively. Each beam delivery system BDS1, BDS2 may comprise beam expanding optics and beam splitting optics.

The two radiation sources 551, 552 are arranged such that their output radiation beams $B_{in}^1$, $B_{in}^2$ cross at an intersection point 553 between the radiation sources 551, 552 and the beam delivery systems BDS1, BDS2.

The lithographic system LS2 further comprises two beam splitting apparatuses 554, 555. Each of the beam splitting apparatuses 554, 555 may comprise a beam splitting apparatus 300, 350, 400, 500 substantially as described above. Each beam splitting apparatus 554, 555 is movable between an inactive position and a deployed position. When disposed in its inactive position, each beam splitting apparatus 554, 555 is disposed close to the intersection point 520 but out of the path of the radiation beams $B_{in}^1$, $B_{in}^2$. When disposed in their respective deployed positions, each beam splitting apparatus 554, 555 is disposed at the intersection point 520 in the path of the radiation beams $B_{in}^1$, $B_{in}^2$. The lithographic system LS2 may comprise additional optics which are operable to steer the two radiation beams $B_{in}^1$, $B_{in}^2$ with sufficient precision such that when the such that when either beam splitting apparatus 554, 555 is disposed in its deployed positions one of the two radiation beams $b_{in}^1$, $B_{in}^2$ is incident upon its beam spot region.

Referring to FIG. 27, the lithographic system LS2 is illustrated with both of the beam splitting apparatuses disposed in their respective inactive positions. Such a configuration may be a default configuration of the lithographic system LS2, when both radiation sources 551, 552 are operating. Each radiation sources 551, 552 emits a radiation beam $B_{in}^1$, $B_{in}^2$ which is received by its corresponding beam delivery system BDS1, BDS2.

Referring to FIG. 28, the lithographic system LS2 is illustrated with the beam splitting apparatus 554 disposed in its deployed position and the beam splitting apparatus 555 disposed in its inactive position. Such a configuration of the lithographic system LS2 may be used in the event that the radiation source 552 is no longer operating (either as part of a planned shut down or when the radiation source 552 is out of order). Only the radiation source 551 emits a radiation beam $B_{in}^1$, which is received by its corresponding beam splitting apparatus 554.

In the manner described above, with reference to FIGS. 20 to 26, first portion of the radiation beam $B_{in}^1$ is incident on, and reflected by, the upper surfaces of a plurality of spokes on the beam splitting apparatus 554, so as to form a first branch radiation beam $B_1$. A beam spot region of the beam splitting apparatus 554 is substantially coincident with the intersection point 553 and the grazing incidence angle of the first radiation beam $B_{in}^1$ is such that the first branch radiation beam $B_1$ propagates along substantially the same optical path as a radiation beam $B_{in}^2$ from the radiation source 552 does when the lithographic system LS2 is in the configuration shown in FIG. 27. Therefore, the first branch radiation beam $B_1$ is received by the second beam delivery system BDS2.

A second portion of the radiation beam passes through the gaps between the spokes of the beam splitting apparatus 554 so as to form a second branch radiation beam $B_2$. Therefore, the second branch radiation beam $B_2$ is received by the first beam delivery system BDS1.

Similarly, when the radiation source 551 is not operating, the first beam splitting apparatus 554 can be disposed in its inactive position and the second beam splitting apparatus 555 can be disposed in its deployed position so as to split the radiation beam $B_{in}^2$ output by the radiation source 552 between the two beam delivery systems BDS1, BDS2.

The lithographic system LS2 therefore provides a system wherein two radiation sources 551, 552 may operate in parallel, each providing radiation to a different set of lithographic apparatuses via a beam delivery system BDS1, BDS2. When one of the radiation sources 551, 552 is not operating, the beam splitting apparatuses 554, 555 may be used to split the radiation beam output by the other radiation source into two branch radiation beams $B_1$, $B_2$ such that each beam delivery system BDS1, BDS2 is supplied with, for example, around 50% of the radiation beam from the operational radiation source.

Advantageously, other than a total intensity, the branch radiation beams $B_1$, $B_2$ received by the beam delivery systems BDS1, BDS2 have similar beam parameters (cross-section, divergence, position) to the radiation beams $B_{in}^1$, $B_{in}^2$ output by the radiation sources 551, 552. For example, when the input radiation beam from one of the radiation sources 551, 552 has a circular cross section, the branch radiation beams output by the beam splitting apparatus 554, 555 will also have a circular cross section. In contrast, other solutions for compensating for a radiation source that is not operating, by splitting the output of another radiation source, may produce branch radiation beams with a different (for example elliptical) cross sectional shape. With such other solutions therefore, additional correcting mirrors may be necessary to restore the branch radiation beams to the shape of the original radiation beam.

A further advantage of the lithographic system LS2 over other solutions for compensating for a radiation source that is not operating is that there is less loss of radiation. The beam delivery system (and the lithographic apparatuses served by it) associated with the operating radiation source can receive 50% of the original radiation beam. The beam delivery system (and the lithographic apparatuses served by it) associated with the non-operating radiation source can receive a percentage of the original radiation beam given by 50% multiplied by reflectivity of the rotating beam splitting apparatus. The reflectivity of the rotating beam splitting apparatus is likely to be of the order of 98% and therefore the lithographic apparatuses served by the non-operating free electron laser can receive around 49% of the original radiation beam. In contrast, other splitting solutions will provide a percentage of the original radiation beam given by 50% multiplied by the reflectivities of a plurality of (at least three) additional mirrors. The reflectivity of the additional mirrors is likely to be of the order of 98% and therefore with such an alternative solution, all of the lithographic apparatuses can receive at most around 47% of the original radiation beam.

In an alternative embodiment, the lithographic system LS2 may only comprise one rotating beam splitting apparatus arranged such that its orientation can be changed in order to serve either radiation source 551, 552.

In an alternative embodiment, the two radiation beams $B_{in}^1$, $B_{in}^2$ output by the two radiation sources 551, 552 do not cross at an intersection point. For such embodiments, when only one of the radiation sources 551, 552 is operating, additional optical elements can be used to guide the radiation beam output by the operational radiation source toward a beam splitting apparatus 554, 555.

The rotating beam splitting apparatuses 300, 350, 400, 500, 550 described above may be provided with a cooling system. Two alternative cooling systems are shown schematically in FIGS. 29 and 30 respectively.

Figure 29:
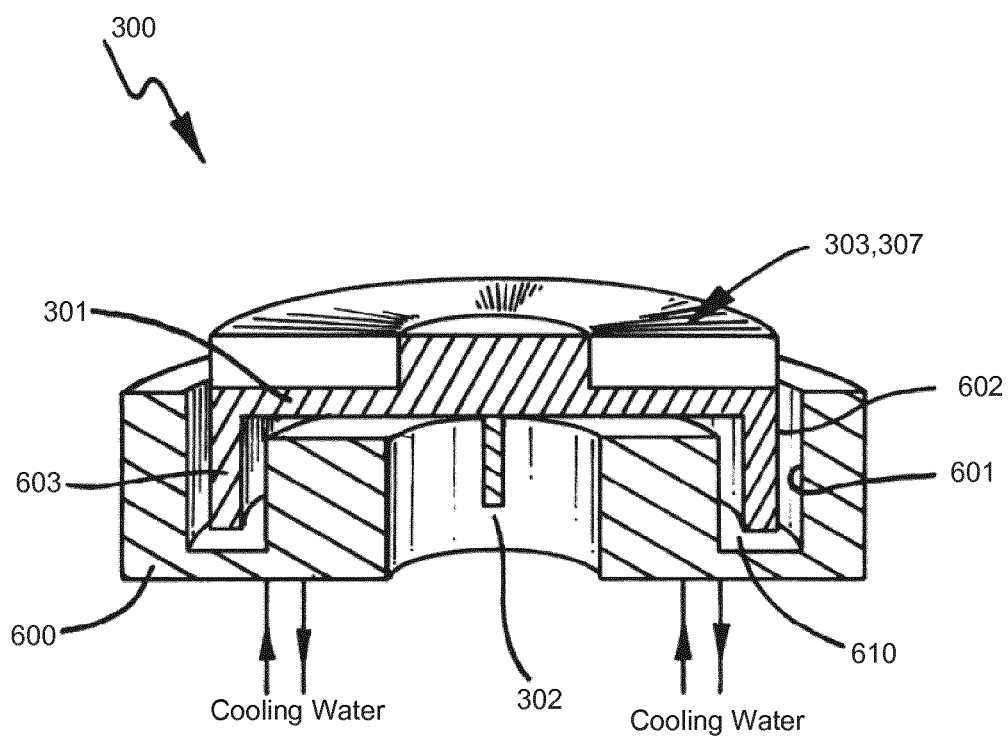
FIG. 29 is a schematic illustration of a cooling system for the beam splitting apparatus.

Referring to FIG. 29, an arrangement is shown in which the rotating body 301 of the beam splitting apparatus 300 is cooled by a static cooling device 600. Heat is transferred between the rotating body 301 and the static cooling device 600 primarily through radiation. The static cooling device 600 is mounted around the rotating body 301. For example, a lower portion of the rotating body 301 may comprise an axially extending annular protrusion 603, which may be received within an annular groove in the cooling body 600.

Opposed surfaces of the body 301 and the static cooling device 600 are provided with coatings 601, 602 of a high emissivity material to promote radiation by the body 301 and absorption of the emitted radiation by the static cooling device 600. A narrow gap 610 is provided between the rotating body 301 and the static cooling device 600. The gap 610 may be filled with a gas such as hydrogen, which may provide additional cooling of the body 301 by thermal conduction. The static cooling device 600 may be provided with channels for receiving a flow of fluid such as, for example, water, to transport heat away from the cooling device 600.

Advantageously, the arrangement shown in FIG. 29 allows water cooling of the rotating body without using rotating water couplings. This avoids, or at least significantly reduces, the risk of water leakage.

Figure 30:
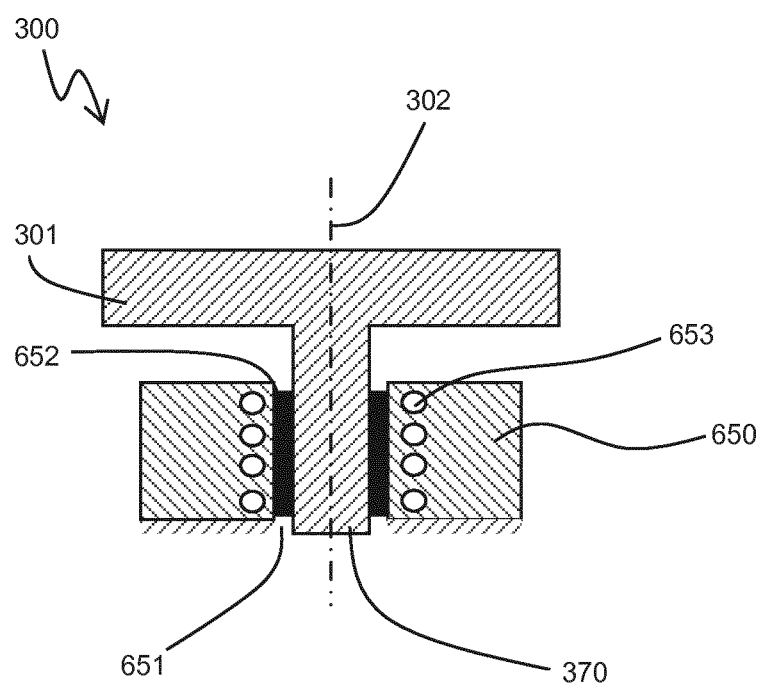
FIG. 30 is a schematic illustration of another cooling system for the beam splitting apparatus.

Referring to FIG. 30, an arrangement is shown wherein the rotating body 301 of the beam splitting apparatus 300 is cooled by a static cooling device 650, heat being transferred between the rotating body 301 and the static cooling device by a layer of liquid metal.

The beam splitting apparatus 300 comprises a shaft 370, which extends axially from the body 301, along the rotation axis 302. The static cooling device 650 is mounted adjacent to the shaft 370. A narrow gap 651 is provided between the shaft 370 and the static cooling device 650. The gap 651 is filled with layer of liquid metal 652, which is kept in place by capillary forces. The metal may comprise a fusible alloy which melts at a relatively low temperature. For example, the metal may comprise an alloy of gallium and indium, which may contain 75.5% gallium by weight and 24.5% indium by weight. Such an alloy has a melting point of 15.7° C. The static cooling device 650 is provided with channels 653 for receiving a flow of fluid such as, for example, water, to transport heat away from the cooling device 650.

In an alternative embodiment, static cooling device 650 may be mounted adjacent to a lower surface of the rotating body 301, said a lower surface being axially facing and opposite to the reflective surface formed by the upper axial surfaces 305 of the plurality of spokes 303. A narrow gap 651 may be provided between the body 301 and the static cooling device 650, the layer of liquid metal being disposed in said gap.

Advantageously, the arrangement shown in FIG. 30 allows water cooling of the rotating body without using rotating water couplings. This avoids, or at least significantly reduces, the risk of water leakage. The use of a liquid metal layer to transfer heat is a robust technique which is compatible with ultra-high vacuum conditions and high angular velocities of the shaft 370.

Alternatively, the rotating beam splitting apparatuses 300, 350, 400, 500 described above may be provided with any other suitable cooling system. For example, the cooling system may comprise one or more air bearings, wherein a (rotating) shaft of the beam splitting apparatus is received within bore in a (static) bearing bush and a thin film of pressurized gas is provided between the shaft and the bearing bush. Heat may flow away from the body of the beam splitting apparatus along the shaft and may conducted from the shaft to the bearing bush since a small gas-filled gap, for example with a dimension of the order of 10 µm, has a high thermal conductance. The bearing bush may be water-cooled so as to form a static cooling device.

A plurality of beam splitting apparatuses 300, 350, 400, 500 substantially as described above may be combined to form a beam splitting apparatus that is operable to split an incoming radiation beam into more than two outgoing branch radiation beams as is now described.

Figure 31:
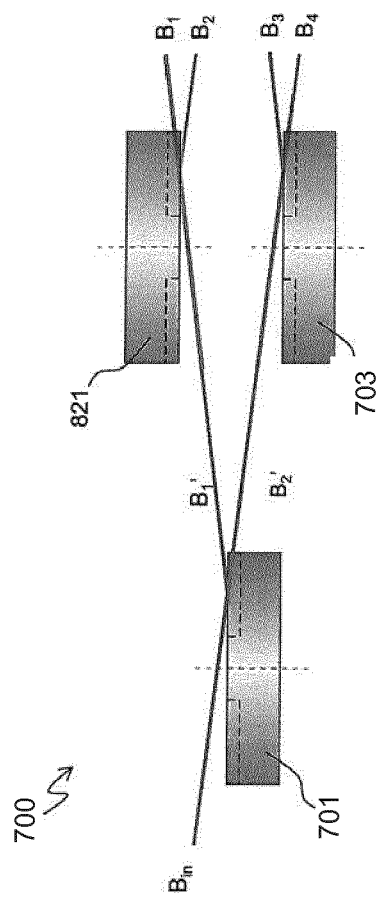
FIG. 31 is a schematic illustration of an embodiment of a composite beam splitting apparatus comprising a plurality of individual beam splitting apparatuses.

Referring to FIG. 31, a beam splitting apparatus 700 that is operable to split an incoming radiation beam into more than two outgoing branch radiation beams comprises a plurality of rotating beam splitting apparatuses 701, 702, 703. Each of the rotating beam splitting apparatuses 701, 702, 703 may comprise a beam splitting apparatus 300, 350, 400, 500 substantially as described above.

In this embodiment, the beam splitting apparatus 700 comprises a primary rotating beam splitting apparatus 701 that is arranged to receive an incoming radiation beam $B_{in}$ and output two branch radiation beams $B_1'$, $B_2'$. The beam splitting apparatus 700 further comprises two secondary rotating beam splitting apparatuses 702, 703. The first secondary rotating beam splitting apparatus 702 is arranged to receive the first branch radiation beam $B_1'$ produced by the primary rotating beam splitting apparatus 701 and to output two branch radiation beams $B_1$, $B_2$. The second secondary rotating beam splitting apparatus 703 is arranged to receive the second branch radiation beam $B_2'$ produced by the primary rotating beam splitting apparatus 701 and to output two branch radiation beams $B_3$, $B_4$.

The spokes and the gaps of each of the individual beam splitting apparatuses 701, 702, 703 may be substantially the same size. Alternatively, the spokes and the gaps may have different sizes as desired.

As explained above, in general, as the upper surfaces of the plurality of spokes of the primary rotating beam splitting apparatus 701 move through the beam spot region 308, the intensities of the first and second branch radiation beams $B_1'$, $B_2'$ will vary with time as a greater or lesser amount or the incoming radiation is reflected or transmitted at different times. The secondary rotating beam splitting apparatuses 702, 703 may be substantially the same size as the primary rotating beam splitting apparatus 701 and may rotate at substantially the same rate. For such embodiments, the relative intensities of the branch radiation beams $B_1$, $B_2$, $B_3$, $B_4$ are dependent upon the relative phase between the rotation of the secondary rotating beam splitting apparatuses 702, 703 and the primary rotating beam splitting apparatus 701. Therefore by adjusting the relative phases of the rotation of the secondary rotating beam splitting apparatuses 702, 703 and the primary rotating beam splitting apparatus 701 the relative intensities of the branch radiation beams $B_1$, $B_2$, $B_3$, $B_4$ may be adjusted. Therefore, the beam splitting apparatus 700 has some flexibility and is operable to vary the portions of the incoming radiation beam $B_{in}$ that are directed towards each of the branch radiation beams $B_1$, $B_2$, $B_3$, $B_4$.

In alternative embodiments, the tree-like structure of the beam splitting apparatus 700 may be extended by providing additional levels of individual beam splitting apparatuses. For example, the tree-like structure of the beam splitting apparatus 700 may be extended by providing four tertiary beam splitting apparatuses to provide a beam splitting apparatus operable to split the incoming radiation beam $B_{in}$ into eight radiation beams.

Figure 32:
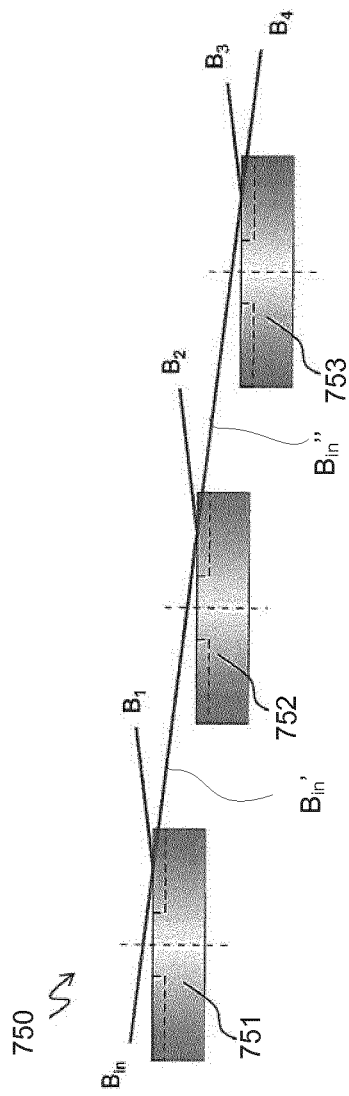
FIG. 32 is a schematic illustration of another embodiment of a composite beam splitting apparatus comprising a plurality of individual beam splitting apparatuses.

Referring to FIG. 32, a beam splitting apparatus 750 that is operable to split an incoming radiation beam into more than two outgoing branch radiation beams. Beam splitting apparatus 750 comprises a plurality of rotating beam splitting apparatuses 751, 752, 753 arranged in a linear array. Each of the rotating beam splitting apparatuses 751, 752, 753 may comprise a beam splitting apparatus 300, 350, 400, 500 substantially as described above.

In this embodiment, each rotating beam splitting apparatus 751, 752, 753 is arranged to receive an incoming radiation beam and output first and second branch radiation beams. The first branch radiation beams may, for example, be directed towards the illumination system IL of one of the lithographic apparatuses of a lithographic system similar to that shown in FIG. 1. With the exception of the last beam splitting apparatus 753, the second branch radiation beams are directed towards the next beam splitting apparatus in the array.

Accordingly, a first rotating beam splitting apparatus 751 is arranged to receive an incoming radiation beam $B_{in}$ and output first and second branch radiation beams $B_1$, $B_{in}'$. The second branch radiation beam $B_{in}'$ is directed towards the second rotating beam splitting apparatus 752. The second rotating beam splitting apparatus 752 receives the radiation beam and outputs first and second branch radiation beams $B_2$, $B_{in}''$. The second branch radiation beam $B_{in}''$ beam is directed towards and a third beam splitting apparatus 753. The third rotating beam splitting apparatus 753 receives this radiation beam and outputs first and second branch radiation beams $B_3$, $B_4$. Branch radiation beams $B_1$, $B_2$, $B_3$ and $B_4$ may, for example, each be directed toward the illumination system IL of a different one of the lithographic apparatuses of a lithographic system similar to that shown in FIG. 1.

As with beam splitting apparatus 700 described above, the relative intensities of the branch radiation beams $B_1$, $B_2$, $B_3$, $B_4$ are dependent upon the relative phases between the rotation of each of the secondary rotating beam splitting apparatuses 751, 752 and 753. Therefore by adjusting the relative phases of the rotation of the rotating beam splitting apparatuses 751, 752, 753 the relative intensities of the branch radiation beams $B_1$, $B_2$, $B_3$, $B_4$ may be adjusted. Therefore, the beam splitting apparatus 750 has some flexibility and is operable to vary the portions of the incoming radiation beam $B_{in}$ that are directed towards each of the branch radiation beams $B_1$, $B_2$, $B_3$, $B_4$.

In order to ensure that the branch radiation beams $B_1$, $B_2$, $B_3$, $B_4$ output by the beam splitting apparatus 750 have substantially the same intensity, in general the spokes and the gaps of each individual beam splitting apparatus 751, 752, 753 may have different sizes. For example, in order to ensure that the branch radiation beams $B_1$, $B_2$, $B_3$, $B_4$ output by the beam splitting apparatus 750 have substantially the same intensity, in some embodiments the ratio of the sizes of the gaps to the spokes may be 3:1 for the first beam splitting apparatus 751, 2:1 for the second beam splitting apparatus 752 and 1:1 for the third beam splitting apparatus 753. These ratios are dependent upon the relative phases of the rotation of the rotating beam splitting apparatuses 751, 752, 753

It will be appreciated that any number of individual beam splitting apparatuses may be provided in the linear array as desired.

Figure 33:
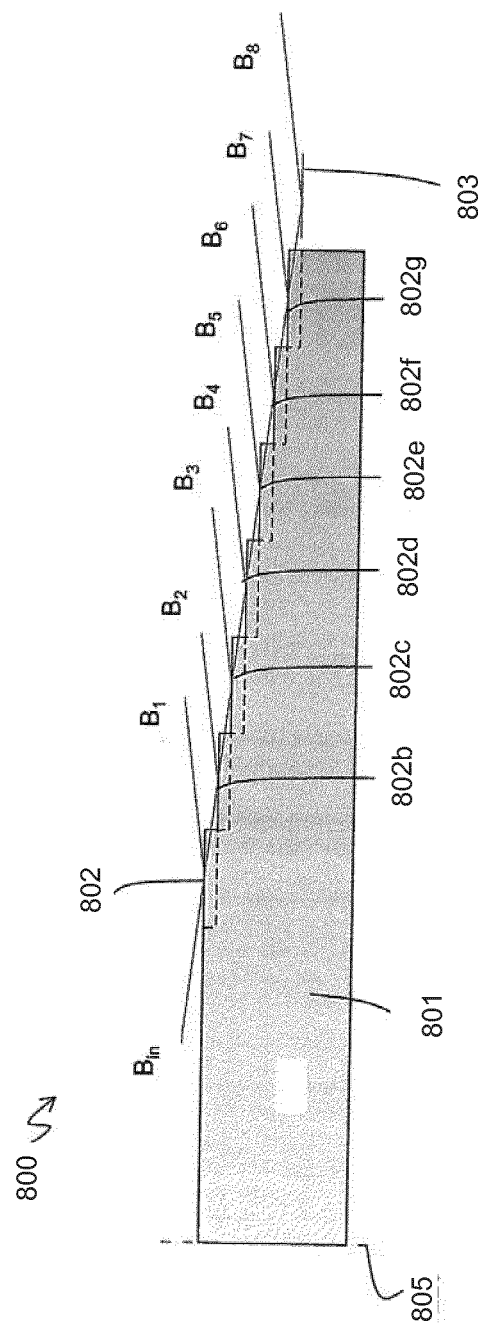
FIG. 33 is a side cross sectional view of another embodiment of a beam splitting apparatus, which may form part of a lithographic system described herein.

Referring to FIG. 33, an alternative beam splitting apparatus 800 is illustrated. The beam splitting apparatus 800 may be, or may form part of, the beam splitting apparatus 20 shown in FIG. 1. As with beam splitting apparatuses 300, 350, 400, 500, beam splitting apparatus 800 comprises a generally disc-shaped body 801 and a mechanism (not shown) operable to rotate said body 801 about a rotation axis 805. Beam splitting apparatus 800 differs from beam splitting apparatuses 300, 350, 400, 500 of FIGS. 20 to 26 in that an axially facing surface of the body 801 of the apparatus 800 is stepped in a radial direction. This divides the axially facing reflective surface into a plurality of surfaces 802a-802g. A central reflective surface 802a is generally circular and the remaining surfaces 802b-802g are of the form of a plurality of concentric annuli.

Each of the plurality of surfaces 802a-802g comprises a plurality of generally radially extending spokes (not shown) separated from each other by respective gaps 307 (not shown). The plurality of generally radially extending spokes and gaps on each surface may be substantially similar to the spokes of any one of beam splitting apparatuses 300, 350, 400, 500.

In all other aspects, beam splitting apparatus 800 may be generally similar to any one of beam splitting apparatuses 300, 350, 400, 500.

Each of the plurality of reflective surfaces 802a-802f comprises a beam spot region arranged to receive a radiation beam $B_{in}$, or a portion thereof. The incoming radiation beam is incident upon the central reflective surface 802a which forms and outputs first and second branch radiation beams. The first branch radiation beam $B_1$ is reflected by the spokes on the central reflective surface 802a. The second branch radiation beam passes through the gaps on the central reflective surface 802a and is directed towards a second reflective surface 802b. Each reflective surface 802b-802f receives a portion of the radiation beam $B_{in}$ that passes through the gaps of each of the preceding reflective surfaces and outputs first and second branch radiation beams. The first branch radiation beam $B_2$-$B_7$ comprises a portion of radiation that has been reflected by the spokes of the reflective surface. The second branch radiation beam is directed towards and next reflective surface. A portion of radiation that passes through the gaps of all of the reflective surfaces 802a-802f forms a final branch radiation beam B8, which may be directed towards subsequent optics by a grazing incidence mirror 803.

The beam splitting apparatus 800 therefore allows an incoming radiation beam $B_{in}$ to be split into a plurality (for example eight) outgoing branch radiation beams $B_1$-$B_8$.

Figure 35:
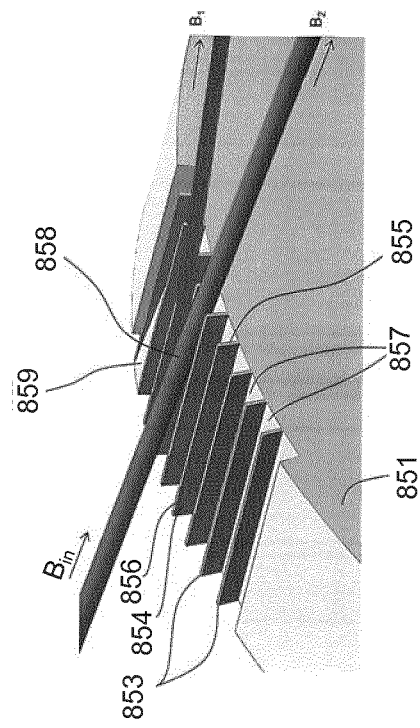
FIG. 35 is a perspective view of the beam splitting apparatus of FIG. 34.
Figure 34:
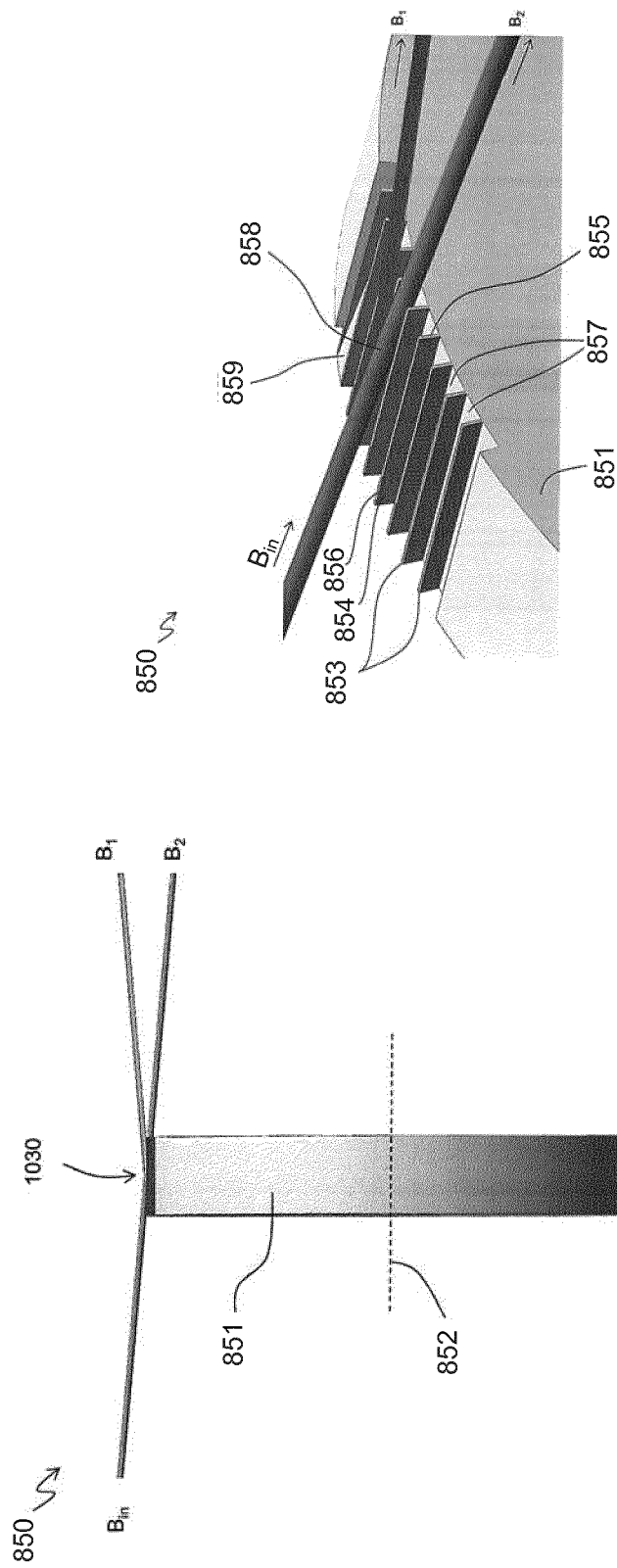
FIG. 34 is a side view of another embodiment of a beam splitting apparatus, which may form part of a lithographic system described herein.

Referring to FIGS. 34 and 35, an alternative beam splitting apparatus 850 is illustrated. The beam splitting apparatus 850 comprises a generally disc-shaped body 851 and a mechanism (not shown) operable to rotate said body 851 about a rotation axis 852. For example, the disc-shaped body 851 may comprise a shaft extending along the rotation axis 852. The shaft may be supported by one or more bearings, for example two bearings. The shaft may be driven to rotate by any suitable mechanism such as a motor or engine.

The beam splitting apparatus 850 further comprises a plurality of radially extending spokes 853. Each spoke comprises two radially extending side walls 854, two axially facing walls 855 and a radially facing surface 856. The shape of the radially facing surface 856 of each spoke is therefore generally rectangular. The radially facing surface 856 of each spoke is formed from a reflective material. The spokes 853 are separated from each other by a plurality of gaps 857. As such, the radially facing surfaces 856 of the plurality of spokes 853 form a plurality of discrete reflective elements. Each of the spokes 853 is substantially the same size and shape and each of the gaps 857 is substantially the same size and shape. Therefore, the radially facing surfaces 856 of the plurality of spokes 853 form a periodic array of discrete reflective elements. A pitch of the periodic array at a given radial point is given by the angular extent of one radially facing surface 856 and one gap 857.

The beam splitting apparatus 850 comprises a beam spot region 858 arranged to receive a radiation beam $B_{in}$. The beam spot region 858 is disposed on a radially facing surface of the body 851, which is formed from the radially facing surfaces 856 of the spokes 853.

As the body 851 rotates about the rotation axis 852, the periodic array moves such that the plurality of reflective elements (formed by the radially facing surfaces 856 of the spokes 853) move through the beam spot region 858. A first portion of the radiation beam is incident on, and reflected by, the radially facing surfaces 856 of the spokes 853 so as to form a first branch radiation beam $B_1$. A second portion of the radiation beam passes through the gaps 857 between the reflective elements so as to form a second branch radiation beam $B_2$. For convenience, in FIG. 35 the spokes 853 and gaps 857 only extend around a portion of the circumference of the body 851. However, in practice the spokes 853 and gaps 857 extend around the entire circumference of the body 851.

The beam splitting apparatus 850 therefore provides an alternative arrangement that allows an incoming radiation beam $B_{in}$ to be split into outgoing first and second branch radiation beams $B_1$, $B_2$.

An advantage of this embodiment 850 is that since the beam spot region 858 is disposed on a radially facing surface of the body 851, each of the reflective elements is generally rectangular in shape, rather than an annular sector. This allows the incoming radiation beam to approach at smaller grazing incidence angles more easily. To provide for smaller grazing incidence angles, only the (axial) thickness of the body 851 needs to be increased. This is in contrast to the embodiments 300, 350, 400, 500 described above wherein in order to accommodate smaller grazing incidence angles the radius of the body would need to be increased. Further, as the grazing incidence angle decreases the reflective elements formed by the spokes 853 remain rectangular.

Another advantage is that the incoming radiation beam $B_{in}$ does not cross, or pass close to, the rotation axis 852. As a result, bearings and actuators may be placed on both sides of the body 851, allowing for a symmetric, more balanced design.

The spokes 853 may be tapered outwards in a direction of increasing radius. This will provide an undercut similar to that employed by the beam splitting apparatus 300 of FIG. 24. For such embodiments, the side walls 854 no longer extend in a purely radially direction. By providing a sufficient radial taper, the fraction of radiation incident upon the side walls 854 may be reduced or eliminated.

The radially facing surfaces 856 of the spokes 853 may be flat. Alternatively, the radially facing surfaces 856 of the spokes 853 may be curved, for example, having a curvature that follows the disc shaped body 851.

An inclined ramp 859 may be provided in the gaps 857 between the spoke 853, arranged such that a surface of the ramp 859 is generally parallel to the incoming radiation beam $B_{in}$. Advantageously, such ramps 859 increase the stiffness and thermal conductivity of the beam splitting apparatus 850 without interfering with the incoming radiation beam $B_{in}$.

The (reflected) first branch radiation beam $B_1$ beam will be astigmatically divergent along the axial direction, whereas the (transmitted) second branch radiation beam $B_2$ is undistorted. This may reduce thermal loads on optical elements that receive the first branch radiation beam $B_1$.

Figure 36:
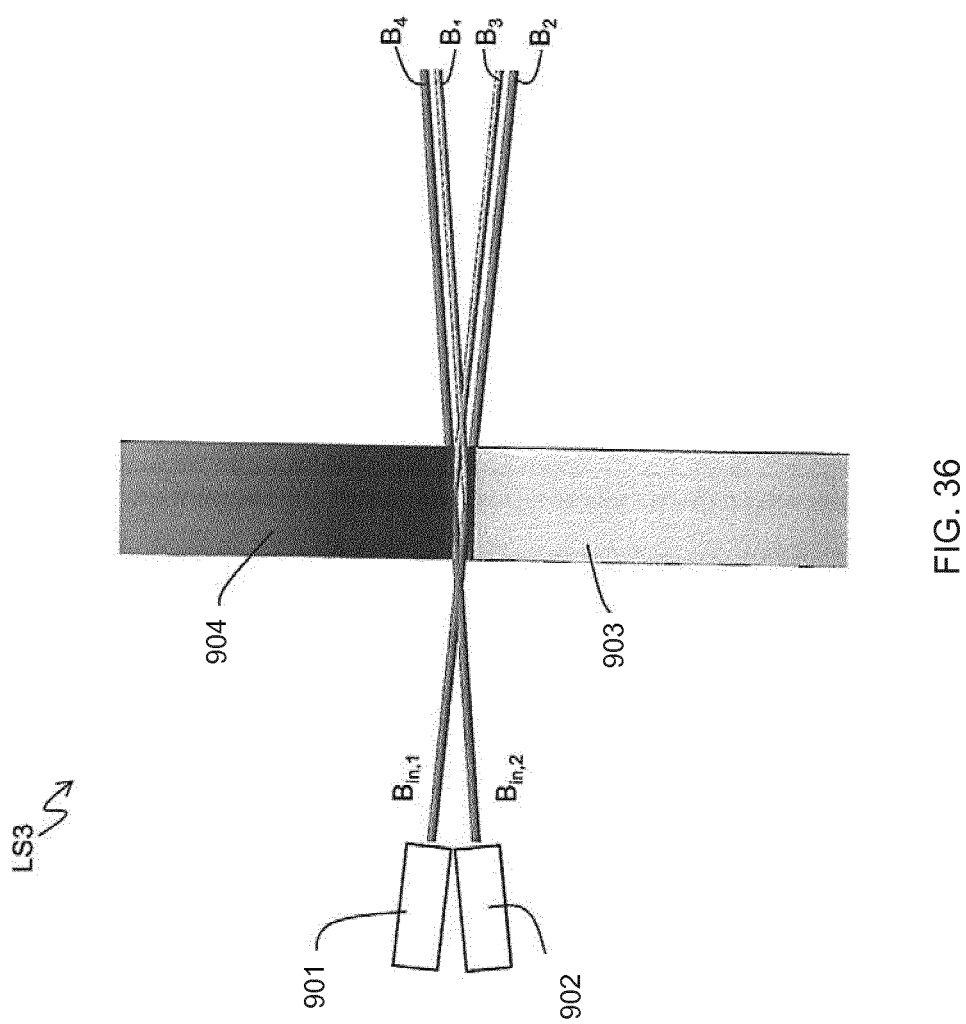
FIG. 36 is a schematic illustration of another embodiment of a lithographic system comprising two beam splitting apparatus.

Referring to FIG. 36, a portion of a lithographic system LS3 comprising two radiation sources 901, 902 is shown. The lithographic system LS3 further comprises two beam splitting apparatuses 903, 904 substantially as shown in FIGS. 34 and 35 and described above.

A radiation beam $B_{in,1}$ output by radiation source 901 is received by a beam spot region of the first beam splitting apparatus 903. A first portion of this radiation beam $B_{in,1}$ is incident on, and reflected by, radially facing surfaces of the spokes so as to form first branch radiation beam $B_1$. A second portion of the radiation beam $B_{in,1}$ passes through the gaps between the reflective elements so as to form a second branch radiation beam $B_2$. A radiation beam $B_{in,2}$ output by radiation source 902 is received by a beam spot region of the second beam splitting apparatus 904. A first portion of this radiation beam $B_{in,2}$ is incident on, and reflected by, the radially facing surfaces of the spokes so as to form a first branch radiation beam $B_3$. A second portion of the radiation beam $B_{in,2}$ passes through the gaps between the reflective elements so as to form a second branch radiation beam $B_4$.

The two beam splitting apparatuses 903, 904 are arranged such that their axes of rotation are substantially parallel and their beam spot regions are spatially close together. With such an arrangement, it is possible to produce two composite beams, each comprising two sub-beams from separate free electron lasers that are parallel and very close together. One composite beam comprises branch radiation beams $B_1$ and $B_4$, the other composite beam comprises branch radiation beams $B_2$ and $B_3$. The arrangement LS3 of FIG. 36 is advantageous because it is not required to move optical components in and out of the paths of the radiation beams $B_{in,1}$, $B_{in,2}$ output by radiation sources 901, 902 when one radiation source 901, 902 is not operating. This arrangement LS3 may allow the same optics to be used when (a) both radiation sources 901, 902 are operating and (b) when only one of the radiation sources 901, 902 is operating. To fully exploit this feature, the lithographic system LS3 may comprise a movable optical element for the optical path of each composite radiation beam, which is arranged to correct for the divergence introduced in the reflected branch radiation beams $B_1$ and $B_3$. When both radiation sources 901, 902 are operating, these optical element may be moved out of the path of a corresponding radiation beam and, when only one radiation source 901, 902 is operating these optical elements may be moved into the path of a corresponding composite radiation beam. With such all optical elements downstream of these optical elements may be substantially the same regardless of whether both radiation sources 901, 902 are operating or not.

Embodiments of beam splitting apparatuses have been described above which comprise a periodic array of reflective elements is provided on a disc-shaped body, which is arranged to rotate about an axis so as to move the periodic array through the beam spot region. However, alternative embodiments may comprise a periodic array of reflective elements provided on a body, which is arranged to move in alternate directions along a path (for example a linear path) so as to move the periodic array through the beam spot region.

Embodiments of beam splitting apparatuses have been described above which comprise a periodic array of reflective elements wherein all of the reflective elements direct radiation in substantially the same direction to form a first branch radiation beam and a second branch radiation beam is formed by radiation that passes through gaps between the reflective elements. In alternative embodiments, the periodic array of reflective elements may comprise reflective elements arranged to direct radiation in a plurality of different directions to form a plurality of branch radiation beams. In some embodiments, the periodic array of reflective elements may not comprise gaps between reflective elements.

Whilst embodiments of a radiation source SO1, SO2 have been described and depicted as comprising a free electron laser FEL, it should be appreciated that a radiation source may comprise any number of free electron lasers FEL. For example, a radiation source may comprise more than one free electron laser FEL. Alternatively, the radiation source SO1, SO2 may not comprise a free electron laser and may, for example, comprise a laser produced plasma (LPP) or a discharge produced plasma (DPP) radiation source.

A free electron laser produces a radiation beam with a smaller bandwidth than LPP or DPP sources. Such a small bandwidth may result in speckle (spatial intensity variations due to interference) at the patterning device MA, which is undesirable. With a rotating beam splitting apparatus as described above, the speckle pattern at the patterning device MA will vary with time as well, and will tend to be averaged out so as to improve the uniformity of illumination of the patterning device MA.

Features of any one of the embodiments of beam splitting apparatuses described above may be combined with any other of the embodiments of beam splitting apparatuses described above as appropriate. For example, an inclined ramp 859 provided in the gaps 857 between the spokes 853 of beam splitting apparatus 850 has been described above that is arranged such that a surface of the ramp 859 is generally parallel to the incoming radiation beam $B_{in}$. Such a ramp may be provided with any of the other embodiments of a beam splitting apparatus 300, 350, 400, 500. Advantageously, such ramps would increase the stiffness and thermal conductivity of the beam splitting apparatuses without interfering with the incoming radiation beam.

In any of the above described embodiments of a beam splitting apparatus 300, 350, 400, 500, 800, 850 a reflective surface of the spokes may be curved, for example to compensate for energy differences or shape changes induced by other optical components in a beam delivery system.

Generally, it will be appreciated that the term "grazing incidence angle" refers to the angle between the propagation direction of an incident radiation beam and a reflective surface that it is incident upon. This angle is complementary to the angle of incidence, i.e. the sum of the grazing incidence angle and the angle of incidence is a right angle.

FIGS. 37 to 40 below illustrate different example arrangements of the undulator 24 of FIGS. 3 and 4. In each case it is to be understood that the radiation beam B emitted from the described undulator arrangement is as described above with reference to FIG. 3.

Figure 37:
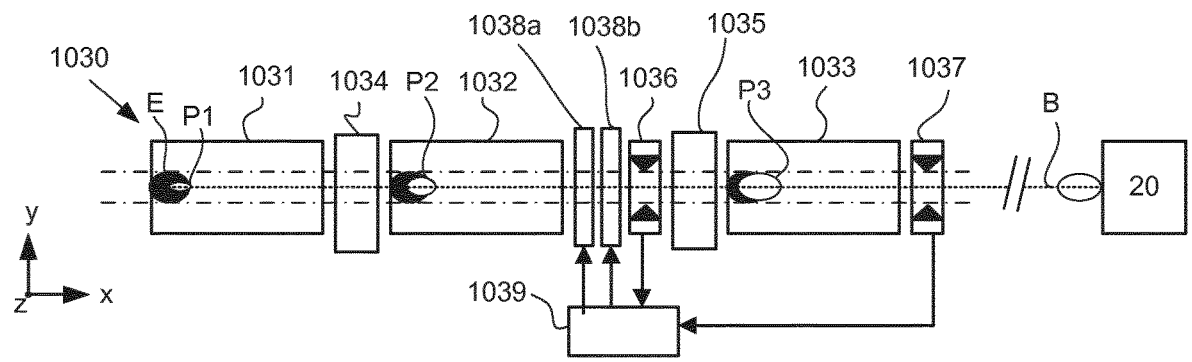
FIG. 37 is a schematic illustration of an undulator according to an embodiment described herein.

An undulator 1030 which may be used to implement the undulator 24 in one embodiment is schematically illustrated in FIG. 37. The undulator 1030 comprises a plurality of undulator modules 1031, 1032, 1033 through which the bunched electron beam E is transmitted. An envelope of the electron beam E as it passes through the undulator 1030 is depicted by dot-dash line. While only three modules 1031, 1032, 1033 are shown in FIG. 37, it is to be understood that more or fewer modules may be provided. The undulator modules 1031, 1032, 1033 may be implemented in any appropriate way, but as described above generally comprise a plurality of magnets which produce a periodic magnetic field. For each undulator module 1031, 1032, 1033, a portion of a volume around a central axis of the undulator module may be considered to be a "good field region" (not shown). The good field region is a volume around the central axis in which the magnitude and direction of the magnetic field at a particular point is substantially equal to values at the closest point on axis of undulator. An electron bunch propagating within the good field region will satisfy the resonant condition of equation (1) and therefore will amplify radiation. Further, an electron beam E propagating within the good field region should not experience significant unexpected disruption due to uncompensated magnetic fields.

Photon bunches P1, P2, P3 are shown generally overlapping with the electron bunch E at the beginning of each undulator module 1031, 1032, 1033 respectively. It can be seen that the photon bunch increases along the longitudinal axis of the undulator 1030 from left to right in the Figure. Due to a phenomenon commonly known as optical guiding, the photon bunches P1, P2, P3 generally follow the electron beam E within each undulator module 1031, 1032, 1033. Optical guiding is a consequence of two effects. The first effect is a result of light refraction within the electron beam E. Because the real part of the refraction index of the electron beam is maximal close to or at the electron beam center, the electron beam guides light in a similar manner to an optical fiber. The second effect is light amplification, because the gain of the FEL is highest where the current density is highest (that is close to or at the center of the electron beam E).

Between the undulator modules (known as drift space), the photons and electrons are decoupled (i.e. they do not interact with each other).

The bunched electron beam E has a finite emittance and will therefore increase in diameter unless refocused. The undulator 1030 therefore further comprises two refocusing elements 1034, 1035 each positioned between a different pair of adjacent modules (the modules 1031,1032 and 1032, 1033 respectively). Where additional modules are provided, a refocusing element may be provided between each module. The refocusing elements 1034, 1035 may comprise, for example, quadrupole magnets.

The undulator 1030 further comprises two beam position monitors (BPMs) 1036, 1037 adapted to measure a deviation from an ideal position of the electron beam E within the undulator 1030 at two different axial locations. Although the envelope shown in FIG. 37 follows a uniform path, in practice the electron beam E may deviate from this path such that the envelope is distorted. This distortion may be detected by the BPMs 1036, 1037. The BPMs 1036, 1037 may implemented in any of a number of ways as will be readily appreciated the skilled person.

Deviation of the trajectory of the electron beam E within an undulator will cause similar deviation of the trajectory of the radiation beam B. As a result of this deviation, the radiation beam B may not reach, or may not fall upon an optimal or acceptable portion of downstream optics such as optics within a beam expander, or within the beam splitting apparatus 20. It has been realised, however, that distortion of the trajectory of the radiation beam B may be addressed within the undulator itself, and may be addressed in the final modules of the undulator.

The undulator 1030 further comprises two electron beam steering units 1038a, 1038b positioned between the module 1032 and the BPM 1036. The electron beam steering units 1038a, 1038b are arranged to steer the electron beam E, in both horizontal (z) and vertical (y) directions. The BPMs 1036, 1037 are connected to a control unit 1039 arranged to receive signals indicative of a position of the electron beam E from each of the BPMs 1036, 1037. The control unit 1039 is arranged to determine an amount by which the trajectory of the electron beam E deviates from a desired trajectory and to control the beam steering units 1038a, 1038b to steer the electron beam E such that it substantially follows the desired trajectory.

Due to the distance between the exit of the undulator 24 and any immediately downstream optics (which may be, for example, a beam expander, or optics within the beam splitting apparatus 20), the lithographic system LS is more sensitive to changes in the tilt of the radiation beam B (i.e. the angle between the propagation direction of the radiation beam B and the longitudinal axis of the undulator 24) than it is to translation of the radiation beam B (i.e. an offset between the propagation direction of the radiation beam B and the longitudinal axis of the undulator 24). The arrangement 1030 shown in FIG. 37 provides a system which is able to correct a tilt of the radiation beam B at the exit of the undulator 24, where correction of the tilt is most effective.

In this way, the undulator 1030 provides an arrangement which is able to align the electron beam E, and therefore the radiation beam B, with an ideal axis of propagation. Alternatively, or additionally, because the lithographic system LS is more sensitive to the tilt of the radiation beam B than to translation of the radiation beam B, the undulator 1030 may be used to produce an electron beam E that is parallel to a desired axis of propagation of the radiation beam B where an amount of translation of the radiation beam B away from an ideal axis of propagation is within a tolerance. In this way, the radiation beam B may still be properly processed by downstream optical elements. In an embodiment, downstream optical elements may themselves be translated in response to detected translations of the radiation beam B.

It will be appreciated that the positions and numbers of the components depicted in the undulator 1030 are merely exemplary. For example, more than two BPMs may be provided, and more or fewer beam steering units may be provided. In alternative embodiments, the steering units 1038a, 1038b and the BPMs 1036, 1037 may be positioned differently within the undulator 1030. It has been determined to be advantageous, however, that the steering units are placed relatively close to the output of the undulator 1030, to reduce the effect of additional causes of displacement or instability on the electron beam E and, consequently, the radiation beam B.

Figure 38:
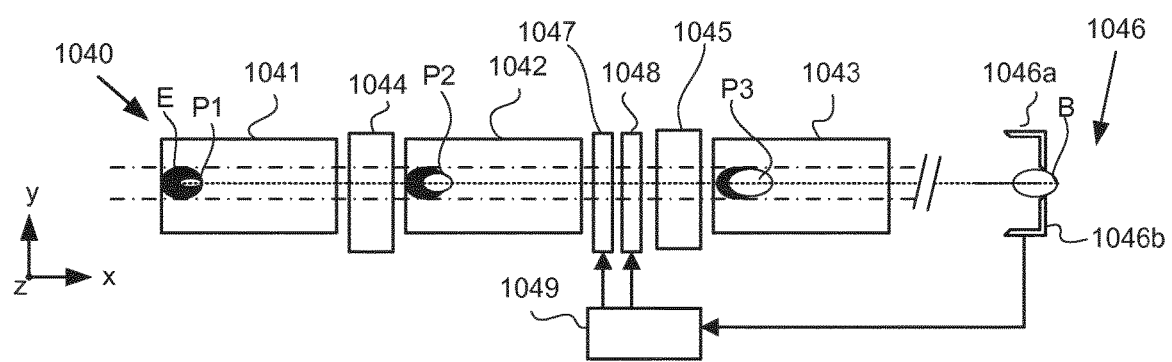
FIG. 38 is a schematic illustration of an undulator according to an alternative embodiment.

FIG. 38 illustrates an alternative undulator 1040 that may be used to provide, for example, the undulator 24 of FIG. 3 or 4. The undulator 1040 comprises a plurality of modules 1041, 1042, 1043. While only three modules are shown in FIG. 38, it is to be understood that more or fewer modules may be provided. The undulator 1040 further comprises two refocusing elements 1044, 1045 positioned between the modules 1041, 1042 and 1042, 1043 respectively, which may be implemented similarly to the refocusing modules 1032, 1033 of FIG. 37. The undulator 1040 further comprises an EUV intensity distribution sensor 1046 arranged to measure an intensity distribution within the radiation beam B. The intensity distribution sensor 1046 may be implemented in any suitable way as will be readily apparent to the skilled person.

The intensity distribution sensor 1046 is depicted as comprising two parts, 1046a, 1046b vertically separated (in the y-direction). In this way, for example, if the part 1046a detects an increase in EUV power and the part 1046b simultaneously detects a decrease in EUV power, it may be determined that the beam has shifted in the y-direction towards the sensor 1046a. It will be appreciated, that the intensity distribution sensor 1046 may comprise other parts. For example, the intensity distribution sensor 1046 may also comprise parts separated in the z-direction, and may comprise parts separated in the x-direction. Further, the intensity distribution sensor may comprise parts separated in more than one direction. The undulator 1040 further comprises two electron beam steering units 1047, 1048 positioned between the module 1042 and the refocusing element 1045. The electron beam steering units 1047, 1048 are arranged to steer the electron beam E within the undulator in both horizontal (z-) and vertical (y-) directions.

The intensity distribution sensor 1046 is connected to a control unit 1049 and is arranged to transmit signals indicating an intensity distribution within the radiation beam B to the control unit 1049. The control unit 1049 is arranged to: process the received indications from the intensity distribution sensor 1046; and to compare the intensity distribution within the radiation beam B with a desired intensity distribution. If the intensity distribution indicated by the intensity distribution sensor 1046 deviates from the desired intensity distribution, the control unit 1049 transmits control signals to the beam steering units 1047, 1048 to steer the electron beam E, and therefore the radiation beam B so that the intensity distribution of the radiation beam B is closer to the desired intensity distribution.

In this way, the centre of the radiation beam B may be directed toward a centre position of a beam acceptance centre (or a sweet spot) of downstream optics.

While shown as part of the undulator 1040, in an embodiment, one or more intensity distribution sensors 1046 may be placed at the entrance to, and/or exit of, the downstream optics. The intensity distribution sensor 1046 may however be placed at any position along the path of the radiation beam B.

As described above, the path followed by the electron beam E through the undulator 24 may be sinusoidal and planar, with the electrons periodically traversing the central axis, or may be helical, with the electrons rotating about the central axis. Generally, for helical paths, a tilt of the electron beam E within the undulator 24 should not exceed 1/10ρ, where ρ is the Pierce parameter. In an embodiment, the Pierce parameter may be of the order of 0.1% indicating that an amount of steering performed by the steering units 1038a, 1038b or 1047, 1048 is likely to be less than 100 µrad.

The bending of a relativistic electron beam is described by the equation (4):

$$1/r = ecB/w \qquad (4)$$

where r is the bending radius, e is the charge of an electron, B is the magnetic field, and w is the energy of the beam. From this it can be shown that the product of the magnetic field strength B in Tesla and the bending radius r in meters is approximately given by the energy w of the electron beam E in MeV divided by 300. (i.e. $B*\rho(T*m) \approx E$ (MeV)/300). For embodiments wherein the steering units comprise a steering magnet of having a length of approximately 0.1 m, a bend angle of 10 µrad may be achieved with a magnetic field of approximately $2*10^{-4}$ T while a bend angle of approximately 100 µrad can be achieved with a magnetic field of 2 mT. As such, steering the electron beam E through bends of less than 100 µrad can be achieved with relatively small magnetic fields which may be quickly established within the steering units 1038a, 1038b and 1047, 1048.

Figure 39:
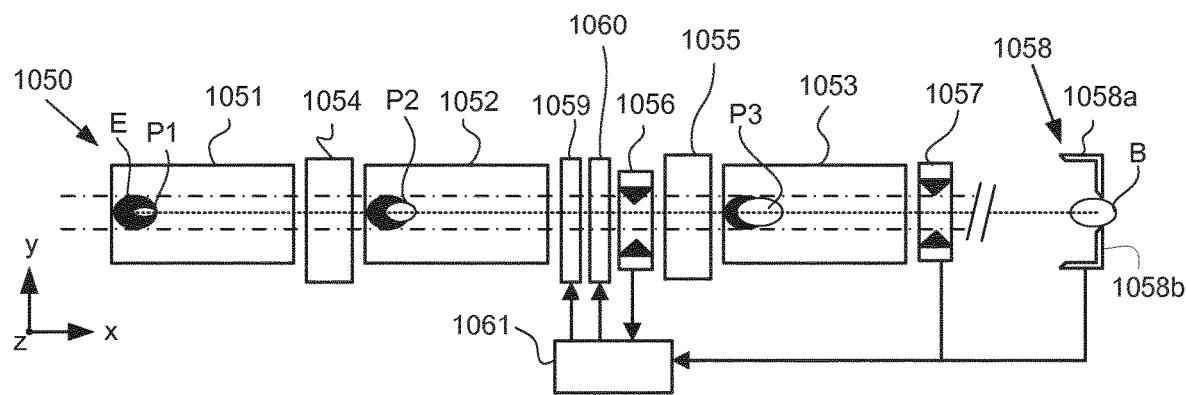
FIG. 39 is a schematic illustration of an undulator according to a further embodiment.

It will be appreciated that the features of the arrangements depicted in the arrangements of FIGS. 37 and 38 may be combined. FIG. 39 illustrates an undulator 1050 which may be used to provide the undulator 24 and which comprises modules 1051, 1052, 1053 and refocusing elements 1054, 1055. The undulator 1050 further comprises BPMs 1056, 1057 which are equivalent to the BPMs 1036, 1037 of the arrangement of FIG. 37. The undulator 1050 further comprises an intensity distribution sensor 1058 (having parts 1058a, 1058b) which is equivalent to the intensity distribution sensor 1046 in the arrangement of FIG. 38. The undulator 1050 further comprises beam steering units 1059, 1060 arranged to receive instructions from a control unit 1061. In the undulator 1050, the control unit 1061 is arranged to receive signals indicative of a trajectory of the electron beam E from the BPMs 1056, 1057 and to receive signals indicative of a distribution of EUV radiation within the radiation beam B from the intensity distribution sensor 1058. In this way, the control unit 1061 may steer the electron beam E (using the steering units 1059, 1060) in dependence upon deviations within both the trajectory of the electron beam E and/or an intensity distribution of the radiation beam B.

Figure 40:
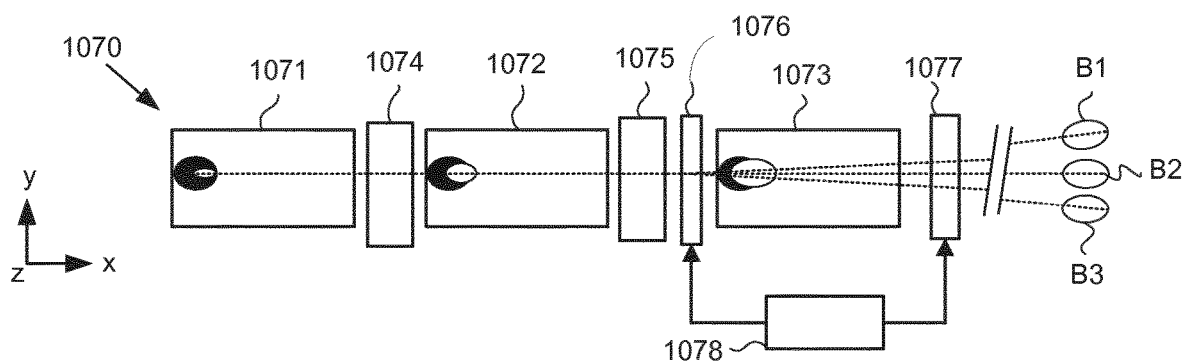
FIG. 40 is a schematic illustration of an undulator according to a further embodiment.

FIG. 40 illustrates an undulator 1070 that may be used to implement the undulator 24 in an alternative embodiment. For clarity, the electron beam envelope is not depicted in FIG. 40. The undulator 1070 comprises three modules 1071, 1072, 1073 and two refocusing elements 1074, 1075. The module 1073 is a planar module. That is, the path followed by the electrons of the electron beam E within the module 1073 is sinusoidal and planar, rather than helical. The modules 1071, 1072 may be helical or planar. The undulator 1070 further comprises a first steering unit 1076 placed before the module 1073 and a second steering unit 1077 placed after the module 1073. A control unit 1078 is in communication with both the first and second steering units 1076, 1077.

The control unit 1077 is arranged to provide instructions to the first steering unit 1076 to actively, and periodically, alter the trajectory of the electron beam E and thereby redistribute the radiation beam B in the far-field. In particular, the steering unit 1076 may be controlled to periodically deflect the electron beam E through a deflection angle. The undulator 1070 may therefore sequentially direct the radiation beam B along different and spatially separated trajectories so as to provide separate EUV radiation beams B1, B2, B3 to different ones of the lithographic apparatus LA1-LA20. It will be appreciated that while only three radiation beams B1, B2, B3 are shown in FIG. 40, more or fewer radiation beams may be provided. For example, a respective radiation beam may be provided for each lithographic apparatus LA1 to LA20.

In such embodiments, the beam splitting apparatus 20 may not be required, or may be simplified. For example, by deflecting the electron beam E so as to provide a respective separate radiation beams for each lithographic apparatus, it is not required to split a single radiation beam for provision to those multiple lithographic apparatus. Alternatively, where more than one radiation beam is provided, but a separate radiation beam is not provided each lithographic apparatus, each radiation beam need be split into fewer beams by a beam splitting apparatus for provision to each lithographic apparatus.

Where multiple radiation beams are provided by the undulator 1070, each radiation beam may be provided with respective downstream optics, such as respective beam expanders, or respective beam splitters.

Alternatively or additionally, the control unit 1078 may cause the steering unit 1076 to periodically sweep the electron beam E through a predetermined angle with substantially constant angular speed. In example embodiments, the electron beam E may be swept through angles of 10 μrad, 100 μrad or 1000 μrad, although it will be appreciated that the electron beam E may be swept through other angles.

It may be desirable to produce a radiation beam with a substantially flat-top intensity distribution (also known as a top-hat intensity distribution). This may be achieved by conditioning optics downstream of the FEL. By sweeping the electron beam E, however, the intensity profile of the resulting radiation beam B, when averaged over a number of emitted pulses, may comprise a substantially flat-top intensity distribution in the far-field, with increased divergence compared to a non-swept beam. A radiation beam B produced by sweeping the electron beam E through an angle may therefore not need to be conditioned by conditioning optics to provide a flat-top distribution. Further, while further expansion of the radiation beam B may still be performed by downstream expanding optics, any required expansion will be reduced.

The second steering unit 1077 is arranged after the module 1073 to redirect the electron beam E altered by the first steering unit 1076 towards the steering unit 25 and the dump 26. Both the steering unit 1076 and the steering unit 1077 steer the electron beam E in the plane perpendicular to the magnetic field lines in the module 1073.

While the steering unit 1076 is placed before the final module 1073 of the undulator 1070, in other embodiments, the steering unit 1076 may be placed before a module that is not the last module of the undulator 1070 (for example the module 1072). In preferred embodiments, however, the steering unit 1076 is placed within a final portion of the undulator. For example, the steering unit may be placed before module that is closer to an exit of the undulator 1070 than it is to an entrance of the undulator 1070.

It will also be appreciated that the embodiment of FIG. 39 may be combined with the embodiments of FIGS. 37 to 38. For example, BPMs may be provided in the arrangement of FIG. 39 to ensure that the electron beam is swept through the correct angular range. Similarly, one or more intensity distribution modules may be provided to monitor an intensity distribution of the single (averaged over time) or multiple radiation beams provided by an undulator arranged similarly to the undulator 1070.

Figure 41:
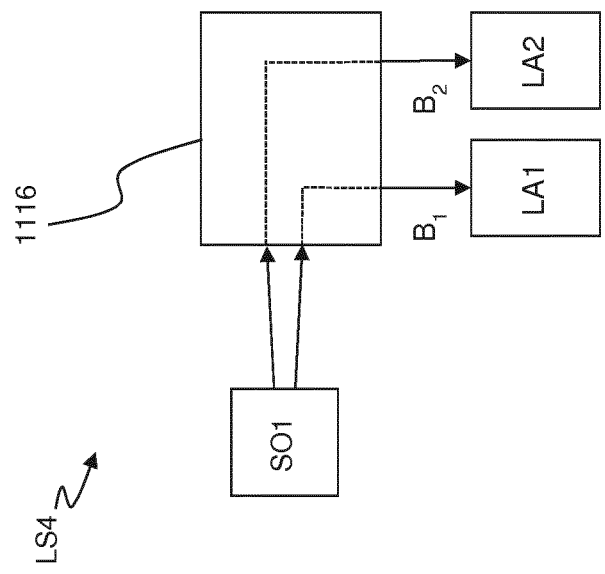
FIG. 41 is a schematic illustration of a lithographic system according to an embodiment described herein.

FIG. 41 shows a lithographic system LS4 according to one embodiment of the invention. The lithographic system LS4 comprises a radiation source SO1 and two lithographic apparatuses LA1-LA2. The radiation source SO1 is configured to generate two extreme ultraviolet (EUV) radiation beams $B_1$-$B_2$. In this embodiment, each of the EUV radiation beams $B_1$-$B_2$ generated by the radiation source SO1 is directed to a different one of the lithographic apparatuses LA1-LA2, by optics 1116. Optics 1116 may comprise beam expanding optics that are arranged to increase the cross sectional area of the radiation beams $B_1$-$B_2$.

Figure 42:
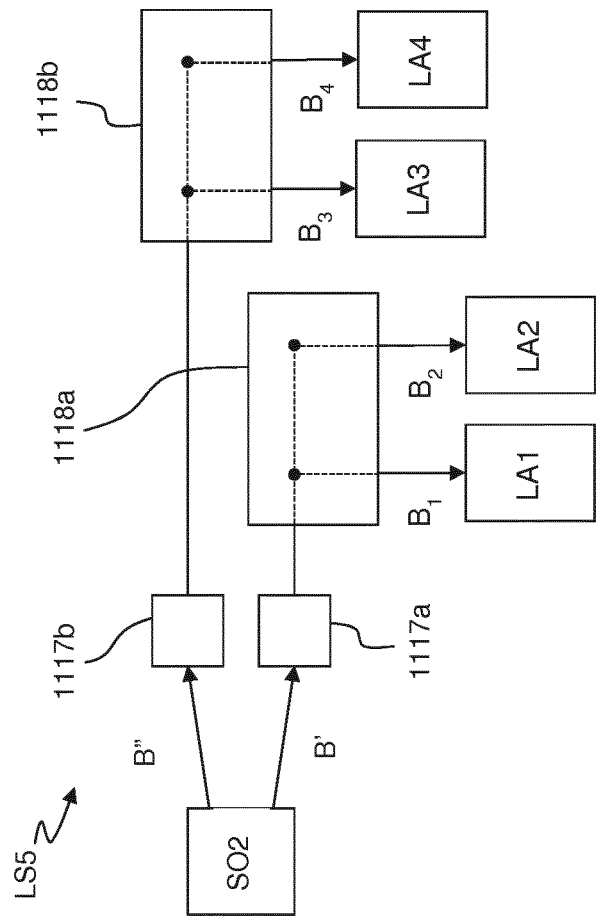
FIG. 42 is a schematic illustration of a lithographic system according to another embodiment.

FIG. 42 shows a lithographic system LS5 according to another example embodiment of the invention. The lithographic system LS5 comprises a radiation source SO2 and four lithographic apparatuses LA1-LA4. The radiation source SO2 is configured to generate two EUV radiation beams B',B". In this embodiment, each of the EUV radiation beams B',B" generated by the radiation source SO2 is split into two branch radiation beams. The lithographic system LS5 comprises beam expanding optics 1117a, 1117b and beam splitting apparatus 1118a, 1118b respectively in the path of the radiation beams B'-B" generated by the radiation source SO2. The lithographic apparatuses LA1-LA4 of FIGS. 41, 42 may be substantially as described above, with reference to FIG. 2.

The beam expanding optics 1117a, 1117b are arranged to increase the cross sectional area of the radiation beams B'-B". Advantageously, this decreases the heat load on optical components (such as mirrors) downstream of the beam expanding optics 1117a, 1117b. This may allow the mirrors downstream of the beam expanding optics to be of a lower specification, with less cooling, and therefore less expensive. Additionally or alternatively, it may allow the downstream mirrors to be nearer to normal incidence. Once expanded by the beam expanding optics 1117a, 1117b, radiation beam B' is split into two branch radiation beams $B_1$, $B_2$ by beam splitting apparatus 1118a and radiation beam B" is split into two branch radiation beams $B_3$, $B_4$ by beam splitting apparatus 1118b. Each beam splitting apparatus 1118a, 1118b may comprise one or more beam splitting apparatuses as described above. Beam expanding optics may not be provided in all embodiments, and in particular may not be necessary with particular beam splitting apparatuses.

The radiation sources SO1, SO2 of FIGS. 41, 42 are configured to generate a plurality of EUV radiation beams and comprises a free electron laser. As described above with reference to FIGS. 3, 4, a free electron laser comprises an electron source and accelerator, which are operable to produce a bunched relativistic electron beam, and a periodic magnetic field through which the bunches of relativistic electrons are directed. The periodic magnetic field is produced by an undulator and causes the electrons to follow an oscillating path about a central axis. As a result of the acceleration caused by the magnetic structure the electrons spontaneously radiate electromagnetic radiation generally in the direction of the central axis. The relativistic electrons interact with radiation within the undulator. Under certain conditions, this interaction causes the electrons to bunch together into microbunches, modulated at the wavelength of radiation within the undulator, and coherent emission of radiation along the central axis is stimulated.

The path followed by the electrons may be sinusoidal and planar, with the electrons periodically traversing the central axis, or may be helical, with the electrons rotating about the central axis. The type of oscillating path may affect the polarization of radiation emitted by the free electron laser. For example, a free electron laser which causes the electrons to propagate along a helical path may emit elliptically polarized radiation, which may be preferred for exposure of a substrate W by some lithographic apparatuses.

Figure 43:
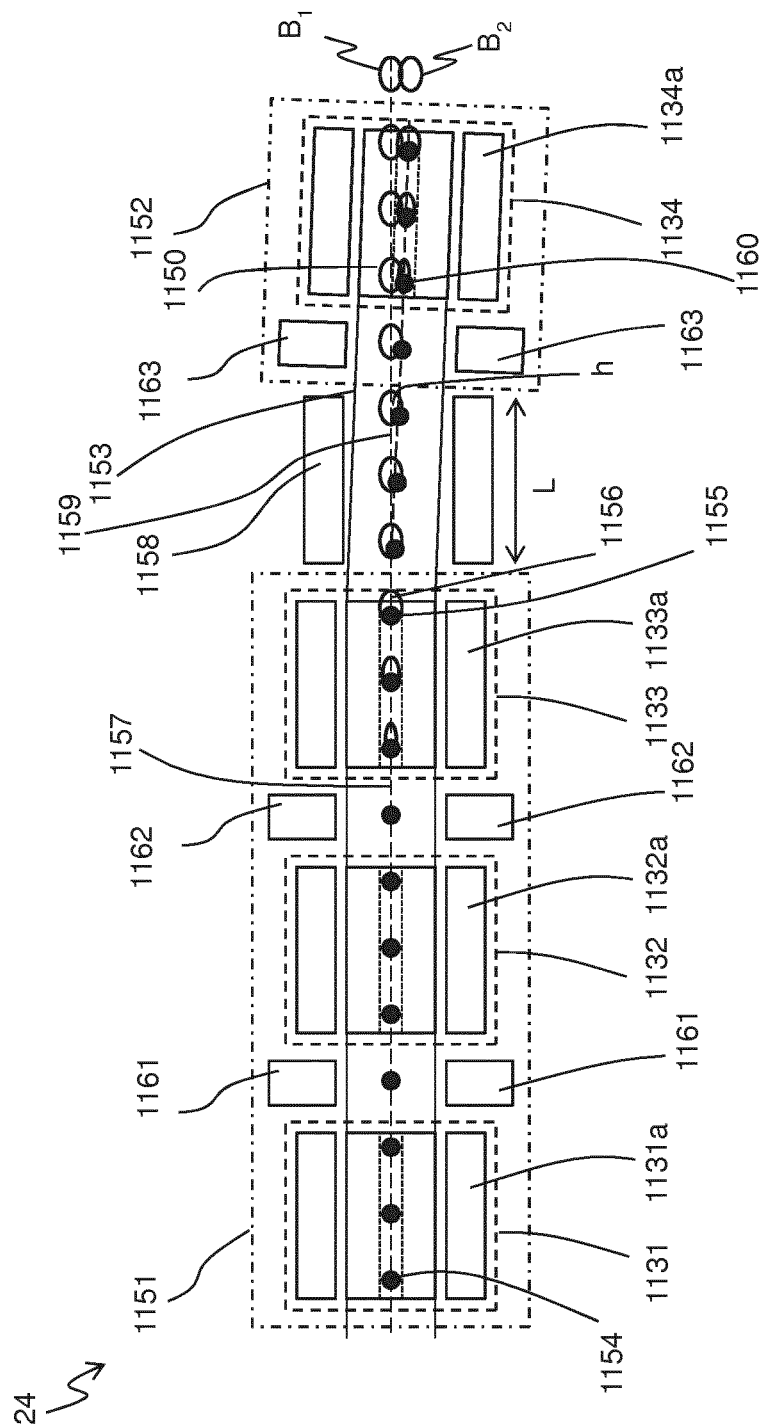
FIG. 43 is a schematic illustration of an undulator according to an embodiment described herein.

Referring to FIG. 43, an example embodiment of the undulator 24 is shown, which comprises four undulator modules 1131, 1132, 1133, 1134. The undulator modules 1131, 1132, 1133, 1134 are arranged in series such that the electron beam E passes through each of the undulator modules in turn, starting with module 1131 and finishing with module 1134. Each of the undulator modules 1131, 1132, 1133, 1134 comprises an entrance and an exit. Each module 1131, 1132, 1133, 1134 further comprises a periodic magnet structure 1131a, 1132a, 1133a, 1134a, which is operable to produce a periodic magnetic field and is arranged so as to guide the relativistic electron beam E produced by the electron source 21 and linear accelerator 22 along a periodic path between the entrance and the exit of that module 1131, 1132, 1133, 1134. As a result, within each undulator module 1131, 1132, 1133, 1134, the electrons radiate electromagnetic radiation generally in the direction of a central axis of their periodic path through that module.

The undulator modules 1131, 1132, 1133, 1134 shown in FIG. 43 are helical (i.e. the electron beam E follows a helical path through each undulator module). In alternative embodiments of the invention some or all of the undulator modules 1131, 1132, 1133, 1134 may be planar and some or all of the undulator modules 1131, 1132, 1133, 1134 may be helical.

As electrons move through each undulator module 1131, 1132, 1133, 1134, they interact with the electric field of the radiation, exchanging energy with the radiation. In general the amount of energy exchanged between the electrons and the radiation will oscillate rapidly unless conditions are close to the resonance condition as described above equation (1).

A region around a central axis of the undulator module 1131, 1132, 1133, 1134 may be considered to be a "good field region". The good field region may be a volume around the central axis wherein, for a given position along the central axis of the undulator module 1131, 1132, 1133, 1134, the magnitude and direction of the magnetic field within the volume are substantially constant. An electron bunch propagating within the good field region may satisfy the resonant condition of Eq. (1) and will therefore amplify radiation. Further, an electron beam E propagating within the good field region should not experience significant unexpected disruption due to uncompensated magnetic fields.

Each of the undulator modules 1131, 1132, 1133, 1134 may have a range of acceptable initial trajectories. Electrons entering an undulator module 1131, 1132, 1133, 1134 with an initial trajectory within this range of acceptable initial trajectories may satisfy the resonant condition of Eq. (1) and interact with radiation in that undulator module 1131, 1132, 1133, 1134 to stimulate emission of coherent radiation. In contrast, electrons entering an undulator module 1131, 1132, 1133, 1134 with other trajectories may not stimulate significant emission of coherent radiation.

For example, generally, for helical undulator modules electron beam E should be substantially aligned with a central axis of the undulator module. A tilt or angle between the electron beam E and the central axis of the undulator module should generally not exceed $1/10\rho$, where $\rho$ is the Pierce parameter. Otherwise the conversion efficiency of the undulator module (i.e. the portion of the energy of the electron beam E which is converted to radiation in that module) may drop below a desired amount (or may drop almost to zero). In an embodiment, the Pierce parameter of an EUV helical undulator module may be of the order of 0.001, indicating that the tilt of the electron beam E with respect to the central axis of the undulator module should be less than 100 μrad.

For a planar undulator module, a greater range of initial trajectories may be acceptable. Provided the electron beam E remains substantially perpendicular to the magnetic field of a planar undulator module and remains within the good field region of the planar undulator module, coherent emission of radiation may be stimulated.

As electrons of the electron beam E move through a drift space between each undulator module 1131, 1132, 1133, 1134, the electrons do not follow a periodic path. Therefore, in this drift space, although the electrons overlap spatially with the radiation, they do not exchange any significant energy with the radiation and are therefore effectively decoupled from the radiation.

The bunched electron beam E has a finite emittance and will therefore increase in diameter unless refocused. Therefore, the undulator 24 further comprises a mechanism for refocusing the electron beam E in between one or more pairs of adjacent modules 1131, 1132, 1133, 1134. Referring to FIG. 43, the undulator 24 comprises three quadrupole magnets 1161, 1162, 1163: a first quadrupole magnet 1161 between the first and second undulator modules 1131, 1132; a second quadrupole magnet 1162 between the second and third undulator modules 1132, 1133; and a third quadrupole magnet 1163 between the third and fourth undulator modules 1133, 1134. The quadrupole magnets 1161, 1162, 1163 reduce the size of the electron bunches and keep the electron beam E within the good field region of the undulator 24. This improves the coupling between the electrons and the radiation within the next undulator module, increasing the stimulation of emission of radiation.

An electron which meets the resonance condition as it enters the undulator 24 will lose (or gain) energy as it emits (or absorbs) radiation, so that the resonance condition is no longer satisfied. Therefore, in some embodiments the undulator 24 may be tapered. That is, the amplitude of the periodic magnetic field and/or the undulator period may vary along the length of the undulator 24 in order to keep bunches of electrons at or close to resonance as they are guided though the undulator 24. The tapering may be achieved by varying the amplitude of the periodic magnetic field and/or the undulator period within each undulator module 1131, 1132, 1133, 1134 and/or from module to module.

As described above, the interaction between the electrons and radiation within the undulator 24 produces a spread of energies within the electron bunches. The tapering of the undulator 24 may be arranged to maximise the number of electrons at or close to resonance. For example, the electron bunches may have an energy distribution which peaks at a peak energy and the tapering may be arranged to keep electrons with this peak energy at or close to resonance as they are guided though the undulator 24. Advantageously, tapering of the undulator 24 has the capacity to significantly increase conversion efficiency. For example, the use of a tapered undulator 24 may increase the conversion efficiency by a factor of more than 2. Tapering of the undulator 24 may be achieved by reducing the undulator parameter K along its length. This may be achieved by matching the undulator period and/or the magnetic field strength $B_0$ along the axis of the undulator to the electron bunch energy to ensure that they are at or close to the resonance condition. Meeting the resonance condition in this manner increases the bandwidth of the emitted radiation.

The undulator 24 comprises a plurality of sections, each section comprising one or more undulator modules. Referring to FIG. 43, the undulator 24 comprises two undulator sections 1151, 1152. The first undulator section 1151 comprises three undulator modules 1131, 1132, 1133 and the second undulator section 1152 comprises one undulator module 1134. The electron beam E comprises a plurality of spaced apart electron bunches, which enter the undulator 24 from the left side and move from left to right. The electron beam passes through a beam line pipe 1153, which comprises a metal pipe within the undulator 24. The electron beam line pipe 1153 may have a diameter of around 5 mm to 5 cm. In some embodiments, the electron beam line pipe 1153 may have a diameter of around 10 mm to 20 mm. For a planar undulator the electron beam line pipe 1153 may have a rectangular cross section, with a shorter dimension of around 10 mm to 20 mm in a direction of the magnetic field.

A first electron bunch 1154 is shown entering the first undulator section 1151. A second electron bunch 1155 is shown at the end of the first undulator section 1151. As a result of the interaction of the electron beam with radiation within the first three undulator modules 1131, 1132, 1133 (as described above), the second electron bunch has developed micro-bunching and is accompanied by an associated photon bunch 1156. The photon bunches 1156 exiting the first undulator section 1151 form a pulsed radiation beam $B_1$.

The photon bunch 1156 is shown generally overlapping with the electron bunch 1155, with the photon bunch increasing along a central axis 1157 of the first undulator section (from left to right in FIG. 43). Due to a phenomenon commonly known as optical guiding, photon bunches generally follow their respective electron bunches within each undulator section 1151, 1152. Optical guiding is a consequence of two effects. The first effect is due to light amplification within the undulator modules 1131, 1132, 1133, 1134, since the gain of the free electron laser FEL is highest where the current density is highest (that is close to or at the center of the electron bunches). This first effect will only promote optical guiding within each undulator module 1131, 1132, 1133, 1134. The second effect is a result of light refraction within the electron beam E. Because the real part of the refraction index of the electron beam is maximal close to or at the center of the electron bunches, the electron beam E guides light in a similar manner to an optical fiber.

The undulator 24 further comprises a steering unit disposed between one or more pairs of adjacent undulator sections. Referring to FIG. 43, the undulator 24 comprises a steering unit 1158 disposed between the first and second undulator sections 1151, 1152. The steering unit 1158 bends the electron beam by an angle 1159 with respect to the axis 1157 of the first undulator section 1151 along which the radiation beam $B_1$ exiting the first undulator section 1151 propagates. A third electron bunch 1160 is shown after the steering unit 1158. Radiation beam $B_1$ continues to propagate along the axis 1157 of the first undulator module 1151 while the electron bunch 1160 is shifted with respect to radiation beam $B_1$ by a separation distance h, which is dependent on the bending angle 1159 and length L of the steering unit 1158.

The steering unit 1158 is arranged to alter a trajectory of the electron beam E exiting the first undulator section 1151 so that when the electron beam E enters the second undulator section 1152 the electron beam E is at least partially separated from the radiation beam $B_1$ exiting the first undulator section 1151. Therefore, although the electron beam E follows a periodic path within the second undulator section 1152, at least a portion of the radiation beam $B_1$ exiting the first undulator section 1151 does not overlap spatially with the electron beam E as it propagates through the second undulator section 1152. As a result, the electron beam E does not interact with this portion of the radiation beam $B_1$ whilst propagating through the second undulator section 1152. The electron beam E is effectively partially decoupled from the radiation beam $B_1$ as it propagates through the second undulator section 1152.

The separation distance h may be such that electron bunch 1160 is completely decoupled from photon bunch 1150, or may be such that electron bunch 1160 partially overlaps with photon bunch 1150. A decoupling of each electron bunch from its previously generated photon bunch is possible with relatively small bending angles and bending field lengths because the electron and photon bunches both have diameters of the order of 100 µm or less. For example, a decoupling may be achieved with a bending angle of around 100 µrad and a bending field length of around 1 m.

The angle 1159 through which the electron beam E is bent in the steering unit 1158 may exceed a divergence of the EUV radiation beam $B_1$ exiting the first undulator section 1151. The divergence of the EUV radiation beam $B_1$ exiting the first undulator section 1151 may for example be around 100 µrad. For such embodiments, in the far field the free electron laser FEL will produce a plurality (in this example two) of EUV radiation beams that do not overlap and can be conditioned and used independently.

Alternatively or additionally the angle 1159 through which the electron beam E is bent in the steering unit 1158 may be smaller than the divergence of the EUV radiation beam $B_1$. For such embodiments, the EUV radiation beams will at least partially overlap in the far field and the undulator may therefore be used to provide a desired intensity distribution.

The steering unit 1158 may include magnets arranged to decrease aberrations due to the energy spread developed within electron bunch during FEL process. These may comprise higher order magnets (for example sextupoles, octupoles).

The steering unit 1158 and the first and second undulator sections 1151, 1152 are arranged such that the electron beam enters the entrance of the second undulator section 1152 with an initial trajectory within the range of acceptable trajectories for the first undulator module 1134 of the second undulator section 1152. Therefore, the electron beam E will interact with radiation in the second undulator section 1152 to stimulate emission of coherent radiation (producing a second radiation beam $B_2$). In the embodiment shown in FIG. 43 the undulator modules 1131, 1132, 1133, 1134 are helical. Therefore to ensure that the electron beam E enters the entrance of the second undulator section 1152 with an initial trajectory within the range of acceptable trajectories for the first undulator module 1134 within the second undulator section 1152, the first and second undulator sections 1151, 1152 are arranged so that their central axes are not aligned. This allows the electron beam E to still fall within the good field region of the second undulator section 1152 despite being bent through angle 1159 by the steering unit 1158. The second undulator section 1152 may also be shifted in a direction of the central axis 1157 of the first undulator module 1151 (to the right in FIG. 43) in order to improve matching of the electron beam E and a central axis of the second undulator section 1152.

The angle 1159 through which the electron beam E is bent in the steering unit 1158 may be sufficiently small that all of the radiation beams resulting in such arrangement fit within electron beam line pipe 1153.

The electron beam line pipe 1153 may substantially follow the path that the electron beam E is to take through the undulator 24, while still allowing enough space for the portion of the radiation beam $B_1$ that is effectively decoupled from the electron beam E. Advantageously, this allows the electron beam E to remain substantially in the centre of the beam line pipe 1153, thereby minimising losses due to wakefields. Alternatively, the beam line pipe 1153 may be aligned with the axis 1157 of the first undulator section 1151.

After leaving the undulator 24, the two radiation beams $B_1$, $B_2$ are emitted by the free electron laser FEL and may be supplied to the lithographic apparatuses of a lithographic system LS4, LS5. The two radiation beams $B_1$, $B_2$ comprise EUV radiation.

Optionally, one of the two radiation beams $B_1$, $B_2$ (or a portion thereof) may be guided to the entrance of one of the undulator sections, for example the first electron section 1151. This may serve as a seed radiation source, which is amplified by stimulated emission within the first undulator section 1151. A radiation beam used in this manner may have low power, for example less than few hundred Watts. Therefore mirrors that are placed close to undulator 24 output may be used to guide the radiation beam.

Although the above described embodiment 24 comprises two undulator sections 1151, 1152 and a single steering unit 1151, other numbers of undulator sections and steering units may alternatively be used. This allows for more than two radiation beams to be output by the undulator 24.

Figure 44:
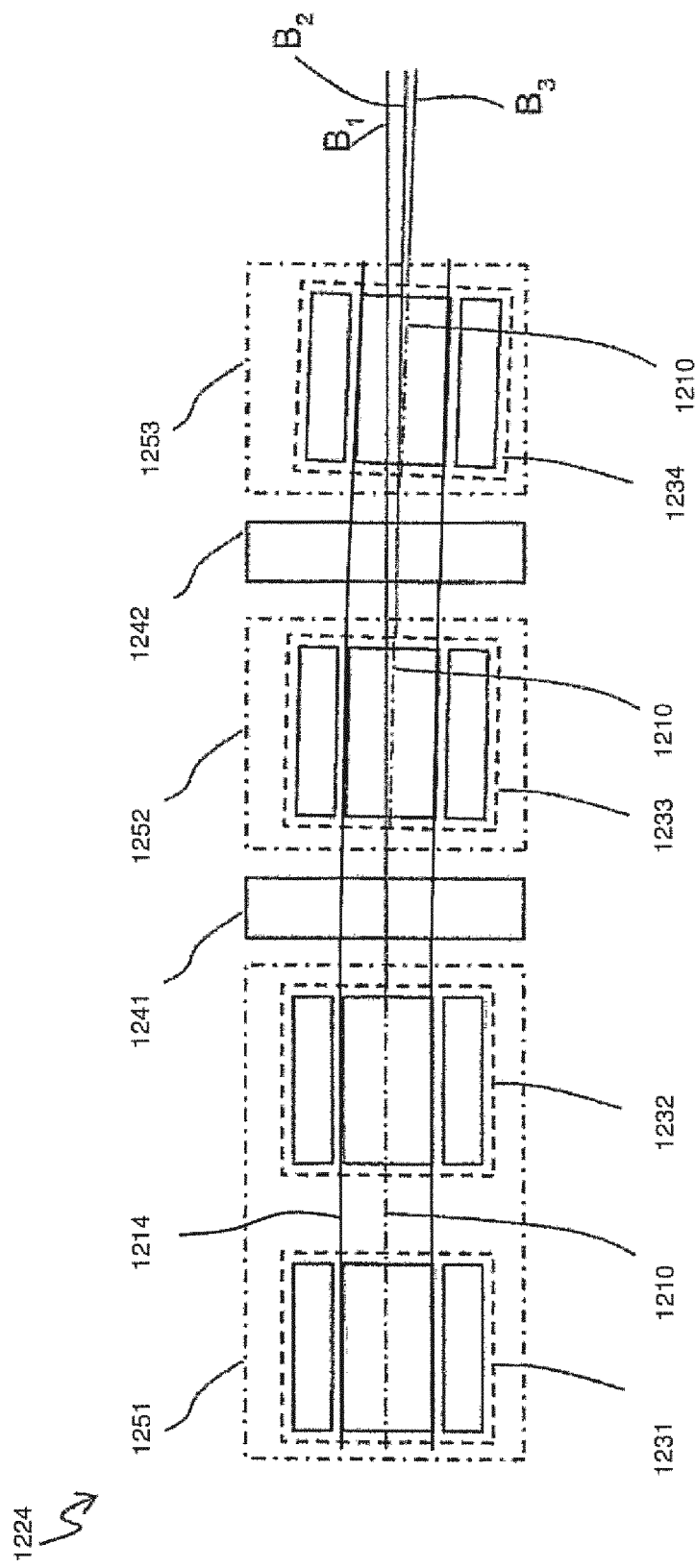
FIG. 44 is a schematic illustration of an undulator according to an alternative embodiment.

Referring to FIG. 44, an alternative embodiment of an undulator 1224 is shown, comprising three undulator sections 1251, 1252, 1253. For ease of explanation, some features shown in FIG. 43 are not depicted in FIG. 44. A first undulator section 1251 comprises two undulator modules 1231, 1232; a second undulator section 1252 comprises one undulator module 1233; and a third undulator section 1253 comprises one undulator module 1234. The electron beam E comprises a plurality of spaced apart electron bunches, which enter the undulator 1224 from the left side and move from left to right. The electron beam E passes through a beam line pipe 1214, which comprises a metal pipe within the undulator 1224. The electron beam E follows a trajectory 1210 that runs along the centre of the beam line pipe 1214.

As the electron beam E propagates through the first undulator section 1251 it interacts with radiation in undulator modules 1231, 1232, generating a radiation beam $B_1$.

A steering unit 241 is arranged to alter a trajectory of the electron beam E exiting the first undulator section 1251 so that when it enters the second undulator section 1252 the electron beam E is at least partially decoupled from the radiation beam $B_1$ exiting the first undulator section 1251. As a result, the electron beam E does not interact with at least a portion of the radiation beam $B_1$ exiting the first undulator section 1251 whilst propagating through the second undulator section 1252 or the third undulator section 1253. The radiation beam $B_1$ exiting the first undulator section 1251 is output by the free electron laser.

The steering unit 241 and the first and second undulator sections 1251, 1252 are arranged such that the electron beam E enters the entrance of the second undulator section 1252 with an initial trajectory within the range of acceptable trajectories for the first undulator module 1233 of the second undulator section 1252. Therefore, the electron beam E will interact with radiation in the second undulator section 1252 to stimulate emission of coherent radiation (producing radiation beam $B_2$). As with the previous embodiment, this is achieved by arranging the first and second undulator sections 1251, 1252 so that their central axes are not aligned.

A steering unit 1242 is arranged to alter a trajectory of the electron beam E exiting the second undulator section 1252 so that when it enters the third undulator section 1253 the electron beam E is at least partially decoupled from the radiation beam $B_2$ exiting the second undulator section 1252. As a result, the electron beam E does not interact with at least a portion of the radiation beam $B_2$ exiting the second undulator section 1252 whilst propagating through the third undulator section 1253. The radiation beam $B_2$ exiting the second undulator section 1252 is output by the free electron laser.

The steering units 1241, 1242 are arranged to alter the trajectory of the electron beam E such that the electron beam E and each of the radiation beams $B_1$, $B_2$, $B_3$ are accommodated within the electron beam line pipe 1214 and do not hit its walls. Advantageously, this avoids loss of radiation and heating up of the electron beam line pipe 1214. For embodiments wherein the undulator sections 1251, 1252, 1253 are planar, the steering units 1241, 1242 may be arranged such that a trajectory of the electron beam E remains substantially in one plane (substantially perpendicular to the magnetic field generated by the undulator 1224). Advantageously, this allows the beam line pipe 1214 to remain small in the direction perpendicular to said plane, which in turn allows a separation between magnets in the undulator 1224 to remain small. For embodiments, wherein the undulator sections 1251, 1252, 1253 are helical, the steering units 1241, 1242 may be arranged such that the directions of the electron beam E in each undulator section 1251, 1252, 1253 lie substantially on a cone. Advantageously, this allows a diameter of the beam line pipe 1214 to remain small while still accommodating the electron beam E and all generated radiation beams.

The steering unit 1242 and the second and third undulator sections 1252, 1253 are arranged such that the electron beam E enters the entrance of the third undulator section 1253 with an initial trajectory within the range of acceptable trajectories for the first undulator module 1234 within the third undulator section 1253. Therefore, the electron beam E will interact with radiation in the third undulator section 1253 to stimulate emission of coherent radiation (producing radiation beam $B_3$).

In alternative embodiments to those described above with reference to FIGS. 43 and 44, each undulator section may comprise any number of undulator modules and in general different undulator sections may comprise different numbers of undulator modules. In some embodiments, the first undulator section may comprise more undulator modules than subsequent undulator modules.

Figure 45:
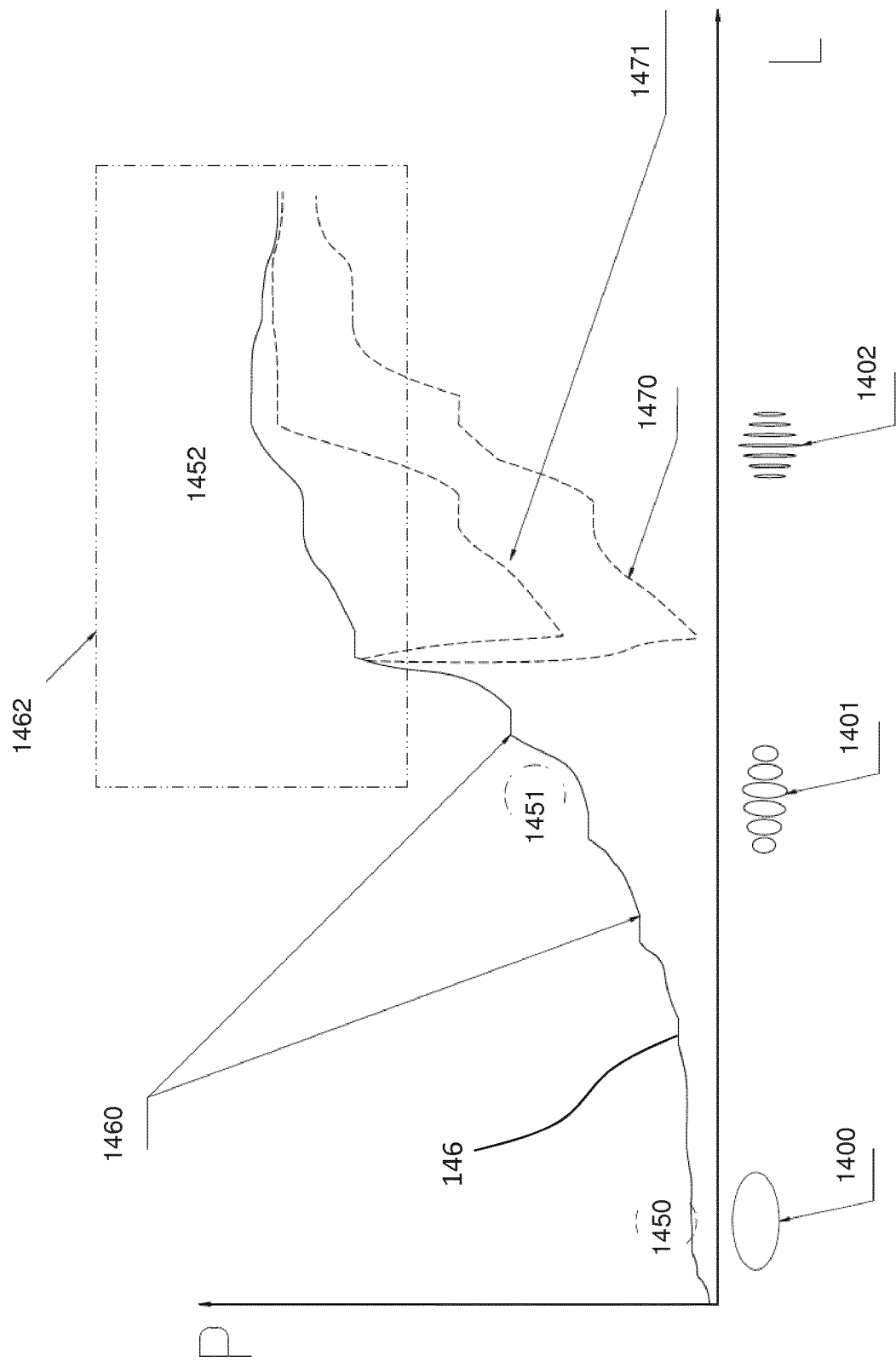
FIG. 45 is an illustration of radiation power growth through a known undulator for a free electron laser.

FIG. 45 shows a plot of the power of laser radiation as a function of distance L travelled through a conventional undulator (i.e. an undulator comprising a single undulator section). A single electron bunch 1400 enters the undulator and the free electron laser process starts with noise in a low power region 1450. The free electron laser process leads to micro-bunching of the electron bunch as it travels through the undulator leading to a build-up of laser power. During an exponential growth mode 1451, the electron 1401 are in a moderately micro-bunched state 1401. The micro-bunching increases until the electron bunches are in a fully micro-bunched state 1402 and the radiation power reaches saturation 1452.

Within each undulator module of an undulator, as the relativistic electrons in each bunch interacts with its corresponding photon bunch, the radiation power changes. Within drift spaces (regions between undulator modules) the electrons do not follow a periodic path and are therefore decoupled from the radiation. The radiation power therefore remains substantially constant within these regions, indicated by regions 1460 in FIG. 45.

The majority of radiation is extracted from each electron bunch in a part of the undulator 1462, in which micro-bunching is fully developed.

In embodiments of the present invention, photons and associated electron bunches are separated or partially separated between two adjacent undulator sections, for example by deflecting the electron beam E in the drift space between these undulator sections. If this decoupling, or partial decoupling, of the electron beam E from its associated photon beam occurs when micro-bunching is fully, or nearly fully, developed then lasing rapidly resumes in a next undulator section. A build-up of radiation power (illustrated by a plot 1470 in FIG. 45) in a next undulator section occurs over a smaller distance than in the first undulator section where the free electron laser process starts from noise. If the photons associated with the electron bunches are only partially removed, a build-up of radiation power in a next undulator section may occur within an even shorter distance (illustrated by a plot 1471 in FIG. 45).

Figure 46:
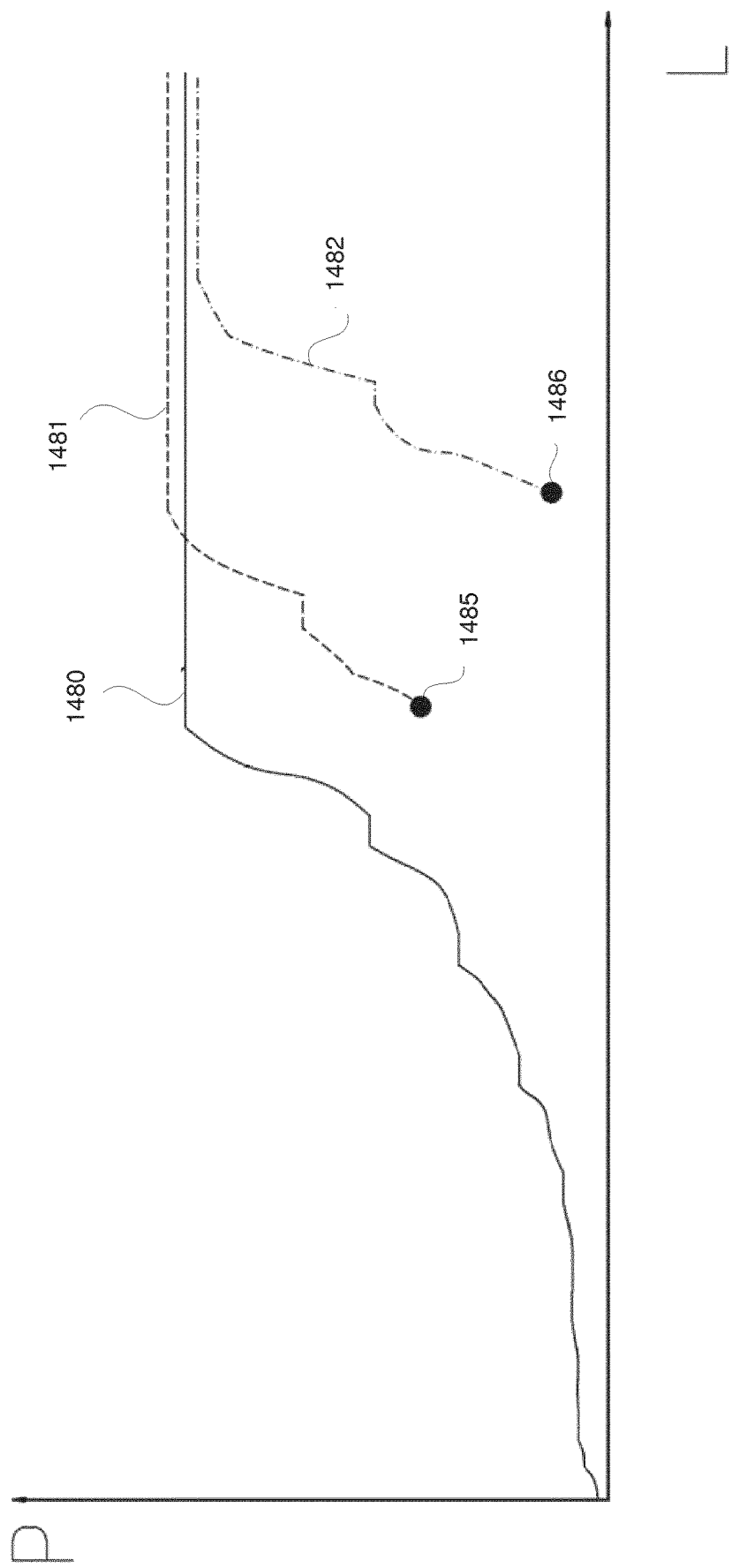
FIG. 46 is an illustration of radiation power growth through an undulator according to an embodiment described herein.

Referring to FIG. 46, plots 1480, 1481, 1482 illustrate a power of respectively photon beams $B_1$, $B_2$, $B_3$ emitted using an undulator according to an embodiment of the present invention as a function of distance L travelled through the undulator. The three photon beams $B_1$, $B_2$, $B_3$ are emitted using an undulator comprising three undulator sections (e.g. as in the embodiment shown in FIG. 44). Plot 1480 shows the power of the first EUV radiation beam $B_1$ produced in the first undulator section; plot 1481 shows the power of the second EUV radiation beam $B_2$ produced in the second undulator section after a first bending of the electron beam E; and plot 1482 shows the power of the third EUV radiation beam $B_3$ produced in the third undulator section after a second bending of the electron beam E. In this example, after each bending of the electron beam E, lasing restarts with part of the power of the radiation beam from the previous undulator section seeding the new beam (1485, 1486). That is, a portion of the first radiation beam $B_1$ seeds the second radiation beam $B_2$, setting an initial value 1485 of curve 1481; and a portion of the second radiation beam $B_2$ seeds the third radiation beam $B_3$, setting an initial value 1486 of curve 1482.

As shown in FIG. 46, in general each of the plurality of radiation beams produced by an undulator according to an embodiment of the invention may have a different power. The power of each radiation beam does not change significantly after photons of that radiation beam have been separated from the electron beam E because only a very small portion of each radiation beam is used to seed the next undulator section. Radiation of differing power may be used to seed and/or restart lasing in the EUV beam after each bending of the electron beam E.

In alternative embodiments, after each undulator section, the electron beam E is completely separated from the radiation beam generated in that undulator section such that no portion of the radiation beam interacts with the electron beam E in the next undulator section. In such embodiments, lasing in each new undulator section may start from noise. However, because the microbunches still exist, the increase in coherent radiation can be much faster than in the very first undulator section.

An amount of tapering of the undulator 24 (i.e. how the undulator parameter K varies along the length of the undulator 24), a focusing of electron beam (also known as the lattice design) and the length and/or number of magnets per individual undulator module are parameters of an undulator 24 which can be tuned to tailor the performance of the free electron laser FEL. For example, the tapering and the focusing may be chosen so that some or each of the radiation beams output by the free electron laser FEL have sufficient power to supply a single lithographic apparatus and/or another EUV consuming device. Additionally or alternatively, they may be chosen so that the pre-micro-bunched electron beams leaving one undulator section develop photon beams with sufficient power to drive a lithographic apparatus tool or other device consuming EUV within a certain number of undulator modules in the next undulator section. These pre-micro-bunched electron beams leaving one undulator section may be partially seeded by a portion of the radiation beam leaving that section. Preferably, pre-micro-bunched electron beams are able to develop photon beams with sufficient power to drive a lithographic apparatus tool or other device consuming EUV within one or a few undulator modules.

Although example embodiments described with reference to FIG. 43, 44 relate to undulators with two or three undulator section and radiation beams, alternative embodiments may comprise more undulator sections and radiation beams.

In some embodiments, in addition to the steering unit, a drift space between each pair of undulator sections may comprise phase adjusting units arranged to provide optimal matching between seeding photon bunches and electron bunches. The phase adjusting units may for example comprise small undulator modules with field-controlled K values. Such phase adjusters can be used to control the power of one of the individual radiation beams.

The K-values of the undulator modules in any undulator section may be independently adjustable, and/or the magnets within each undulator module may be independently adjustable. This provides control over the power of each of the plurality of radiation beams.

The steering units may comprise electron beam shifting elements, which may be operable to shift the electron beam E in a direction substantially perpendicular to its propagation direction by up to few hundred μm. The electron beam shifting elements may be adjustable. Such arrangement provides independent control of the overlap of electron beam with radiation beams and an angle of separation between the radiation beams. The electron beam shifting elements may comprise a pair of dipole magnets.

The electron beam E may be transversely expanded before being bent by a steering unit and may be transversely compressed back to its original dimensions afterwards. This may reduce degradation of bunch emittance of the electron beam E due to, for example, Coherent Synchrotron Radiation. Therefore, for such embodiments the drift space between each pair of undulator sections may comprise a beam expander, a steering unit and a beam compressor. Alternatively, as will be appreciated by the skilled person, the electron beam E may be bent in a direction parallel to the largest local dimension of the electron beam.

Figure 47:
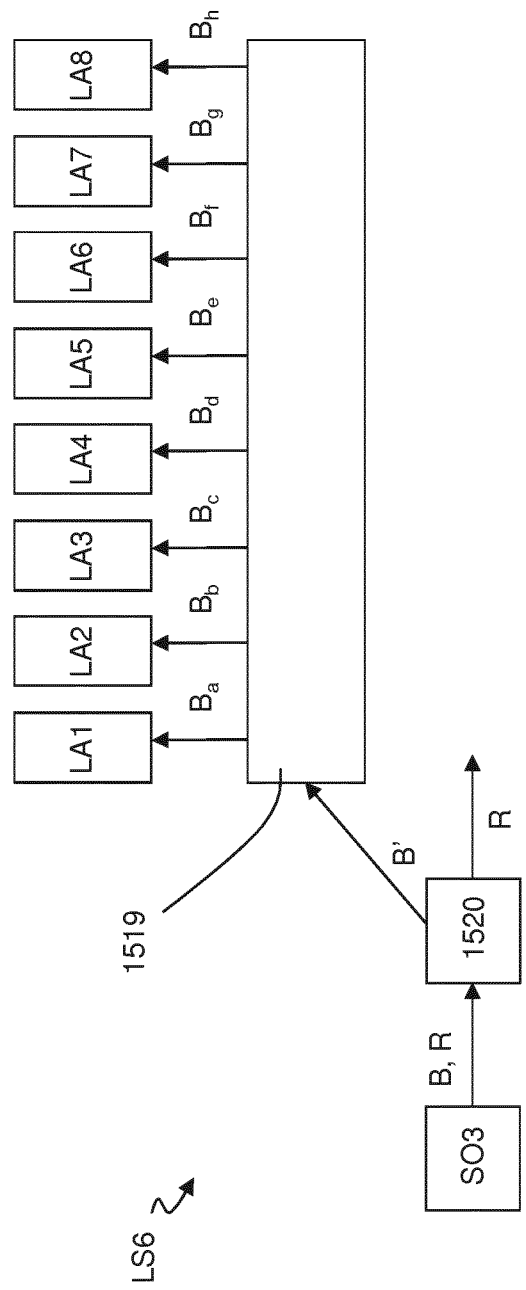
FIG. 47 is a schematic illustration of a lithographic system comprising a first optical element according to an embodiment described herein.

FIG. 47 shows an example lithographic system LS6 comprising a radiation source SO3, a first optical element 1520 according to an embodiment of the invention, a beam delivery system 1519 and eight lithographic apparatuses LA1-LA8. The radiation source SO3 is configured to generate an extreme ultraviolet (EUV) radiation beam B (which may be referred to as a main beam). It will be appreciated that more or fewer lithographic apparatuses may be provided.

The beam delivery system 1519 comprises beam splitting optics. The beam splitting optics splits the main radiation beam B into a plurality of radiation beams $B_a$-$B_h$ (which may be referred to as branch beams), each of which is directed to a different one of the lithographic apparatuses LA1-LA8.

The beam delivery system 1519 may further comprise beam expanding optics. The beam expanding optics may be arranged to increase the cross sectional area of the radiation beam B. This decreases the heat load on mirrors downstream of the beam expanding optics. This may allow the mirrors downstream of the beam expanding optics to be of a lower specification, with less cooling, and therefore less expensive. Additionally or alternatively, it may allow the downstream mirrors to be nearer to normal incidence.

The beam expanding optics may be disposed upstream of the beam splitting optics, such that the main radiation beam B passes through the beam expanding optics before the beam splitting optics. In alternative embodiments, beam splitting optics may be disposed upstream of beam expanding optics. For such embodiments, separate beam expanding optics may be provided for each branch radiation beam $B_a$-$B_h$. In alternative embodiments, the beam delivery system 1519 may not comprise beam expanding optics.

The radiation source SO3, first optical element 1520, beam delivery system 1519 and lithographic apparatuses LA1-LA8 may all be constructed and arranged such that they can be isolated from the external environment. A vacuum may be provided in at least part of the radiation source SO3, first optical element 1520, beam delivery system 1519 and lithographic apparatuses LA1-LA8 so as to minimise the absorption of EUV radiation. Different parts of the lithographic system LS6 may be provided with vacuums at different pressures (i.e. held at different pressures which are below atmospheric pressure).

The lithographic apparatuses LA1-LA8 may be substantially as described above with reference to FIG. 2.

The following discussion relates to a source comprising a free electron laser, and in particular to radiation generated by a free electron laser. It will be appreciated that a free electron laser is not essential to the invention. Embodiments of the invention may incorporate other high power radiation sources.

With reference to FIG. 47, in addition to the main radiation beam B, the undulator 24 of a free electron laser (FEL) emits ionizing radiation R such as, for example, gamma radiation and neutrons. This additional ionizing radiation R is undesirable since it is a health hazard and may be damaging to susceptible materials, such as magnets in actuators and motors.

Therefore the lithographic system LS6 is provided with a reflective first optical element 1520 arranged to deflect a portion of the EUV radiation beam B so as to form a reflected radiation beam B' and to either transmit of absorb the additional ionizing radiation R. The free electron laser may be disposed within a bunker arranged to contain ionizing radiation and the first optical element 1520 may also be disposed within the bunker. In this way, the EUV radiation beam B may be directed towards the beam delivery system 1519 via an aperture in the bunker which is not aligned with the axis of the undulator 24. The additional ionizing radiation R will either be absorbed or will continue to propagate generally in the direction of the axis of the undulator 24 and will be contained by the bunker.

The radiation beam B output by the free electron laser FEL may have a substantially circular cross section and a Gaussian-like intensity profile. The radiation beam B produced by an EUV free electron laser typically has a relatively small etendue. In particular, the EUV radiation beam B produced by a free electron laser FEL has a significantly smaller etendue than an EUV radiation beam that would be generated by a laser produced plasma (LPP) source or a discharge produced plasma (DPP) source (both of which are known in the prior art). For example, the radiation beam B may have a divergence less than 500 μrad, for example less than 100 μrad. The radiation beam B may for example have a diameter of around 50 μm to 100 μm as it leaves the undulator 24.

In order to support high throughput for the eight EUV lithographic apparatus LA1-LA8, the output power of the free electron laser FEL may be of the order of tens of kilowatts, for example around 30 kW. At such powers, since the initial diameter of the radiation beam B produced by the free electron laser is so small, the power density of the radiation beam B will be significant. Further, since the divergence of the radiation beam B produced by the free electron laser is so small, the power density of the radiation beam B will decrease very slowly with increasing distance.

Therefore, the first optical element 1520 is disposed within the bunker that contains the free electron laser FEL but, for thermal reasons, relatively distant from the undulator 24. For example, the first optical element may be disposed around 1520 m from the exit of the undulator 24. For a radiation beam with an initial diameter of the order of 1550 μm and a divergence of around 50 μrad, at a distance of 1520 m from the undulator the diameter of the radiation beam is approximately 2 mm. The thermal load on the first optical element 1520 may be reduced by arranging for the radiation beam B to be incident on the first optical element 1520 at a small grazing incidence angle, for example a grazing incidence angle of around 2 degrees. This will spread the radiation over a larger beam spot area and will also increase the reflectivity of the first optical element 1520. For a radiation beam B with a power of 30 kW, assuming that 5% of the energy of the beam is absorbed by the first optical element 1520, the first optical element 1520 will be subject to a heat load of around 1500 W. At a distance of 1520 m and with a small grazing incidence angle, this heat load may be spread over an area on the surface of the first optical element 1520 of the order of 1 cm². For example, for a circular radiation beam with a beam diameter of 2 mm incident on the first optical element 1520 at a grazing incidence angle of 2 degrees, the heat load is spread over an elliptical area on the surface of the first optical element 1520 of 0.9 cm².

Figure 48:
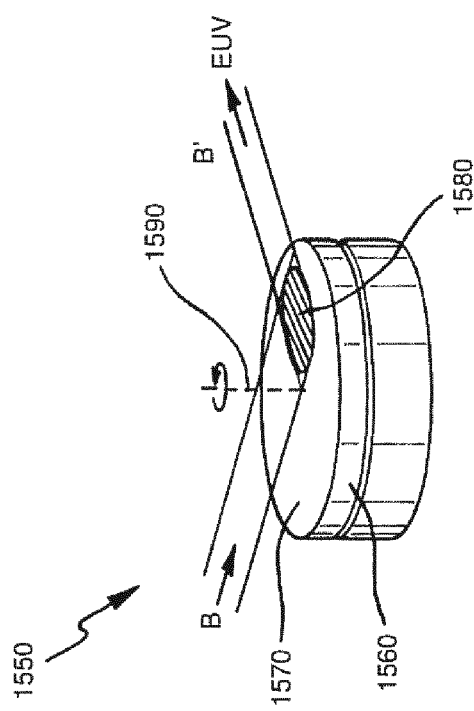
FIG. 48 is a perspective view of an optical element, which may form the first optical element of a lithographic system described herein.

FIG. 48 shows an optical element 1550, which may form the first optical element 1520 of the lithographic system LS6. The optical element 1550 comprises a generally disc-shaped body 1560 and a reflective surface 1570 provided on the body 1560 for receiving the radiation beam B from the free electron laser FEL so as to form a beam spot region 1580. The optical element 1550 is arranged such that the radiation beam B is incident on the reflective surface 1570 at a small grazing incidence angle, for example, a grazing incidence angle of around 2 degrees. Therefore, the beam spot region 1580 is an elongate ellipse shape.

The optical element 1550 further comprises a movement mechanism (not shown) that is operable to rotate the body 1560 about a rotation axis 1590. For example, the disc-shaped body 1560 may comprise a shaft extending along the rotation axis 1590. The shaft may be supported by one or more bearings, for example two bearings. The shaft may be driven to rotate by any suitable mechanism such as a motor or engine.

A direction along, or parallel to, the rotation axis 1590 may be referred to as an axial direction. A direction running to or from the rotation axis 1590 and perpendicular to said rotation axis 1590 may be referred to as a radial direction.

The reflective surface 1570 is disposed on an axially facing surface of the body 1560. As the movement mechanism rotates the body 1560 about the rotation axis 1590, the reflective surface 1570 rotates, causing the beam spot region 1580 to move over the reflective surface 1570. The beam spot region 1580 follows a periodic path, in particular a circular path, over the reflective surface 1570. Therefore, as the body 1560 rotates, the beam spot region 1580 traces out an annular shaped region of the reflective surface 1570.

In some embodiments, the reflective surface 1570 may be curved in order to cause expansion of the beam B. For example, the reflective surface may form part of a sphere or part of a torus. In the below embodiments it is described that curvature of the reflective surface 1570 may arise from heat transfer from the radiation beam into the body 1560. Curvature caused by such heat transfer may be additional curvature where the reflective surface 1570 is curved without such heat transfer.

In general, a two dimensional surface may curve differently in different directions. In the following, it will be appreciated that "a curvature of a surface in a given direction at a given point on said surface" means a curvature of the curve that is formed by the intersection of said surface and a plane containing the normal vector of the surface at that point and a vector in said given direction.

A fraction of the power of the radiation beam B is absorbed by the optical element 1550, causing the reflective surface 1570 to heat up. Since the movement mechanism is operable to move the reflective surface 1570 such that the beam spot region 1580 moves over the reflective surface 1570, the power absorbed by the optical element 1550 is spread over a larger area, decreasing the density of the heat load. This allows the optical element 1550 to receive radiation beams with higher power densities, in contrast to static optical elements of the same or similar dimension.

The optical element 1550 will absorb a fraction of the energy of the radiation beam B, causing a temperature gradient extending generally axially away from the reflective surface 1570. Heat will flow down this temperature gradient, axially away from the reflective surface 1570 and through the body 1560. As a result of the axial temperature gradient, different parts of the body 1560 will expand differently, which will cause the reflective surface 1570 to distort such that the reflective surface becomes convex, curving in the radial direction.

For a body with two opposed surfaces separated by a distance d (the thickness of the body), if a heat load of Q Watts is applied evenly to one of the surfaces, ignoring edge effects, the difference in temperature ΔT between the two surfaces is given by:

$$\Delta T = \frac{d}{\lambda A} Q, \tag{5}$$

where A is the area over which the heat is applied and is the thermal conductivity of the body. The body 1560 may for example be formed from silicon which has a thermal conductivity of around 150 Wm$^{-1}$K$^{-1}$. For a radiation beam B with a power of 30 kW, assuming that 5% of the energy of the beam is absorbed by the first optical element 1550, the first optical element 1550 will be subject to a heat load of around 1500 W. For an incoming radiation beam B with a diameter of 2 mm and a grazing incidence angle of 2 degrees, the beam spot region 1580 is an ellipse with a minor axis length of 2 mm and a major axis length of around 58 mm. Therefore, if the major axis of the ellipse extends in a radial direction the heat load will be spread out around an annular region of the reflective surface 1570 with a radial extent of around 58 mm. If the inner radius of the annular region is 80 mm then the area over which the heat load is applied will be around 0.04 m$^2$. If the axial thickness of the body 1560 is 1520 mm then this heat load of 1500 W over an area of 0.04 m$^2$ will result in a temperature difference of around 5 K across the two opposite axially facing surfaces of the body 1560.

For a body with two opposed surfaces separated by a distance d (the thickness of the body), if one of the two opposed surfaces is heated evenly such that there is a temperature ΔT between the two surfaces then the heated surface will become convex, with a radius of curvature R given by:

$$R = \frac{d}{\alpha \Delta T}, \tag{6}$$

where α is the thermal expansion coefficient of the body. The thermal expansion coefficient of silicon is 2.5×10$^{-6}$ K$^{-1}$. Therefore, the radius of curvature of the reflective surface 1570 (using the example dimensions above and assuming a temperature difference of 5 K), will be around 1600 m. The reflective surface 1570 will therefore act like a cylindrical lens with a focal length f (in the plane of incidence of radiation beam B) given by f=bR/2, where R is the radius of curvature and b is the grazing incidence angle of the radiation beam B in radians. For a radius of curvature of 1600 m and a grazing incidence angle of 0.035 radians (equivalent to 2 degrees), the focal length will be around 28 m.

Note that in the above calculations, for simplicity it has been assumed that the heat load from the radiation beam is spread uniformly over a fixed (annular) area of the reflective surface 1570. However, in general, the heat load may vary across the fixed area. The heat load on any given portion of the fixed area is dependent upon the intensity distribution of the radiation beam B, the grazing incidence angle and the path that the beam spot region 1580 follows over the reflective surface 1570 as the body 1560 rotates. Therefore, in general, in addition to the axial temperature gradient there will be a temperature gradient in the plane of the reflective surface 1570, in the radial direction, within the fixed area of the reflective surface 1570. As a result, the reflective surface 1570 will deform differently at different radial positions within the fixed area of the reflective surface 1570. That is, a local radius of curvature in the radial direction at a given location on the reflective surface 1570 will be a function of the radial position of that given location. As a result, the reflective surface 1570 will no longer act as a cylindrical lens. Rather, different parts of the reflective surface 1570 will, in general, have different focal lengths.

The curvature of the reflective surface 1570 that results from the heat load of the radiation beam B may be problematic, especially because the radius of curvature of the reflective surface 1570 is dependent on the incident heat load.

Therefore, the optical element 1550 may further comprise a distortion mechanism for altering a curvature of the reflective surface 1570. The distortion mechanism may be arranged to alter the curvature of the reflective surface 1570 so as to at least partially correct for curvature of the reflective surface 1570 caused by the radiation beam B.

Since the beam spot region 1580 follows a periodic path on the reflective surface 1570, provided the beam spot region moves sufficiently quickly, the curvature of the reflective surface 1570 caused by the radiation beam B in a direction along the period path is negligible. That is, for a given radial position the intensity is the same around the fixed area. The direction of maximum induced curvature is in a direction perpendicular to the periodic path, i.e. in the radial direction. Such a curvature is simpler to correct for using the distortion mechanism.

Figure 49:
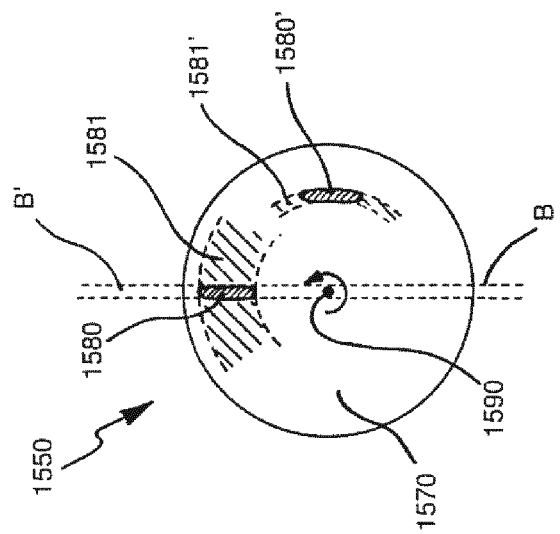
FIG. 49 is a plan view of the optical element of FIG. 48.

As shown in FIG. 49, in some embodiments, the incoming radiation beam B passes over one side of the reflective surface 1570 of the body 1560, through the rotation axis 1590, and approaches the beam spot region 1580. As the radiation beam B is incident upon the beam spot region 1580, its propagation direction is generally in a (local) radial direction (i.e. perpendicular to the rotation axis 1590), with a small axial component (i.e. parallel to the rotation axis 1590). The size of the axial component is determined by the grazing incidence angle of the radiation beam B. Advantageously, for such embodiments, the radial extent of the annular region 1581 (only a portion of this is shown in FIG. 49) of the reflective surface 1570 over which the thermal load is applied is maximised, since it is given by the length of the major axis of the beam spot region 1580 (which is dependent on the diameter of the radiation beam B and the grazing incidence angle).

In alternative embodiments, the radiation beam B may approach the reflective surface in such a way that the beam spot region 1580 that it forms has a different orientation relative to the rotation axis 1590 (i.e. such that the major axis of the beam spot region does not, or does not wholly, extend in the radial direction). For example, referring again to FIG. 49, the incoming radiation beam B may not pass over the rotation axis 1590, and as the radiation beam B is incident upon a beam spot region 1580', its propagation direction may be generally in a (local) tangential direction (i.e. perpendicular to both the rotation axis 1590 and the radial direction), with a small axial component (i.e. parallel to the rotation axis 1590). For such embodiments, the radial extent of the annular region 1581' (only a portion of this is shown in FIG. 49) of the reflective surface 1570 over which the thermal load is applied is given by the diameter of the radiation beam B. Therefore such embodiments have less spreading of the heat than those wherein the major axis of the beam spot region extends in a radial direction.

Due to thermal expansion, the reflective surface 1570 will develop an annular shaped ridge. This ridge will be steeper for beam spot region 1580' than for beam spot region 1580. For embodiments wherein the major axis of the beam spot region extends in a tangential direction, the beam spot region 1580' is generally aligned with the annular ridge. Therefore there will be less height variation of the reflective surface 1570 along the major axis of the beam spot region 1580'. The reflected radiation beam B' may be slightly more sensitive to height variations along the major axis of the beam spot region than along the minor axis of the beam spot region. Additionally, since the incoming radiation beam B does not pass through the rotation axis 1590, the body 1560 of the optical element 1550 can be supported for rotation on both of its opposed axial sides. This allows, for example, a shaft to extend out of the reflective surface 1570 of the body 1560 without blocking the radiation beam B. This may allow, for example, the shaft to be supported by bearings on either side of the body 1560, allowing for easier and more stable implementation than provided by a single-side axle mounting.

A distortion mechanism may be operable to alter a radial curvature of the reflective surface 1570. For example, the distortion mechanism may be operable to apply a generally axial force to a radially outer edge of the body. Various different embodiments of distortion mechanisms are possible. Some examples of distortion mechanisms are now described with reference to FIGS. 50 to 55.

Figure 50:
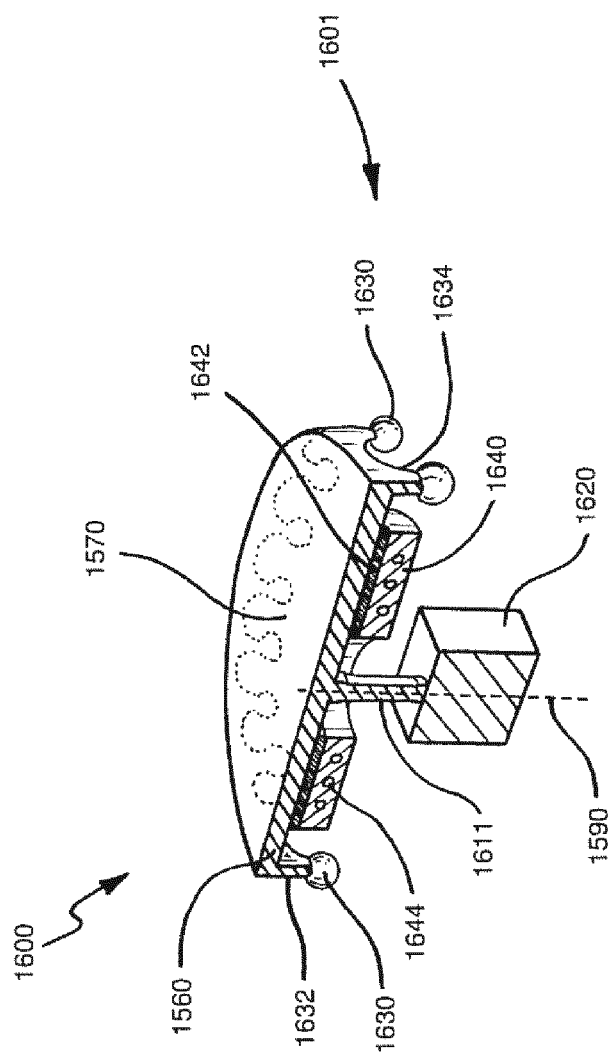
FIG. 50 is a partial cross sectional view of an embodiment of an optical element which may form the optical element of FIGS. 48 and 49.

FIG. 50 shows an optical element 1600, which may form the first optical element 1550 of FIGS. 48 and 49. Features of optical element 1600 that are identical to those of optical element 1550 share common labels and are not described in detail below.

A shaft 1611 extends axially from the body 1560 along the rotation axis 1590. The shaft is supported by one or more bearings (not shown), for example two bearings. The movement mechanism comprises a motor 1620 which is operable to drive the shaft 1611 to rotate.

The optical element 1600 is provided with a distortion mechanism 1601, which comprises a plurality of masses 1630 extending axially away from the generally disc shaped body 1560. Each of the plurality of masses 1630 is generally spherical in shape. In alternative embodiments, the plurality of masses may have another shape. The plurality of masses 1630 are distributed evenly around the circumference of the body 1560.

This distortion mechanism 1601 is suitable for altering a curvature of the reflective surface 1570 as now described. The rotation of the body 1560 causes a centrifugal force to act on the plurality of masses 1630 in an outward radial direction. The centrifugal force generates a moment that acts on a radially outer edge of the body 1560, altering a radial curvature of the reflective surface 1570. The bending moment that is applied to the radially outer edge of the body 1560 is proportional to the square of the rotation rate of the body 1560. Therefore, by altering the rotation rate, the level of distortion of the reflective surface 1570 may be controlled. For example, the rotation rate may be varied in dependence on the heat load applied by the radiation beam B.

For a disc with a radius of around 150 mm, receiving a heat load of 1500 W over an annular region of the reflective surface 1570 with an area of around 0.04 $m^2$, a torque of the order of 0.05 Nm may be used to provide a sufficient bending moment to substantially correct for the deformation caused by the heat load. This could be achieved with, for example, a total mass of around 1 kg, axially displaced from the body by around 5 cm and a rotation speed of 4 rad/s or 0.65 Hz.

Each of the plurality of masses 1630 is connected to the disc shaped body 1560 via an axially extending wall section 1632. The axially extending wall sections 1632 for each pair of adjacent masses 1630 are connected by a wall section 1634. Each wall section 1634 is arcuate. In alternative embodiments, the axially extending wall sections 1632 for each pair of adjacent masses 1630 may be connected by a wall section 1634 with another shape. For example, in some embodiments the wall sections may be forked arcuate wall sections. The wall sections 1634 between each pair of adjacent masses 1630 distribute the moment over the entire circumference of the body 1560. The shape of the wall sections 1634 may be optimized to ensure a substantially even distribution of the moment over the entire circumference of the body 1560.

The distortion mechanism 1601 employed by the first optical element 1600 provides a simple mechanism for altering a curvature of the reflective surface 1570. The amount of curvature can be adjusted by varying the speed of rotation of the body 1560.

The first optical element 1600 may further comprise a cooling mechanism as now described. An example cooling mechanism comprises a static cooling device 1640, disposed adjacent to an axially facing surface of the body 1560 opposite to the reflective surface 1570. A narrow gap is provided between the rotating body 1560 and the static cooling device 1640. The gap is filled with a layer of liquid metal 1642, which is kept in place by capillary forces. The metal may comprise a fusible alloy which melts at a relatively low temperature. For example, the metal may comprise an alloy of gallium and indium, which may contain 75.5% gallium by weight and 24.5% indium by weight. Such an alloy has a melting point of 15.7° C. The static cooling device 1640 is provided with channels 1644 for receiving a flow of fluid such as, for example, water, to transport heat away from the cooling device 1640.

Such a cooling mechanism allows water cooling of the rotating body 1560 without using rotating water couplings. This avoids, or at least significantly reduces, the risk of water leakage. The use of a liquid metal layer to transfer heat is a robust technique which is compatible with ultra-high vacuum conditions (as required for the EUV radiation beam B) and high angular velocities of the body 1560.

In other embodiments, heat may be transferred between the rotating body 1560 and the static cooling device 1640 through radiation. For example, opposed surfaces of the body 1560 and the static cooling device 1640 may be provided with coatings of a high emissivity material to promote radiation by the body 1560 and absorption of the emitted radiation by the static cooling device 1640 across a narrow gap there between. The gap may be filled with a gas such as hydrogen, which may provide additional cooling of the body 1560 by thermal conduction.

Figure 50A:
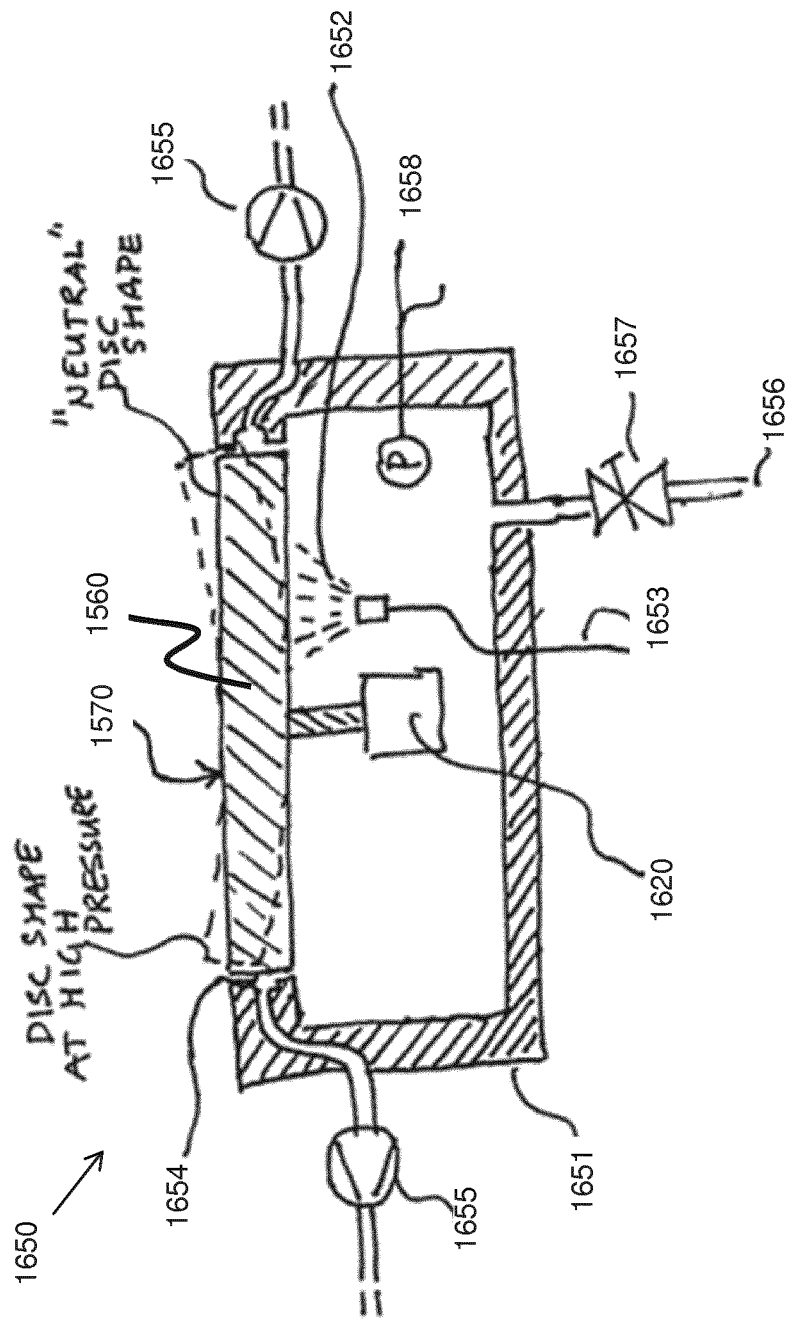
FIG. 50A is a partial cross sectional view of another embodiment of an optical element which may form the optical element of FIGS. 48 and 49.

FIG. 50A shows an alternative optical element 1650, which may form the first optical element 1550 of FIGS. 48 and 49. In the arrangement of FIG. 50A, functions of cooling and shape correction are combined. In the optical element 1650, the rotating body 1560 is provided within a housing 1651. The reflective surface 1570 rotating body 1560 forms an upper face of the housing 1651 such that a cavity is formed within the housing beneath the rotating body 1560.

At least one nozzle 1652 is provided within the cavity of the housing 1651 beneath the rotating body 1560. The nozzle 1652 is connected to a supply of coolant fluid (not shown) by a pipe 1653 and is arranged to spray a coolant fluid to the back side of the rotating body 1560. Upon contact with the back side of the rotating body, the coolant fluid evaporates within the housing. For example, to achieve 1 kW of cooling power, 0.5 mL/s of liquid water may be evaporated.

The evaporated coolant vapour is isolated from the vacuum of the beam delivery system using a pumped no-contact seal 1654 at an interface between the rotating body 1560 and the housing 1651. Pumps 1655 pump gas into a pumping channel to prevent the escape of coolant vapour. While only a single pumping channel is shown in FIG. 50A, the seal 1654 may comprise a plurality of pumping stages.

An exhaust 1656 allows coolant vapour to escape the housing 1651. An adjustable valve 1657 allowing pressure within the cavity to be regulated. For example, for water vapour, a pressure of that at room temperature (about 2.5 kPa) will generate a force on the rotating body which will tend to bend the rotating body 1560 in a direction opposite to the direction of deformation due to heat load; by regulating the valve 1657, one is able to adjust the pressure within the cavity such that the rotating body 1560 assumes a "neutral" shape. A pressure sensor 1568 may be provided to monitor a pressure in the cavity.

In an embodiment, the nozzle (or nozzles) 1652 generate a coolant flux onto the back surface of the rotating body 1560 such that the cooling power varies with the radial position on the rotating body 1560, in order to correct for spatial variation in incident heat load. Additionally, by varying the cooling along the radial position on the rotating body 1560, the shape of the thermal deformation may be adjusted with greater freedom.

In an embodiment, at least some coolant does not evaporate, but rather drips from the back surface of the rotating body. In this case, the higher the heat load applied to the rotating body 1560, the more coolant evaporates, the higher the pressure in the cavity, and the higher the resulting force on the rotating body 1560. In this way, the shape correction effect of the pressure can be made self-adapting to adjust to higher heat load.

Figure 51:
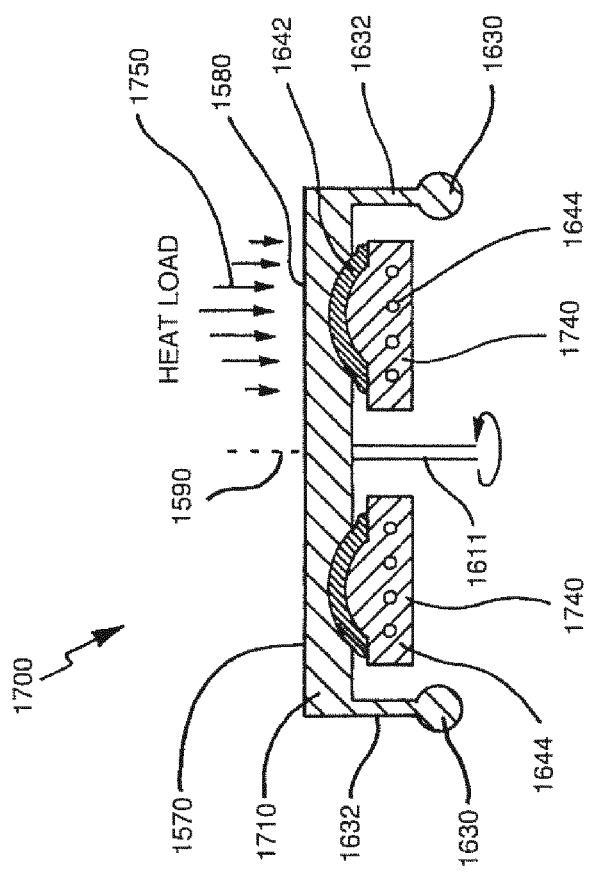
FIG. 51 is a cross sectional view of another embodiment of an optical element which may form the optical element of FIGS. 48 and 49.

FIG. 51 illustrates an alternative optical element 1700, which incorporates a distortion mechanism 1601. Features of optical element 1700 that are identical to those of first optical elements 1550, 1600 share common labels and are not described in detail below.

Optical element 1700 differs from optical element 1600 of FIG. 50 in that it comprises a generally disc shaped body 1710 with an axial thickness which varies in a radial direction. The reflective surface 1570 remains generally flat and the variation in the axial thickness is achieved by altering the shape of an axially facing rear surface of the body 1710, which is opposite to the reflective surface 1570. Further, the optical element 1700 comprises a static cooling device 1740 which has a generally complimentary shape to the axially facing rear surface of the body 1710.

The cross sectional shape of the body 1710 in a plane containing the rotation axis 1590 is such that maximum counter-bending of the reflective surface 1570 occurs at a radial position that receives the largest heat load from the radiation beam B. For example, as discussed above, the radiation beam B output by the free electron laser FEL may have a substantially circular cross section and a Gaussian-like intensity profile. When incident at a small grazing incidence angle, such a circular cross section beam will produce an elongate elliptical beam spot region 1580. Due to the Gaussian-like intensity profile a centre of the elliptical beam spot region 1580 will receive the largest heat load and the edges of the beam spot region 1580 will receive the smallest heat load.

An example heat load from a Gaussian-like radiation beam B is indicated by arrows 1750. For such a heat load, the axial thickness of the body 1710 is smallest at a radial position corresponding to the centre of the beam spot region 1580 and is largest at radial positions corresponding to the edges of the beam spot region 1580.

Such an arrangement allows a different curvature to be applied by the distortion mechanism 1601 at different radial positions by the application of a single generally axial force, in this embodiment provided by the centrifugal force acting on the masses 1630.

Figure 53:
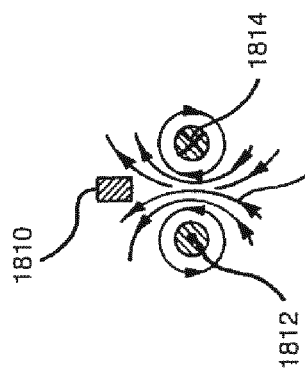
FIG. 53 is a cross sectional view of a portion of the optical element of FIG. 52, showing the magnetic field generated by two electrical coils.
Figure 52:
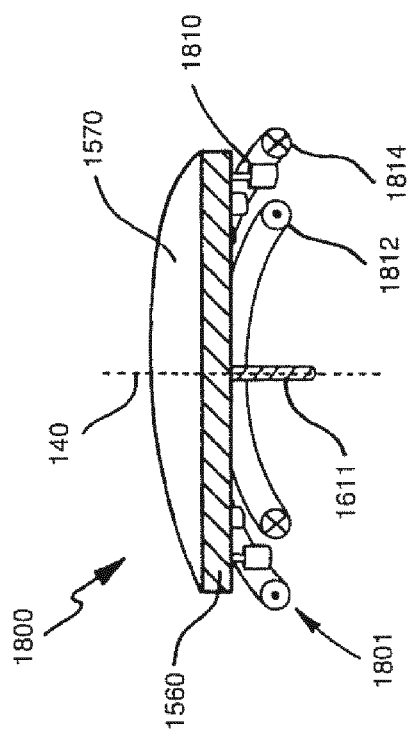
FIG. 52 is a partial cross sectional view of another embodiment of an optical element which may form the optical element of FIGS. 48 and 49.
Figure 54:
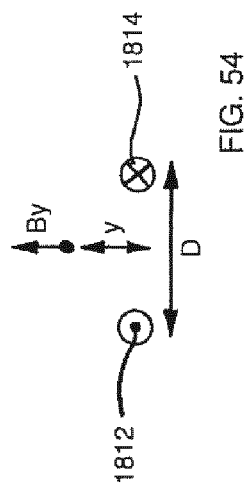
FIG. 54 is a schematic view of the layout of the two electrical coils of the optical element of FIG. 52.

With reference to FIGS. 52 to 54, an optical element 1800 is now described, which may form the optical element 1550 of FIGS. 48 and 49. Features of optical element 1800 that are identical to those of optical elements 1550, 1600, 1700 share common labels and are not described in detail below.

The optical element 1800 is provided with a distortion mechanism 1801, which comprises a plurality of members 1810 extending axially away from the generally disc shaped body 1560. Each of the plurality of members 1810 is formed from a magnetic material and may be of the form of a ferromagnetic plate. Each of the plurality of members 1810 may be formed from a soft magnetic material, which is only magnetised in the presence of an external magnetic field. Such soft magnetic material may be preferred to, for example, permanent magnets because permanent magnets may be affected more by the radiation R emitted from the free electron laser FEL. The plurality of members 1810 are distributed evenly around the circumference of the body 1560. The distortion mechanism further comprises two electrical coils 1812, 1814. The electrical coils 1812, 1814 are stationary, concentric and each form a ring centred on the rotation axis 1590 at substantially the same axial position. A first electrical coil 1812 is disposed radially inwards from the plurality of members 1810 and second electrical coil 1814 is disposed radially outwards from the plurality of members 1810. Each of the coils 1812, 1814 may comprise a multi-strand conductor.

A current passes in opposite directions around the first and second coils 1812, 1814. As shown in FIG. 53, the two coils 1812, 1814 generate a magnetic field 1816 in the vicinity of the plurality of members 1810 which will apply a generally axial force to them. In turn, this generally axial force is transmitted to a radially outer edge of the body 1560.

Therefore, a generally axial force that is applied to a radially outer edge of the body 1560 is generated electromagnetically. This generally axial force will generate a bending moment onto the disc, altering a curvature of the reflective surface 1570. Since a local bending moment will vary with radial distance, an axial thickness of the body 1560 may vary (not shown in FIG. 52). For example, the axial thickness may be largest near the rotation axis 1590, tapering to a smaller thickness towards the edge of the body 1560.

Referring to FIG. 54, the two coils 1812, 1814 are separated radially by a distance D. Each of the plurality of members 1810 is disposed at a radial position which is midway between the two coils 1812, 1814. The magnetic field at this radial position, as a function of the axial distance y from the two coils 1812, 1814 is given by:

$$B_y = \frac{\mu_0 NID}{2\pi\left(y^2 + \frac{D^2}{4}\right)}, \quad (7)$$

where I is the current flowing through the two coils, N is the number of windings in each coil, $\mu_0$ is the magnetic permeability of vacuum, y is the axial distance from the two coils and D is the radial separation of the two coils. Here it is assumed that D and y are much smaller than the diameter of each of the current loops. The maximum field gradient occurs at y=D/2.

Such an arrangement provides a simple mechanism for altering a curvature of the reflective surface 1570. The amount of curvature applied can be adjusted by varying the current through the two electrical coils 1812, 1814.

Figure 55:
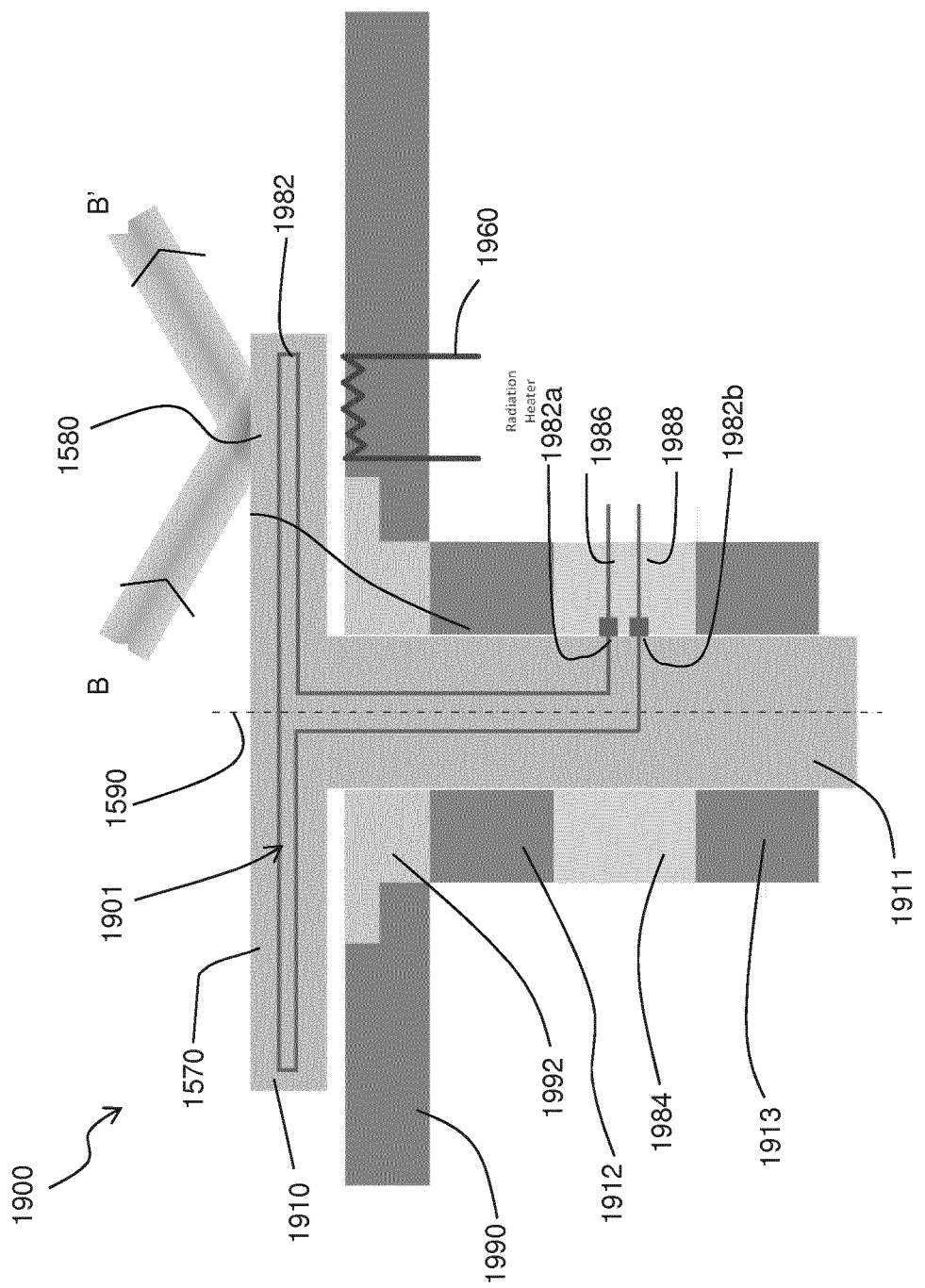
FIG. 55 is a cross sectional view of another embodiment of an optical element which may form the optical element of FIGS. 48 and 49.

FIG. 55 shows an optical element 1900, which may form the optical element 1550 of FIGS. 48 and 49. Features of optical element 1900 that are identical to those of first optical elements 1550, 1600, 1700, 1800 share common labels and are not described in detail below.

The first optical element 1900 comprises an internal cooling system 501, as now described. The internal cooling system 501 comprises one or more channels 1982 for a flow of cooling fluid, such as water, that extend between an inlet 1982a and an outlet 1982b. The one or more channels 1982 are at least partially disposed in a generally disc shaped body 1910 on which the reflective surface 1570 is disposed. The inlet 1982a and outlet 1982b are disposed on a shaft 1911, which is supported for rotation by two bearings 1912, 1913. The channels 1982 extend axially to and from the body 1910 via the shaft 1911.

The internal cooling system 501 further comprises a stationary coolant feed 1984 adjacent to the shaft 1911. The stationary coolant feed 1984 is provided with an inlet 1986 and an outlet 1988. Cool water passes into the stationary coolant feed 1984 via the inlet 1986. As the shaft 1911 rotates, the inlet 1986 is periodically aligned with the inlet 1982a of internal channels 1982, allowing the cool water to pass into the channel 1982 and move towards the rotating body 1910. Heated water passes back down the shaft 1911 from the body 1910. As the shaft 1911 rotates, the outlet 1988 is periodically aligned with the outlet 1982b of internal channels 1982, allowing the heated water to pass from the channel 1982 into the outlet 1988. In alternative embodiments, the stationary coolant feed 1984 and/or the shaft 1911 may be provided with a first circumferentially extending groove at an axial position corresponding to that of inlet 1982a and inlet 1986 and a second circumferentially extending groove at an axial position corresponding to that of outlet 1982b and outlet 1988. The first circumferentially extending groove allows inlet 1982a to be in continuous fluid communication with inlet 1986 and the second circumferentially extending groove allows outlet 1982b to be in continuous fluid communication with outlet 1988. This may increase the efficiency of the internal cooling system 501.

The optical element 1900 is mounted on a wall 1990 such that the body 1910 is disposed on one side of the wall 1990 and the shaft 1911 extends through an aperture in the wall 1990 to an opposite side. The wall is provided with a vacuum seal 1992 allowing the two sides of the wall 1990 to be maintained at different pressures. For example, the side of the wall on which the body 1910 is disposed may be maintained at high vacuum, as required by the EUV radiation beam B, while the opposite side may be at atmosphere pressure.

The internal cooling system of the optical element 1900 can provide cooling very close to the reflective surface 1570 thus minimizing thermal deformation of the reflective surface 1570. In turn, this can significantly reduce the amount of counter-bending required to correct for the thermal deformation of the reflective surface 1570.

The first optical element 1900 is provided with a distortion mechanism, which comprises a heating element 1960 arranged to apply a thermal load to an axially facing surface of the body 1910 opposite to the reflective surface 1570, in the vicinity of the beam spot region 1580.

The thermal load applied may be generally similar to the thermal load applied by the radiation beam B to the beam spot region 1580. Such an arrangement effectively reduces the axial temperature gradient over the body 1910 and therefore reduces the curvature of the reflective surface in the radial direction that arises as a result of this axial temperature gradient (see Eqs. (5) and (6) above).

Alternatively, the thermal load applied may be generally complementary to the thermal load applied by the radiation beam B to the beam spot region 1580. It is to be understood that a second thermal load is generally complementary to a first thermal load if in regions where the first thermal load is relatively low, the second thermal load is relatively high and vice versa. For example, when the thermal load applied by the radiation beam B to the beam spot region 1580 is Gaussian-like the thermal load applied by heating element 1960 may be higher at the edge of the beam spot region 1580 and lower towards the centre of the beam spot region 1580. Such an arrangement may better correct for the variation in heat load applied by the radiation beam B to different parts of the reflective surface 1570.

Figures 56, 57:
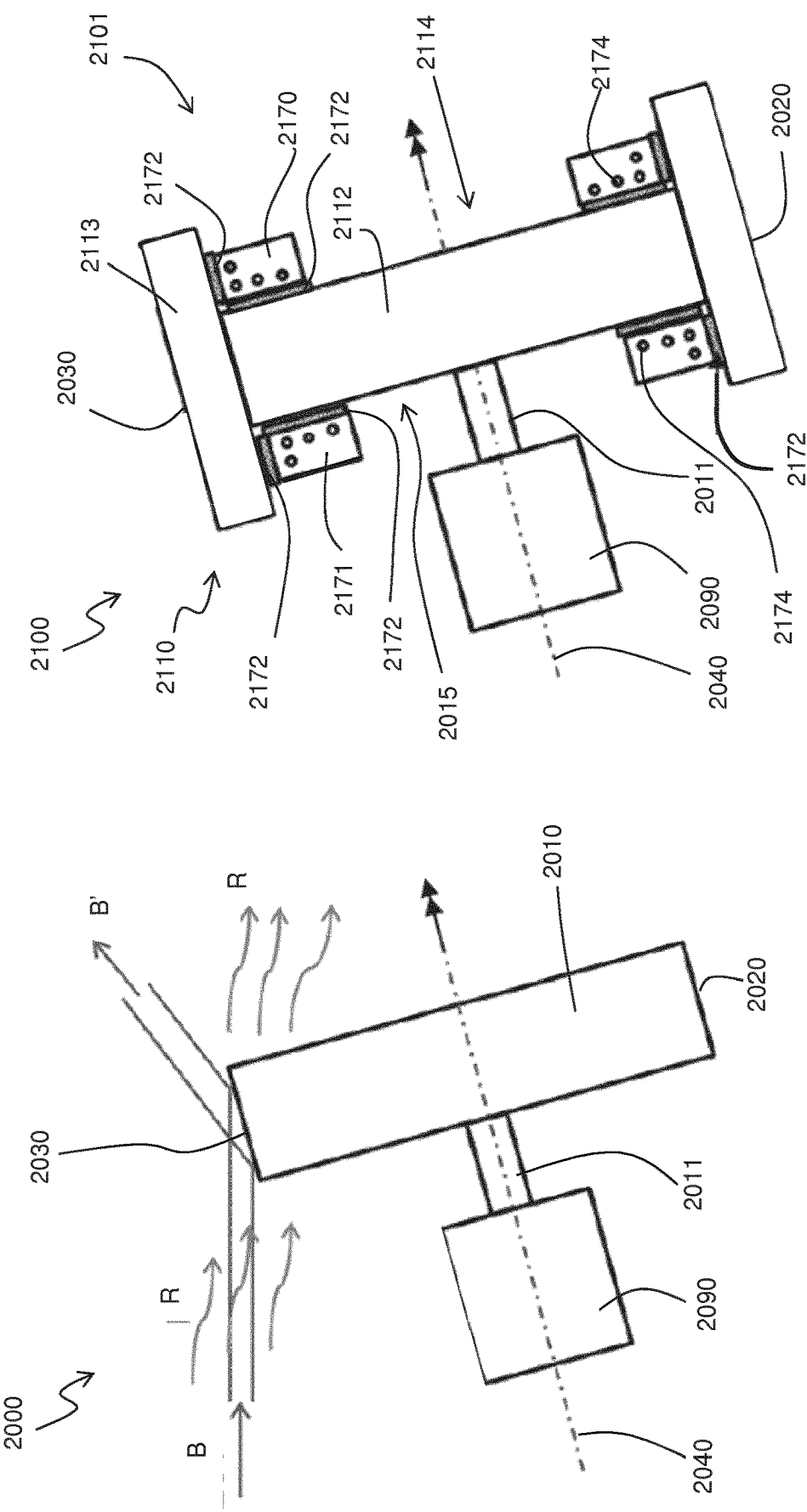
FIG. 56 is a side view of another optical element, which may form the first optical element of a lithographic system described herein.
FIG. 57 is a schematic illustration of an optical element with a cooling system which may form the optical element of FIG. 56.

FIG. 56 shows an optical element 2000, which may form the first optical element 1520 of the lithographic system LS6. The optical element 2000 comprises a generally discshaped body 2010 and a reflective surface 2020 provided on the body 2010 for receiving the radiation beam B from the free electron laser FEL so as to form a beam spot region 2030.

The first optical element 2000 is arranged such that the radiation beam B is incident on the reflective surface 2020 at a small grazing incidence angle, for example, a grazing incidence angle of around 2 degrees (around 0.035 radians). Therefore, the beam spot region 2030 is an elongate ellipse shape. For an incoming radiation beam B with a diameter of 2 mm and a grazing incidence angle of 2 degrees, the beam spot region 2030 is an ellipse with a minor axis length of 2 mm and a major axis length of around 58 mm.

The first optical element 2000 further comprises a movement mechanism that is operable to rotate the body 2010 about a rotation axis 2040. The movement mechanism comprises a shaft 2011 extending from the body 2010 along the rotation axis 2040 and an actuator 2090 arranged to rotate the shaft 2011 about the rotation axis 2040. The shaft 2011 may be supported by one or more bearings (not shown), for example two bearings. For embodiments comprising two bearings, the bearings may be provided on opposite sides of the body 2010. The actuator 2090 may comprise any suitable mechanism such as a motor or engine.

The reflective surface 2020 is disposed on a radially facing surface of the body 2010. As the movement mechanism rotates the body 2010 about the rotation axis 2040, the reflective surface 2020 rotates, causing the beam spot region 2030 to move over the reflective surface 2020. The beam spot region 2030 follows a periodic path over the reflective surface 2020, which extends around the circumference of the body 2010.

A fraction of the power of the radiation beam B is absorbed by the first optical element 2000, causing the reflective surface 2020 to heat up. Since the movement mechanism is operable to move the reflective surface 2020 such that the beam spot region 2030 moves over the reflective surface 2020, the power absorbed by the optical element 2000 is spread over a larger area, decreasing the density of the heat load. Advantageously, this allows the first optical element 2000 to receive radiation beams with higher power densities, in contrast to static optical elements of the same or similar dimensions.

The reflective surface 2020 is disposed on the radially facing surface of the body 2010, which is curved in a tangential direction. Therefore, in a direction perpendicular to the plane of incidence of radiation beam, the first optical element 2000 will increase the divergence of the radiation beam such that the reflected radiation beam B' is more divergent than the incoming radiation beam B. In a direction perpendicular to the plane of incidence of radiation beam, the reflective surface 2020 has a focal length f given by $f=R/(2b)$, where R is a radius of the body 2010 and b is the grazing incidence angle of the radiation beam B in radians. The body 2010 may have a radius of around 0.25 m and a circumference of around 1.6 m. For a body 2010 with a radius of around 0.25 m and a grazing incidence angle of 0.035 radians, the focal length of the reflective surface 2020 is 3.6 m. This curvature is in a tangential direction that is perpendicular to the direction of the radiation beam B. The change in the shape and the divergence of the radiation beam can be corrected for relatively easily using mirrors within the beam delivery system 1519. For example, the beam delivery system 1519 may comprise one or more concave cylindrical mirrors arranged to shape the reflected beam B, for example to a circular shape with a fixed dimension and a limited divergence.

The generally disc shaped body may not be solid. FIG. 57 shows an optical element 2100, which may form the optical element 2000 of FIG. 56. Features of optical element 2100 that are identical to those of first optical element 2000 share common labels and are not described in detail below.

Optical element 2100 comprises a first body portion 2112 and a second body portion 2113. The first and second body portions 2112, 2113 form a generally disc shaped body 2110. The first body portion 2112 is radially inward of the second body portion 2113. An axial thickness of the first body portion 2112 is smaller than an axial thickness of the second body portion 2113 such that the generally disc shaped body 2110 is stepped in cross section, with a generally circular blind bore 2114, 2115 formed on each axially facing surface of the body 2110.

The optical element 2100 is provided with a reflective surface 2020 is disposed on a radially facing surface of the second body portion 2113.

Optical element 2100 further comprises a cooling mechanism 2101 as now described. The cooling mechanism 2101 comprises two generally ring shaped cooling devices 2170, 2171, each disposed in a different one of the generally circular blind bores 2114, 2115 formed on each axially facing surface of the body 2110. Each cooling device has an outer radially facing surface adjacent to an inner radially facing surface of the second body portion 2113 and an axially facing surface adjacent to an axially facing surface of the first body portion 2112. A narrow gap is provided between the rotating body 2110 and each static cooling device 2170, 2171. The gap is filled with layer of liquid metal 2172, which is kept in place by capillary forces. The metal may comprise a fusible alloy which melts at a relatively low temperature. For example, the metal may comprise an alloy of gallium and indium, which may contain 75.5% gallium by weight and 24.5% indium by weight. Such an alloy has a melting point of 15.7° C. The static cooling devices 2170, 2171 are provided with channels 2174 for receiving a flow of fluid such as, for example, water, to transport heat away from the cooling devices 2170, 2171.

Such a cooling mechanism allows water cooling of the rotating body 2110 without using rotating water couplings. This avoids, or at least significantly reduces, the risk of water leakage. The use of a liquid metal layer to transfer heat is a known technique which is compatible with ultra-high vacuum conditions and high angular velocities of the body 2110.

In alternative embodiments, heat may be transferred between the rotating body 2110 and the static cooling devices 2170, 2171 primarily through radiation. For example, opposed surfaces of the body 2110 and the static cooling devices 2170, 2171 may be provided with coatings of a high emissivity material to promote radiation by the body 2110 and absorption of the emitted radiation by the static cooling devices 2170, 2171 across a narrow gap there between. The gap may be filled with a gas such as hydrogen, which may provide additional convective cooling of the body 2110.

The optical element 2100 will absorb a fraction of the energy of the radiation beam B, causing a temperature gradient extending generally radially away from the reflective surface 2020. Heat will flow down this temperature gradient, radially inwards from the reflective surface 2020 and through the body 2110. As a result of the radial temperature gradient, radially different parts of the body 2110 will expand differently, which will cause the reflective surface 2020 to distort such that a curvature of the reflective surface 2020 in the axial direction is altered.

For a body with two opposed surfaces separated by a distance d (the thickness of the body), if a heat load of Q Watts is applied to one of the surfaces, ignoring edge effects, the difference in temperature $\Delta T$ between the two surfaces is given by Eq. (5). For an incoming radiation beam B with a diameter of 2 mm and a grazing incidence angle of 2 degrees, the beam spot region 2030 is an ellipse with a minor axis of 2 mm and a major axis of around 58 mm. Therefore, the heat load will be spread out around a strip of the reflective surface 2020 with a width of around 58 mm and a circumference of around 1.6 m, i.e. an area of around 0.09 $m^2$.

For a body with two opposed surfaces separated by a distance d (the thickness of the body) if one of the two opposed surfaces is heated such that there is a temperature $\Delta T$ between the two surfaces then the heated surface will become convex, with a radius of curvature R given by Eq. (6). It may be desirable to require that the focal length caused by the curvature in the axial direction be above a minimum focal length, for example 3.6 m. Note that this induced curvature in the axial direction is in the plane of incidence of radiation beam. In the plane of incidence of radiation beam B, the focal length is given by f=Rb/2, where R is the radius of curvature and b is the grazing incidence angle in radians. For a grazing incidence angle of 0.035 rad, a minimum focal length of 3.6 m corresponds to a minimum allowed radius of curvature of 206 m. For a disc with an axial dimension of 58 mm, this corresponds to a maximum allowed deformation of the edges of the reflective surface 2020 of 2 µm.

This is achievable for a body 2110 formed from a material such as, for example, silicon carbide (SiC), which has a thermal expansion coefficient of $4 \times 10^{-6}$ $K^{-1}$. For example, if the second body portion 2113 is formed from SiC, has a (radial) thickness of 10 mm, the radial temperature difference across the second body portion 2113 is around 10 K then the radius of curvature is around 1620 m.

Note that in the above calculations, for simplicity, it has been assumed that the heat load from the radiation beam is spread uniformly over a fixed area of the reflective surface 2020. However, in general, the heat load will vary across the fixed area. The heat load on any given portion of the fixed area is dependent upon the intensity distribution of the radiation beam, the grazing incidence angle and the path that the beam spot region 2030 follows over the reflective surface 2020 as the body 2110 rotates. Therefore, in general, in addition to the radial temperature gradient there will be a temperature gradient in the axial direction. As a result, the reflective surface 2020 will deform differently at different axial positions of the reflective surface 2020. That is, a local radius of curvature in the axial direction at a given location on the reflective surface 2020 will be a function of the axial position of that location. As a result, the reflective surface 2020 will no longer act as a cylindrical lens with constant curvature in the axial direction. Rather, a radius of curvature of a given location on the reflective surface 2020 in the axial direction will be dependent upon the axial position of that location. Therefore, in the axial direction, different parts of the reflective surface 2020 will, in general, have different focal lengths and the reflective surface 2020 will no longer act as a cylindrical lens. Note that this thermally induced curvature of the reflective surface 2020 is perpendicular to the intrinsic curvature of the reflective surface 2020 in the tangential direction, which remains substantially unchanged. Correction for the thermally induced curvature, wherein the radius of curvature of the reflective surface 2020 varies axially is challenging. Therefore the body 2110 of optical element 2100 may be shaped so as to at least partially reduce a variation in temperature of the reflective surface 720 caused by the radiation beam B.

The variation in the radius of curvature in the axial direction across the reflective surface 2020 may be eliminated if the temperature of the reflective surface 2020 is constant. Therefore the body 2110 of optical element 2100 may be shaped so as to at least partially reduce a variation in temperature of the reflective surface 720 caused by the radiation beam B. For example, the body 2110 may be shaped so that the thermal resistance of the path followed by the heat as it flows away from the reflective surface 2020 differs for different axial positions on the reflective surface 2020.

For example, the body 2110 may be shaped so as to taper inwards in the radial direction to form a constriction below the reflective surface 720, as now described.

Referring to FIGS. 58 and 59, thermal maps 2200, 2250 are shown for two different geometries of the body 2110. Each map 2200, 2250 shows a temperature variation of the body 2110 both axially (from left to right) and radially (from bottom to top). An upper edge 2201, 2251 of each map 2200, 2250 corresponds to the reflective surface 2020 of the optical element 2100 and a lower edge 2202, 2252 of each map 2200, 2250 corresponds to the rotation axis 2040 of the optical element 2100. The location of two cooling devices 2170, 2171 is indicated schematically on each map 2200, 2250.

The maps 2200, 2250 have been calculated based on a radiation bean B with a two-sigma Gaussian-like intensity distribution depositing a heat load of 1500 W on the reflective surface 2020. A plurality of lines 2210, 2260 indicating constant temperature are shown on each map 2200, 2250 respectively. The spacing between each pair of adjacent lines 2210, 2260 corresponds to a temperature difference of 0.5 K. The temperature is highest at the upper edge 2201, 2251 of each map 2200, 2250. The material is either aluminium or silicon and has a thermal conductivity of around 150 $Wm^{-1}K^{-1}$. Cooling from the axial faces of the body 2110 is at a rate of 5000 $Wm^{-2}K^{-1}$ and the circumference of the body 2110 is 1.5 m.

Map 2200 of FIG. 58 corresponds to a body 2010 with a uniform axial thickness. Map 2250 of FIG. 59 corresponds to a body 2010 with an axial thickness that varies with radius. In particular, moving radially inwards from the reflective surface 2020, the axial thickness of the body initially decreases to form a constriction 2270 and then increases back to the axial thickness of the reflective surface 2020. The variation in the temperature of the reflective surface 2020 is 1.1 K for the body with uniform axial thickness and 0.2 K for the body with a constriction 2270. Therefore, the provision of the constriction 2270 reduces the temperature gradient in the axial direction on the reflective surface 2020 and, as a result, the variation in the radius of curvature across the reflective surface 2020 is reduced.

It will be appreciated that the various embodiments described above may be combined. For example, the first optical element 1520 may comprise a distortion mechanism that is a combination distortion mechanism 1601 (using masses) and distortion mechanism 301 (using magnetism).

Whilst the example embodiments described with reference to FIGS. 47 to 59 comprise a radiation source SO3 comprising a free electron laser FEL, it should be appreciated that a radiation source may comprise any number of free electron lasers FEL. For example, a radiation source may comprise more than one free electron laser FEL. Alternatively, the radiation source SO3 may not comprise a free electron laser and may, for example, comprise a laser produced plasma (LPP) or a discharge produced plasma (DPP) radiation source.

It will be understood that the heat loads and the area over which these are applied described above are by way of example only and that the invention is not limited to the above described values. For example, the radiation beam output by the radiation source may have any power, it may be incident upon the reflective optical element at any grazing incidence angle, the beam spot region may trace out any size area of the reflective surface, and the reflective surface may have any reflectivity.

Although the embodiments of the first optical element 1520 described above comprise a generally disc shaped body that is arranged to rotate about a central rotation axis, movement of the reflective surface such that the beam spot region moves over the reflective surface following a periodic path may be achieved otherwise.

It will be appreciated that the term "axial direction" is a direction along, or parallel to a rotation axis. It will be appreciated that the term "radial direction" is a direction running through a rotation axis and perpendicular to said rotation axis. It will be appreciated that the term "tangential direction" is a direction perpendicular to an axial direction and a radial direction.

It will be appreciated that the term "axially facing surface" is a generally flat surface whose normal is generally in an axial direction. It will be appreciated that the term "radially facing surface" is a generally curved surface whose normal is generally in a radial direction.

It will be appreciated that "curvature of a surface in an axial direction at a given point on said surface" means a curvature of the curve that is formed by the intersection of said surface and a plane containing the normal vector of the surface at that point and a vector in the axial direction. This may be referred to as "an axial curvature of the surface". Similarly, it will be appreciated that "curvature of a surface in a radial direction at a given point on said surface" means a curvature of the curve that is formed by the intersection of said surface and a plane containing the normal vector of the surface at that point and a vector in the radial direction. This may be referred to as "a radial curvature of the surface".

It is a feature of various embodiments described above that an optical system 40 comprising various optical elements as described above may be used to direct the radiation beams B', B" to beam splitting apparatus 20 from where the radiation beams can be provided to one or more of the lithographic apparatus. In alternative embodiments, other optical system arrangements, for example other beam delivery system arrangements, can be provided in which arrangements of optical elements are used to direct a radiation beam from an FEL source to a beam splitter or directly to lithographic apparatus, and/or to shape the radiation beam.

In general, it is important that the optical elements of the optical system are kept in an environment at which there is a sufficiently high pressure of hydrogen (for example, around 1 Pa pressure of hydrogen) or other suitable gas such as helium or, in some cases, argon, oxygen or nitrogen, to prevent or reduce build-up of carbon on the optical elements. The hydrogen can react with the carbon to prevent or reduce carbon deposits. However, the electron beam line of the FEL source must operate at ultra-high vacuum, for example at pressures of around $10^{-8}$ Pa. Therefore, it has been found that the FEL source and the optical system should be separated in such a way as to allow for an increase in the vacuum (decrease in the pressure) between the optical system and the FEL source.

Figures 60, 61:
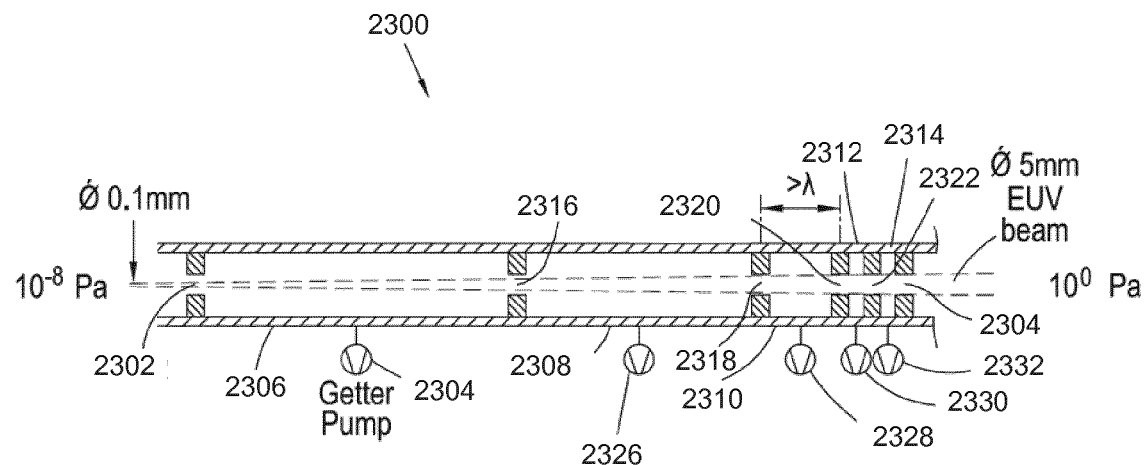
FIG. 60 is a schematic illustration of an apparatus that can be provided between an FEL source and an optical system to provide a suitable variation of pressure between the FEL source and the optical system.
FIG. 61 is a schematic illustration of part of the apparatus of FIG. 60.

In the system of FIGS. 1 to 5, for example, a further apparatus can be provided between the FEL source and the optical system 40 to provide a suitable variation of pressure between the FEL source and the optical system. An example of such a further apparatus 2300 according to one embodiment is shown in FIG. 60.

The apparatus 2300 comprises a long tube (in this case, approximately 50 m long) divided into sections 2306, 2308, 2310, 2312, 2314, separated by walls each with an aperture 2316, 2318, 2320, 2322 through which a radiation beam emitted by the undulator of the FEL source can pass. The apparatus 2300 includes an input aperture 2302 for receiving the beam of radiation from the FEL source and an output aperture 2304 for outputting the beam of radiation, with the input aperture 2302 and the output aperture 2304 being separated by the sections 2306, 2308, 2310, 2312, 2314 also referred to as chambers. The diameter of the radiation beam will usually increase as it travels away from the undulator and, for example, may have a diameter of around 100 microns when it leaves the undulator and may diverge towards a 5 mm diameter after around 50 m. Therefore, the apertures 2316, 2318, 2320, 2322 between the chambers increase with distance from the undulator in the embodiment of FIG. 60. Although five sections or chambers 2306, 2308, 2310, 2312, 2314 are provided in the embodiment of FIG. 60, any suitable number, size and arrangement of sections or chambers can be provided in alternative embodiments to provide a desired pressure variation between input and output apertures.

Each chamber 2306, 2308, 2310, 2312, 2314 includes a respective pumping port and each chamber can be provided with a respective vacuum pump 2324, 2326, 2328, 2330, 2332 for pumping the chamber via the pumping port of the chamber. In the apparatus of FIG. 60, pumps 2326, 2328, 2330, 2332 for pumping chambers 2308, 2310, 2312, 2314 are turbo-molecular pumps. Chamber 2306 is adjacent to the FEL source and in this case a getter pump 2324 is used to pump chamber 2306. Any suitable arrangement and type of vacuum pumps can be used to pump the different chambers in alternative embodiments depending on the pressures that are required to be achieved.

At pressures below $1\times10^{-3}$ Pa, the mean free path of hydrogen molecules becomes >10 m. The thermal velocity of hydrogen at room temperature is about $v_m=1.8$ km/s. This means that in the case of the apparatus of FIG. 60, hydrogen molecules that pass approximately parallel to the EUV beam may not be pumped and may end up in the undulator. This is illustrated in FIG. 61, which shows part of the apparatus of FIG. 60 and in which molecule "3" can be seen to travel ballistically into the undulator of the FEL source. Only a single pump 2326 is shown in FIG. 61 for clarity.

As the pressure in the chambers decreases (moving from right to left in the case of FIG. 60) the number of collisions between molecules becomes smaller and ballistic behaviour of the molecules can become more significant.

In the case of the apparatus of FIG. 60, with a pressure of around 1 Pa at the output aperture 2304 the pressure in chamber 2326 may reach approximately $1 \times 10^{-3}$ Pa. Taking the area of the aperture 2318 between chambers 2308 and 2310 as being $A_2=4$ mm$^2$ and taking the area of the input aperture as being $A_1=1$ cm$^2$ the ballistic gas throughput (for example in Pam$^3$/s) from aperture 2318 to the input aperture 2302 can be taken as being:—

$$Q=A_1 A_2 v_m \rho_1/(2L^2) \qquad (8)$$

Taking the length between aperture 2318 and the input aperture 2302 as being 30 m (compared to a total distance between the input aperture 2302 and output aperture 2304 of around 50 m) the ballistic gas throughput to input aperture 2302 may be just acceptable if a pressure of around $10^{-8}$ Pa is to be maintained in the undulator of the FEL source.

However, it may be desirable to increase the area of aperture 2318 and the other inter-chamber apertures. It may also be desirable to reduce the length of the apparatus 2300, and in consequence the distance L, significantly. The EUV beam is divergent, starting at 0.1 mm diameter in the undulator 24 and expanding to, for example, 5 mm at 50 m distance. However, due to the presence of the steering unit 25 (shown in FIGS. 3, 4) it may be more convenient to place the input aperture at, for example, 10 m distance from the undulator, where the EUV beam has a diameter of around 1 mm. Including a margin, one could use an aperture of diameter 2 mm (3 mm$^2$ area). In some embodiments of the FEL, the divergence of the EUV beam or the distance from the undulator may be larger, requiring a larger aperture size. It may be desirable to keep apparatus 2300 within the buildings 31', 31" or within other shielded area, and reduction in length of the apparatus 2300 may have a significant impact in reducing construction size. However, increases in aperture area and reduction in length of the apparatus 2300 would be expected to increase the ballistic gas throughput to the FEL source. Furthermore, the actual pressure in the intermediate chamber 2310 is difficult to control and predict precisely in practice. If the pressure in the chamber 2310 were to be, for example, around $1 \times 10^{-4}$ Pa then there would be significant ballistic gas transport from the next chamber 2312, which may have a pressure of around $1 \times 10^{-2}$ Pa, to the FEL source. Increased ballistic gas transport to the FEL source may result in an unacceptably high gas pressure in the undulator of the FEL source.

Figure 62:
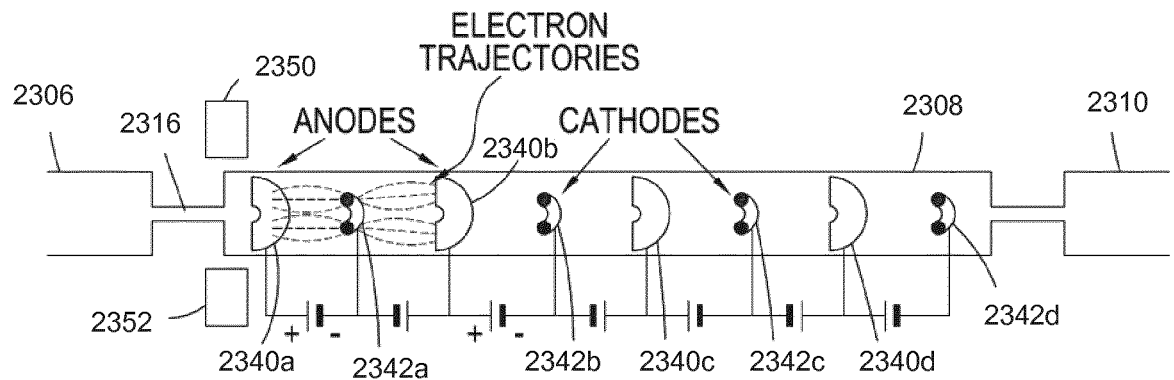
FIG. 62 is a schematic illustration of an electron source installed in a chamber of the embodiment of FIG. 60.

FIG. 62 is a schematic illustration of part of apparatus 2300 according to an embodiment. In the embodiment of FIG. 62 electron sources in the form of pairs of ring-shaped anodes 2340a, 2340b, 2340c, 2340d and cathodes 2342a, 2342b, 2342c, 2342d are provided in chamber 2308 of apparatus 2300 around the radiation beam path. The cathodes and anodes form part of a thermionic emission apparatus that includes heating components (not shown) for heating the cathodes to emit electrons via thermionic emission and power and control apparatus (not shown) for applying suitable electric potential difference between the anodes and cathodes and for controlling the quantity and energy of electrons emitted by the cathodes in operation.

In the embodiment of FIG. 62 the cathodes are formed of LaB$_6$ or CeB$_6$, for instance as sold by Electron Microscopy Sciences®, which are suitable for high current densities and medium-high vacuum conditions. However, any suitable materials for the cathodes and anodes can be used in alternative embodiments.

The pumps, pumping ports and other chambers of the apparatus 2300 are not shown in FIG. 62 for clarity.

A pair of magnets 2350, 2352 is also provided, which are operable to apply a magnetic field in the region of the chamber 2308 near the aperture 2316 in order to alter trajectories of ionized gas atoms or molecules.

In operation of the apparatus 2300, the various pumps 2324, 2326, 2328, 2330, 2332 are operated to maintain vacuums in the chambers 2306, 2308, 2310, 2312, 2314 whilst the FEL source is operational to produce a radiation beam that passes through the apparatus 2300 between the input aperture 2302 and the output aperture 2304. The radiation beam has a wavelength of between 4 nm and 25 nm in this case.

At the same time the electron sources are operated to provide a flow of electrons through the chamber between the cathodes 2342a, 2342b, 2342c, 2342d and anodes 2340a, 2340b, 2340c, 2340d.

At least some of the electrons emitted by the cathodes 2342a, 2342b, 2342c, 2342d interact with and ionize hydrogen (or other atoms or molecules) present in the chamber 2308. The magnetic field applied by the magnets 2350, 2352 causes the ions to change direction and hit a wall of the chamber 2308 or the aperture between chambers 2308 and 2306, which breaks the ballistic trajectories and allows pumping using regular vacuum pumps, for example pump 2326 of chamber 2308 or pump 2324 of chamber 2306. Thus, the use of the electron source to ionize atoms or molecules, and the magnetic field, can be used to alter the trajectory of gas atoms or molecules following ionization to enable pumping of the gas atoms or molecules and to decrease ballistic transport of the gas atoms or molecules to the input aperture 2302 and consequently to the undulator. The strength of the magnetic field applied by the magnets 2350, 2352 can be selected, based on the size of the chambers and other operating parameters, to ensure that most or all of the ionized gas atoms or molecules collide with the walls of the chamber or aperture. For example, hydrogen ions at v=1.8 km/s will have a curvature radius R=my/(Be)=0.2 mm for an applied magnetic field of B=0.1 T or 2300 mm for an applied magnetic field of B=0.1 mT (roughly the earth's magnetic field). Thus, in some embodiments no external magnetic field is applied to disrupt the ballistic trajectories of the ionized gas atoms or molecules and instead the background magnetic field (e.g. the earth's magnetic field) is used to disrupt the ballistic trajectories and cause collisions with the walls of the chamber or aperture.

In some variants of the embodiment of FIG. 62, or other embodiments that use cathode and anode arrangements, the walls of the chamber are set at a lower potential than the cathodes in order to increase the electron density at the centre of the chamber, thereby to increase the probability of collisions between the electrons and gas atoms or molecules.

A pair of magnets 2350, 2352 is used to alter the trajectories of ionized atoms or molecules, in this case ionized hydrogen molecules, in the embodiment of FIG. 61. In alternative embodiments an electric field rather than a magnetic field may be used to alter the trajectories of ionized atoms or molecules. Any suitable arrangement for applying an electric field may be used. For example a suitable electrical potential may be applied to a wall of the chamber 2308, chamber 2306, or to a wall of the aperture between the chambers 2308, 2306 or to a further component of the apparatus positioned within or near to a chamber or aperture, to attract or repel the ionized atoms or molecules.

In the embodiment of FIG. 62, the electron source is operated in such a way as to provide electrons with a desired energy or range of energies. The ionization interaction cross section of the electrons depends on their energies and so by suitable control of the electron energies the probability of ionization of hydrogen molecules (or indeed other atoms or molecules) occurring can be increased. The variation of interaction cross sections for electron collisions with hydrogen molecules are described in "Cross Sections and Related Data for Electron Collisions with Hydrogen Molecules and Molecular Ions", H. Tawara et al, J. Phys. Chem. Ref. Data, Vol. 19, No. 3, 1990 and suitable electron energies can be selected from data provided in that paper, for example based on the plot of FIG. 2 of that paper. According to the paper, the collision cross section for ionization of hydrogen molecules is about $\sigma=1\times10^{-20}$ m$^2$ at 100 eV electron energy. If the path length over which ballistic hydrogen molecules can interact with the electrons is X, then the current density should satisfy:—

$$J >> ev_m/(\sigma X) = 0.5 \text{ A/cm}^2 \qquad (9)$$

assuming X=5 m and e=1.6×10$^{-19}$ C. This appears to be a manageable current density in practice.

In some modes of operation of the embodiment of FIG. 62, the electron source is controlled so that the electrons (in the absence of, or until they have, collisions) have a desired value of kinetic energy, for example between 20 eV and 2400 eV, optionally between 60 eV and 100 eV, further optionally around 80 eV, when they pass through the regions of the chamber where hydrogen molecules having a ballistic trajectory that would take them to the input aperture 2302 are most likely to be present. For example, the electron source may be controlled so that the electrons have the desired value of kinetic energy when they pass through the centre of the chamber 2308.

Any suitable arrangement of anodes and cathodes may be provided to form the electron source. For example, in a variant of the embodiment of FIG. 62, each anode and cathode pair includes a further anode (not shown in FIG. 62) for example in the form of a mesh or grid, positioned close to the cathode and acting as an accelerating anode to accelerate the electrons to have a desired kinetic energy or range of kinetic energies. The other anode 2340a, 2340b, 2340c, 2340d of each pair then acts as a collecting electrode to collect the electrons after passage through the chamber 2308. The use of the further anode may, in some arrangements, reduce the variation in kinetic energy of electrons during their travel between the further anode and anode, and in some arrangements may enable the kinetic energies to remain within a desired range during that travel. Any other suitable electron source arrangement may be used, based for example on any known thermionic, hot cathode, field emission or other techniques.

In order to increase the probability of collision between one or more of the electrons and hydrogen molecules in the chamber, in some embodiments measures are taken to increase the length of the path followed by the electrons through at least the part of the chamber where hydrogen molecules following a ballistic trajectory leading to the input aperture 2302 may be most likely to be present. For instance, in some embodiments, an applied electric or magnetic field is used to alter trajectories of the electrons in the chamber. An example of an electron source and magnetic field arrangement according to one such embodiment is illustrated schematically in FIG. 63.

Figure 63:
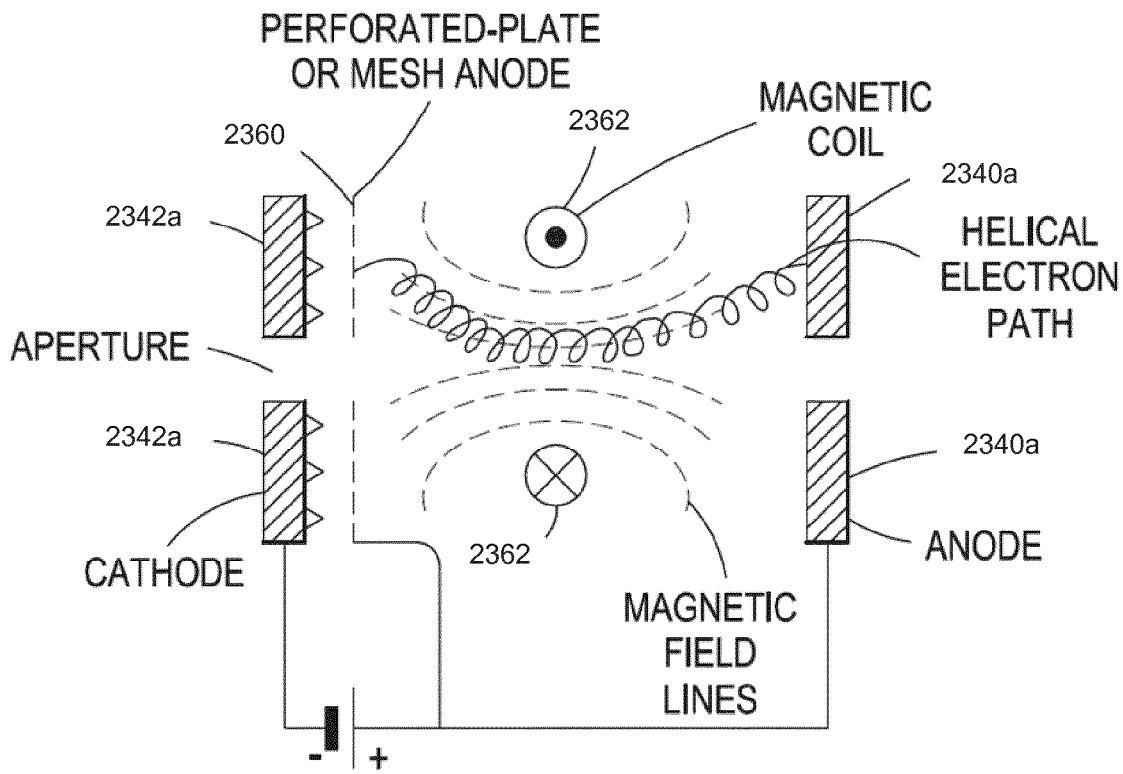
FIG. 63 is a schematic illustration of an electron source comprising a cathode and anode arrangement according to an alternative embodiment.

FIG. 63 is a cross sectional view through part of a chamber, for example chamber 2308, of the apparatus 2300 and shows one of the ring shaped cathodes 2342a and an associated one of the ring shaped anodes 2340a. It can be seen that both the cathode 2342a and anode 2340a include an aperture that is aligned with the apertures 2316, 2318 of the chamber 2308 to allow the passage of the radiation beam from the FEL source. In this embodiment a further accelerating anode 2360, in the form of a perforated plate or mesh is provided as part of the cathode arrangement. A magnet coil arrangement 2362 is also provided, which in operation is used to apply a magnetic field to the part of the chamber through which electrons from the cathode 2342a pass. The magnet coil arrangement in this case comprises a magnet coil whose plane is perpendicular to the path of the radiation beam from the FEL source. The magnetic field applied by the magnet coil arrangement 2362 causes the electrons to follow an at least partially helical path between the cathode arrangement and the anode 2340a, as illustrated schematically in FIG. 63 for one electrode, thereby increasing the current density and the chances of collision between electrons and hydrogen molecules.

Any other suitable arrangement of anodes and cathodes, and magnetic or electric fields to alter the trajectory of electrons emitted by the cathodes can be provided in alternative embodiments, so as to alter the trajectory of the electrons to follow any desired paths. One such alternative embodiment is illustrated schematically in FIG. 64, which provides a cross sectional view through part of a chamber, for example chamber 2308, of the apparatus 2300 and shows a planar cathode 2370 and associated planar anode 2372 aligned above and below, respectively, the path followed by the radiation beam provided by the FEL source. In this case a magnet coil arrangement (not shown in FIG. 64) is provided that applies a magnetic field between the planar cathode 2370 and anode 2372 to cause the electrons passing from the cathode 2372 to the anode 2370 to follow an at least partially helical path.

Figure 65:
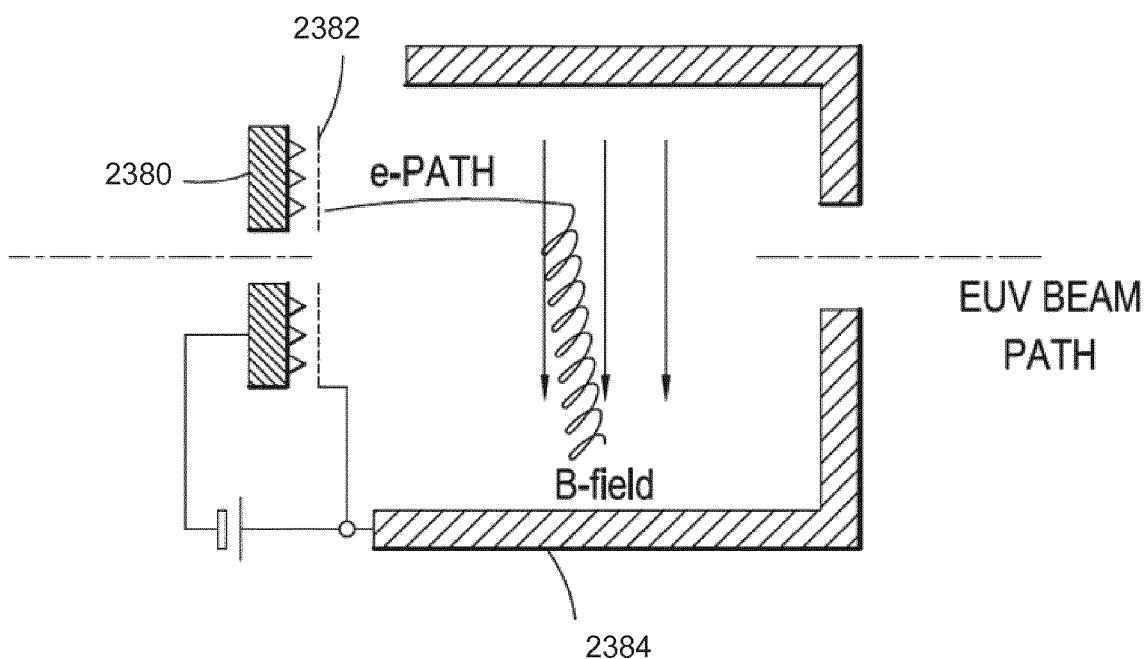
FIG. 65 is a schematic illustration of an electron source comprising a cathode and anode arrangement according to a further alternative embodiment.

A further alternative embodiment is shown schematically in FIG. 65, which provides a cross sectional view through part of a chamber, for example chamber 2308, of the apparatus 2300 and shows a ring shaped cathode 2380 that includes an aperture that is aligned with the apertures 2318, 2320 of the chamber 2308 to allow the passage of the radiation beam from the FEL source, and an anode 2384. In this embodiment a further accelerating anode 2382, in the form of a perforated plate or mesh is provided as part of the cathode arrangement. The anode 2384 is a planar anode arranged perpendicular to the cathode and aligned along a wall of the chamber 2310. In this case a magnetic coil arrangement (not shown) applies a magnetic field perpendicular to the radiation beam path and causes the electrons to follow an at least partially helical path as they travel to the anode 2382.

Figure 64:
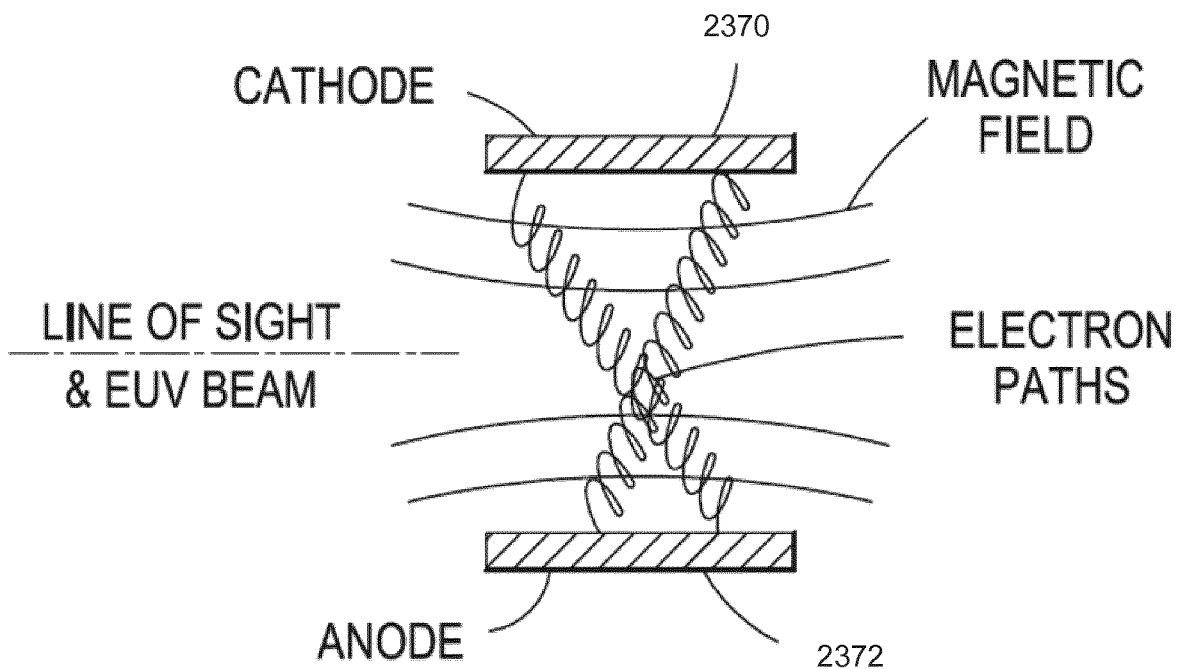
FIG. 64 is a schematic illustration of an electron source comprising a cathode and anode arrangement according to another alternative embodiment.

In the embodiments of FIGS. 63 to 65, a magnetic field source in the form of an electromagnet can be used to alter the trajectory of the electrons, and the magnetic field source is separate from the magnets 2350, 2352 that are used to alter the trajectories of the ionized hydrogen molecules or other gas atoms or molecules. In alternative embodiments, a single magnet, for example a single magnet coil arrangement, may be used both to alter the trajectory of the electrons and to alter the trajectory of the ionized hydrogen molecules. In other embodiments, no additional magnetic field source is operated to alter the trajectories of the ionized gas atoms or molecules and instead the background magnetic field (e.g. the earth's magnetic field) is sufficient to alter the trajectories of the ionized gas atoms or molecules to the required extent.

In the embodiments of FIGS. 62 to 65, the use of magnetic fields to alter the trajectories of both electrons and ionized atoms or molecules (in particular, ionized hydrogen molecules) has been described. In alternative embodiments electric fields instead of or as well as magnetic fields can be used to alter the trajectories of either or both the electrons and the ionized atoms or molecules. The electric fields in such embodiments can be provided using any suitable components, for example any suitable electric field source. In some embodiments an electric field can be provided by applying a suitable electrical potential to a wall of one of the chambers, or a passage between chambers, or to some other component of the apparatus within or near one or more of the chambers or the apertures between chambers.

Embodiments described in relation to FIGS. 62 to 65 use cathode and anode arrangements to generate electrons by way of thermionic emission. Any other suitable arrangements to generate electrons or other particles or radiation for ionizing hydrogen or other atoms or molecules can be used in alternative embodiments. For example, in one embodiment, a relatively heavy noble gas, such as neon, argon, krypton, or xenon, is injected in the chamber. The absorption cross section of xenon for EUV is about 500 times higher than that of hydrogen, which will be in a permanently ionized state due to the presence of EUV radiation. Moreover, EUV ionization will yield electrons at 88 eV, which is close to the optimal energy for the ionization of hydrogen gas. In an embodiment, an ion source such as a duoplasmatron is used to generate a proton beam, with ion energies around 100 eV. These protons can be trapped in a magnetic field of, for example, 0.1 Tesla, and have enough energy to ionize multiple hydrogen atoms.

Figure 66:
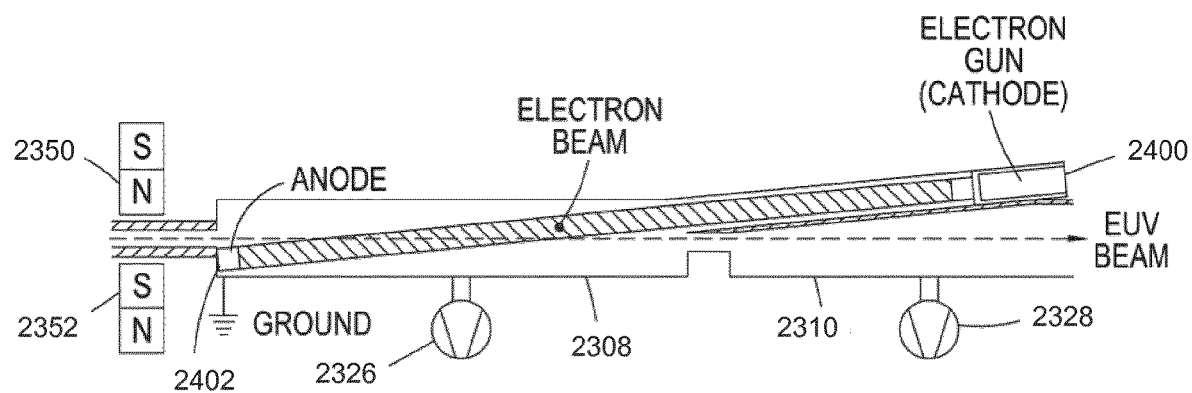
FIGS. 66 and 67 are schematic illustrations showing further alternative electron source arrangements.

FIG. 66 shows an arrangement for generating an electron beam for ionizing hydrogen or other atoms or molecules within chambers 2308 and 2310 according to an alternative embodiment. In this case an electron gun arrangement 2400 including a cathode for producing a collimated beam of electrons is provided in chamber 2308 and is arranged to direct the collimated beam of electrons to an anode 2402 within chamber 2308 so as to ionize hydrogen or other atoms or molecules within chamber 2308, chamber 2310 or the aperture between them.

Figure 67:
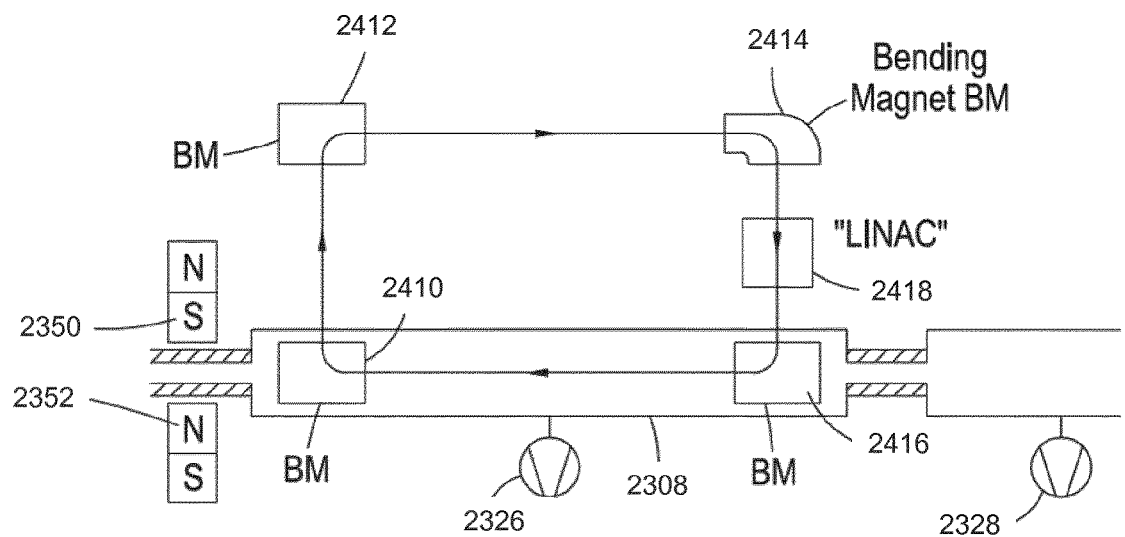

FIG. 67 shows an alternative arrangement for generating an electron beam for ionizing hydrogen or other atoms or molecules within chamber 2308 according to a further alternative embodiment. In this case an arrangement of bending magnets 2410, 2412, 2414, 2416 and a linear accelerator (LINAC) 2418 are arranged to provide a recirculating beam of electrons of appropriate energy to ionize hydrogen or other atoms or molecules within chamber 2308.

In embodiments described in relation to FIGS. 62 to 67, anode or cathode arrangements, or other arrangements for producing electrons for ionizing hydrogen or other atoms or molecules, for example oxygen, argon or nitrogen, are provided in apparatus 2300. Apparatus 2300 is described above as having a length of around 50 m between input aperture 2302 and output aperture 2304. However, by using ionizing electrons to reduce ballistic passage of hydrogen molecules to the input aperture 2302, in some embodiments the length of the apparatus 2300 can be reduced whilst still maintaining desired pressure levels in operation at the undulator of the FEL laser and the beam delivery system (for example, around $10^{-8}$ Pa at the undulator and around 1 Pa at the beam delivery system or other optical system). For example in variants of the embodiments of FIGS. 62 to 67 the distance between the input aperture 2302 and output aperture 2304 is reduced to around 10 m to 20 m.

Figure 68:
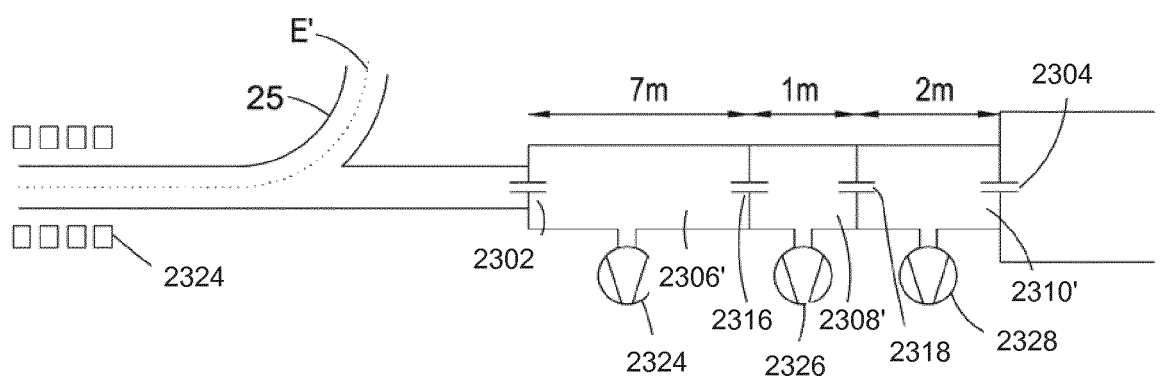
FIG. 68 is a schematic illustration of an apparatus according to a further embodiment.

A further, reduced length embodiment is illustrated schematically in FIG. 68, in which the length of the apparatus between the input aperture and the aperture is reduced to around 10 m. In this embodiment, the anode and cathode arrangements of the embodiment of FIG. 62 or of other embodiments, and associated magnetic or electric field source (omitted in some variants of the embodiment) are positioned in chamber 2306'. Chamber 2306' has a length of around 7 m, chamber 2308' has a length of around 1 m, and chamber 2310' has a length of around 2 m.

In the embodiment of FIG. 68, pumps 2324, 2326 and 2328 pump at around 100 litres/second. Apertures 2302, 2316, 2318 each have a length of 50 mm and a diameter of 3 mm, aperture 2304 has a length of 5 mm and a diameter of 3 mm, and chambers 2306', 2308' and 2310' have a diameter of 100 mm. With this configuration, chamber 2310' can be expected to be a pressure of $1 \times 10^{-2}$ Pa and have a mean free path for hydrogen molecules of 1 m. With the length (2 m) of chamber 2310', it can be assume that the molecules passing through aperture 2318 are not beamed too much (e.g. not have a ballistic trajectory directed toward aperture 2302). Chambers 2308', 2306' will have pressures of around $1 \times 10^{-5}$ Pa and $1 \times 10^{-8}$ Pa respectively, not counting the effect of beaming from aperture 2318 towards aperture 2302. Without ionizing equipment, you would get $-5 \times 10^{-8}$ Pa inside the undulator (e.g. 5 m of 10 mm diameter pipe). If a mistake were to be made in dimensioning pump 2328 and aperture 2304, resulting in a much lower pressure (e.g. $1 \times 10^{-3}$ Pa) inside chamber 2310', then p1 in the equation (8) becomes not $1 \times 10^{-2}$ Pa (from chamber 2310') but rather 1 Pa (the pressure upstream), since there will not be enough gas collisions inside 2310 to break the molecular beam. That would result in 100× more molecular beam flux towards the undulator, and 100× more pressure. Thus, it can be understood that correct selection of apparatus dimensions, pump capacities and other apparatus parameters can be important. Tolerances and sensitivity of the operating pressure in the undulator to parameter variations can be improved by increasing the length of the apparatus in some cases.

Although five chambers 2306, 2308, 2310, 2312, 2314 are provided in apparatus 2300 according to the embodiment of FIG. 60, any suitable number of chambers and vacuum pumps can be provided in alternative embodiments to provide the desired pressures at the input to and output from the apparatus, and in some variants or embodiments the use of electrons or other particles or radiation to ionize hydrogen or other atoms or molecules can enable a reduced number of chambers to be provided.

Although embodiments have been described in which the radiation source comprises a free electron radiation source, in alternative embodiments any suitable radiation source for providing radiation of a desired wavelength may be used. For example, in some embodiments the radiation source comprises a synchrotron radiation source.

Although embodiments have been described in relation to the ionizing of hydrogen molecules, the embodiments can also be used to ionize and remove other gas atoms or molecules that may be present in some cases, for example oxygen, argon or nitrogen. Electron energies or other ionizing particles or radiation may be selected accordingly.

Any suitable magnitude of electric or magnetic field may be used to alter the trajectory of electrons or other charged particles, or the trajectory of ionized gas atoms or molecules, and the appropriate size of field may be selected based, for example, on the particular size, materials and/or arrangement of components and/or desired operating parameters in particular embodiments.

Figure 69:
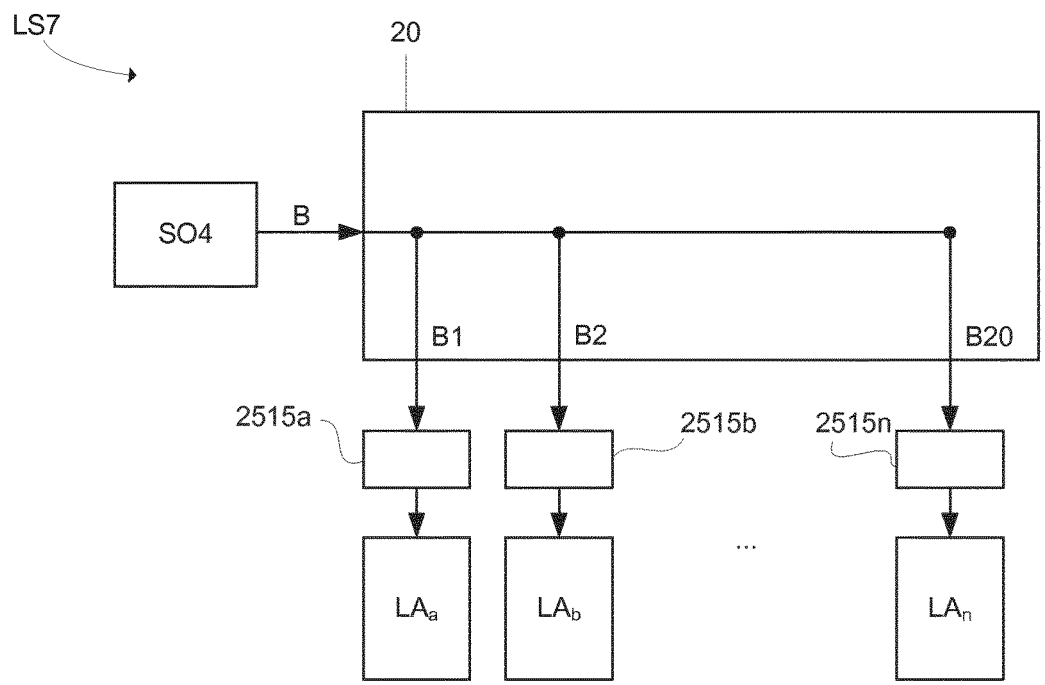
FIG. 69 depicts a lithographic system comprising a beam splitting apparatus according to an embodiment of the invention.

FIG. 69 shows an example lithographic system LS7. The lithographic system LS7 is similar to the lithographic system LS of FIG. 1 and includes the beam splitting apparatus 20 according to one embodiment of the invention. The lithographic system LS7 further comprises a radiation source SO4 and a plurality of lithographic apparatuses $LA_a$-$LA_n$. For example, there may be 20 lithographic apparatuses.

Where the source SO4 comprises a free electron laser, the source SO4 may output relatively high-power radiation. For example, a free electron laser source SO4 may output a radiation beam B that provides branch radiation beams B1 to B20 each of the order of 1 kW. For some lithographic apparatus, it may be desirable to reduce an amount of radiation that is received at the lithographic apparatus. For example, a substrate of a lithographic apparatus may comprise a layer of resist which requires a dose of radiation of approximately 5 mJ/cm$^2$. Receipt of a high-power branch radiation beam at that lithographic apparatus may cause difficulties in ensuring that the resist is provided with a suitable dose of radiation. One way to decrease the dose of radiation received at a portion of the substrate is to move the substrate with respect to the radiation incident upon the substrate (scanning). It may be difficult, however, to achieve a sufficiently high scan speed to achieve a desired dose of radiation at the substrate.

In embodiments of the present invention, the branch radiation beams B1-B20 are directed through a respective attenuator 2515a-2515n. Each attenuator 2515a-2515n is arranged to adjust the intensity of a respective branch radiation beam B1-B20 before the branch radiation beam B1-B20 passes into the illumination system IL of its corresponding lithographic apparatus $LA_a$-$LA_n$.

Figure 70A:
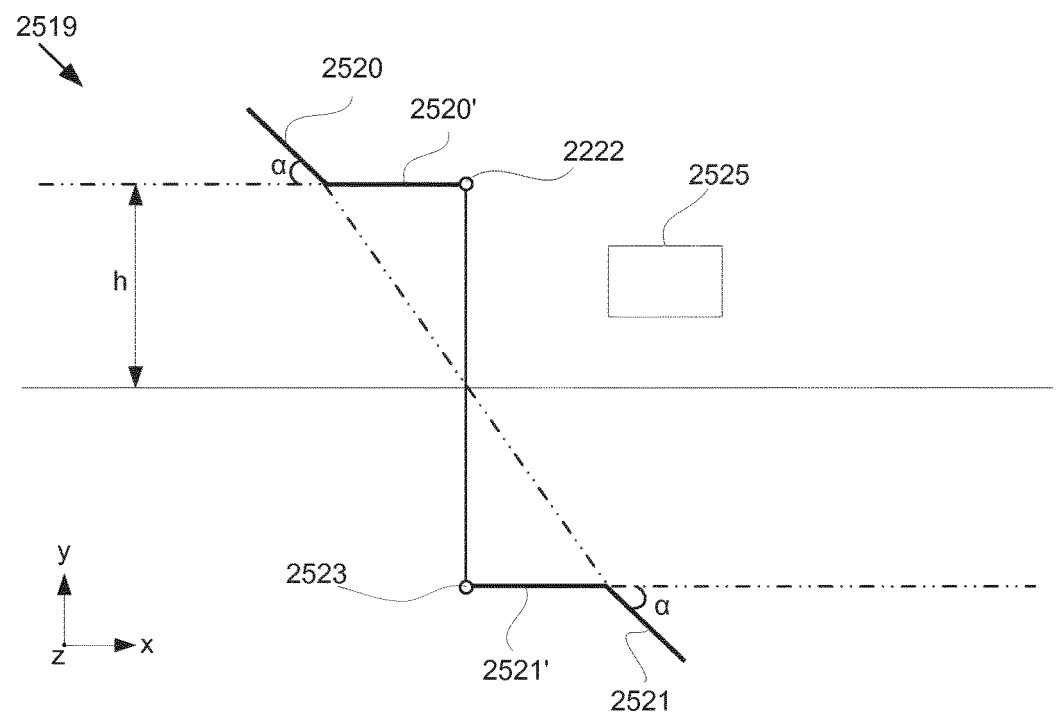
FIGS. 70A, 70B are schematic illustrations of an attenuation apparatus of the lithographic system of FIG. 69.
Figure 70B:
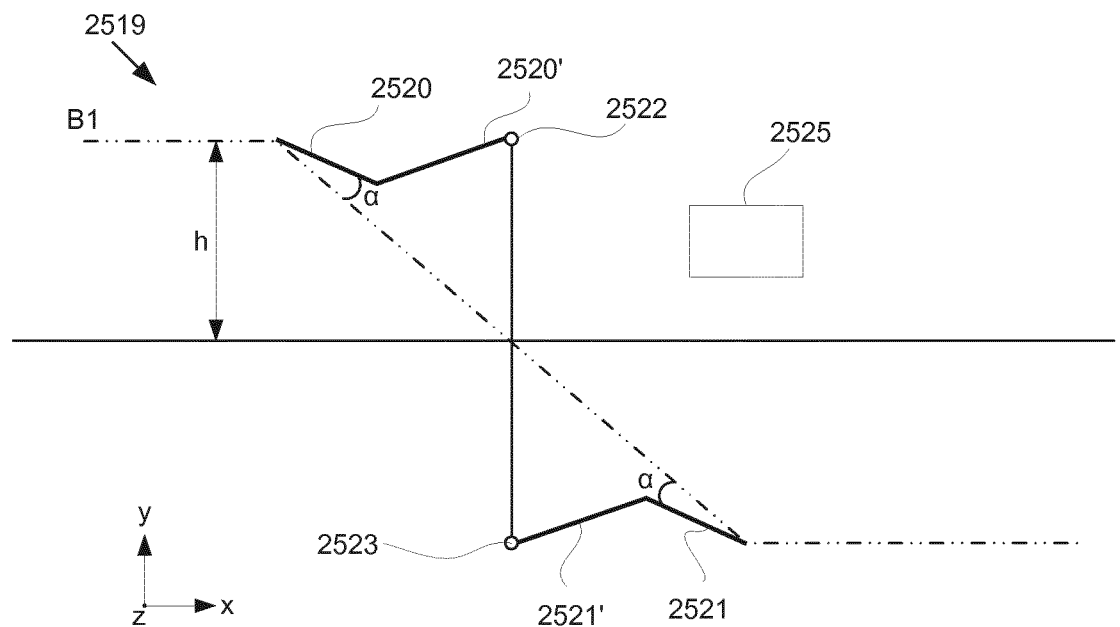

Referring to FIGS. 70a, 70b there is illustrated an example of a first attenuation apparatus 2519 that may be provided by the attenuator 2515a. The branch laser beam B1 is depicted in dashed-dot outline. The attenuator 2515a comprises a first mirror 2520 and a second mirror 2521. The second mirror 2521 is separated, in a depicted y-direction, from the first mirror 2520 by a distance 2h. The second mirror 2521 is arranged so that the branch radiation beam B1 entering the attenuator 2515a is incident on a reflective surface of the first mirror 2520 and reflected by the reflective surface towards a reflective surface of the second mirror 2521. The second mirror 2521 is angled so as to direct the branch radiation beam B1 towards the lithographic apparatus $LA_a$ (not shown in FIG. 70).

The first mirror 2520 is connected to a first pivot point 2522 via an arm 2520', while the second mirror is connected to a second pivot point 2523 via an arm 2521'. A first adjustment means (not shown) is provided to rotate about the first pivot point 2522, and a second adjustment means (not shown) is provided to rotate the second mirror 2521 around the second pivot point 2523. The first and second adjustment means may take any appropriate form as will be readily apparent to the skilled person. For example, the adjustment means may comprise to suitable motors disposed at the pivot points 2522, 2523 and connected to the arms 2520', 2521'.

Through rotation of the mirrors 2520, 2521 about the pivot points 2522, 2523, an angle of incidence a of the mirrors 2520, 2521 with respect to the branch radiation beam B1 may be adjusted. It will be appreciated that as the mirrors 2520, 2521 are disposed at the same angle of incidence a, after reflection by the mirrors 2520, 2521, the branch radiation beam B1 propagates in the same direction as before reflection by the mirrors 2520, 2521.

The mirrors 2520, 2521 are arranged to reflect the branch radiation beam B1 with what is commonly referred to as grazing (or glancing) incidence reflection. In FIG. 70a, the mirrors 2520, 2521 are shown disposed at a maximum angle of incidence a, such that the branch radiation beam is incident on a bottom portion (with respect to the y-direction) of the mirror 2520 and a top portion (with respect to the y-direction) of the mirror 2521. In some embodiments, the maximum value of the angle α may be, for example, an angle of approximately 10 degrees.

In FIG. 70b, the mirrors 2520, 2521 are shown disposed at a minimum angle α of incidence such that the branch radiation beam B1 is incident on a top portion of the mirror 2520 and a bottom portion of the mirror 2521. The minimum value of the angle α may be, for example, an angle α of approximately 1 degrees. In the depicted example, therefore, the mirrors 2520, 2521 are rotatable about the respective pivot points 2522, 2523 between angles of incidence of 1 degrees to 10 degrees. It will be appreciated that in other embodiments, the arrangement and/or size of mirrors 2520, 2521 may be different so as to allow a larger or smaller angular range. For example, the pivot points 2522, 2523 may be selected so as to increase or decrease the useful angular range of the mirrors 2520, 2521. Further, while the mirrors 2520, 2521 are each shown as being arranged to rotate around a fixed pivot point, this is merely exemplary. It will be appreciated that the angle of incidence of the mirrors 2520, 2521 may be adjusted using any other appropriate adjustment means as will be readily apparent to the skilled person. In an embodiment, the mirrors 2520, 2521 may both be arranged to rotate about the same pivot point. By appropriate selection of the position of the pivot points 2522, 2523, a displacement of the outgoing branch radiation beam B1 with respect to the incoming branch radiation beam B1, (i.e. 2h in the embodiment of FIGS. 70a, 70b), can be made substantially constant for angles α within a predetermined, relatively small range (a shown in FIGS. 70a, 70b). For larger angular ranges of the angle α, however, where the displacement of the outgoing branch radiation beam with respect to the incoming branch radiation beam is to be substantially constant, at least one of the mirrors 2520, 2521 or both, may be provided with translational means suitable to translate one or both of the mirrors 2520, 2521 in the y-direction.

The reflectance of each of the mirrors 2520, 2521 is a function of the angle of incidence a between the mirror 2520, 2521 and the branch radiation beam B1. For example, for an incidence angle of 2 degrees, approximately 98% (in a theoretical case of a mirror having a ruthenium (Ru) coating having perfectly flat surface) of the incident radiation may be reflected at each of the mirrors 2520, 2521. That is, when angled at 2 degrees, radiation reflected by one of the mirrors 2520, 2521 is reduced by 2% compared to the intensity of the radiation that is incident on that mirror. As such, where both of the mirrors 2520, 2521 are disposed at an angle α f 2 degrees, the intensity of the branch radiation beam B1 is reduced by approximately 4% through reflection by the mirrors 2520, 2521.

For an incidence angle of 10 degrees (the maximum angle used in the example above), approximately 90% of the incident radiation may be reflected at each of the mirrors 2520, 2521. That is, when the angle of incidence is 10 degrees, the intensity of the reflected radiation is approximately 10% less than the incident radiation. As such, where both of the mirrors 2520, 2521 are disposed at an angle of incidence a of 10 degrees, the intensity of the branch radiation B1 is reduced by approximately 20% through reflection by the mirrors 2520, 2521.

From the above description, it will be appreciated that by adjustment of the angle α between 1 and 10 degrees, the intensity of the branch radiation beam B1 received at the lithographic apparatus LA$_a$ may be varied between 2% and 20%.

In some embodiments the angle of incidence of the mirrors 2520, 2521 may be adjusted at a frequency of up to 1 KHz, thereby providing a rapid adjustment mechanism for the attenuation of the branch laser beam B1. The first and second adjustment means may be connected to a controller 2525. The controller 2525 may be arranged to receive instructions indicating a desired intensity of the branch radiation beam B1 to be received at the lithographic apparatus LA$_a$. In response to receipt of such instructions, the controller may be arranged to control the adjustment means to adjust the angle of incidence a of the mirrors 2520, 2521 to achieve a desired attenuation of the branch radiation beam B1 and thereby a desired intensity at the lithographic apparatus LA$_a$.

The controller 2525 may be part of a feedback control loop arranged to detect an intensity of the branch radiation beam B1 received at the lithographic apparatus LA$_a$ and to adjust the attenuation of the branch radiation beam B1 in order to maintain the intensity at the lithographic apparatus LA$_a$ at a predetermined value or within a predetermined range.

In other embodiments, the angles of incidence of each of the mirrors 2520, 2521 may be adjustable independently of one another. While this would result in a change in the direction of propagation of the branch radiation beam B1, this may beneficially increase the number possible attenuation values in, for example, embodiments in which the angle of incidence of a mirror 2520, 2521 is adjustable only in discrete steps.

It will be appreciated that while the embodiments described above are described with reference to the attenuator 2515a, the attenuators 2515b-2515n may be similarly implemented.

Figure 71:
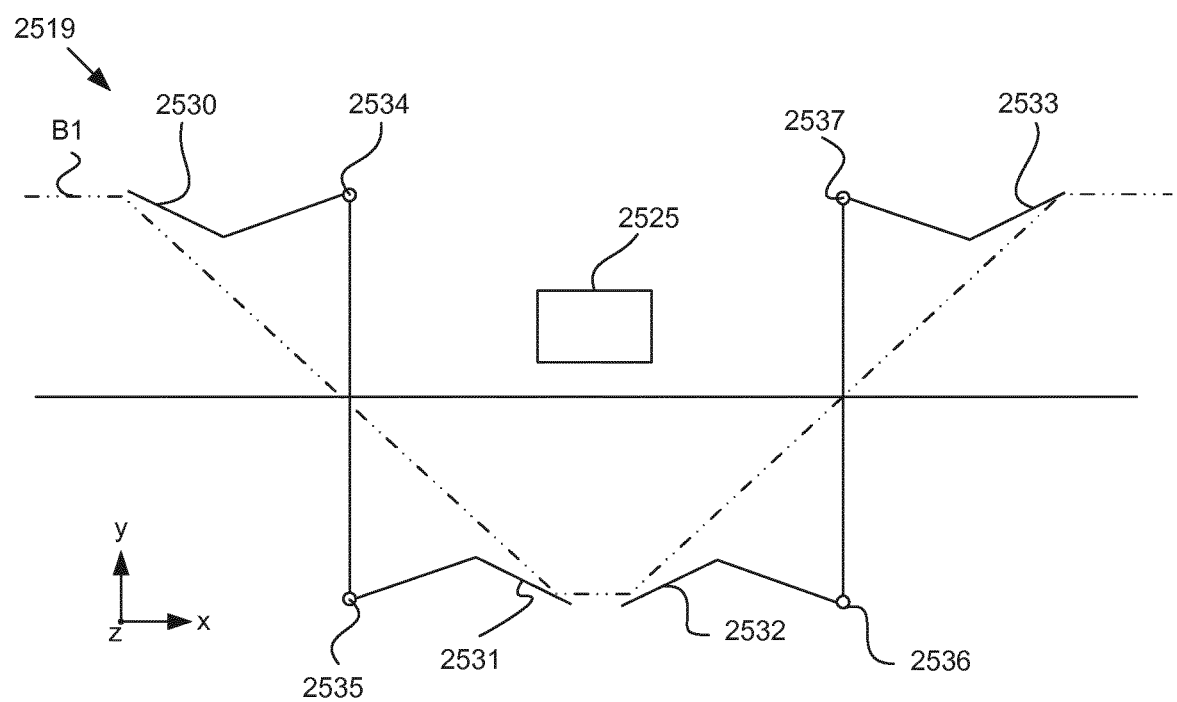
FIG. 71 is a schematic illustration of an alternative attenuation apparatus of the lithographic system of FIG. 69.

Referring to FIG. 71, there is illustrated an alternative embodiment of a first attenuation apparatus 2519 that may be provided within the attenuator 2515a. In the embodiment of FIG. 71, the first attenuation apparatus 2519 comprises four mirrors 2530, 2531, 2532, 2533. The mirrors 2530, 2531 are arranged similarly to the mirrors 2520, 2521 as described above with reference to FIGS. 70a, 70b. In particular, the first mirror 2530 is provided with first adjustment means arranged to rotate the mirror 2530 about a first pivot point 2534 to which the mirror 2530 connects via an arm 2530'. The second mirror 2531 is provided with a second adjustment means arranged to rotate the mirror 2531 about a second pivot point 2535 to which the mirror 2531 connects via an arm 2531'.

The mirrors 2532, 2533 are arranged similarly to the mirrors 2530, 2531, but may be considered to be a "mirroring" of the arrangement of the first mirror 2530 and the second mirror 2531 along a an axis perpendicular to the direction propagation of the branch radiation beam B1. In particular, the third mirror 2532 is disposed at the same position in the y-direction as the second mirror 2531 and is arranged to receive radiation reflected from the second mirror 2531. The third mirror is provided with a third adjustment means arranged to rotate the mirror 2532 about a third pivot point 2536. The third mirror 2532 is arranged to reflect received radiation towards the fourth mirror 2533 which is separated from the second mirror 2532 in the y-direction by a distance of 2h (i.e. the fourth mirror 2533 is at the same position in the y-direction as the first mirror 2530). The fourth mirror 2533 is provided with a fourth adjustment means arranged to rotate the mirror 2533 about a fourth pivot point 2537. The fourth mirror 2533 arranged to direct radiation to the lithographic apparatus LA$_a$ (not shown in FIG. 71).

Where the angle of incidence a of each of the first to fourth mirrors 2530-2533 is the same, the branch radiation beam B1 exits the attenuator 2515a in the same direction and at the same position in the y-direction as it enters the attenuator 2515a. Additionally, by using four mirrors, each being operable to adjust the angle of incidence through a range of 1 degrees and 10 degrees, a possible attenuation range of the attenuator 2515a is increased from a range of 2% to 20% (in the arrangement of FIG. 70) to a range of 4% to 40% (i.e. a possible transmission range of 96% to 60% of the radiation entering the attenuator 2515a). It will be appreciated that where a greater minimum attenuation is acceptable, the greater range of attenuation achievable in the embodiment of FIG. 71 may be advantageous.

Further, the embodiment of FIG. 71 may be utilised to provide the same or a similar attenuation range to that which may be provided by the embodiment of FIG. 70 with a smaller effect on the polarisation of the branch radiation beam B1. That is, due to the smaller angle of incidence a required to achieve a particular attenuation, the combined effect of the four mirrors 2530 to 2533 on the P and S polarisation components of the branch radiation beam B1 is smaller than the combined effect of the two mirrors 2520, 2521 for a given attenuation. This is particularly the case for attenuations of or approaching 20% (i.e. as the angle of incidence a of each mirror 2520, 2521 approaches 10 degrees).

In some embodiments it may be desired to retain, as far as possible, a generally circular polarisation exhibited by the branch radiation beam B1 before it enters the attenuator 2515a. In this case, an attenuation range of approximately 2% to 20% may be achieved with an angular adjustment range of between approximately 1 degrees and 5 degrees. This embodiment may therefore be particularly beneficial for having a reduced effect on the polarisation of the branch radiation beam B1.

Further, in the arrangement of FIG. 71, translational means for providing translational correction of one or more of the mirrors 2530 to 2533 are not required. The outgoing beam has the same angle and position as the incoming beam for all values of alpha (when angles alpha are equal for all four mirrors). Put another way, any change in the distance 2h caused by the mirrors 2530, 2531 is "reversed" by the mirrors 2532, 2533, such that translation of the mirrors in the y-direction is not required to ensure that the branch radiation beam B1 leaves the attenuator 2515a at the same position as it enters.

FIG. 71 may be considered to show two sets of two mirrors; a first set containing the mirrors 2530, 2531 and a second set containing the mirrors 2532, 2533. It will be appreciated that in other embodiments additional mirrors, or additional sets of mirrors may be provided to further increase the possible attenuation range, or to reduce alterations to the polarisation of the branch radiation beam B1.

In addition to the first attenuation apparatus described above, a second attenuation apparatus may be provided within one or more of the attenuators 2515a to 2515n. The second attenuation apparatus may provide a fixed attenuation. Alternatively, the second attenuation apparatus may provide an adjustable attenuation apparatus that is adjustable at a slower rate, and/or with a higher range of possible attenuation values.

Figure 72A:
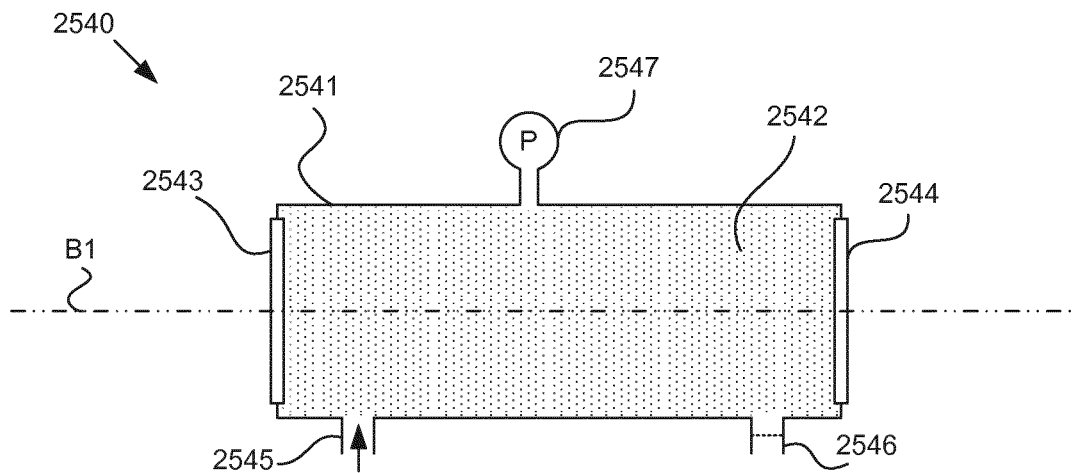
FIGS. 72A, 72B are schematic illustrations of further attenuation apparatus of the lithographic system of FIG. 49.

FIG. 72a schematically depicts an example of a second attenuation apparatus 2540 that may be provided in combination with, or in the alternative to, a first attenuation apparatus as described above with reference to FIGS. 3 and 4. While referred to herein as "first" and "second" attenuation apparatus, it is to be understood that this does not imply an ordering. Indeed, where provided in combination, the branch radiation beam B1 may pass through either one of the first or second attenuation apparatus before passing through the other.

Where one of the first or second attenuation apparatus provides a larger attenuation (for example, where the second attenuation apparatus provides an attenuation factor of 10), it may be desirable to place the second attenuation apparatus after (with respect to the direction of propagation of the branch radiation beam B1) sensors that monitor an intensity of the radiation, for example, for a control loop.

The attenuation apparatus 2540 comprises a housing 2541 defining a chamber 2542. The housing 2540 may define a chamber 2541 of any shape. For example, the housing 2541 may be generally tubular. The chamber 2542 is closed at a first end by a first window 2543 and at a second, opposing end, by a second window 2544. An inlet 2545 is provided to allow a controlled amount of a gas, into the chamber 2542. A valve 2546 may also be provided to allow a controlled flow of gas from the chamber 2542. A pressure monitor 2547 is provided to monitor a pressure within the chamber 2542. The pressure monitor 2547 may be any form of pressure monitor. By providing a gas flow, rather than a fixed, enclosed gas medium, energy absorbed by the gas may be removed. The amount of energy thus removed may be substantial where the attenuation apparatus 2540 provides a large attenuation factor (such as a factor of 10).

The inlet 2545 allows the introduction into the chamber 2542 of an EUV absorbing gas. It will be appreciated that the particular gas introduced into the chamber 2542 may be selected in dependence upon a desired level of EUV absorption. As an example, however, gasses such as Hydrogen, Helium and/or Argon may be suitable. The windows 2543, 2544 are constructed so as to provide a high transmittance for EUV radiation and may be constructed to provide a high absorbance to other wavelengths of electromagnetic radiation. For example, the windows may comprise what are commonly referred to as spectral purity filters, which filter radiation outside of the EUV wavelength, but which allow the transmission of EUV radiation. Such spectral purity filters may be constructed in any appropriate way as will be apparent to those skilled in the art. For example, the windows 2543, 2544 may be constructed from molybdenum (Mo) and zirconium silicide (ZrSi). The Mo/ZrSi stack may be capped on one or both sides with molybdenum silicide (MoSi). In an alternative example the windows 2543, 2544 may be formed from polysilicon (pSi) One or both of the sides of the polysilicon film may be capped with a silicon nitride (SiN) layer. Other materials, for example graphene, may be suitable for use in the windows 2543, 2544. The thickness of the windows 2543, 2544 may be selected in dependence upon a maximum pressure desired within the chamber 2542, which itself may be selected in dependence upon a desired attenuation.

The branch radiation beam B1 enters the second attenuation apparatus 2540 through the first window 2543 and is attenuated by way of interaction with the fluid within the chamber 2542, before exiting the attenuation apparatus 2540 through the second window 2544. An attenuation of the branch radiation beam B1 caused by passage through the chamber 2542 may be varied by varying the type, amount or pressure of gas within the chamber 2542.

The pressure sensor, gas inlet and gas valve may be in communication with a controller such as the controller 2525 (FIGS. 3, 4), or a separate controller. The controller may be operable to control the gas inlet 2545 and the gas valve 2546 to achieve a desired pressure within the chamber 2542. The desired pressure within the chamber 2542 may be selected so as to achieve a desired attenuation of the branch radiation beam B1 to be caused by the second attenuation apparatus. Alternatively or additionally, a desired pressure within the chamber 2542 may be selected to maintain a pressure within the chamber 2542 within a predetermined safe range.

Figure 72B:
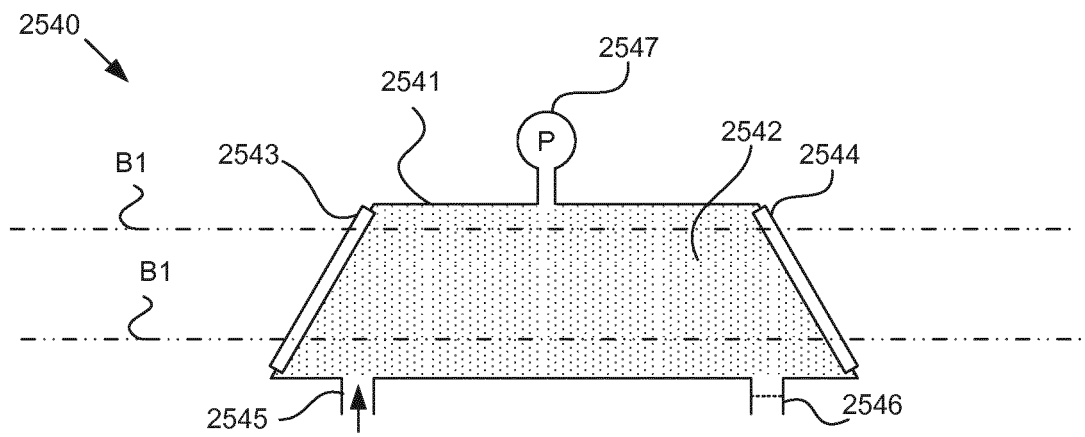

An alternative embodiment of the second attenuation apparatus is illustrated in FIG. 72b in which like components have been provided with like reference numerals. In the example embodiment of FIG. 72a, both of the windows 2543, 2544 are perpendicular to the direction of propagation of the branch radiation beam B1 along their length. As such, the path of the branch radiation beam B1, through the chamber 2542, is the same length irrespective of the position at which the branch radiation beam B1 enters the chamber 2542. In the alternative example shown in FIG. 72b, the windows 2543, 2544 are angled towards each other with respect to the direction of propagation of the branch radiation beam B1. In this way, where the branch radiation beam B1 enters the chamber 2542 at one position, it will travel a shorter distance through the chamber 2542 than when the branch radiation beam B1 enters the chamber 2542 at a different, lower (in the y-direction in FIG. 72) position. As such, attenuation of the branch radiation beam can be varied by varying the position at which branch radiation beam B1 enters the chamber 2542. Moreover, this arrangement can also be used to generate an intensity gradient over the cross section of the light beam. Such an intensity gradient may be used to correct for intensity variations over the illumination field.

Generally, the range in which attenuation of the branch radiation beam B1 may be varied using the second attenuation apparatus of FIGS. 72a, 72b is larger than the range of attenuation adjustment achievable with the first attenuation apparatus of FIGS. 70a, 70b and 71. However, the speed with which the attenuation may be adjusted is slower than that of the first attenuation apparatus. For example, the chamber 2542 may be emptied of gas in order to decrease the attenuation. However, this may take a significant length of time compared to the time required to adjust the mirrors 2530 to 2533, for example.

Figure 73:
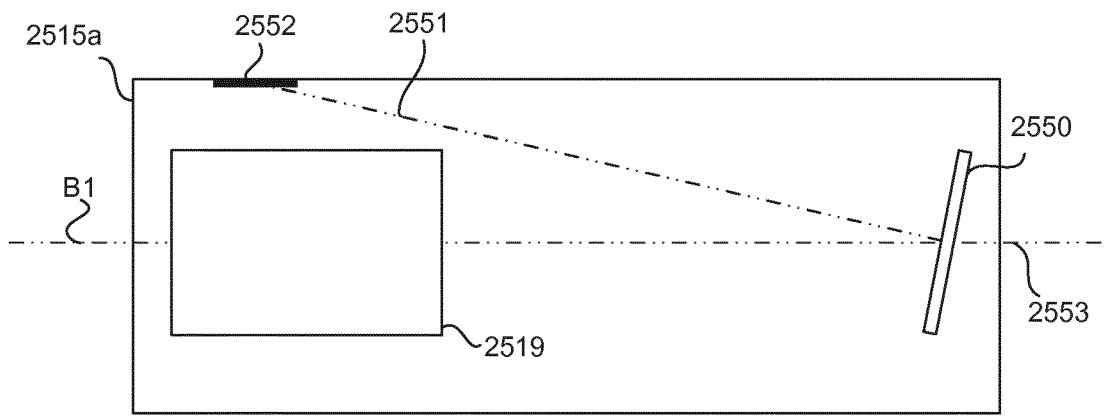
FIG. 73 is a schematic illustration of a further attenuation apparatus of the lithographic system of FIG. 69.

Referring to FIG. 73, there is shown a further alternative embodiment, in which a second attenuation apparatus is provided by an EUV reflective membrane 2550 disposed in the path of the branch radiation beam B1 at a near-normal angle of incidence. The membrane 2550 may be constructed similarly to the windows 2543, 2544 described above. The membrane 2550 may be of any suitable dimensions depending on the construction and materials used.

The branch radiation beam B1 leaves the first attenuation apparatus 2519 and is incident upon the membrane 2550. The membrane 2550 is oriented so as to create an angle of incidence of the branch radiation beam B1 which causes a portion 2551 of the branch radiation beam B1 to be reflected towards a radiation dump 2552 disposed on a wall of the attenuator 2515a. A portion 2553 of the branch radiation beam B1 is transmitted through the membrane 2550. It will also be appreciated that a portion of the branch radiation beam B1 not reflected will be absorbed by the membrane 2550. The angle of incidence of the branch radiation beam B1 and the membrane 2550 may be a near-normal incidence angle substantially avoiding reflection radiation towards the previous optical element (i.e. the first attenuation apparatus 2519 in FIG. 73.

In FIG. 73, the reflective membrane 2550 is disposed after the first attenuation apparatus 2519 (with respect to the direction of propagation of the branch radiation beam B1) within the attenuator 2515a, however in other embodiments, the order of attenuation apparatus within the attenuator 2515a may be otherwise. It will further be appreciated that a plurality of membranes such as the membrane 2550 may be provided in sequence to further increase an attenuation of the branch attenuation beam B1.

Further, while it is described above that an attenuator may comprise a first and second attenuation apparatus, it will be appreciated that an attenuator may comprise further attenuation apparatus. For example, the embodiments of FIG. 73 may be combined with other embodiments, to provide an attenuator with an attenuation apparatus of FIG. 3 or 4, an attenuation apparatus of FIG. 72a, 72b and an attenuation apparatus comprising a membrane such as the membrane 2550. Other configurations are also possible.

While it is described above that a respective attenuator 2515a-2515n is provided for each branch radiation beam, it will be appreciated that in other embodiments, an attenuator may be provided for only one or some of the branch radiation beams. Further, a single attenuator may be provided for a plurality of branch radiation beams. That is, while the attenuators 2515a-2515n are shown disposed outside of the beam splitting apparatus 20, in other embodiments, an attenuator as described herein may be disposed within the beam splitting apparatus 20 so as to attenuate a plurality of branch radiation beams. For example, to attenuate all of the branch radiation beams $B_b$-B20 together, an attenuator may be provided immediately after the branching of the first branch radiation beam B1. Indeed, as will be apparent to the skilled person from the teaching herein, any combination or configuration of attenuators may be provided.

More generally, it will be readily appreciated from the teaching herein that an attenuator 15 as generally described above may be positioned elsewhere within the lithographic system before the substrate. For example, with reference to FIG. 2, an attenuator may be positioned within the illuminator IL.

Figure 74:
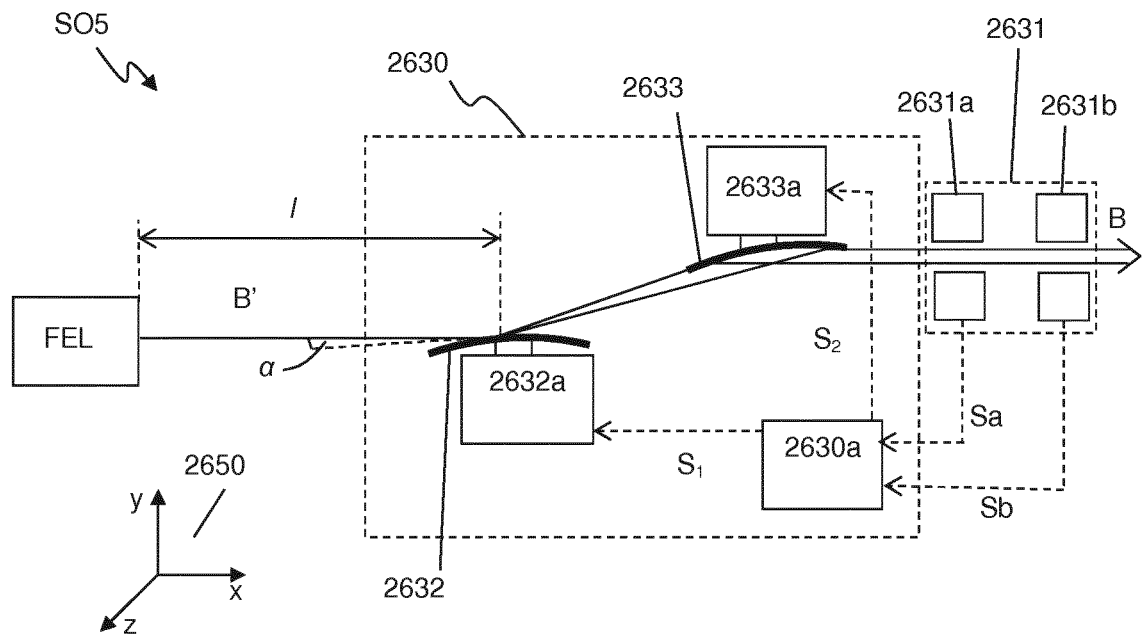
FIG. 74 is a schematic illustration of a radiation source according to an embodiment described herein.

Referring to FIG. 74, there is now described an alternative embodiment of the radiation source SO5, which comprises a free electron laser FEL (which may be, for example, substantially as described with reference to FIG. 3), an optical system 2630 and a sensor apparatus 2631. The optical system 2630 comprises: a first optical element 2632, a second optical element 2633, a controller 2630a, a first actuator 2632a, and a second actuator 2633a. The first and second actuators 2632a, 2633a are operable to move the first and second optical elements 2632, 2633 respectively in response to a received signal $S_1$, $S_2$ from controller 2630a. The optical system 2630 is arranged to receive the beam of radiation B' from the free electron laser FEL and, using the first and second movable optical elements 2632, 2633, to increase a cross-sectional area of the beam B' (e.g. to increase the diameter of the beam if the beam has a circular cross-section, or increase the height and width of the beam if the beam has a rectangular cross-section). This larger beam B is output by the optical system 2630 and is received by the beam splitting apparatus 20 (FIG. 1).

The sensor apparatus 2631 comprises two sets of sensors 2631a, 2631b spaced apart along the direction of propagation of the beam B. Each set of sensors 2631a, 2631b comprises sensors arranged around the periphery of the beam B such that deviation of the radiation beam from a desired position will cause overlap of an edge of the beam with one or more sensors. For example, for embodiments wherein the radiation beam B output by the optical system 2630 is circular, the sensing elements may be distributed around the circumference of a circle in the y-z plane, the diameter of the circle substantially matching that of the radiation beam B. Any other suitable form of sensor apparatus may be used.

The sensor apparatus 2631 provides two output signals Sa, Sb, each signal being indicative of the position of the beam after it has propagated by a different distance. The controller S is arranged to process the signals Sa, Sb to determine the direction of propagation of the beam B. The controller may also determine the position of the beam B. The controller 2630a is operable to move the one or more movable optical elements 2632, 2633 using actuators 2632a, 2633a in response to the signal S from the sensor apparatus 2631, to compensate for changes in the direction of the beam B' produced by the free electron laser FEL. The controller 2630a and the first and second actuators 2632a, 2633a form an adjustment mechanism of the optical system 2630. The optical elements 2632, 2633 may also be used to compensate for changes in the position of the beam B' produced by the free electron laser FEL.

As used in this context, the edge of the beam B may be defined as the point where the intensity has dropped below a pre-set threshold. The pre-set threshold may for example be a percentage of the maximum intensity.

Each sensor of each sensor set 2631a, 2631b may output a signal indicative of the amount of radiation incident upon it. Each of these signals may be sent to the controller 2630a separately or as combined signals Sa, Sb.

By analysing the amount of radiation incident upon each of the plurality of sensors, the position of the radiation beam B may be determined. For example, for embodiments wherein the radiation beam is circular, if there is a difference in the amount of radiation incident on two diametrically opposed sensing elements then the centre of the radiation beam B is closer to the sensing element that receives more radiation. Once the position of the radiation beam for each sensor set 2631a, 2631b has been determined in this manner, the direction of the radiation beam may be determined. If this differs from the desired direction of the radiation beam B, the controller 2630a may be operable to move the first and second optical elements 2632, 2633 to correct for this.

The sensor sets 2631a, 2631b of the sensor apparatus 2631 may be movable. This may allow for changes in the shape of the radiation beam B and/or intensity profile to taken into account.

Each of the first and second optical elements 2632, 2633 comprises a mirror and may be provided with an active cooling mechanism. For example, each mirror may be provided with a supply of cooling fluid such as, for example, water or carbon dioxide ($CO_2$). However, there is a limit to the power density that an optical element can absorb and dissipate, without sustaining damage.

For a given output power of the free electron laser FEL, the power density that the first optical element 2632 downstream of the free electron laser FEL receives is dependent upon: (i) the initial size and divergence of the radiation beam B' as it leaves the undulator 24 of the free electron laser FEL; and (ii) the distance between the undulator 24 and the first optical element 2632. The power density that the first optical element 2632 receives decreases as the distance between the free electron laser FEL and the first optical element 2632 increases.

The radiation beam produced by an EUV free electron laser typically has a relatively small etendue. In particular, the EUV radiation beam B' provided by the free electron laser FEL has a significantly smaller etendue than an EUV radiation beam that would be generated by a laser produced plasma (LPP) source or a discharge produced plasma (DPP) source (both of which are known in the prior art). For example, the radiation beam B' produced by the free electron laser FEL may have a divergence less than 500 μrad, for example less than 100 μrad, and may for example have a diameter of around 50 μm. The radiation beam B' produced by the free electron laser FEL may for example have a diameter of around 50 μm.

The output power of the free electron laser FEL may be of the order of tens of kilowatts, in order to support high throughput for one or more EUV lithographic apparatus. At these powers, since the initial diameter of the radiation beam B' produced by the free electron laser FEL is so small, the power density will be significant. For example, the initial power density of a free electron laser with an output power of 30 kW and initial beam diameter of 50 μm will be of the order of $1.5 \times 10^{13}$ W/m². Even assuming an absorption rate of the order of 10% (which may be the case for a grazing incidence mirror), this power density is too large to be practically handled by the first optical element 2632 without damaging it.

In embodiments of the present invention, the first optical element 2632 is a convex grazing incidence mirror. Preferably, the first optical element 2632 is formed from material which is a good conductor of heat such as, for example, copper, with a coating that maximizes reflectivity and minimizes absorption such as, for example, ruthenium (Ru). The convex grazing incidence mirror may have any suitable shape such as, for example, spherical, astigmatic or a-spherical. The angle between the radiation beam B' and the surface of the first optical element 2632 is small, which provides two benefits: (a) it enlarges the beam spot size on the first optical element 2632, lowering the power density; and (b) it lowers the absorption coefficient, reducing the fraction of the incident power which is absorbed, and must be dissipated, by the first optical element 2632. The angle between the radiation beam B' and the surface of the first optical element 2632 is preferably below about 10 degrees, since the reflectivity of the first optical element 2632 drops significantly as the angle increases above 10 degrees. Since the first optical element 2632 is convex, its radius of curvature sets a lower limit of the angle between the radiation beam B' and the surface of the first optical element 2632. Preferably the angle is in the range 0.5 to 10 degrees, more preferably in the range 1 to 5 degrees, and most preferably in the range 1 to 3 degrees.

For a circular beam B', since the first optical element 2632 is a grazing incidence mirror, the beam spot size on the first optical element 2632 will be an ellipse. Neglecting the curvature of the first optical element 2632, the length of the minor axis of the ellipse will be the diameter, d, of the beam B' and the length of the major axis will be the ratio of the diameter, d, of the beam B' to the sine of the angle, a, between the radiation beam B' and the surface of the first optical element 2632, i.e. d/sin(a).

Again, neglecting the curvature of the first optical element 2632, for a circular beam B' with the first optical element 2632 being a grazing incidence mirror, the power density, PD, absorbed by the first optical element 2632 is given by:

$$PD = f_a(\alpha) \times \sin \alpha \times PD_0, \qquad (10)$$

where a is the angle between the radiation beam B' and the surface of the first optical element 2632, $f_a(\alpha)$ is the fraction of the power absorbed by the first optical element 2632 (which is dependent upon $\alpha$), and $PD_0$ is the ratio of the power of the beam B' to its cross sectional area (i.e. the initial power density of the beam).

In one example, the angle $\alpha$ between the radiation beam B' and the surface of the first optical element 2632 is 2.5 degrees. At this angle, around 8% of the incident power may be absorbed by the first optical element 2632. Taking into account the enlarged spot size and the reduced absorption fraction, the power density absorbed by the first optical element 2632 for the above example of a free electron laser with an output power of 30 kW and initial beam diameter of 50 μm would be reduced to the order of $5.3 \times 10^{10}$ W/m². However, this power density is still too large to be practically handled by the first optical element 2632 without damaging it.

As the radiation beam B' propagates, it increases in size. The increase in size between two points will be proportional to the product of the distance between the two points and the tangent of half the divergence. Neglecting the curvature of the first optical element 2632, for a circular beam B' normally incident upon the first optical element 2632 the power density, Pd, absorbed by the first optical element 2632 is given by:

$$Pd = f_a \times \left(\frac{d_1}{d_1 + 2l \tan(\theta/2)}\right)^2 \times Pd_i, \qquad (11)$$

where $f_a$ is the fraction of the power absorbed by the first optical element 2632, $d_1$ is the initial beam diameter, B is the divergence of the beam B', l is the distance between the undulator 24 and the first optical element 2632, and $Pd_i$ is the ratio of the power of the beam B' to its initial cross sectional area (i.e. the initial power density of the beam).

Since the divergence of the radiation beam B' produced by the free electron laser FEL is so small, in order for the size of the beam to increase significantly (corresponding to a significant reduction in the power density absorbed by the first optical element 2632), the beam must travel a significant distance. For example, it may be necessary for the distance between the undulator 24 and the first optical element 2632 to be of the order of tens of metres in order for the power density on the first optical element 2632 to be sufficiently low that its surface coating is not damaged. A distance between the undulator 24 and the first optical element 2632 of around 10 m may be too small and 100 m may be unnecessarily large. The distance between the undulator 24 and the first optical element 2632 may for example be in the range 30 m to 80 m, for example it may be around 50 m. The distance between the undulator 24 and the first optical element 2632 at which damage of the first optical element is avoided will depend upon material properties of the surface coating and substrate of the first optical element and upon the effectiveness of a cooling system used to cool the first optical element (in addition to depending upon the power density of the beam).

For the above example of a free electron laser with: an output power of 30 kW, an initial beam diameter of 50 μm, an angle, α, between the radiation beam B' and the surface of the first optical element 2632 of 2.5 degrees, a divergence of 100 μrad, and a distance between undulator 24 and the first optical element 2632 of 50 m, the power density on the first optical element 2632 may be reduced to the order of $4.4 \times 10^8$ W/m². With sufficient cooling, such a power density may be absorbed and dissipated by the first optical element 2632 without damaging it.

In general, for a given initial beam diameter, power and divergence the power density PD absorbed by the first optical element 2632 may be varied by altering: (i) the angle α between the radiation beam B' and the surface of the first optical element 2632; and/or (ii) the distance l between the undulator 24 and the first optical element 2632. The range of acceptable values of angle α will be dependent upon the distance l and vice versa. The range of acceptable values of angle α may also be constrained by the radius of curvature of the first optical element 2632 (to avoid the possibility that the first optical element curves away from the radiation beam B' to such an extent that part of the radiation beam misses the first optical element).

When the distance between the undulator 24 of the free electron laser FEL and the first optical element 2632 is of the order of tens of metres, the placement of the beam spot on the first optical element 2632 will be strongly dependent upon the initial direction of the radiation beam B' leaving the undulator 24. A very small variation in this direction may cause the spot at the first optical element 2632 to move a significant distance. The distance l is sufficiently large that small relative mechanical movement of components of the radiation source SO5 and/or the buildings they are housed in can give rise to a large displacement of the spot on the first optical element 2632. The controller 2630a and the first and second actuators 2632a, 2633a form an adjustment mechanism of the optical system 2630.

The adjustment mechanism of the optical system 2630 (provided by the controller 2630a and the first and second actuators 2632a, 2633a) and the sensor apparatus 2631 provide an active feedback loop which allows the first optical element 2632 to be placed sufficiently far from the undulator 24 so that it is not damaged whilst ensuring that the direction and position of the beam B output by the optical system 2630 remain stable. Therefore, advantageously, the combination of a free electron laser FEL and this active feedback loop allows a high power EUV radiation beam to be available for lithography.

Since the first optical element 2632 is convex, it will increase the divergence of the EUV radiation beam, decreasing the heat load on mirrors downstream in the optical path. This may allow the mirrors downstream to be of a lower specification, with less cooling and therefore less expensive. Additionally or alternatively, it may allow the downstream mirrors to be nearer to normal incidence.

Referring to FIG. 74, relative to the reference set of axes 50, the axis of the undulator 24 is in the x direction. The radiation beam B' will generally propagate in the x direction. Each of the first and second optical elements 2632, 2633 is operable to move linearly in the y and z directions and is operable to rotate about the x and z axes. This freedom allows the optical system 2630 to correct for deviations in the direction of propagation of the radiation beam from the x direction.

For example, a so called beam-pointing error may occur, wherein the radiation beam B' is not propagating in the x-direction but instead is propagating at a slight angle to the x-direction. The pointing error may for example be such that the direction of the radiation beam B' includes a component in the y direction. This may be corrected for by rotating the first and second optical elements 2632, 2633 around the z-direction. Rotation of the first optical element 2632 may be used to direct the radiation beam B' such that it is incident upon the centre of the second optical element 2633, and rotation of the second optical element may be used to ensure that the radiation beam B' is propagating in the x-direction when it exits the optical system 2630.

A pointing error in which the direction of the radiation beam includes a component in the z-direction may be corrected for in a similar manner by rotating the first and second optical elements 2632, 2633 around the x-direction. A pointing error in which the radiation beam includes components in the y and z directions may be corrected for by rotating the first and second optical elements 2632, 2633 in both the x and z directions.

The first optical element 2632 may be translatable in the y and z-directions. Translation in the y and z-directions may be used to ensure that the radiation beam B' is incident at or close to the centre of the first optical element. If the radiation beam B' has deviated such that it is no longer incident upon centre of the first optical element 2632 then the translation of the first optical element in the y and/or z directions may be performed until the radiation beam B' is at or close to the centre of the first optical element. The position of the radiation beam B' on the first optical element 2632 may for example be monitored by a camera or some other sensor (not illustrated).

Translation of the second optical element 2633 in the y and z-directions may not be needed in order to correct for beam pointing errors. However, the second optical element 2633 may be translatable in the y and z-directions in order to allow for correction of other errors. Translation of the second optical element 2633 may for example be used to provide correction or modification of the cross-sectional shape of the radiation beam (e.g. if the optical elements 2632, 2633 have an aspherical shape or other complex shape).

Figure 75:
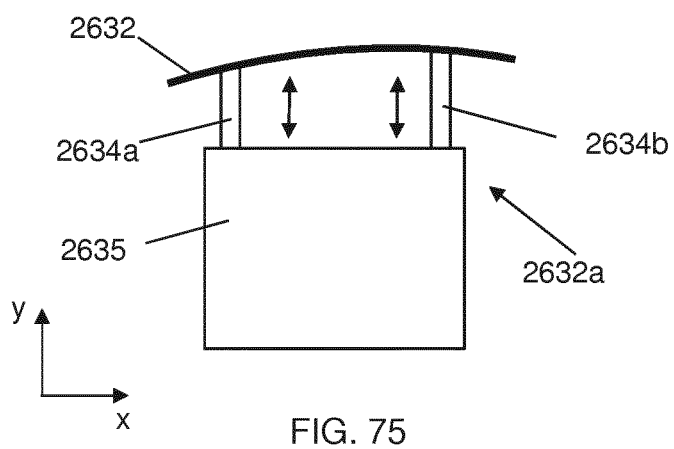
FIG. 75 is a schematic illustration of an optical element and an actuator of the radiation source of FIG. 74.

FIG. 75 represents schematically in more detail the first optical element 2632 and the associated actuator 2632a. The actuator 2632a includes three actuator elements which are connected between the first optical element 2632 and a base 2635 of the actuator. Each actuator element is located at or adjacent to a corner of the optical element (the three actuator elements are arranged in the form of three corners of a triangle). Two of the actuator elements 2634a, 2634b are shown schematically in FIG. 75. The actuator elements 2634a, 2634b may for example be piezo-electric actuators, or may be any other suitable form of actuator. Each actuator element 2634a, 2634b is individually operable to move a corner of the first optical element in the y-direction (as indicated by double-headed arrows). This allows the first optical element to be rotated around the z-axis or around the x-axis as desired. Operating all of the actuator elements together will provide translation of the first optical element 2632 in the y-direction. A separate actuator element may be used to provide translation of the first optical element 2632 in the z-direction. The separate actuator element may for example be used to translate the base 2635 in the z-direction, thereby moving the first optical element 2632 in the z-direction. Similarly, a separate actuator element may be used to provide translation in the x-direction. The separate actuator element may for example be used to translate the base 2635 in the x-direction, thereby moving the first optical element 2632 in the x-direction.

Although the above description of actuator elements 2634a, 2634b refers to them being at or adjacent to corners of the first optical element 2632, it is not necessary that the first optical element have corners (it may for example be elliptical). In general, arranging the actuator elements as three corners of a triangle allows for easily controllable rotation and translation of the first optical element (irrespective of the shape of the first optical element). However, any suitable arrangement of actuator elements may be used. For example, an arrangement of six actuator elements may be used, the actuator elements being mounted in pairs on the base and being mounted in different pairs on the optical element (arrangements of this type are referred to as a Stuart platform or Hexapod).

One or more bellows that can vary in length may extend between the first optical element 2632 and the base 2635, and may act to transmit heat from the first optical element to the base. The transfer of heat may be facilitated by fixed material within the bellows with high heat conductivity. Additionally or alternatively, one or more flexible pipes may deliver cooling fluid to and from the mounting plate via the bellows. Additionally or alternatively, flexible heat pipes, in which a liquid is evaporated at the hot side and vapour is condensed at the cold side, can be used to transfer heat away from the optical element.

The actuator 2633a for the second optical element 2633 may have a similar configuration to the actuator 2632a for the first optical element 2632. In an embodiment, the separate actuator used to provide translation in the z-direction may be omitted.

The controller 2630a may be operable to determine whether or not the position and/or direction of the radiation beam B differs from a desired direction and if so, how the first and second optical elements 2632, 2633 need to move in order to return the radiation beam B to the desired direction. The controller 2630a may then convert this information into two signals $S_1$, $S_2$ for the two actuators 2632a, 2633a in order to move the first and second optical elements 2632, 2633 accordingly. The controller 2630a may comprise a processor (not shown) which may implement the above described functions. The processor may calculate in real time how the first and second optical elements 2632, 2633 must be moved in response to given input signals Sa, Sb from the sensor apparatus 2631. Additionally or alternatively, the processor may access this information from a look up table or the like which may be stored in a memory (not shown).

The second optical element 2633 has a concave shape such that the divergence of the outgoing beam is substantially zero. The shape of the second optical element 2633 may substantially match that of the first optical element 2632 and may be, for example, spherical, astigmatic or aspherical. Therefore, downstream of the second optical element 2633, the beam is substantially collimated. Advantageously, this allows other optical elements that condition branch radiation beams B1-B3 (see FIG. 1) before they enter the lithographic apparatuses LA1, LA2 or mask inspection apparatus MIA, to be identical or at least very similar. This is beneficial from a manufacturing point of view.

It may be preferable for the beam that is received by the beam splitting apparatus 20 to have a different shape and/or intensity distribution to that output by the undulator 24. For example, a rectangular shape may be preferable to a circular beam for consecutive knife edge extraction mirrors within the beam splitting apparatus 20. The shape and/or intensity distribution of the radiation may be altered by the optical system 2630 by, for example, using first and second optical elements with a-spherical optical surfaces. It will be appreciated that for different beam B shapes, different arrangements of sensing elements in the sensor apparatus 2631 may be used so that the distribution of sensing elements substantially matches the shape of the beam B.

Although the above described embodiment of a radiation source SO5 comprises one free electron laser FEL, a radiation source according to an embodiment of the invention may comprise two or more free electron lasers.

Figure 76:
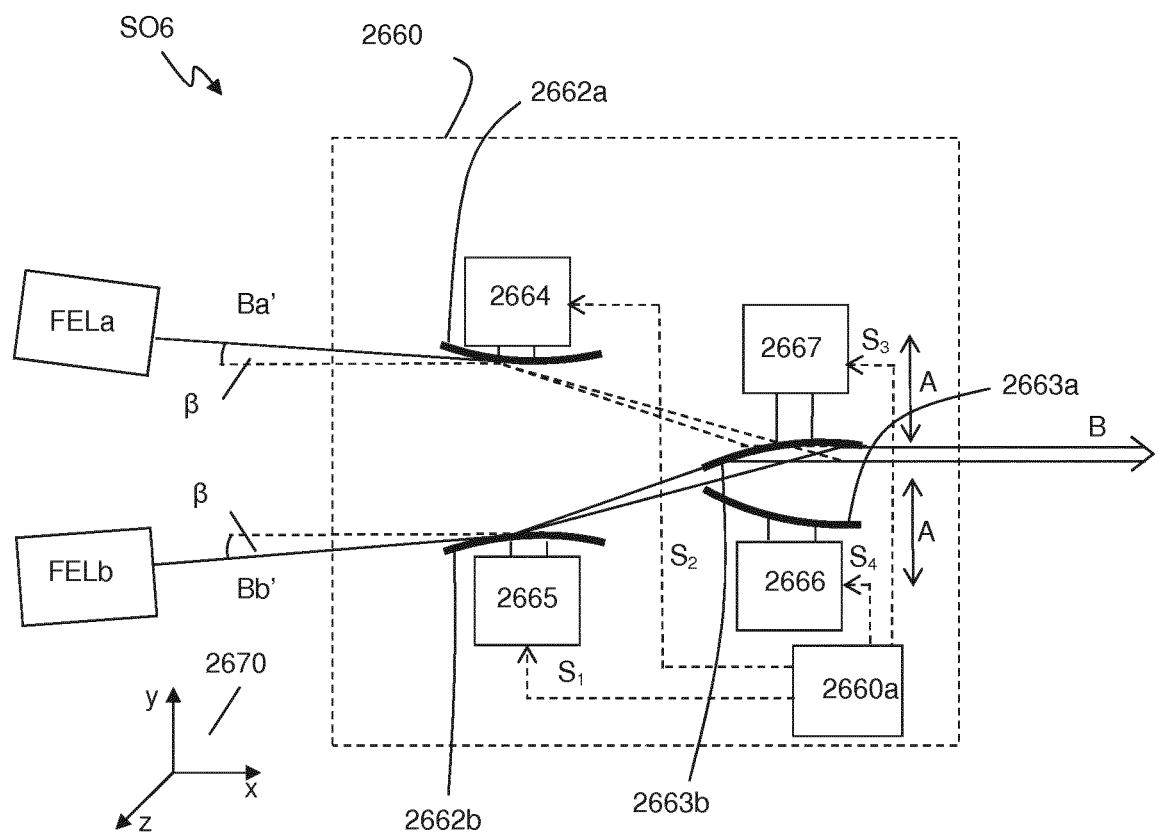
FIG. 76 is a schematic illustration of a further radiation source according to an embodiment described herein.

Referring to FIG. 76, a second embodiment of a radiation source SO6 according to the invention comprises two free electron lasers FELa, FELb, an optical system 2660 and a sensor apparatus (not shown in order to reduce the complexity of the drawing). Each of the free electron lasers FELa, FELb is operable to produce a beam of EUV radiation B', B" and may be substantially the same as the free electron laser FEL described above in relation to the first embodiment of a radiation source SO5. Such an arrangement provides redundancy, allowing one of the free electron lasers FELa, FELb to operate when the other free electron laser is being repaired or undergoing maintenance. Thus, one of the free electron lasers FELa, FELb is always available for use.

The optical system 2660 comprises four movable optical elements: first and second optical elements 2662a, 2663a associated with a first one of the free electron lasers FELa; and first and second optical elements 2662b, 2663b associated with a second one of the free electron lasers FELb. The optical system further comprises a controller 2660a and an actuator 2664, 2665, 2666, 2667 for each of the movable optical elements 2662a, 2662b, 2663a, 2663b. Each of the four actuators 2664, 2665, 2666, 2667 is operable to move one of the of the movable optical elements 2662a, 2662b, 2663a, 2663b response to a received signal $S_1$, $S_2$, $S_3$, $S_4$ from controller 2660a.

Each of the first optical elements 2662a, 2662b performs substantially the same function for its respective free electron laser FELa, FELb as the first optical element 2632 does for free electron laser FEL described above in relation to the first embodiment of a radiation source SO5. Both of the first optical elements 2662a, 2662b are arranged to direct the radiation beam B', B" received from their respective free electron lasers FELa, FELb to substantially the same location.

The optical system 2660 is arranged to selectively receive a beam of radiation B', B" from one of the free electron lasers FELa, FELb and, using the first and second movable optical elements associated with that free electron laser FELa, FELb, to increase a cross-sectional area of the beam B' to produce a beam B with a larger diameter. This larger beam B that is output by the optical system 2660 is received by the beam splitting apparatus 20.

As with the first embodiment SO5, the sensor apparatus (not shown) is operable to determine a position and direction of the beam B output by the optical system 2660 and to send a signal S indicative thereof to the controller 2660a. The controller 2660a is operable to move the first and second optical elements corresponding to the free electron laser FELa, FELb that is operating in response to signal S to compensate for changes in the direction of the beam B', B" produced by that free electron laser FELa, FELb. The controller 2660a and the four actuators 2664, 2665, 2666, 2667 form an adjustment mechanism of the optical system 2660.

In addition to the functionality described above in relation to the second optical element 2633 of the first embodiment SO5, each of the second optical elements 2663a, 2663b is operable to move in the y direction over a greater distance, as indicated by arrow A between an in use position, wherein it is arranged to receive radiation from its associated free electron laser FELa, FELb via its associated first optical element, and a storage position, wherein it is retracted out of the path of the radiation. In use, one of the free electron lasers, for example FELb in FIG. 76, is switched on and the other free electron laser is switched off (for example to allow for maintenance). The second optical element 2663b associated with the free electron laser FELb that is switched on is disposed in its in use position and the other second optical element is in its storage position.

Advantageously, such an arrangement allows the beam of radiation B output by the optical system 2660 to be in substantially the same position and direction regardless of which free electron laser FELa, FELb is operating.

A control mechanism (not shown) may be provided for moving the two second optical elements 2663a, 2663b between their in use and stored positions as appropriate.

Relative to the reference set of axes 2670 in FIG. 76, the beam of radiation B output by the optical system 2660 is generally in the x direction. The axis of each of the two free electron laser FELa, FELb, along which their output radiation beams B', B" propagate are disposed at a small angle β relative to the x axis. This allows the physical separation between the two free electron lasers FELa, FELb to be larger than that between the two first optical elements. This is advantageous since it may be preferable for instance for system stability for the two first optical elements 2662a, 2662b to be relatively close, say of the order 1 metre apart, whereas the free electron lasers FELa, FELb are very large apparatuses and may necessarily need to be separated by a significantly larger distance. The distance A between the undulators of the two free electron lasers FELa, FELb is given by:

$$\Delta = 2l \tan(\beta) + 2k \tan(2\alpha + \beta) \quad (12)$$

where, l is the distance between the undulators of the free electron lasers FELa, FELb and the first optical elements 2662a, 2662b, α is the angle between the radiation beam B' and the surface of the first optical element 2662a, 2662b and k is the distance between the first optical elements 2662a, 2662b and the second optical elements 2663a, 2663b. For sufficiently large 1 and k:

$$\Delta = 2\beta(l+k) + 4k\alpha. \quad (13)$$

Figure 77:
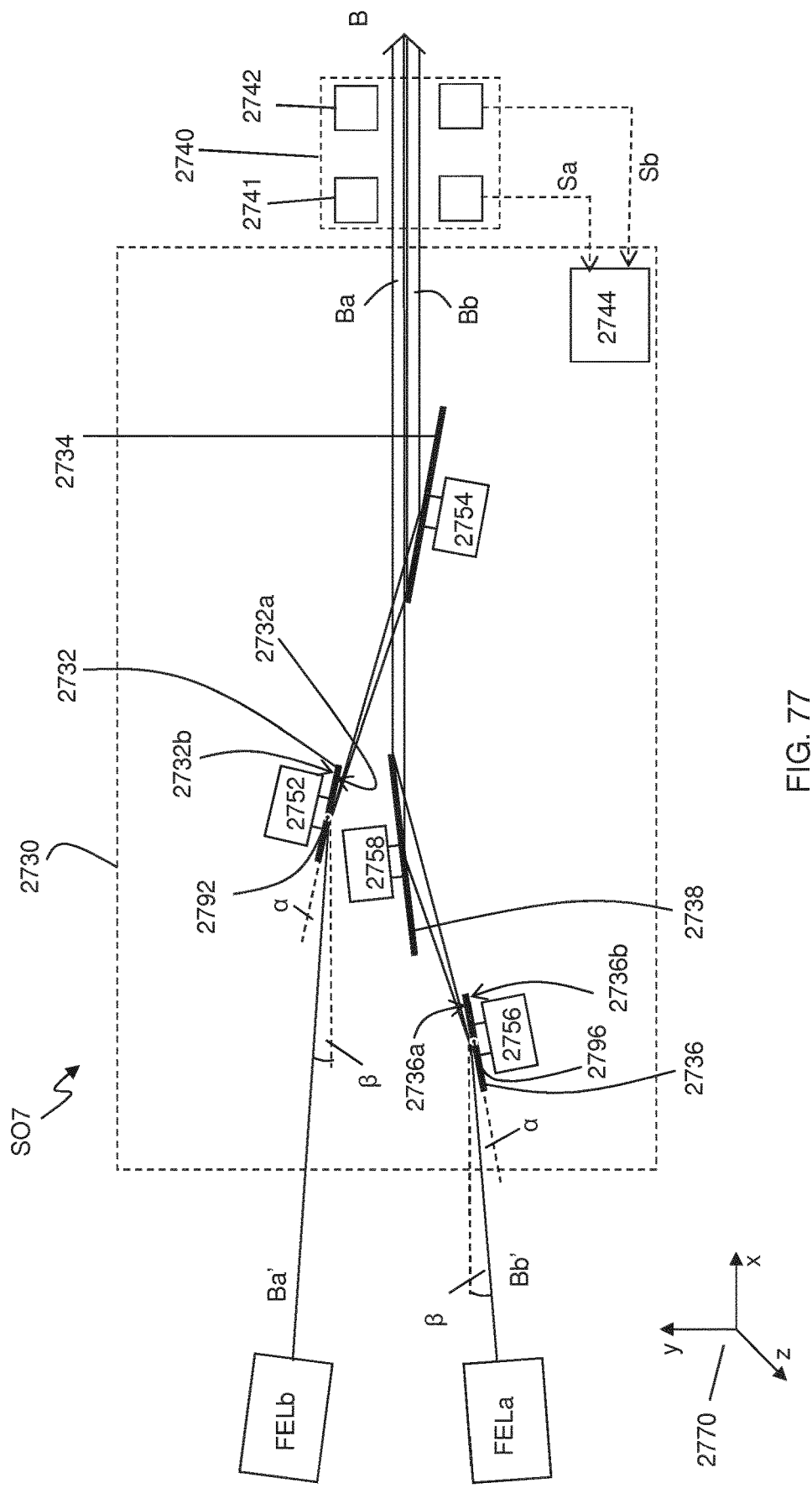
FIG. 77 is a schematic illustration of a further radiation source according to an embodiment described herein.

Referring to FIG. 77, a radiation source SO7 comprises two free electron lasers FELa, FELb and an optical system 2730.

Each of the free electron lasers FELa, FELb is selectively operable to produce a beam of EUV radiation Ba', Bb'. That is, each of the free electron lasers FELa, FELb is switchable between an on state wherein it produces a beam of EUV radiation and an off state wherein it does not. Each of the free electron lasers FELa, FELb may be said to be on when disposed in its on state, and may be said to be off when disposed in its off state.

Each of the beams of EUV radiation Ba', Bb' output by the free electron lasers FELa, FELa may have a substantially circular cross section and a Gaussian intentsity profile. As described above, the radiation beam produced by an EUV free electron laser typically has a relatively small etendue. For example, the radiation beams Ba', Bb' produced by the free electron lasers FELa, FELb may have a divergence less than 500 μrad, for example less than 100 μrad, and may for example have a diameter of around 50 μm as they leave their respective undulators 24.

Referring again to FIG. 77, the optical system 2730 is arranged to receive a beam of radiation Ba', Bb' from each of the free electron lasers FELa, FELa and to output an output radiation beam B. The radiation beam B that is output by the optical system 2730 is received by the beam splitting apparatus 20 (see FIG. 1).

The optical system 2730 comprises four optical elements: first and second optical elements 2732, 2734 associated with a first one of the free electron lasers FELa; and first and second optical elements 2736, 2738 associated with a second one of the free electron lasers FELb. The optical elements 2732, 2734, 2736, 2738 are arranged to alter the size and shape of the cross section of the radiation beams Ba', Bb' from the free electron lasers FELa, FELb.

In particular, the first optical elements 2732, 2736 are convex mirrors, which act to increase the cross sectional area of the radiation beams Ba', Bb' from the free electron lasers FELa, FELb. Although in FIGS. 77, 79 and 80 the first optical elements 2732, 2736 appear to be substantially flat in the x-y plane they are in fact convex both in this plane and in the z direction. Since the first optical elements 2732, 2736 are convex, they will increase the divergence of the EUV radiation beams Ba', Bb', decreasing the heat load on mirrors downstream of them. The first optical element 2732 may be referred to as a diverging optical element arranged to increase the cross sectional area of the radiation beam Ba' received from the first free electron laser FELa. The first optical element 2736 may be referred to as a diverging optical element arranged to increase the cross sectional area of the radiation beam Bb' received from the second free electron laser FELb. This may allow the mirrors downstream to be of a lower specification, with less cooling, and therefore less expensive. Additionally or alternatively, it may allow the downstream mirrors to be nearer to normal incidence. In practice, the radiation beam B output by the radiation source SO7 may be split by a plurality of consecutive, static, knife edge mirrors arranged in series in the path of the beam B. Increasing the size of the beam B (by, for example, using convex mirrors as the first optical elements 2732, 2736) reduces the accuracy with which the mirrors must be located in the beam B path. Therefore, this allows for more accurate splitting of the output beam B by the splitting apparatus 20.

The second optical elements 2734, 2738 are concave and are complementary in shape to the first optical elements such that the beams leaving the second optical elements 2734, 2738 have substantially zero divergence. The second optical element 2734 may be referred to as a converging optical element arranged to reduce a divergence of the radiation beam Ba' received from the first free electron laser FELa to substantially zero after the cross sectional area of that radiation beam Ba' has been increased by first optical element 2732. The second optical element 2738 may be referred to as a converging optical element arranged to reduce a divergence of the radiation beam Bb' received from the second free electron laser FELb to substantially zero after the cross sectional area of that radiation beam Bb' has been increased by first optical element 2736. Therefore, downstream of the second optical elements 2734, 2738 the beams are substantially collimated. Again, although in FIGS. 77, 79 and 80 the second optical elements 2734, 2738 appear to be substantially flat in the x-y plane they are in fact concave both in this plane and in the z direction.

It may be preferable for the output beam B, which is received by the beam splitting apparatus 20, to have a different shape and/or intensity distribution to that output by the free electron lasers FELa, FELb. For example, a rectangular shape may be preferable to a circular beam for consecutive knife edge extraction mirrors within the beam splitting apparatus 20. Therefore, in addition to increasing the cross sectional area of the radiation beams Ba', Bb', the optical elements 2732, 2734, 2736, 2738 act to alter the cross sectional shape of the radiation beams Ba', Bb'. In particular, the optical elements 2732, 2734, 2736, 2738 are astigmatic or aspherical and are shaped so as to ensure that the radiation beams Ba, Bb leaving the second optical elements 2734, 2738 are more rectangular in shape than the radiation beams Ba', Bb' produced by the free electron lasers FELa, FELb. For example, the optical elements may be shaped so that the beams Ba, Bb leaving the second optical elements 2734, 2738 are generally rectangular but with rounded corners, although other shapes are also possible. The two dimensions of such a rectangular shape may be related to radii of curvature of the optical elements in two perpendicular directions such as, for example, in the x-y plane and in the z direction. Advantageously, this allows the mirrors that are used to split the output radiation beam B into branch radiation beams before they enter the lithographic apparatuses, to be identical or at least very similar. This is especially beneficial from a manufacturing point of view.

In the present example, it is described that eight branch radiation beams Ba-B8 are provided for eight lithographic apparatus LA1-LAB. It will be appreciated that as illustrated in FIG. 1, additional lithographic apparatuses may be provided.

When both of the free electron lasers FELa, FELb are on, the optical system 2730 is operable to combine their radiation beams Ba', Bb' to form a composite radiation beam. In this embodiment, this is achieved by offsetting the first and second optical elements 2732, 2734 of the first free electron laser FELa from those 2736, 2738 of the second free electron laser FELb in the x direction so that the beams Ba, Bb leaving the second optical elements 2734, 2738 are both adjacent to each other and mutually parallel. In particular, the first and second optical elements 2732, 2734 of the first free electron laser FELa are disposed "downstream" (with respect to the direction of propagation of the laser beams Ba', Bb') of those 2736, 2738 of the second free electron laser FELb.

Such an arrangement, the optical system 2730 is operable to combine the two radiation beams Ba', Bb' to form a composite radiation beam, provides a radiation source SO7 with two free electron lasers FELa, FELb, wherein the radiation source SO7 is able to continue to produce an output radiation beam in the event that one of the free electron lasers FELa, FELb is off. This may allow, for example, one of the free electron lasers FELa, FELb to be repaired or to undergo maintenance. However, advantageously, embodiments of the invention also allow both free electron lasers FELa, FELb to operate simultaneously when required or desired. Thus, if both of the free electron lasers FELa, FELb are operational they can both be producing radiation for a lithographic system such as the lithographic system LS.

Figure 78A:
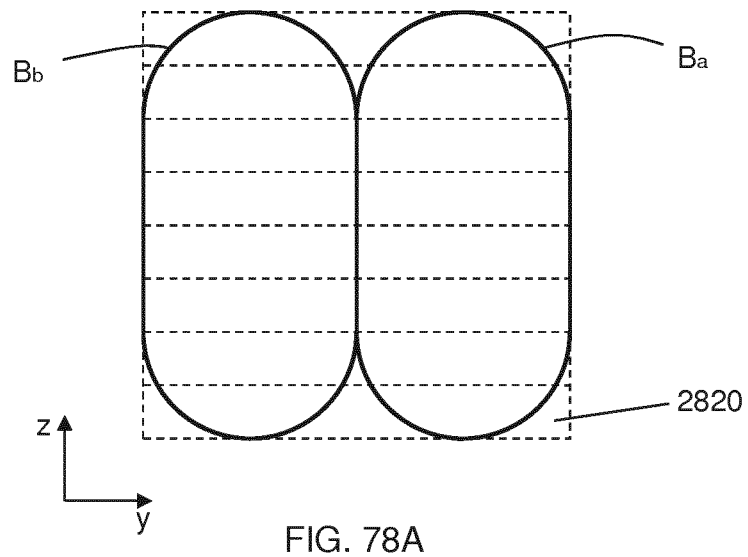

The composite beam is the output radiation beam B output by the optical system 2730. The cross sectional profile of the composite radiation beam B output by the optical system 2730 is shown in FIG. 78, the edge of the composite radiation beam B being defined as the point where its intensity has dropped below a pre-set threshold. FIG. 78 also illustrates eight portions 2820 of the output beam B, which correspond to the eight branch radiation beams Ba-B8 that may be produced by the beam splitting apparatus 20 using eight substantially identical consecutive knife edge extraction mirrors (not shown). FIG. 78A shows an embodiment wherein each branch radiation beam Ba-B8 comprises a portion of radiation from each of the two radiation beams Ba', Bb' whereas FIG. 78B shows an embodiment wherein each branch radiation beam Ba-B8 comprises radiation exclusively from one or the other of the two radiation beams Ba', Bb'.

Each of the free electron lasers FELa, FELb may have scheduled and/or unscheduled down time during which they are off. In the event that one of the free electron lasers is off, for example the first one FELa, the effect on the lithographic apparatuses LA1-LA20 will be different for the two different embodiments shown in FIGS. 78A and 78B respectively.

In the case of the embodiment shown in FIG. 78A, all of the lithographic apparatuses LA1-LA20 will receive some radiation, although only half of that which they would receive when both free electron lasers FELa, FELb are on. Unless the optics which delivers the branch radiation beams Ba-B8 to the illuminators IL of the lithographic apparatuses LA1-LA20 is altered, for such embodiments only half of the facetted field mirror device 10 (FIG. 2) will be illuminated. Under these conditions, it may be the case that either: (a) all of the mirrors of the facetted field mirror device 10 are either illuminated completely of not illuminated at all; or (b) at least some of the mirrors of the facetted field mirror device 10 are only partially illuminated. If each of the mirrors of the facetted field mirror device 10 is either completely illuminated or not illuminated at all, by suitable configuration of the facetted field mirror device 10 and the facetted pupil mirror device 11 it can be arranged that the illuminators IL of the lithographic apparatuses LA1-LA20 produce a suitable illumination pattern for illumination of a mask MA. This is achieved by directing the mirrors so that the illuminated mirrors are substantially evenly distributed over the pupil plane of the illuminator IL. This results in a loss of performance. However, if the some of the mirrors of the facetted field mirror device 10 are only partially illuminated, these conditions can result in a large non-uniformity (tilt) in the field at the mask MA. This can be avoided by suitable re-design of the facetted field mirror devices 10 to ensure that no mirrors are partially illuminated, however, this is somewhat impractical. Furthermore, the effect of partial illumination of some of the mirrors can be reduced by increasing the total number of mirrors (for example by using MEMS devices and using, for example, more than 100,000 mirrors).

Figure 78B:
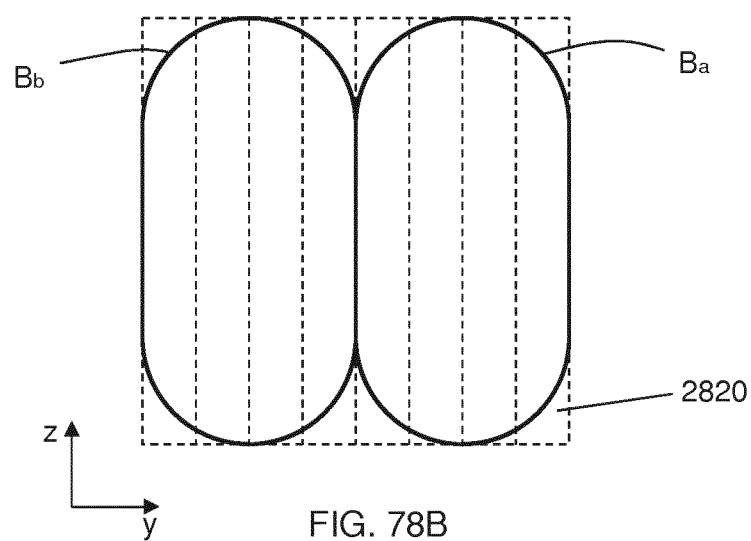

In the case of the embodiment shown in FIG. 78B, half of the lithographic apparatuses LA1-LA20 will receive the same amount of radiation as when both free electron lasers FELa, FELb are on but the other half will receive no radiation.

In order to address the problems of: (a) only illuminating half of the facetted field mirror devices 10; and/or (b) only providing half of the lithographic apparatuses LA1-LA20 with radiation, the optical system 2730 is adjustable and is operable to vary the cross sectional profile (size and/or shape) of the beams of radiation Ba, Bb leaving the second optical elements 2734, 2738. For this purpose, the optical system 2730 further comprises: a controller 2744; and an actuator 2752, 2754, 2756, 2758 for each of the optical elements 2732, 2734, 2736, 2738. Each of the four actuators 2752, 2754, 2756, 2758 is operable to move one of the optical elements 2732, 2734, 2736, 2738 in response to a received signal (not shown) from the controller 2744.

In particular, when one of the two free electron lasers FELa, FELb is off the optical system 2730 may be operable to adjust so that the radiation beam Ba, Bb leaving the second optical element 2734, 2738 corresponding to the other free electron laser FELa, FELb has generally the same size, shape and position as the combined radiation beam B would have if both free electron lasers FELa, FELb were on. Alternatively the optical system 2730 may be operable to adjust so that the radiation beam Ba, Bb leaving the second optical element 2734, 2738 corresponding to the free electron laser FELa, FELb that is on so as to be at least closer in size, shape and position of the combined radiation beam B than it would be when both lithographic apparatuses are on. As a result, each lithographic apparatus LA1-LA20 will receive a branch radiation beam Ba-B8 that illuminates substantially all of its facetted field mirror device 10 but which has half the power that would be received if both free electron lasers FELa, FELb were on. Advantageously, this means that the beam splitting apparatus and the lithographic apparatuses LA1-LA20 need not change and all lithographic apparatuses LA1-LA20 in the lithographic system LS can continue to operate without any significant loss of performance. For the avoidance of doubt, as referred to in this context performance means the quality of images imparted to, for example, a substrate W by the lithographic apparatuses LA1-LA20. As will be apparent to the skilled person, when only one of the free electron lasers FELa, FELb is operating the power of the radiation available to each lithographic apparatus LA1-LA20 will be reduced (for two free electron lasers FELa, FELb of equal power it will be halved). Therefore when only one free electron laser FELa, FELb is operating, the speed of operation of each lithographic apparatus LA1-LA20 will be reduced (for example by a factor of 2) but the quality will not be significantly affected.

Figure 79:
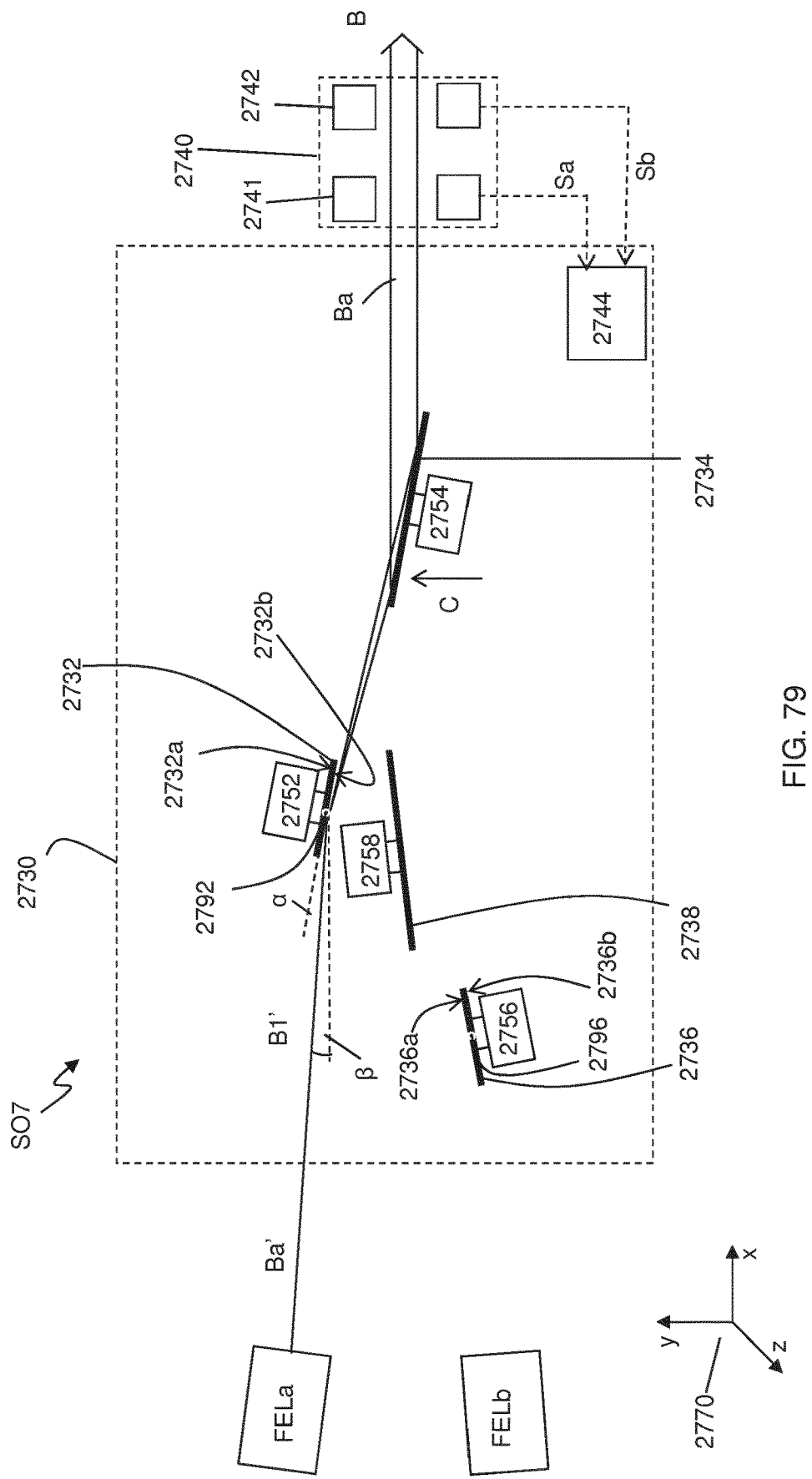
FIG. 79 is a schematic illustration of the radiation source shown in FIG. 77 when a first of the two free electron lasers is off.
Figure 80:
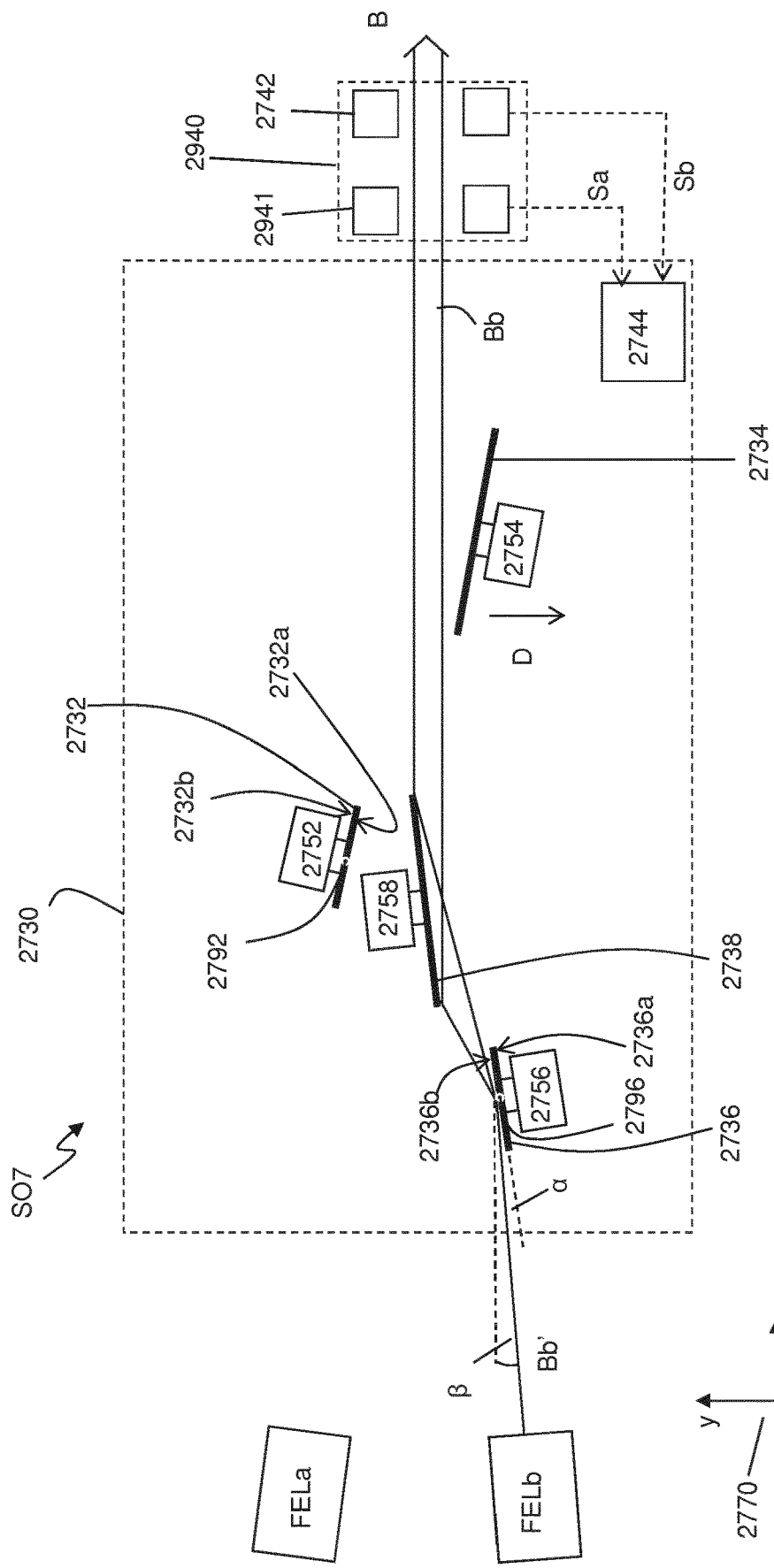
FIG. 80 is a schematic illustration of the radiation source shown in FIG. 77 when a second of the two free electron lasers is off.
Figure 81:
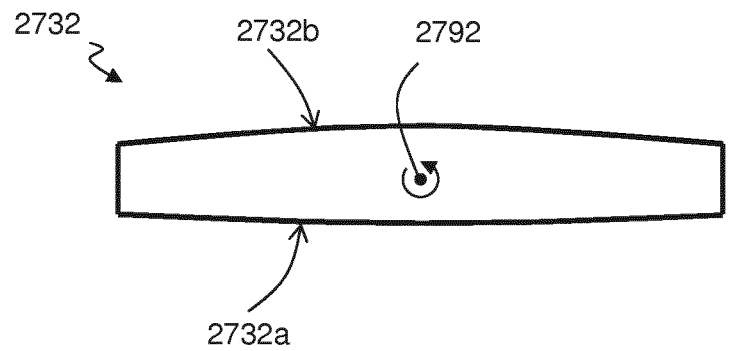
FIG. 81 depicts a cross section of a first optical element of the radiation source shown in FIGS. 77, 79 and 80 in the x-y plane.

Referring to FIGS. 79 and 80, to achieve this, the optical system 2730 is operable to vary the divergence of the first optical elements 2732, 2736 in a direction in the x-y plane (i.e. perpendicular to the z direction) and to move the second optical element 2738 of the second free electron laser FELb in the y direction. Each of the first optical elements 2732, 2736 comprises two opposing surfaces with different radii of curvature. For example, referring to FIG. 81, the first optical element 2732 corresponding to the first free electron laser FELa comprises first 2732a and second 2732b opposing surfaces. Actuator 2752 is operable to rotate the first optical element 2732 about an axis 2792 in the z direction. The divergence of the first optical element 2732 is be varied by rotating it about the axis 2792 in the z direction by 180 degrees so as to place a different one of the opposing surfaces 2732a, 2732b in the path of the radiation beam Ba'. When both free electron lasers FELa, FELb are on the radiation beam Ba' from the first free electron laser FELa is incident upon the first surface 2732a. When only the first free electron laser FELa is on the first optical element 2732 is rotated such that the radiation beam Ba' is incident upon the second surface 2732b, which has half the radius of curvature of the first surface 2732a (and therefore produces twice the divergence). Similarly, the first optical element 2736 corresponding to the second free electron laser FELb comprises two opposing surfaces 2736a, 2736b and actuator 2756 is operable to rotate it about an axis 2796 in the z direction so as to vary its divergence.

In an alternative example embodiment, two or more first optical elements with different radii of curvature may be provided for each free electron laser FELa, FELb and the divergence of the first optical element 2732, 2736 may be varied by moving a first optical element out of the path of the radiation beam Ba', Bb' and replacing it with another one with a different radius of curvature.

Referring again to FIG. 79, a configuration wherein the first free electron laser FELa is on and the second free electron laser FELb is off is illustrated. The first optical element 2732 for the first free electron laser FELa has been rotated about its axis 2792 by 180 degrees so as to place its second surface 2732b in the path of the radiation beam Ba'. Furthermore, the second optical element 2734 is moved up in the y direction (as indicated by arrow C). When incident upon the second surface 2732b, the radiation beam Ba' from the first free electron laser FELa will illuminate twice the area of the second optical element 2734 as it would if it were incident upon the first surface 2732a. Since the divergence of the second optical element 2734 is the same, but the beam is spread over twice the area, the radiation beam Ba leaving the second optical element 2734 has substantially zero divergence.

Referring to FIG. 80, a configuration wherein the second free electron laser FELb is on and the first free electron laser FELa is off is illustrated. The first optical element 2736 for the second free electron laser FELb has been rotated about its axis 2796 by 180 degrees so as to place its second surface 2736b in the path of the radiation beam Bb'. Furthermore, the second optical element 2734 corresponding to the first free electron laser FELa is moved down in the y direction (as indicated by arrow D). The radiation beam Bb' from the second free electron laser FELb will illuminate twice the area of the second optical element 2738 as it would if the first surface 2736a of the first optical element 2736 was in the path of the radiation beam Bb'. Since the divergence of the second optical element 2738 is the same, but the beam is spread over twice the area, the radiation beam Bb leaving the second optical element 2738 has substantially zero divergence.

Figure 82:
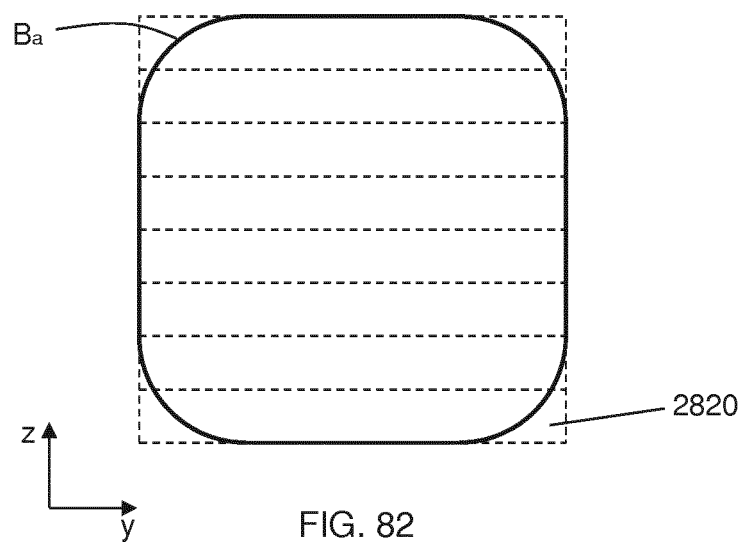

The beam profile produced by the radiation source SO7 when only the first free electron laser FELa is on is shown in FIG. 82. The beam profile produced by the radiation source SO7 when only the second free electron laser FELb is substantially identical to that shown in FIG. 82.

The radiation source SO7 may comprise one or more sensors (not shown) that are operable to determine whether the two free electron lasers FELa, FELb are on or off. Such sensors may send signals indicative of the state of the two free electron lasers FELa, FELb to the controller 2744. Additionally of alternatively, the radiation source SO7 may comprise user interface which may allow a user to manually input the state of two free electron lasers FELa, FELb (for example in the case of planned downtime).

Relative to the reference set of axes 2770 in FIGS. 77, 79 and 80, the output beam of radiation B output by the optical system 2730 propagates generally in the x direction. The axis of each of the two free electron lasers FELa, FELb, along which their output radiation beams Ba', Bb' propagate are disposed at a small angle β relative to the x axis. This allows the physical separation between the two free electron lasers FELa, FELb to be larger than that between the two first optical elements 2732, 2736. This is advantageous since it may be preferable, for instance for system stability, for the two first optical elements 2732, 2736 to be relatively close, say of the order 1 metre apart, whereas the free electron lasers FELa, FELb are very large apparatuses and may necessarily need to be separated by a significantly larger distance.

The radiation source SO7 further comprises a sensor apparatus 2740. The sensor apparatus 2740 comprises two sets of sensors 2741, 2742 spaced apart along the direction of propagation of the output beam B. Each set of sensors 2741, 2742 comprises sensors arranged around the periphery of the output beam B such that deviation of the radiation beam from a desired position will cause overlap of an edge of the beam with one or more sensors. For example, the sensing elements may be distributed around the perimeter of a region in the y-z plane that substantially matches the intensity distribution of the radiation beam B. For example, the sensing elements may be distributed around the lines marking the shape of the beam profiles shown in FIG. 78 or FIG. 82. Any other suitable form of sensor apparatus may be used.

The sensor apparatus 2740 provides two output signals Sa, Sb, each signal being indicative of the position of the output beam B after it has propagated by a different distance. The controller 2744 is arranged to process the signals Sa, Sb to determine the direction of propagation of the output beam B. The controller may also determine the position of the beam B. The controller 2744 is operable to move the optical elements 2732, 2734, 2736, 2738 using actuators 2752, 2754, 2756, 2758 in response to the signals Sa, Sb from the sensor apparatus 2740, to compensate for changes in the direction of the beams Ba', Bb' produced by the free electron lasers FELa, FELb. The controller 2744 and the four actuators 2752, 2754, 2756, 2758 form an adjustment mechanism of the optical system 2730. The optical elements 2732, 2734, 2736, 2738 may also be used to compensate for changes in the position of the beams Ba', Bb' produced by the free electron lasers FELa, FELb.

As used in this context, the edge of the output beam B may be defined as the point where the intensity has dropped below a pre-set threshold. The pre-set threshold may for example be a percentage of the maximum intensity.

Each sensor of each sensor set 2741, 2742 may output a signal indicative of the amount of radiation incident upon it. Each of these signals may be sent to the controller 2744 separately or as combined signals Sa, Sb.

By analysing the amount of radiation incident upon each of the plurality of sensors, the position of the output radiation beam B may be determined. For example, for embodiments wherein the sensing elements are distributed around the perimeter of a region in the y-z plane that substantially matches the intensity distribution of the output radiation beam B, if there is a difference in the amount of radiation incident on two diametrically opposed sensing elements then the centre of the output radiation beam B is closer to the sensing element that receives more radiation. Once the position of the radiation beam for each sensor set 2741, 2742 has been determined in this manner, the direction of the radiation beam may be determined. If this differs from the desired direction of the output radiation beam B, the controller 2744 may be operable to move the optical elements 2732, 2734, 2736, 2738 to correct for this.

The sensor sets 2741, 2742 of the sensor apparatus 2740 may be movable. This allows for changes in the output beam shape B and/or intensity profile to taken into account. For example, the sensor sets may moveable so that they can be distributed according to the beam profile shown in FIG. 78 when both free electron lasers FELa, FELb are on and they can be distributed according to the beam profile shown in FIG. 82 when only one of the free electron lasers FELa, FELb is on.

The radiation beams Ba', Bb' supply EUV radiation to the lithographic apparatuses LA1-LA20 and the optical system 2730 forms the first part of a set of dedicated optical components that direct the radiation from the free electron lasers FELa, FELb to the lithographic apparatuses LA1-LA20.

Each of the optical elements 2732, 2734, 2736, 2738 comprises a mirror and may be provided with an active cooling mechanism. For example, each mirror may be provided with a supply of cooling fluid such as, for example, water or carbon dioxide ($CO_2$). However, there is a limit to the power density that an optical element can absorb and dissipate, without sustaining damage.

For a given output power of the free electron lasers FELa, FELb, the power density that the first optical element 2732, 2736 downstream of the corresponding free electron laser FELa, FELb receives is dependent upon: (i) the initial size and divergence of the radiation beam Ba', Bb' as it leaves the undulator 24 of that free electron laser FELa, FELb; and (ii) the distance between the undulator 24 of that free electron laser FELa, FELb and its corresponding first optical element 2732, 2736. The power density that each first optical element 2732, 2736 receives decreases as the distance between that first optical element 2732, 2736 and its corresponding free electron laser FELa, FELb increases.

In embodiments of the present invention, the first optical elements 2732, 2736 are grazing incidence mirrors. Preferably, the first optical elements 2732, 2736 are formed from a material which is a good conductor of heat such as, for example, copper, with a coating that maximizes reflectivity and minimizes absorption such as, for example, ruthenium (Ru). The angle $\alpha$ between the radiation beam Ba', Bb' output by each free electron laser FELa, FELb and the surface of its corresponding first optical element 2732, 2736 is small, which provides two benefits: (a) it enlarges the beam spot size on the first optical elements 2732, 2736, lowering the power density; and (b) it lowers the absorption coefficient, reducing the fraction of the incident power which is absorbed, and must be dissipated, by the first optical elements 2732, 2736. The angle $\alpha$ between each radiation beam Ba', Bb' and the surface of the corresponding first optical element 2732, 2736 is preferably below about 10 degrees, since the reflectivity of the first optical elements 2732, 2736 drops significantly as the angle increases above 10 degrees. Since the first optical elements 2732, 2736 are convex, their radii of curvature set lower limits of the angle between the radiation beam Ba', Bb' and the surface of the corresponding first optical element 2732, 2736. Preferably the angle $\alpha$ is in the range 0.5 to 10 degrees, more preferably in the range 1 to 5 degrees, and most preferably in the range 1 to 3 degrees.

As the radiation beams Ba', Bb' propagate, they increase in size. The increase in size between two points will be proportional to the product of the distance between the two points and the tangent of half the divergence.

Since the divergence of the radiation beams Ba', Bb' produced by the free electron lasers FELa, FELb is so small, in order for the size of the beam to increase significantly (corresponding to a significant reduction in the power density absorbed by the first optical elements 2732, 2736), the beams must travel a significant distance. For example, it may be necessary for the distance between the undulator 24 of each free electron laser FELa, FELb and its corresponding first optical element 2732, 2736 to be of the order of tens of metres in order for the power density on the first optical elements 2732, 2736 to be sufficiently low that their surface coatings are not damaged. A distance between each undulator 24 and its corresponding first optical element 2732, 2736 of around 10 m may be too small and 100 m may be unnecessarily large. The distance may for example be in the range 30 m to 80 m, for example it may be around 50 m. In general, the distance between the undulator 24 of each free electron laser FELa, FELb and its corresponding first optical element 2732, 2736 at which damage of the first optical element is avoided will depend upon material properties of the surface coating and substrate of the first optical element and upon the effectiveness of a cooling system used to cool the first optical element (in addition to depending upon the power density of the beam).

In general, for a given initial beam diameter, power and divergence the power density absorbed by each first optical element 2732, 2736 may be varied by altering: (i) the angle α between the surface of that first optical element 2732, 2736 and the radiation beam Ba', Bb' incident upon it; and/or (ii) the distance L between that first optical element 2732, 2736 and its corresponding undulator 24. The range of acceptable values of angle α will be dependent upon the distance L and vice versa. The range of acceptable values of angle may also be constrained by the radius of curvature of the first optical element 2732, 2736 (to avoid the possibility that the first optical element curves away from the radiation beam Ba', Bb' to such an extent that part of the radiation beam misses the first optical element).

When the distance L between the undulator 24 of each free electron laser FELa, FELb and its corresponding first optical element 2732, 2736 is of the order of tens of metres, the placement of the beam spot on the first optical element 2732, 2736 will be strongly dependent upon the initial direction of the radiation beam Ba', Bb' leaving that undulator 24. A very small variation in this direction may cause the spot at the first optical element 2732, 2736 to move a significant distance. The distance L is sufficiently large that small relative mechanical movement of components of the radiation source SO7 and/or the buildings they are housed in can give rise to a large displacement of the spot on the first optical element 2732, 2736.

The controller 2744 and the four actuators 2752, 2754, 2756, 2758 provide an active feedback loop which allows each of the first optical elements 2732, 2736 to be placed sufficiently far from the undulator 24 of its corresponding free electron laser FELa, FELb so that it is not damaged whilst ensuring that the direction and position of the output beam B output by the optical system 2730 remains stable. Therefore, advantageously, the combination of free electron lasers (which have very small etendues) and this active feedback loop allows a high power EUV radiation beam to be available for lithography. In particular, it allows for a radiation source SO7 that has an output radiation beam with a sufficiently large power to serve a plurality (for example eight) lithographic apparatuses.

Referring to FIGS. 77, 79 and 80, relative to the reference set of axes 2770, the axes of the free electron lasers FELa, FELb are nominally disposed in the x-y plane and at a small angle β to the x axis. The output radiation beam B will generally propagate in the x direction. Each of the optical elements 2732, 2734, 2736, 2738 is operable to move linearly in the y and z directions and is operable to rotate about the x and z axes. This freedom allows the optical system 2730 to correct for deviations in the direction of propagation of the radiation beams Ba', Bb' from their nominal directions.

For example, a so called beam-pointing error may occur, wherein one of the radiation beams Ba', Bb' is not propagating at an angle β to the x-direction but instead is propagating at a slightly different angle. The pointing error may for example be such that the direction vector of the radiation beam Ba', Bb' lies in the x-y plane but makes a different angle with the x axis. This may be corrected for by rotating the first 2732, 2736 and second 2734, 2738 optical elements around the z-direction. Rotation of the first optical element 2732, 2736 may be used to direct the radiation beam Ba', Bb' such that it is incident upon the second optical element 2734, 2738, and rotation of the second optical element 2734, 2738 may be used to ensure that the output radiation beam B is propagating in the x-direction when it exits the optical system 2730.

A pointing error in which the direction of the radiation beam Ba', Bb' includes a component in the z-direction may be corrected for in a similar manner by rotating the first 2732, 2736 and second 2734, 2738 optical elements around the x-direction. A pointing error in which the radiation beam Ba', Bb' includes components in the y and z directions may be corrected for by rotating the first 2732, 2736 and second 2734, 2738 optical elements in both the x and z directions.

The first optical elements 2732, 2736 may be translatable in the y and z-directions. Translation in the y and z-directions may be used to ensure that the radiation beam Ba', Bb' is incident at or close to the centre of the first optical element. If the radiation beam Ba', Bb' has deviated such that it is no longer incident upon centre of the first optical element 2732, 2736 then the translation of the first optical element in the y and/or z directions may be performed until the radiation beam Ba', Bb' is at or close to the centre of the first optical element 2732, 2736. The position of the radiation beam Ba', Bb' on the first optical element 2732, 2736 may for example be monitored by a camera or some other sensor (not illustrated).

Translation of the second optical elements 2734, 2738 in the y and z-directions may not be needed in order to correct for beam pointing errors. However, the second optical elements 2734, 2738 may be translatable in the y and z-directions in order to allow for correction of other errors. Translation of the second optical elements 2734, 2738 may for example be used to provide correction or modification of the cross-sectional shape of the radiation beam (e.g. if the optical elements have an aspherical shape or other complex shape).

The controller 2744 may be operable to determine whether or not the position and/or direction of the output radiation beam B differs from a desired direction and if so, how the optical elements 2732, 2734, 2736, 2738 need to move in order to return the output radiation beam B to the desired direction. The controller 2744 may then convert this information into two signals for the actuators 62, 64, 66, 68 in order to move the optical elements 2732, 2734, 2736, 2738 accordingly. The controller 2744 may comprise a processor (not shown) which may implement the above described functions. The processor may calculate in real time how the optical elements 2732, 2734, 2736, 2738 must be moved in response to given input signals Sa, Sb from the sensor apparatus 2740. Additionally or alternatively, the processor may access this information from a look up table or the like which may be stored in a memory (not shown).

Figure 83:
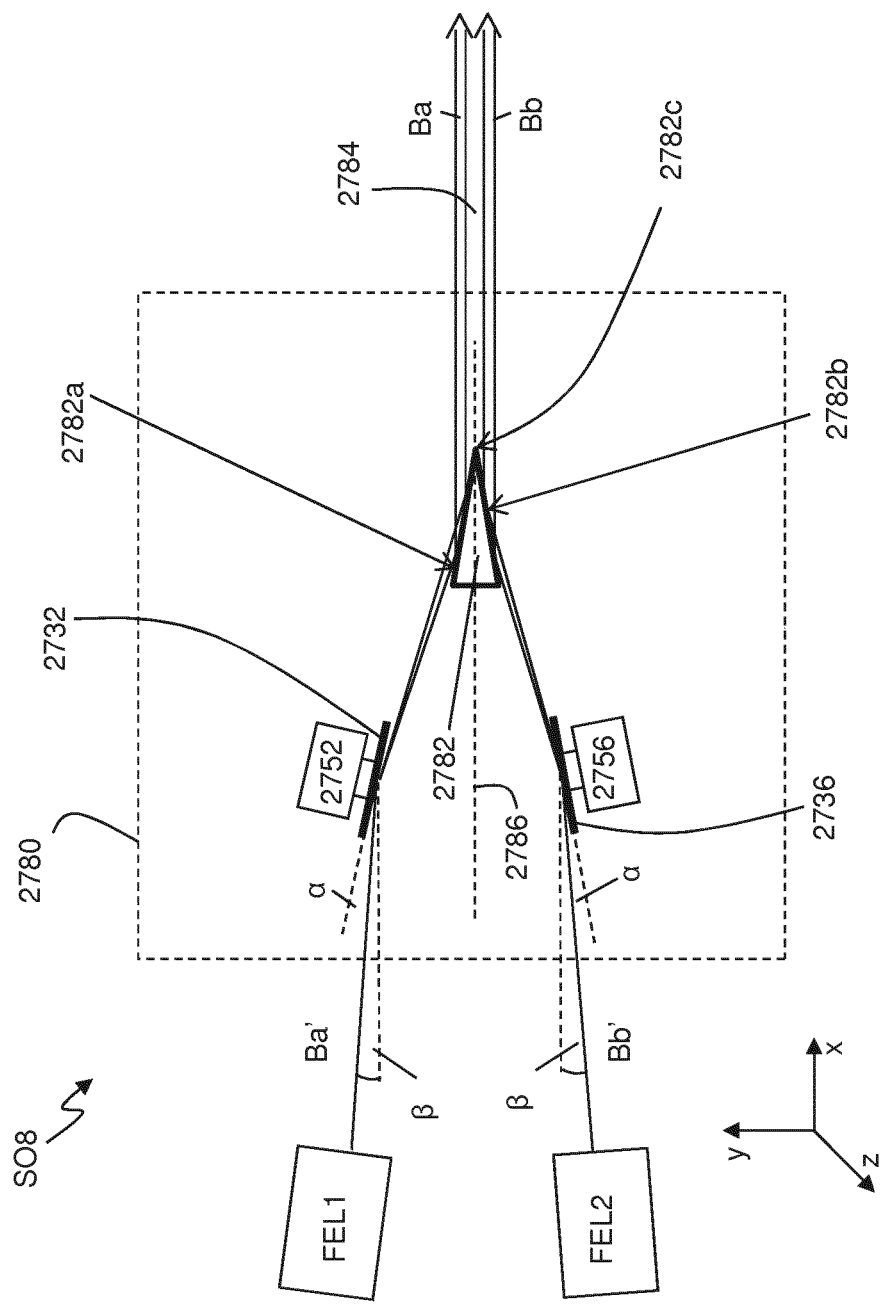
FIG. 83 is a schematic illustration of a further radiation source according to an embodiment described herein.
Figure 84:
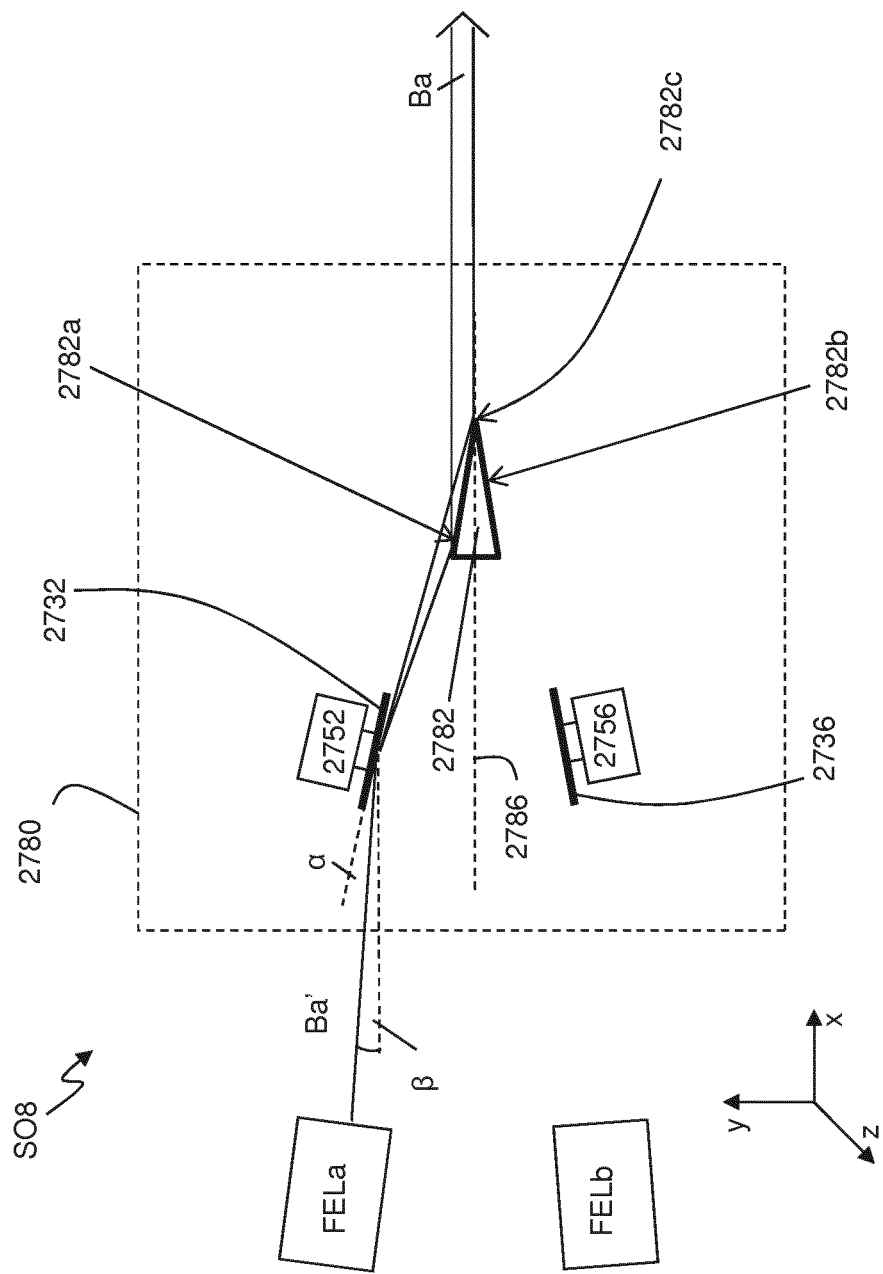
FIG. 84 is a schematic illustration of the radiation source shown in FIG. 83 when a first of the two free electron lasers is off.

The optical layout of the optical system 2730 of the first embodiment (FIGS. 77, 79 and 80) is not symmetric with respect to the two free electron lasers FELa, FELb, which may lead to slightly different optical properties for the radiation originating from different free electron lasers FELa, FELb. With reference to FIGS. 83 and 84, another embodiment of a radiation source SO8 is described. Like components in the two embodiments share common labels.

The radiation source SO8 comprises two free electron lasers FELa, FELb and an optical system 2780. The optical system 2780 comprises two first optical elements 2732, 2736, which are equivalent to those of optical system 2730 although they are disposed at generally the same position in the x direction. The optical system 2760 further comprises a single second optical element 2782. The second optical element 2782 is generally wedge shaped and comprises two reflective surfaces 2782*a*, 2782*b*. A first one of the reflective surfaces 2782*a* acts as a second optical element for the first free electron laser FELa and a second of the reflective surfaces 2782*b* acts as a second optical element for the second free electron laser FELb. Both of the reflective surfaces are concave and may have an astigmatic or a-spherical shape matching that of the first optical elements 2732, 2736.

Figure 85A:
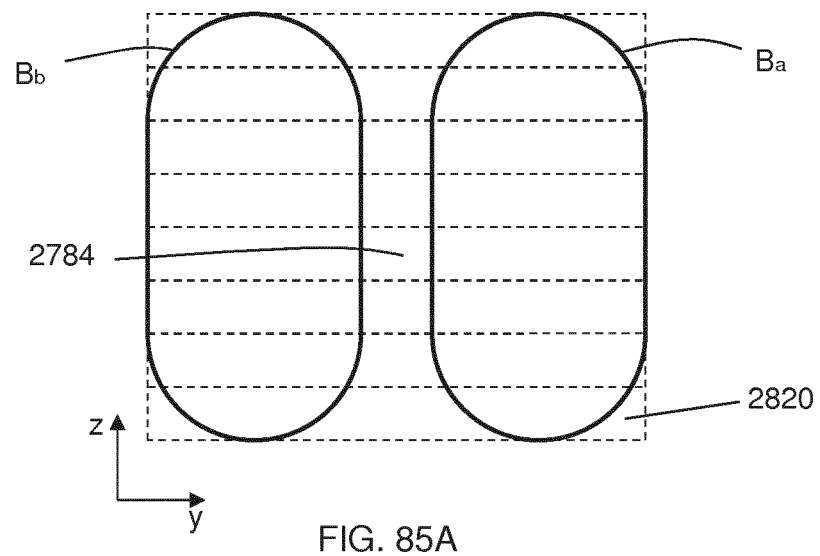
Figure 85B:
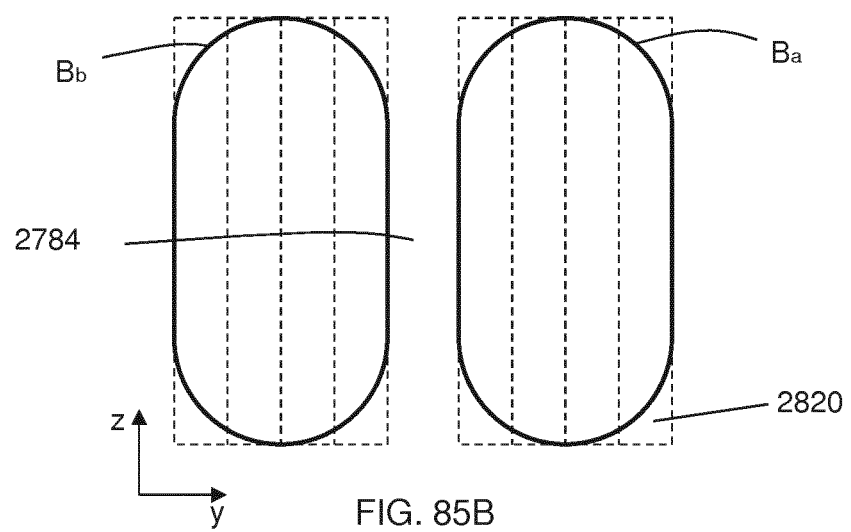

Similarly to the first embodiment SO, when both free electron lasers FELa, FELb are on, the optical system 2780 will act to increase the size of the radiation beams Ba', Bb', alter their shape and output a combined radiation beam B. However, as shown in FIG. 85, in contrast to the first embodiment SO, the combined beam B output by the optical system 2780 of the embodiment SO8 has a gap 2784 separating the contributions from the two free electron lasers FELa, FELb.

Although the second optical element 2782 is wedge shaped it cannot taper to a point at the intersection 2782*c* between the first and second reflective surfaces 2782*a*, 2782*b*. The second optical element 2782 is provided with at least a minimum thickness at the intersection 2782*c* so that the thermal conductivity of the second optical element 2782 can dissipate the absorbed radiation power from the radiation beams Ba', Bb'. The minimum size of the gap 2784 in the intensity distribution of the combined radiation beam B is determined by the minimal required thickness of the second optical element 2782 at the intersection 2782*c*.

In principle, this gap 2784 does not present any problem for the beam extracting optical elements within the beam splitting apparatus 20, which can be designed and positioned such that substantially the entire facetted field mirror device 10 of each lithographic apparatus LA1-LA20 is illuminated. For example, referring to FIG. 85B, the beam extracting optical elements may be arranged, as illustrated by regions 2820, such that the gap 2784 does not effect any of the branch radiation beams Ba-B8.

In some embodiments, similarly to the first embodiment SO, first optical elements 2732, 2736 are operable to rotate about axes 2792, 2796 in the z direction to alter their divergence, as described above in relation to the first embodiment SO. For such embodiments, the surfaces 2782*a*, 2782*b* of the second optical element 2782 are of sufficient size to accommodate a single radiation beam from one of the free electron lasers FELa, FELb (see FIG. 84). The shape of the radiation beam B output by the optical system 2780 will be as shown in FIG. 82. Note that when only one free election laser FELa, FELb is on, the radiation beam B output by the optical system 2780 does not have a gap 2784 and will be shifted either up or down in the y direction. Therefore the beam splitting apparatus 20 will have to be altered when switching between use of one free electron laser FELa, FELb and two free electron lasers FELa, FELb, unless the gap 2784 is negligibly small and the second optical element 2782 can be moved in the y direction to ensure the output radiation beam B is centred on the dashed line 2786.

The embodiment of a radiation source SO8 may incorporate any or all compatible features of the first embodiment of a radiation source SO as desired or appropriate. For example, although not shown in FIGS. 83 and 84, radiation source SO8 may further comprise a sensor apparatus and the optical system 2780 may further comprises a controller and an actuator for each of the optical elements 2732, 2736, 2782. Each of the actuators may be operable to move one of the optical elements 2732, 2736, 2782 to compensate for changes in the direction of the beams of radiation produced by the two free electron lasers FELa, FELb.

Figure 86:
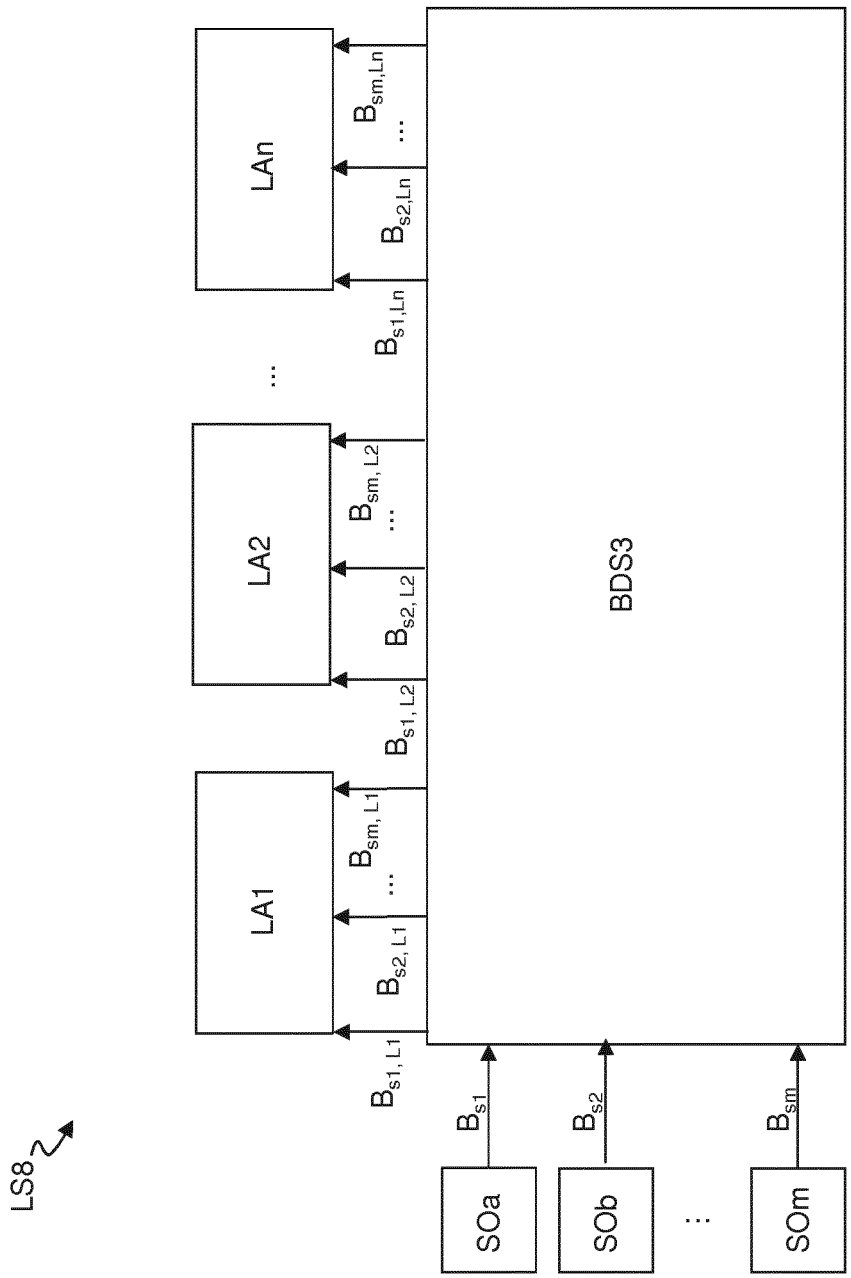
FIG. 86 is a schematic illustration of a further embodiment of a lithographic system.

FIG. 86 shows a lithographic system LS8 comprising m radiation sources SOa-SOm, a beam delivery system BDS3 and n lithographic apparatuses LA1'-LAn'. Each of the radiation sources SOa-SOm is selectively operable to produce an extreme ultraviolet (EUV) radiation beam $B_{S1}$-$B_{Sm}$ (which may be referred to as a main beam). That is, each of the radiation sources SOa-SOm is switchable between an on state wherein it produces a main radiation beam and an off state wherein it does not. Each of the radiation sources SOa-SOm may be said to be on when disposed in its on state, and may be said to be off when disposed in its off state. The beam delivery system BDS3 is arranged to receive the main radiation beams $B_{S1}$-$B_{Sm}$ produced by each of the radiation sources SOa-SOm and to direct a portion of each main radiation beam to each lithographic apparatus LA1'-LAn' as now described.

The beam delivery system BDS3 comprises beam splitting optics. The beam splitting optics splits each main radiation beam $B_{S1}$-$B_{Sm}$ into n separate radiation beams (which may be referred to as branch beams), each of which is directed to a different one of the n lithographic apparatuses LA1'-LAn'. For example, the main radiation beam $B_{S1}$ output by the first radiation source, is split into n branch radiation beams $B_{S1,L1}$-$B_{S1,Ln}$, the main radiation beam $B_{S2}$ output by the second radiation source, is split into n branch radiation beams $B_{S2,L1}$-$B_{S2,Ln}$ and the main radiation beam $B_{Sm}$ output by the mth radiation source, is split into n branch radiation beams $B_{Sm,L1}$-$B_{Sm,Ln}$. In the following, it will be understood that a branch radiation beam referred to as branch radiation beam $B_{Si,Lj}$ refers to the portion of radiation output by the ith radiation source, which is directed to the jth lithographic apparatus.

The beam delivery system BDS3 may comprise m beam splitting optics, arranged such that a different one of said m beam splitting optics is provided for each individual main radiation beam $B_{S1}$-$B_{Sm}$. Beam guiding optics may be arranged to guide branch radiation beams output by each of the m beam splitting optics to the lithographic apparatuses. Optionally, for such embodiments beam combining optics may be provided to combine the branch radiation beams output by the m beam splitting optics into n composite radiation beams, each of which is directed towards a different lithographic apparatus LA1'-LAn'. For example, a single branch radiation beam from each of the m main radiation beams $B_{S1}$-$B_{Sm}$ may be combined into each composite radiation beam. For example, beam combining optics may be arranged to form a composite radiation beam comprising branch radiation beams $B_{S2,L1}$, $B_{S2,L1}$, . . . $B_{Sm,L1}$ that is directed to the first lithographic apparatus LA1'. Such an arrangement may reduce the complexity of the beam guiding optics since all of the branch radiation beams within a given composite radiation beam may share a single set of beam guiding optics. Each composite radiation beam may for example comprise a plurality of substantially parallel closely spaced branch radiation beams (i.e. with no spatial overlap).

Alternatively, the beam delivery system BDS3 may comprise beam combining optics arranged to combine the m main radiation beams output by the m radiation sources SOa-SOm into a single composite radiation beam. For such embodiments, a single set of beam splitting optics may be arranged to split the single composite radiation beam into n composite radiation beams, each of which is directed towards a different lithographic apparatus LA1'-LAn'.

The beam delivery system BDS3 may further comprise beam expanding optics and/or beam shaping optics. The beam expanding optics may be arranged to increase the cross sectional area of one or more of the main radiation beams $B_{S1}$-$B_{Sm}$ or the branch radiation beams formed therefrom. This decreases the power density of the heat load on mirrors downstream of the beam expanding optics. This may allow the mirrors downstream of the beam expanding optics to be of a lower specification, with less cooling, and therefore less expensive. Further, the lower power density on such mirrors results in less deformation of their optical surfaces due to thermal expansion. Additionally or alternatively, reducing the power density of the heat load on downstream mirrors may allow these mirrors to receive the main radiation beams $B_{S1}$-$B_{Sm}$, or the branch radiation beams formed therefrom at a larger grazing incidence angle. For example, the mirrors may receive radiation at a grazing incidence angle of 5 degrees rather than, say, 2 degrees. The beam shaping optics may be arranged to alter the cross sectional shape and/or the intensity profile of one or more of the main radiation beams $B_{S1}$-$B_{Sm}$ or the branch radiation beams formed therefrom.

In alternative embodiments, the beam delivery system BDS3 may not comprise beam expanding optics or beam shaping optics.

In some embodiments, the beam delivery system BDS3 may comprise beam reducing optics, which may be arranged to decrease the cross sectional area of one or more of the main radiation beams $B_{S1}$-$B_{Sm}$ or the branch radiation beams formed therefrom. As discussed above, beam expanding optics may reduce the power density of the heat load received by mirrors within the beam delivery system BDS3, which may be desirable. However, beam expanding optics will also increase the size of said mirrors, which may be undesirable. Beam expanding optics and beam reducing optics may be used to reach a desired beam size, which may be the smallest beam cross section that results in optical aberrations below a given threshold level.

The radiation sources SOa-SOm, beam delivery system BDS3 and lithographic apparatuses LA1'-LAn' may all be constructed and arranged such that they can be isolated from the external environment. A vacuum may be provided in at least part of the radiation sources SOa-SOm, beam delivery system BDS3 and lithographic apparatuses LA1'-LAn' so as to minimise the absorption of EUV radiation. Different parts of the lithographic system LS8 may be provided with vacuums at different pressures (i.e. held at different pressures which are below atmospheric pressure). Different parts of the lithographic system LS8 may, for example, be maintained under ultra-high vacuum (UHV) conditions, except for a partial hydrogen pressure. The partial hydrogen pressure may be well below 10 Pa, for example below 1 Pa.

Figure 87:
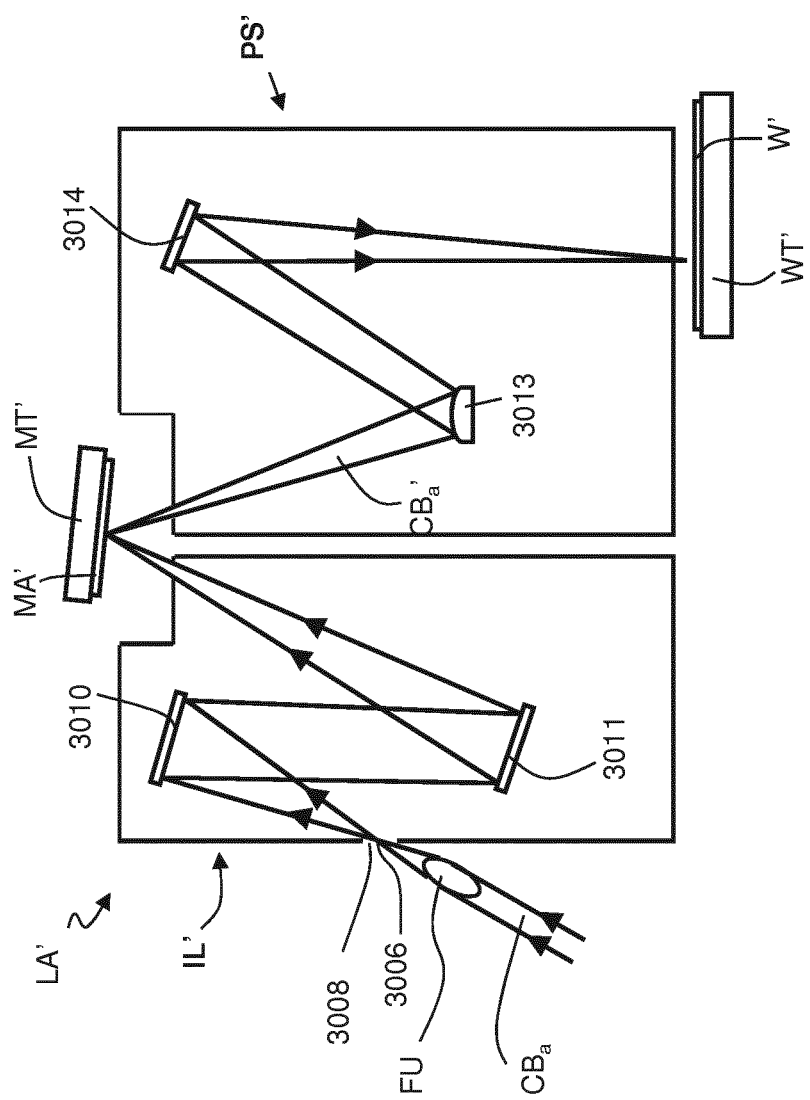
FIG. 87 is a schematic illustration of a lithographic apparatus that may form part of a lithographic system described herein.

FIG. 87 shows a lithographic apparatus LA', which comprises a focusing unit FU, an illumination system IL, a support structure MT configured to support a patterning device MA (e.g. a mask), a projection system PS and a substrate table WT configured to support a substrate W. Each of the lithographic apparatuses LA1'-LAn' may be substantially identical to the lithographic apparatus LA' of FIG. 87 as now described.

The illumination system IL is configured to receive a radiation beam $CB_a$ though an opening 3008 in an enclosing structure of the illumination system IL. The opening 3008 may, for example, have a diameter of the order of a few millimetres. A first optical element of the illumination system IL comprises a facetted field mirror device 3010 and has a non-zero numerical aperture. For example, the facetted field mirror device 3010 may have a numerical aperture of around 0.22 and a focal point at or near to the opening 3008. Therefore the focusing unit FU is arranged to focus the radiation beam $CB_a$ at or near to the opening 3008 such that the facetted field mirror device 3010 is substantially fully illuminated by the radiation.

Although not shown in FIG. 87 for clarity, the lithographic apparatus LA' is arranged to receive a composite radiation beam $CB_a$, comprising a plurality of substantially parallel adjacent radiation sub-beams. For example, the first lithographic apparatus of FIG. 86 is arranged to receive a composite radiation beam comprising branch radiation beams $B_{S2,L1}$, $B_{S2,L1}$, ... $B_{Sm,L1}$. Further, also not shown on FIG. 87 for clarity, focusing unit FU comprises a plurality of focusing optics, each being arranged to receive a different one of the radiation sub-beams that are received by the lithographic apparatus LA'. As will be described further below, the plurality of focusing optics are arranged to focus each of the radiation sub-beams received by the lithographic apparatus LA' at different intermediate foci. The different intermediate foci are arranged around an optical axis of the facetted field mirror device 3010 in close proximity to it, such that at the facetted field mirror device 3010 the radiation from each of the different radiation sub-beams partially overlaps and the facetted field mirror device 3010 is completely illuminated by each of the radiation sub-beams. For clarity, only a single intermediate focus 3006 has been shown in FIG. 87.

The illumination system IL is configured to condition the radiation beam $CB_a$ that is received by that lithographic apparatus LA1' before it is incident upon the patterning device MA. For this purpose, a second optical element of the illumination system IL comprises a facetted pupil mirror device 3011. The faceted field mirror device 3010 and faceted pupil mirror device 3011 together provide the radiation beam $CB_a$ with a desired cross-sectional shape and a desired angular distribution. The radiation beam $CB_a$ passes from the illumination system IL and is incident upon the patterning device MA held by the support structure MT. The patterning device MA reflects and patterns the radiation beam to form a patterned beam $CB_a'$. In alternative embodiments, the illumination system IL may include other mirrors or devices in addition to or instead of the faceted field mirror device 3010 and faceted pupil mirror device 3011. The illumination system IL may for example include an array (or matrix) of independently moveable mirrors. The independently moveable mirrors may for example measure less than 1 mm across. The independently moveable mirrors may for example be microelectromechanical systems (MEMS) devices.

Following reflection from the patterning device MA' the patterned radiation beam $CB_a'$ enters the projection system PS'. The projection system PS' is configured to project the patterned radiation beam $CB_a'$ onto a substrate W' held by the substrate table WT'. For this purpose, the projection system PS' comprises a plurality of mirrors 3013, 3014 which are configured to project the patterned radiation beam $CB_a'$ onto the substrate W'. The projection system PS' may apply a reduction factor to the patterned radiation beam $CB_a'$, so as to form an image with features that are smaller than corresponding features on the patterning device MA'. For example, a reduction factor of 4 may be applied. The projection system PS' may apply a different reduction factor to the patterned radiation beam $CB_a'$ in each of two mutually perpendicular directions (which may be referred to as the x and y directions). Although the projection system PS' has two mirrors in FIG. 87, the projection system may include any number of mirrors (e.g. six mirrors). The substrate W' may include previously formed patterns. Where this is the case, the lithographic apparatus LA' aligns the patterned radiation beam $CB_a'$ with a pattern previously formed on the substrate W'.

Each of the radiation sources SOa-SOm is configured to generate an EUV radiation beam $B_{S1}$-$B_{Sm}$. These m EUV radiation beams $B_{S1}$-$B_{Sm}$ have a sufficient combined power to supply each of the lithographic apparatuses LA1'-LAn'. Each of the radiation sources may comprise a free electron laser. Alternatively, the radiation source may be implemented in any other way and may, for example, comprise a laser produced plasma (LPP) radiation source.

The following discussion relates to radiation generated by a free electron laser but it will be appreciated that a free electron laser is not essential to the invention. Embodiments of the invention may incorporate other high power radiation sources with relatively small etendues.

The radiation beam B output by the free electron laser FEL may have a substantially circular cross section and a Gaussian-like intensity profile. The radiation beam B produced by an EUV free electron laser typically has a relatively small etendue. In particular, the EUV radiation beam B produced by a free electron laser FEL has a significantly smaller etendue than an EUV radiation beam that would be generated by a laser produced plasma (LPP) source or a discharge produced plasma (DPP) source (both of which are known in the prior art). For example, the radiation beam B may have a divergence less than 500 μrad, for example less than 100 μrad. The radiation beam B may for example have a diameter of around 50 μm to 100 μm at its beam waist, as it leaves the undulator 24.

In free space (i.e. with a refractive index of 1), the etendue of a radiation beam at an infinitesimal surface element dS in an optical system is given by the product of the area of the surface dS, the solid angle dΩ subtended by radiation crossing (or emitted by) the surface element and the cosine of the angle between the normal to the surface element and the direction of the radiation crossing that point. In general, the etendue of a radiation beam at an extended surface S is given by integrating over the solid angle subtended by radiation crossing (or emitted by) each surface element (to account for the fact that light may cross each point on the surface at a range of angles) and integrating over the surface (to sum the contributions from all such surface elements). For a light source operable to produce a well collimated radiation beam, as is produced by a free electron laser, the etendue of the light source may be estimated by the product of the area of the light source and the solid angle into which light is emitted. Further, for such a light source the solid angle into which light is emitted is given by (using small angle approximations) $\pi\theta^2$, where θ is the half divergence of the light source. Therefore the etendue of a such a light source is given by $G=\pi A\theta^2$, where A is the area of the light source, from which it can be seen that the etendue of a free electron laser with a beam waist diameter of 50 μm and a full divergence of 100 μrad is around $1.5\times10^{-11}$ mm$^2$.

The etendue of a radiation beam cannot decrease as it propagates an optical system. The etendue of a radiation beam remains constant as it propagates through a perfect optical system in free space, i.e. an optical system with perfect reflections and refractions. However, as a radiation beam propagates through an optical system which spreads out radiation, for example by scattering and/or diffraction, its etendue will increase. The higher the quality of the optical elements (for example mirrors and lenses) in the optical system, the smaller the increase in etendue will be.

In light of the above, for embodiments wherein the m radiation sources SOa-SOm comprise free electron lasers, the main radiation beams $B_{S1}$-$B_{Sm}$ each have a very small etendue and, further, this etendue will either remain constant or increase by a relatively small amount as the radiation propagates from each light source to the lithographic apparatuses LA1'-LAn'. As a result, the etendue of the radiation that is projected onto the first optical element of each lithographic apparatus LA1'-LAn' (for example the faceted field mirror device 3010 shown in FIG. 87) will also be very small. Therefore, the diameter of the intermediate focus formed by each free electron laser will be relatively small.

As discussed above, the first optical element of the illumination system IL' of each lithographic apparatus LA1'-LAn' has a non-zero numerical aperture, which may be of the order of around 0.22. That is, the solid angle subtended by the first optical element at its focal point (which is at or near to the opening 3008) is significantly larger than the solid angle into which each free electron laser emits radiation. If the etendue of the radiation remains substantially constant, this means that the diameter of the intermediate focus formed by each free electron laser will be significantly smaller than (the already small) diameter of the beam waist diameter of each main radiation beam $B_{S1}$-$B_{Sm}$.

Embodiments of the present invention exploit the fact that radiation sources SOa-SOm with sufficiently small etendue, in combination with a high quality beam delivery system BDS3, form sufficiently small intermediate foci at each lithographic apparatus LA1'-LAn' to allow two or more such intermediate foci to be closely spaced. By arranging these intermediate foci around an optical axis of the facetted field mirror device 3010 in close proximity to it, the radiation from each of the different branch radiation beams received by a given lithographic apparatus can partially overlap at the facetted field mirror device 3010 such that the facetted field mirror device 3010 is completely illuminated by each of the branch radiation beams.

Although embodiments of the invention are herein described with particular reference to free electron lasers, it will be apparent that the radiation sources SOa-SOm may comprise any other type of radiation source with a sufficiently small etendue.

Various embodiments of focusing units FU for lithographic apparatuses LA1'-LAn' and beam delivery systems BDS3 for use with an embodiment of the lithographic system LS8 of FIG. 86 comprising two radiation sources SOa, SOb (i.e. m=2) are now described.

Figure 88:
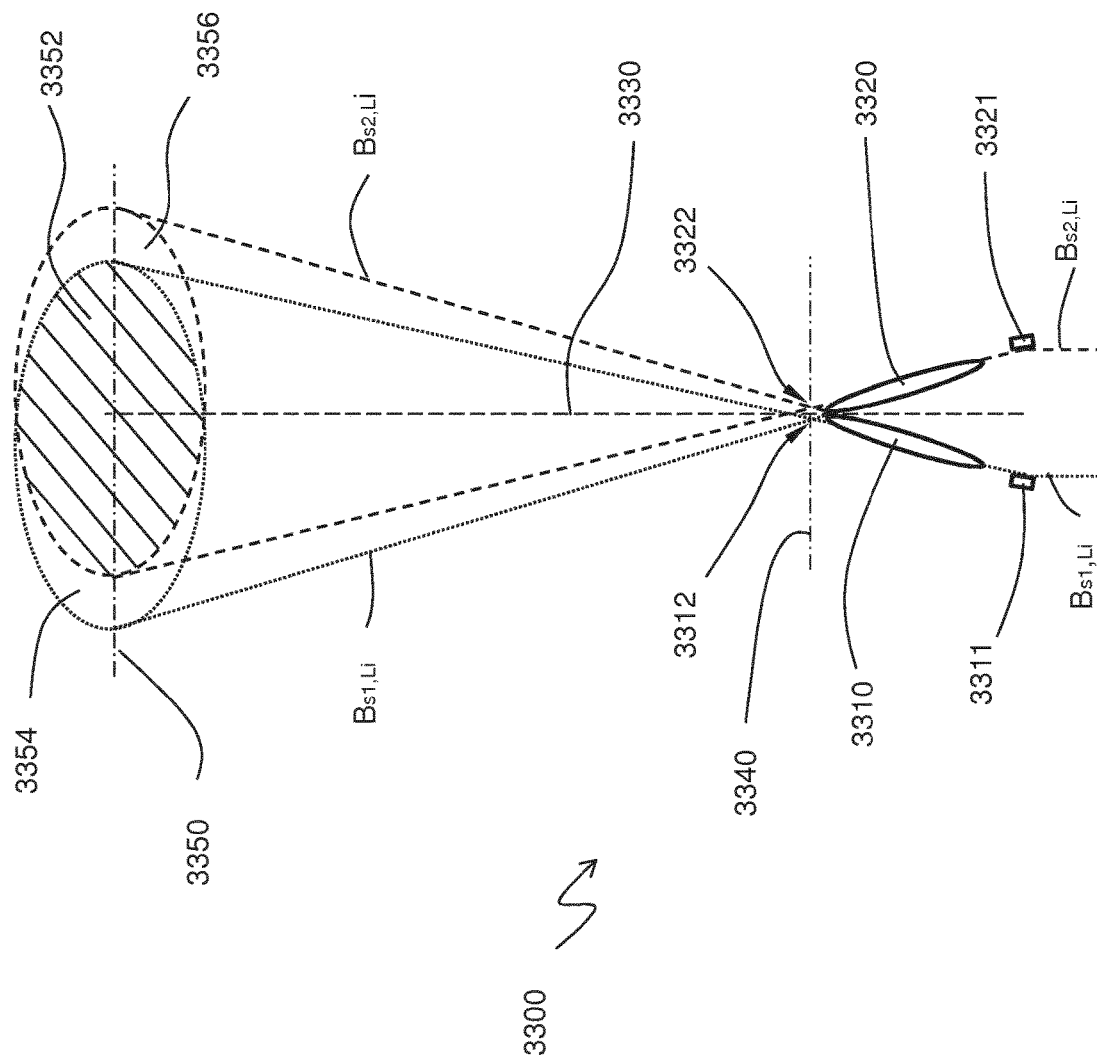
FIG. 88 is a schematic illustration of a focusing unit that may form part of the lithographic apparatus of FIG. 87.

FIG. 88 shows a schematic layout of a focusing unit 3300, which may form the focusing unit FU of each of the lithographic apparatuses LA1'-LAn'.

Focusing unit 3300 comprises two focusing elements 3310, 3320, each of which is arranged to receive an input radiation beam and focus it at an intermediate focus. In particular, each focusing element 3310, 3320 comprises a Wolter collector, which uses two curved grazing incidence mirrors that are arranged to receive a generally parallel radiation beam and focus it to a focal point. The radiation beams received by focusing elements 3310, 3320 may, for example, comprise the ith branch radiation beams $B_{S1,Li}$, $B_{S2,Li}$ from each of two radiation sources SOa, SOb.

Figure 90:
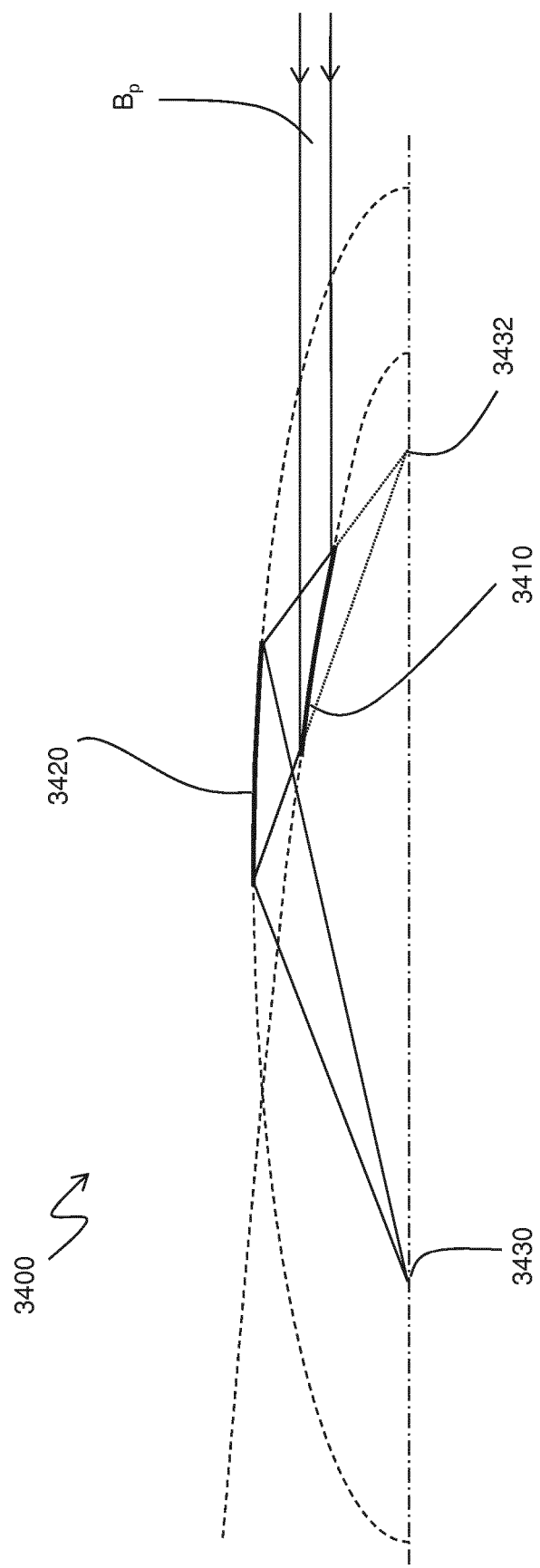
FIG. 90 is a schematic illustration of a type III Wolter collector which may form part of the focusing unit of FIG. 88.

Each focusing element 3310, 3320 may comprise a type III Wolter collector. FIG. 90 shows a cross sectional view of a type III Wolter collector 3400. The collector comprises an inner, convex parabolic mirror 3410 and an outer, concave elliptical mirror 3420. When a generally parallel input radiation beam is incident upon the parabolic mirror 3410, it is reflected onto the elliptical mirror 3420, reflected by the elliptical mirror 3420 and focused to a focal point 3430 of the collector 3400. As it propagates away from the parabolic mirror 3410, the radiation beam appears to originate from a focal point 3432 of the parabolic mirror 3410, which coincides with a first focal point of the elliptical mirror 3420. As a result, after reflection form the elliptical mirror 3420, the focal point 3430 of the collector 3400 coincides with a second focal point of the elliptical mirror 3420. Such an arrangement allows EUV or X-ray radiation to be focused using reflective grazing incidence optics.

The two focusing elements 3310, 3320 are arranged adjacent to each other, symmetrically about a central axis 3330 of the focusing unit 3300. Each of the focusing elements 3310, 3320 is provided with a grazing incidence steering mirror 3311, 3321 respectively. The grazing incidence steering mirrors 3311, 3321 are arranged to control the direction of branch radiation beams $B_{S1,Li}$, $B_{S2,Li}$ as they approach focusing elements 3310, 3320 respectively. Each focusing element 3310, 3320 and its associated grazing incidence steering mirror 3311, 3321 may be referred to as a focusing optics.

Steering mirror 3311 is arranged to receive a generally parallel branch radiation beam $B_{S1,Li}$ which is on one side of and generally parallel to the central axis 3330. Steering mirror 3311 alters the direction of branch radiation beam $B_{S1,Li}$ as it approaches focusing element 3310. As can be seen most clearly in FIG. 89, focusing element 3310 focuses the branch radiation beam $B_{S1,Li}$ to an intermediate focus 3312 which lies in a focal plane 3340 of the focusing unit 3300. The intermediate focus is 3312 is disposed on one side of the central axis 3330, separated by a distance x (in the focal plane 3340).

Similarly, steering mirror 3321 is arranged to receive a generally parallel branch radiation beam $B_{S2,Li}$ which is generally parallel to the central axis 3330, on the opposite side of the central axis 3330 to branch radiation beam $B_{S1,Li}$. Steering mirror 3321 alters the direction of branch radiation beam $B_{S2,Li}$ as it approaches focusing element 3320. As can be seen most clearly in FIG. 89, focusing unit 3320 focuses the branch radiation beam $B_{S2,Li}$ to an intermediate focus 3322 which lies in the focal plane 3340 of the focusing unit 3300. Intermediate focus is 3322 is disposed on an opposite side of the central axis 3330 to intermediate focus 3312 and is separated from the central axis 3330 by a distance x (in the focal plane 3340).

On an opposite side of the focal plane 3340 to the two focusing elements 3310, 3320 the two branch radiation beams $B_{S1,Li}$, $B_{S2,Li}$ are divergent, their divergence being determined by the diameter of the incoming branch radiation beams $B_{S1,Li}$, $B_{S2,Li}$ and the curvature of the mirrors within each of the focusing elements 3310, 3320. Close to the focal plane 3340 of the focusing unit 3300, the two divergent branch radiation beams $B_{S1,Li}$, $B_{S2,Li}$ remain spatially separated. However, as can be seen in FIG. 88, at a sufficiently large distance from the focal plane 3340 of the focusing unit 3300, for example, in plane 3350 the two beams partially overlap. An overlap region 3352 of plane 3350 receives radiation from both of the two branch radiation beams $B_{S1,Li}$, $B_{S2,Li}$. A first edge region 3354 of plane 3350 only receives radiation from branch radiation beam $B_{S1,Li}$ and second edge region 3356 of plane 3350 only receives radiation from branch radiation beam $B_{S2,Li}$. By reducing the distance x in the focal plane 3340 separating each of the intermediate foci 3312, 3322 from the central axis 3330, the size of the overlap region 3352 in plane 3350 can be increased.

The grazing incidence steering mirrors 3311, 3321 may be arranged to control the direction of branch radiation beams $B_{S1,Li}$, $B_{S2,Li}$ as they approach focusing elements 3310, 3320 respectively so as to maximise the overlap between the two branch radiation beams $B_{S1,Li}$, $B_{S2,Li}$ in plane 3350. Additionally or alternatively, the grazing incidence steering mirrors 3311, 3321 and the two focusing elements 3310, 3320 may be arranged to ensure that the direction of each of the branch radiation beams $B_{S1,Li}$, $B_{S2,Li}$ as they leave focusing elements 3310, 3320 is generally aligned with the central axis 3330. Such an arrangement minimises the difference between the angle at which each of the two branch radiation beams $B_{S1,Li}$, $B_{S2,L1}$ approaches plane 3350. In turn, this minimises any shift of the intensity profile of the radiation beam $CB_a$ that is incident upon the patterning device MA'.

In use, the focusing unit 3300 is disposed proximate to the opening 3008 in the enclosing structure of the illumination system IL' of a lithographic apparatus, for example the ith lithographic apparatus LAi of lithographic system LS8. The focusing unit 3300 is arranged such that its central axis 3330 is generally aligned with an optical axis of the first optical element of the lithographic apparatus LAi (for example the faceted field mirror device 3010). Further, the focusing unit 3300 is arranged such that a focal point of the first optical element of the lithographic apparatus LAi lies in, or close to, the focal plane 3340 of the focusing unit 3300. With such an arrangement, the focusing unit 3300 can focus the two branch radiation beams $B_{S1,Li}$, $B_{S2,Li}$ to the two intermediate foci 3312, 3322 at or near to the opening 3008. The facetted field mirror device 3010 is disposed within the overlap of the two branch radiation beams $B_{S1,Li}$, $B_{S2,Li}$. For example, the facetted field mirror device 3010 may be disposed in the overlap region 3352 of the plane 3350 shown in FIG. 88. Therefore, substantially the entire field of the facetted field mirror device 3010 is illuminated by both branch radiation beams $B_{S1,Li}$, $B_{S2,Li}$. It will be appreciated that "the entire field of the facetted field mirror device 3010" comprises all those parts of the facetted field mirror device 3010 that project onto the substrate W', regardless of any pattern imparted to the radiation beam by the lithographic apparatus LAi. That is, when those parts of the facetted field mirror device 3010 receive radiation, and no pattern is imparted to the radiation beam, that radiation will propagate through the lithographic apparatus LAi to the substrate W'.

In some embodiments, the focusing unit 3300 may be arranged such that a focal point of the first optical element of the lithographic apparatus LAi lies close to, but not in, the focal plane 3340 of the focusing unit 3300. Such a defocusing of the branch radiation beams $B_{S1,Li}$, $B_{S2,Li}$ increases the size of the light spots in the plane 3340. The facetted field mirror device 3010 is arranged to form an image of these light spots on each of the mirrors of the faceted pupil mirror device 3011. Therefore, arranging for a focal point of the first optical element of the lithographic apparatus LAi to lie close to, but not in, the focal plane 3340 of the focusing unit 3300 will, in turn, increases the size of the beam spots that are imaged onto the mirrors of the faceted pupil mirror device 3011. This may be beneficial since it reduces the power densities of the heat load on the mirrors of the faceted pupil mirror device 3011 (and likewise on any mirror downstream that is located in a pupil plane).

With such an arrangement, the radiation which is received by the first and second edge regions 3354, 3356 does not illuminate the facetted field mirror device 3010 and is therefore discarded. By reducing the distance x in the focal plane 3340 separating each of the intermediate foci 3312, 3322 from the central axis 3330, the fraction of radiation that is discarded in this manner can be decreased. For a free electron laser with a beam waist diameter of 50 μm and a full divergence of 100 μrad, the intermediate foci 3312, 3322 may be disposed sufficiently close to the central axis 3330 to ensure that the radiation that is received by the first and second edge regions 3354, 3356 and is therefore discarded is only a very small percentage of the radiation received by the lithographic apparatus LAi. For example, the distance x between each of the two intermediate foci 3312, 3322 and the central axis may be of the order of 3 mm and the radius of each of the branch radiation beams $B_{S1,Li}$, $B_{S2,Li}$ in the plane of the facetted field mirror device 3010 may be of the order of 225 mm. For such an arrangement, it can be shown that the ratio of the size of each of the first and second edge regions 3354, 3356 to the size of the overlap region 3352 is around 0.017. Therefore, for embodiments wherein the branch radiation beams $B_{S1,Li}$, $B_{S2,Li}$ have top-hat intensity distributions, 1.7% of the radiation would be discarded. For embodiments wherein the branch radiation beams $B_{S1,Li}$, $B_{S2,Li}$ have Gaussian-like intensity distributions, the intensity of the branch radiation beams $B_{S1,Li}$, $B_{S2,Li}$ in the first and second edge regions 3354, 3356 is relatively low. For a Gaussian-like radiation beam, the intensity at a radius of 2 sigma is 13.5% of the intensity in the centre. Thus for an embodiment wherein the branch radiation beams $B_{S1,Li}$, $B_{S2,Li}$ have Gaussian-like intensity distributions and the first and second edge regions 3354, 3356 are around 2 sigma from the centres of the branch radiation beams $B_{S1,Li}$, $B_{S2,Li}$, only around 1.7%×13.5%=0.23% of the radiation would be discarded.

The use of a focusing unit 3300 comprising a plurality (in this case two) of focusing elements 3310, 3320, each arranged to receive a different radiation beam and project it onto the first optical element of the lithographic apparatus LAi (for example the faceted field mirror device 3010) offers an arrangement that is relatively insensitive to the number of input radiation beams. For example, in the case that one of two radiation sources SOa, SOb is not operating, the facetted field mirror device 3010 of each lithographic apparatus LA1'-LAn' remains substantially fully illuminated by a branch radiation beams from the other source. No active adjustments must be made to the beam delivery system BDS3 (for example to alter the optical paths followed by radiation from the operating radiation source) or to the lithographic apparatuses LA1'-LAn' (for example, to adjust the configurations of the faceted field mirror device 3010 and faceted pupil mirror device 3011) for the lithographic apparatus to continue operating. The power of the radiation received by each lithographic apparatus is reduced (for example by a factor of m/(m−1) when one of m identical radiation sources SOa-SOm is not operating) but otherwise the lithographic system LS8 will remain unaffected.

Figure 91:
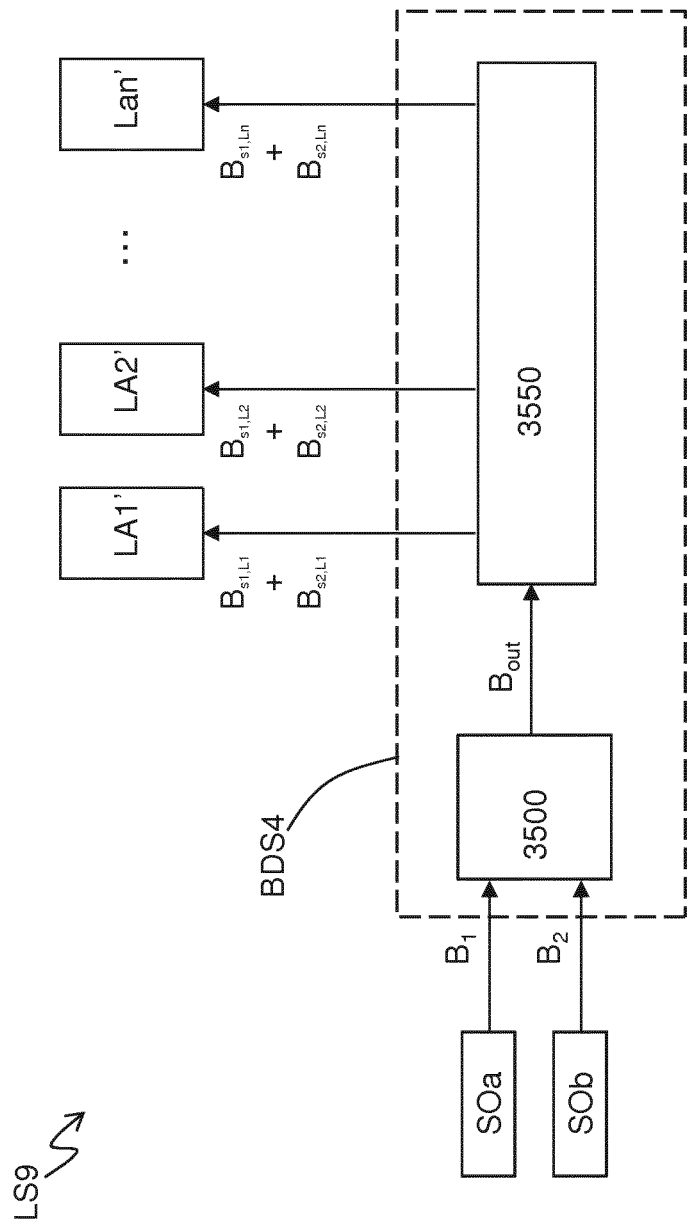
FIG. 91 is a schematic illustration of an example embodiment of a lithographic system of the type shown in FIG. 86.

FIG. 91 shows a lithographic system LS9 which is an embodiment of the lithographic system LS of FIG. 86 comprising two radiation sources SOa, SOb (i.e. m=2). Lithographic system LS9 comprises a beam delivery system BDS4, which comprises beam combining optics 3500 and beam splitting optics 3550. The beam combining optics 3500 is arranged to receive two main radiation beams $B_{S1}$, $B_{S2}$ output by two radiation sources SOa-SOb and to output a single composite radiation beam $B_{out}$. The beam splitting optics 3550 is arranged to receive the single composite radiation $B_{out}$ output by the beam combining optics 3500 and to split it into n composite radiation beams, each of which is directed towards a different lithographic apparatus LA1'-LAn'.

Figure 92:
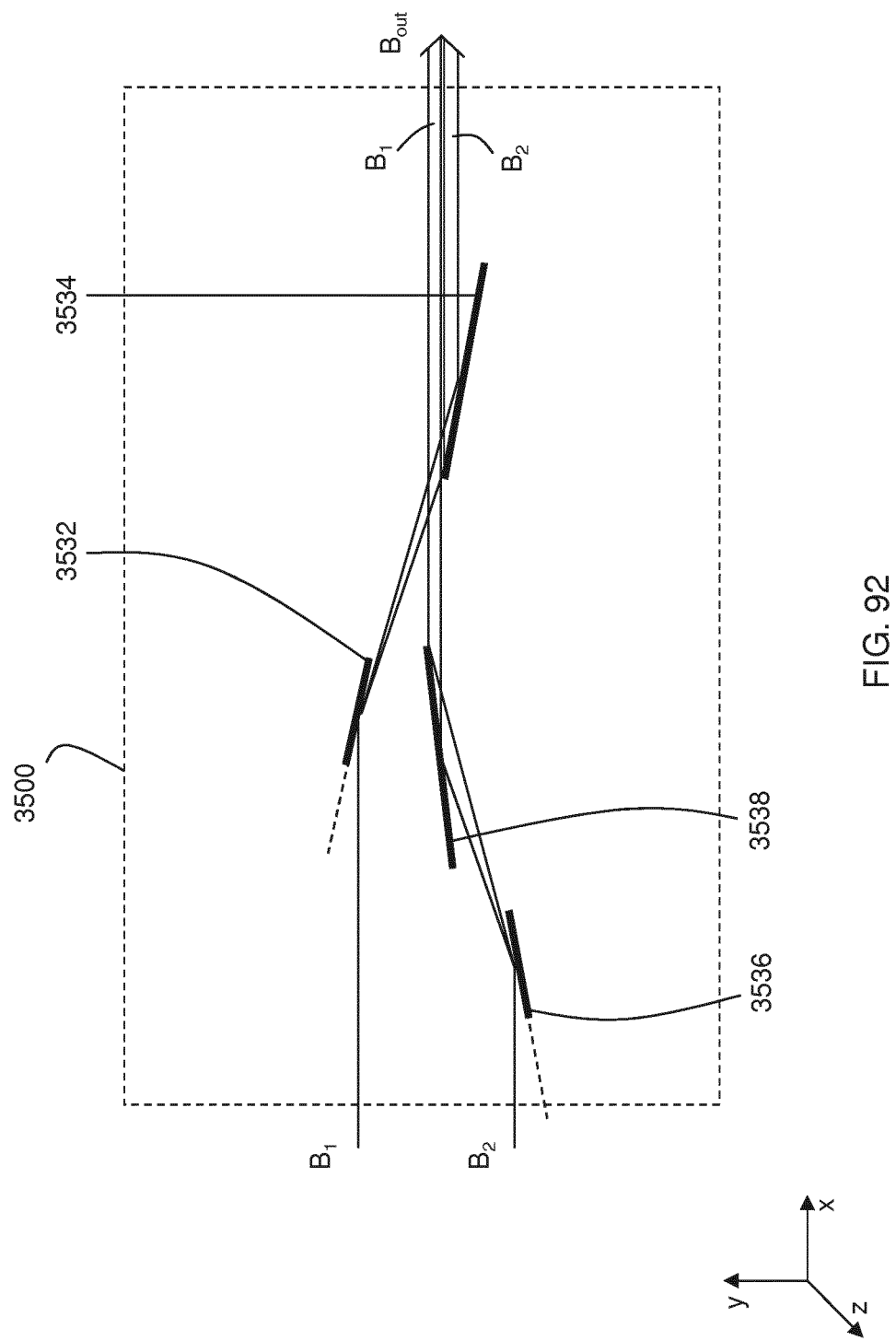
FIG. 92 is a schematic illustration of beam combining optics that may form part of the lithographic system shown in FIG. 92.

FIG. 92 shows a schematic layout of a beam combining optics 3500 which may form part of the lithographic system LS9 of FIG. 91. The beam combining optics 3500 are arranged to receive a main radiation beam $B_{S1}$, $B_{S2}$ (from each of the radiation sources SOa, SOb) and to output an output radiation beam $B_{out}$.

The beam combining optics 3500 comprises four optical elements: first and second optical elements 3532, 3534 associated with a first one of the radiation sources SOa; and first and second optical elements 3536, 3538 associated with a second one of the radiation sources SOb. The optical elements 3532, 3534, 3536, 3538 are arranged to alter the size and shape of the cross section of the main radiation beams $B_{S1}$, $B_{S2}$ from the radiation sources SOa, SOb.

In particular, the first optical elements 3532, 3536 are convex mirrors, which act to increase the cross sectional area of the main radiation beams $B_{S1}$, $B_{S2}$. The first optical elements 3532, 3536 may be referred to as diverging optical elements. Although in FIG. 92 the first optical elements 3532, 3536 appear to be substantially flat in the x-y plane they are in fact convex in this plane. Since the first optical elements 3532, 3536 are convex, they will increase the divergence of the main radiation beams $B_{S1}$, $B_{S2}$, decreasing the heat load on mirrors downstream of them. The radiation beam $B_{out}$ is split into a plurality of composite branch radiation beams by beam splitting optics 3550, which may, for example, comprise a plurality of consecutive, static, knife edge mirrors arranged in series in the path of the beam $B_{out}$. Increasing the size of the beam $B_{out}$ using first optical elements 3532, 3536 reduces the accuracy with which these knife edge mirrors must be located in the path of the radiation beam $B_{out}$. This allows for more accurate splitting of the output beam $B_{out}$ by the splitting optics 3550.

The second optical elements 3534, 3538 are concave and are complementary in shape to the first optical elements such that the beams leaving the second optical elements 3534, 3538 have substantially zero divergence (i.e. are parallel beams). The second optical elements 3534, 3538 may be referred to as converging optical element. Therefore, downstream of the second optical elements 3534, 3538 the beams are substantially collimated. Again, although in FIG. 92 the second optical elements 3534, 3538 appear to be substantially flat in the x-y plane they are in fact concave in either this plane.

Such an arrangement 3500 expands the two main radiation beams $B_{S1}$, $B_{S2}$ in the y direction. In order to also expand the beam in the z direction, another pair of mirrors (a first one convex and a second one concave), which curve in the z direction may be used. Therefore, in order to expand both main radiation beams $B_{S1}$, $B_{S2}$ in both the y and z directions a total of 8 mirrors may be used.

It may be preferable for the output beam $B_{out}$, which is received by the beam splitting optics 3550, to have a different shape and/or intensity distribution to that output by the radiation sources SOa, SOb. For example, for embodiments wherein the beam splitting optics 3550 employs a plurality of consecutive knife edge extraction mirrors, a rectangular shape with a generally top hat intensity profile may be preferable to, for example, a circular beam with a Gaussian-like intensity profile (which may be output by the radiation sources SOa, SOb). Therefore, in addition to increasing the cross sectional area of the radiation beams $B_{S1}$, $B_{S2}$, the optical elements 3532, 3534, 3536, 3538 act to alter the cross sectional shape of the radiation beams $B_{S1}$, $B_{S2}$. In particular, the optical elements 3532, 3534, 3536, 3538 are astigmatic or aspherical and are shaped so as to ensure that the radiation beams $B_{S1}$, $B_{S2}$ leaving the second optical elements 3534, 3538 are more rectangular in shape than the radiation beams $B_{S1}$, $B_{S2}$ produced by the radiation sources SOa, SOb. For example, the optical elements may be shaped so that the beams $B_{S1}$, $B_{S2}$ leaving the second optical elements 3534, 3538 are generally rectangular, although other shapes are also possible. The two dimensions of such a rectangular shape may be related to radii of curvature of the optical elements in two perpendicular directions such as, for example, in the x-y plane and in the z direction. Such a generally rectangular shape allows the mirrors that are used to split the output radiation beam $B_{out}$ into a plurality of branch radiation beams to be identical or at least very similar. This is especially beneficial from a manufacturing point of view.

When both of the radiation sources SOa, SOb are on, the beam combining optics 3500 is operable to combine the two main radiation beams $B_{S1}$, $B_{S2}$ to form a composite radiation beam $B_{out}$. That is, the beams $B_{S1}$, $B_{S2}$ leaving the second optical elements 3534, 3538 are both adjacent to each other and mutually parallel. The beam combining optics 3500 allows all of the branch radiation beams that are directed to each lithographic apparatus LA1'-LAn' to share a single set of optics (for example a single static knife edge mirror within the beam splitting optics 3550 and any additional guiding optics).

Each of the radiation sources SOa, SOb of FIG. 91 may have scheduled and/or unscheduled down time during which they are off. In the event that one of the radiation sources SOa, SOb is off, all of the lithographic apparatuses LA1'-LAn' will receive some radiation, although only half of that which they would receive when both radiation sources are on (assuming that the output of the two radiation sources is substantially the same).

Figure 93:
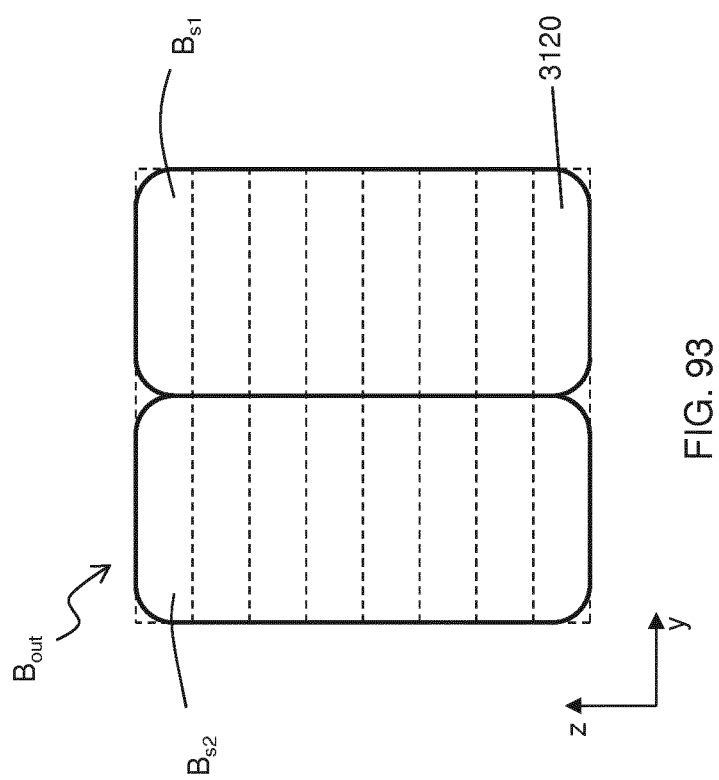
FIG. 93 is an illustration of a cross sectional profile of a composite radiation beam output by the beam combining optics shown in FIG. 92.

The cross sectional profile of the composite radiation beam $B_{out}$ output by the optical system 3500 is shown in FIG. 93, the edge of the composite radiation beam $B_{out}$ being defined as the point where its intensity has dropped below a pre-set threshold. FIG. 93 also illustrates eight portions 3120 of the output beam $B_{out}$, which correspond to eight branch radiation beams produced by a beam splitting optics 3550 using eight substantially identical consecutive knife edge extraction mirrors (not shown). This corresponds to an embodiment of the lithographic system LS9 comprising eight lithographic apparatuses LA1'-LA8 (i.e. n=8). Each portion 3120 comprises a portion of radiation from each of the two radiation beams $B_{S1}$, $B_{S2}$.

Figure 94:
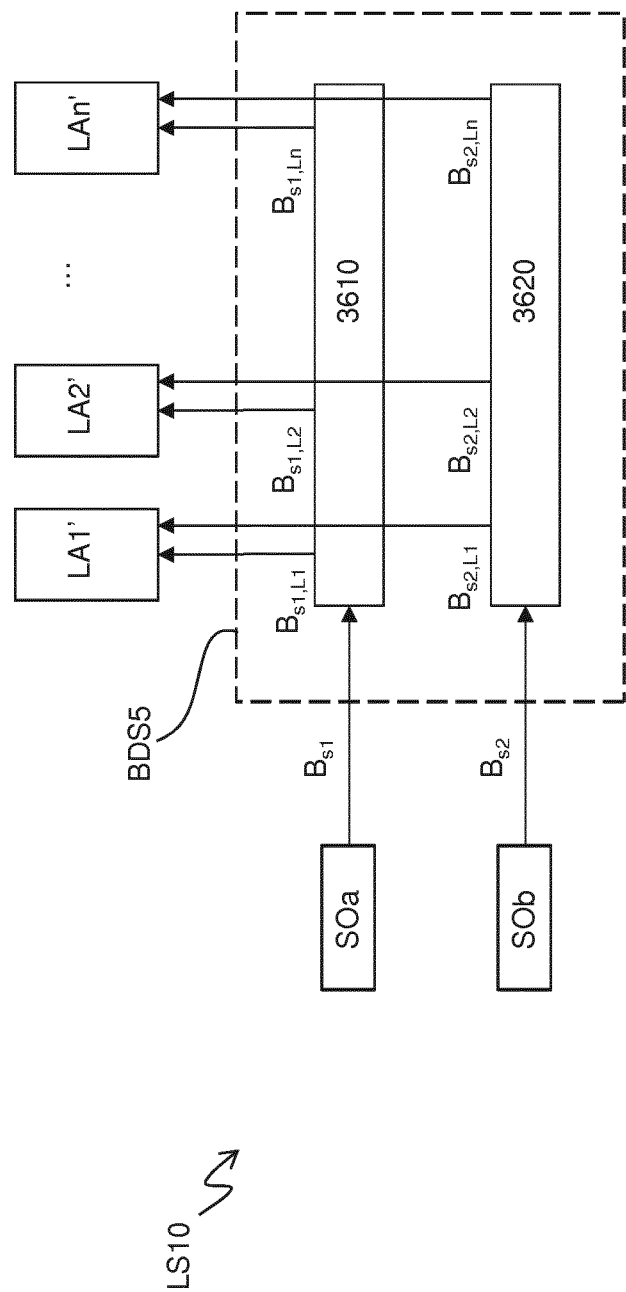
FIG. 94 is a schematic illustration of a further example embodiment of a lithographic system of the type shown in FIG. 86.
Figure 95:
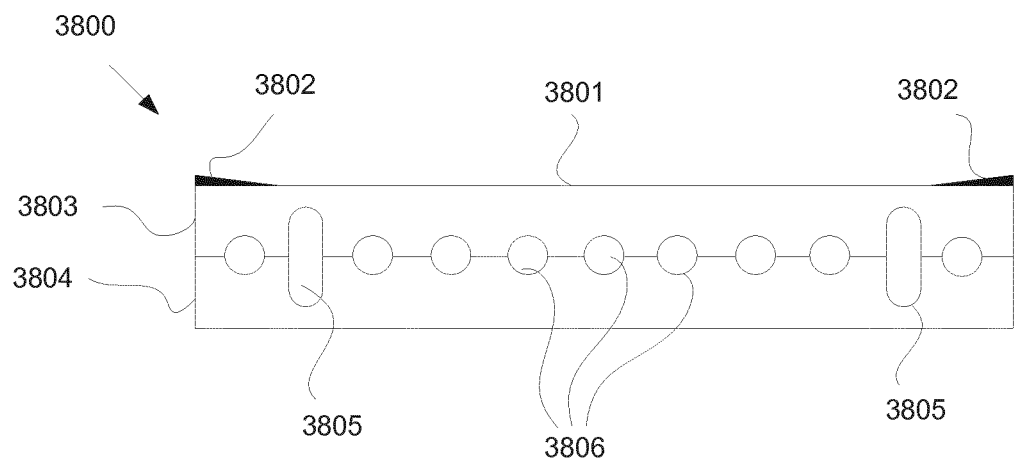
FIG. 95 is schematic illustration of an embodiment of a mirror that may be used in a beam delivery system of a lithographic system described herein.
Figure 96:
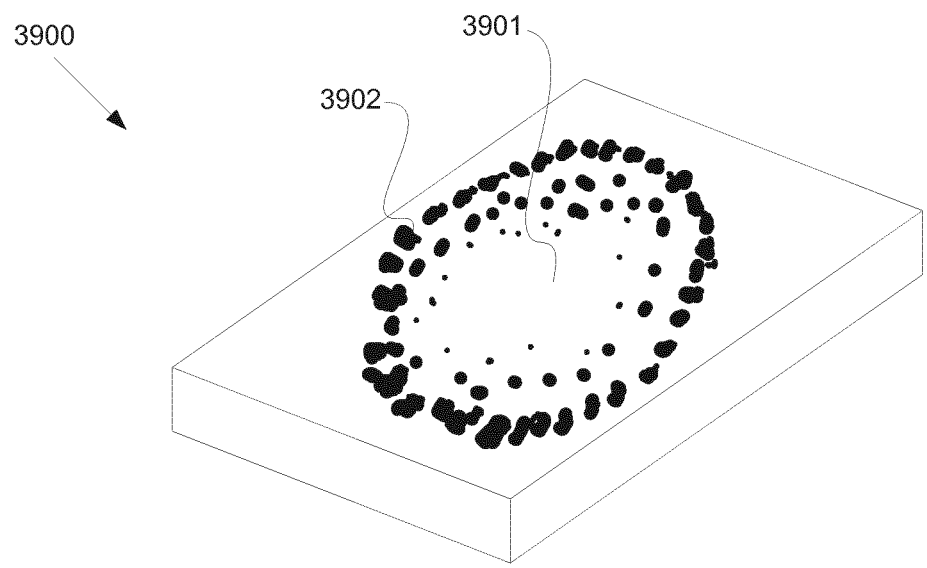
FIG. 96 is a schematic illustration of an alternative embodiment of a mirror that may be used in a beam delivery system.

FIG. 94 shows another lithographic system LS10 which is an embodiment of the lithographic system LS of FIG. 86 comprising two radiation sources SOa, SOb (i.e. m=2). Lithographic system LS10 comprises an alternative beam delivery system BDS5, which comprises two beam splitting optics 3610, 3620. Beam splitting optics 3610 is arranged to receive the main radiation beam $B_{S1}$ output by radiation source SOa and to split it into n composite radiation beams $B_{S2,L1}$-$B_{S1,n}$, each of which is directed towards a different lithographic apparatus LA1'-LAn'. Beam splitting optics 3620 is arranged to receive the main radiation beam $B_{S2}$ output by radiation source SOb and to split it into n composite radiation beams $B_{S1,L1}$-$B_{S2,Ln}$, each of which is directed towards a different lithographic apparatus LA1'-LAn'.

Some or all of the optics within the beam delivery systems BDS3, BDS4, BDS5 may be operable to rotate about one or more axes and or translate in one or more directions. For this purpose, they may be provided with actuators, which may be controlled in response to a received signal from a controller. This may allow the beam delivery system BDS3 to be adjustable so as to correct for variations in the directions of the main radiation beams $B_{S1}$-$B_{Sm}$ output by the radiation sources SOa-SOm. The beam delivery system may further comprise one or more sensor apparatuses, which may be operable to output a signal to the controller that is indicative of the position of one or more radiation beams within the beam delivery system BDS3. Therefore, the sensor apparatuses and the controller may form part of a feed-back loop for correcting for variations in the directions of the main radiation beams $B_{S1}$-$B_{Sm}$ output by the radiation sources SOa-SOm.

As described above, beam delivery systems which deliver a radiation beam produced by one or more sources generally comprise a plurality of optics including a plurality of mirrors. In an embodiment, where the source comprises a free electron laser (FEL) providing a radiation beam of generally Gaussian cross-section, the radiation beam diameter may be clipped by optics within the beam delivery system. For example, a particular mirror geometry may result in an intensity profile of a radiation beam being "clipped" at, for example, 2-3, or 4 sigma. In this case, there will be a sharp transition between "power" and "no power" in the reflected radiation beams. Such "sharp clipping" can cause interference effects that affect the beam profile as the radiation beam propagates. For example, diffraction effects can lead to substantial intensity oscillations over the cross-section of the radiation beam.

One option to reduce intensity oscillations is to use mirrors which clip the radiation beam at a large diameter. For example, the radiation beam may be clipped at 6-sigma rather than 4-sigma. In order to do this, however, mirrors within the beam delivery system would need to be significantly larger to achieve the same peak power density at a centre of the radiation beam.

An alternative method of reducing the effects of "hard clipping" is to provide "soft clipping" of the radiation beam. Soft clipping results in the radiation beam being clipped gradually, rather than with a sharp transition. In an embodiment, an EUV radiation-absorbing material is provided at outer edges of one or more mirrors within the beam delivery system. The radiation-absorbing material may be arranged such that her is a gradual transition from an inner-most portion of the radiation-absorbing material to an outer edge of the mirror, from a maximum reflectivity to a minimum reflectivity. For example, the radiation-absorbing material may be deposited with varying thickness, the thickness increasing from an inner portion to an outer portion. Alternatively, different materials, or compositions of materials, having different radiation-absorbing qualities, may be applied at different portions of the mirror.

The thickness of the radiation-absorbing material may be selected so as to reduce wave-front shift that may be caused by the radiation-absorbing material. In particular, for a thickness of radiation absorbing material $t_{ab}$, wave-front ΔWf shift may be given by:

$$\Delta Wf = 2 * a * t_{ab} \quad (14)$$

where a is the grazing angle in radians. For example, in some embodiments, a may have value of approximately 0.035 rad.

EUV radiation absorbed by the radiation-absorbing material will result in an increase heat load. In order to limit deformation of the mirror due to temperature gradients caused by increased heat loads at the edges of the mirror, in some embodiments outer edges of mirrors (carrying radiation-absorbing material) are thermally insulated from an inner portion of the mirror. FIG. 71 schematically illustrates a cross-section of a mirror 3800 that may be used in one or more components of a beam delivery system described above. The mirror 3800 comprises a reflective surface 3801 which is positioned in the path of a radiation beam provided from a radiation source. The radiation source may be any radiation source as described above.

The mirror 3800 further comprises a radiation-absorbing material 3802 applied to an edge of the mirror 3800. The radiation-absorbing coating is applied so as to have an increasing thickness closer to the edge of the mirror 3800. The radiation-absorbing coating may be any made from any suitable material. By way of example, the radiation coating may be an aluminium, gold, nickel or rhenium. Aluminium may be particularly beneficial as it has a refractive index substantially similar to that of a vacuum for EUV radiation, and hence, little reflection at grazing incidence angles, while still providing absorption of EUV radiation.

The mirror 3800 comprises a top portion 3803 comprising the reflective surface 3801, and a bottom portion 3804. The top portion 3803 and the bottom portion 3804 each comprise cooperating grooves so as to form an insulating gap 3805. The insulating gap 3805 may provide a vacuum, or may be gas-filed. The insulating gap 3805 acts to insulate the edge portion of the mirror 3800, so that local heat loads caused by the absorption of EUV radiation by the radiation-absorbing material 3802 do not cause (or cause reduced) temperature gradients across a center part of the mirror 3800.

The mirror 3800 additionally comprises cooling channels 3806 to carry cooling fluid.

An alternative example of a mirror 3900 is schematically illustrated in FIG. 72. The mirror 3900 comprises a reflective surface 3901 arranged in the path of a radiation beam. A radiation-absorbing material in the form of a plurality of spots 3902 is deposited on the reflective surface 3901 with a varying surface area density. That is, towards an outer edge of the mirror 3900, the spots 3902 cover an increasing portion of the reflective surface 3901. The spots are preferably sufficiently small to allow diffraction from the edges of the spots 3901 to spread out sufficiently so as not to negatively affect the propagation of the radiation beam or cause other negative consequences. For example, the spots may have a diameter of the order of 0.25 mm.

In a further embodiment, the spots 3901 may be reflective rather than absorbing, and arranged so as to reflect incident radiation in a different direction to that of the main radiation beam. For example, reflective spots may be provided by milling appropriate wells into the reflective surface and coating the wells with a reflective coating such as ruthenium.

It will be appreciated from the above that a beam delivery system may comprise a plurality of mirrors (e.g. arrangements to combine radiation beams from two radiation sources, arrangements to split radiation beams for provision to multiple tools, etc.). In an embodiment, a desired clipping of the radiation beam is achieved by soft clipping the radiation beam over a plurality subsequent mirrors. This may be advantageous so as to reduce the heat load experienced by the soft-clipping means of a single mirror. For example, in one example embodiment, a first mirror may provide soft-clipping means along a first two of four edges, with a subsequent (e.g. next) mirror providing soft-clipping means along a second two of four edges. In this way, the two mirrors together provide soft-clipping means along all four edges. In addition to spreading heat load, providing soft-clipping means on different edges of subsequent mirrors allows a diameter of the "soft aperture" to be varied where a diameter of the radiation beam varies or is unknown in advance.

As has been described above with reference to various embodiments of a lithographic system LS11, a lithographic apparatus (e.g. the lithographic apparatus LA$_1$) is provided with a branch radiation beam B$_1$. The branch radiation beam B$_1$ is formed from a main radiation beam B which is emitted from a radiation source SO which comprises at least one free electron laser FEL. For some embodiments of a lithographic system LS11 it is advantageous to provide a lithographic apparatus LA$_1$, with a branch radiation beam B$_1$ which has a desired polarization state. For example, it may be desirable to provide a lithographic apparatus with a branch radiation beam which is circularly polarized.

In general, the polarization of a branch radiation beam B$_1$ which is received by a lithographic apparatus LA$_1$, depends on the polarization of radiation which is emitted from one or more free electron lasers whose output forms part of the branch radiation beam B$_1$ and any changes to the polarization which occur along the optical path of the radiation between the one or more free electron lasers FEL and the lithographic apparatus LA$_1$.

Radiation which is emitted from a free electron laser FEL typically undergoes several reflections at reflective elements (e.g. mirrors) before it is received by a lithographic apparatus LA$_1$. When radiation from a free electron laser undergoes a reflection at a reflective element the polarization of the radiation may be altered. The polarization of a branch radiation beam B$_1$ which is received by a lithographic apparatus LA$_1$, may therefore be different to the polarization of the radiation which is emitted from a free electron laser FEL.

The polarization of radiation which is emitted from a free electron laser FEL depends on the geometry of an undulator 24 which forms part of the free electron laser FEL. In particular the polarization of radiation which is emitted from a free electron laser FEL depends on the factor A (which appears in equation 1) in an undulator 24. In some embodiments the undulator 24 is a helical undulator. If the undulator 24 is a helical undulator then the factor A may be approximately equal to 1 and the undulator may emit radiation which is circularly polarized. As was explained above it may be desirable to provide a lithographic apparatus LA$_1$ with a branch radiation beam B$_1$ which is circularly polarized. However in an embodiment in which the free electron laser FEL emits circularly polarized radiation, changes in the polarization of radiation which is caused by reflective elements along the optical path of a branch radiation beam B$_1$ from the free electron laser FEL to the lithographic apparatus LA$_1$, may result in the branch radiation beam B$_1$ which is provided to the lithographic apparatus LA$_1$ not being circularly polarized. For example, changes to the polarization of the branch radiation beam B$_1$ along its optical path from the free electron laser FEL to the lithographic apparatus LA$_1$ may result in the branch radiation beam B$_1$ being elliptically polarized when it is provided to the lithographic apparatus LA$_1$.

It may be therefore be desirable to configure a lithographic system LS11 such that a branch radiation beam B$_1$ which is provided to a lithographic apparatus LA$_1$, is substantially circularly polarized.

Figure 97A:
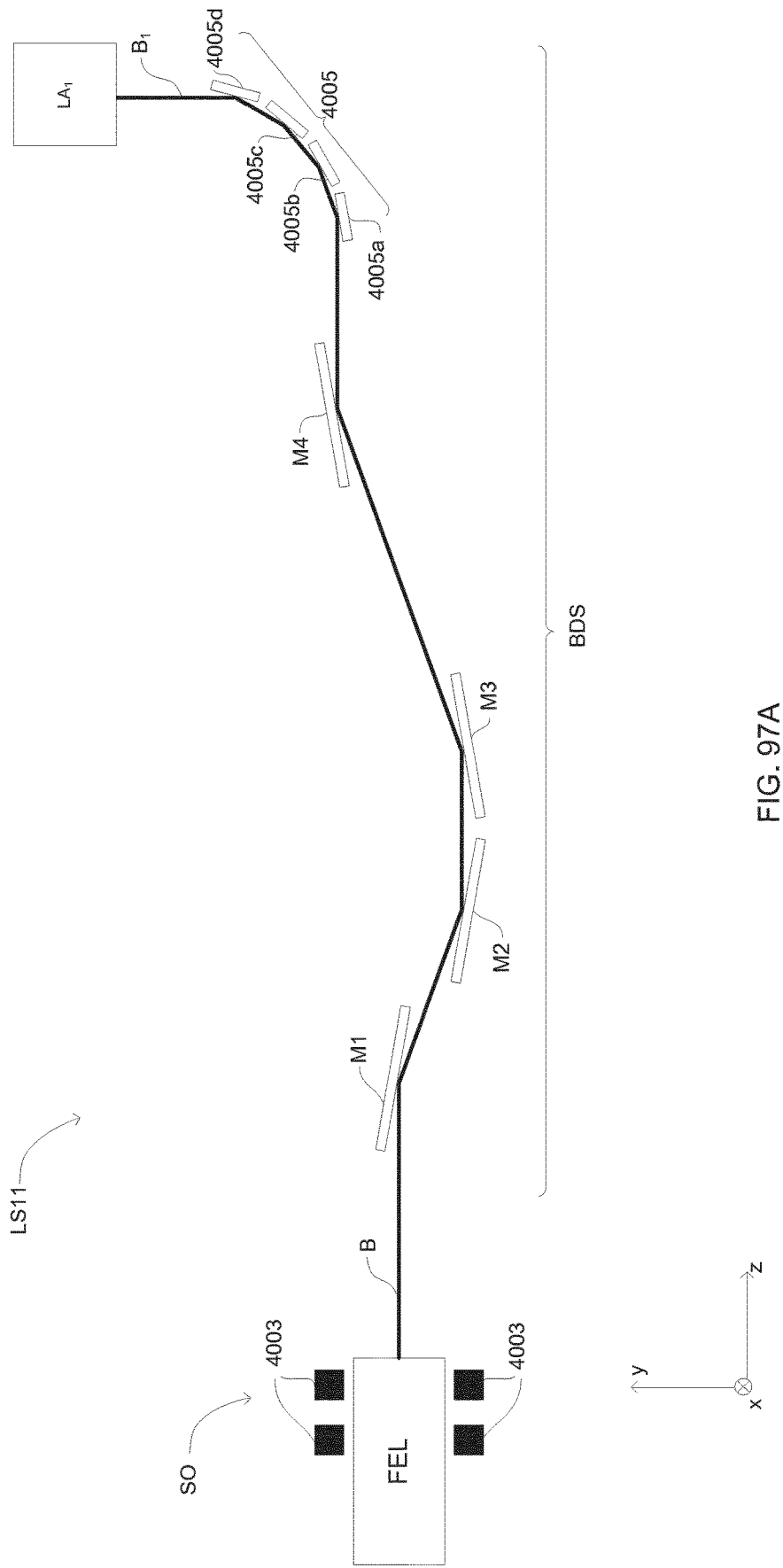
FIGS. 97A and 97B are schematic illustrations of a portion of a lithographic system.
Figure 97B:
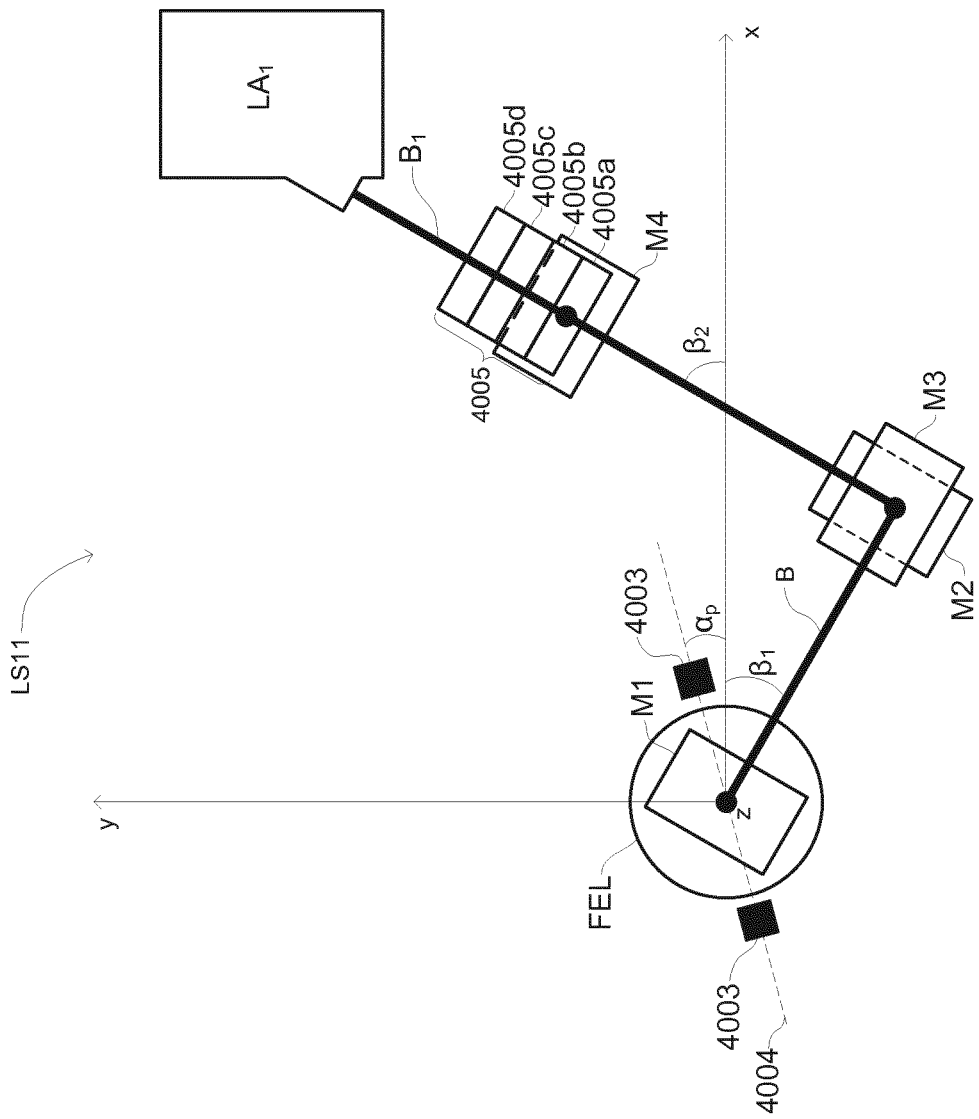

FIGS. 97A and 97B are schematic illustrations of a portion of an embodiment of a lithographic system LS11". The lithographic system LS11" comprises a radiation source SO comprising a free electron laser FEL, a beam delivery system BDS and a lithographic apparatus LA$_1$. In the illustrations of FIGS. 97A and 97B the optical path of radiation which forms a single branch radiation beam B$_1$ which propagates from a free electron laser FEL to a lithographic apparatus LA$_1$ is shown. However it will be appreciated that the lithographic system LS11" may include more lithographic apparatuses and may produce more branch radiation beams than are shown in FIGS. 97A and 97B. For example, portions of a main radiation beam B which is emitted from the radiation source SO may be split off to form other branch radiation beams which may be directed along other optical paths (not shown) to other lithographic apparatuses (not shown).

FIGS. 97A and 97B each depict the same optical path of a branch radiation beam $B_1$ from a free electron laser FEL to a lithographic apparatus $LA_1$. A consistent Cartesian co-ordinate system is used throughout FIGS. 97A and 97B and is shown with labeled axes in each of the figures. FIG. 97A shows the portion of the lithographic system LS11" as projected into a y-z plane and FIG. 97B shows the portion of the lithographic system LS11" as projected into an x-y plane.

The branch radiation beam $B_1$ is directed from the free electron laser FEL to the lithographic apparatus $LA_1$ via four reflective elements M1-M4 and a bending optics 4005. In the embodiment which is depicted in FIGS. 97A-97B bending optics 4005 comprises four reflective elements 4005a-4005d. The branch radiation beam $B_1$ therefore undergoes eight reflections before it is received at the lithographic apparatus $LA_1$. In other embodiments a branch radiation beam may undergo fewer or more reflections than eight on its optical path between a free electron laser FEL and a lithographic apparatus $LA_1$.

When polarized radiation undergoes a reflection at a reflective element it may be considered to be formed from a p-polarized component and an s-polarized component. The p-polarized component is the component of the radiation beam which has a polarization direction which is parallel to a plane of incidence and the s-polarized component is the component of the radiation beam which has a polarization direction which is perpendicular to the plane of incidence. The plane of incidence is the plane in which both the radiation beam which is incident on the reflective element and the radiation beam which is reflected from the reflective element lies.

In the embodiment which is depicted in FIGS. 97A-97B the free electron laser FEL includes a planar undulator. In a planar undulator the factor A is approximately equal to 2 and linearly polarized radiation is emitted. The orientation of the linear polarization of the radiation emitted from a planar undulator depends on the orientation of undulator magnets 4003 which generate a periodic magnetic field in the undulator. As is best seen from FIG. 97B the undulator magnets 4003 lie in a polarization plane 4004 which forms a polarization angle $\alpha_p$ with the x-axis. The plane of linear polarization of the radiation beam B which is emitted from the free electron laser FEL is the polarization plane 4004. The linear polarization of the radiation beam B therefore forms the polarization angle $\alpha_p$ with the x-axis. In practice a free electron laser FEL may include many more magnets 4003 than are shown in FIGS. 97A and 97B.

The radiation beam B is initially incident on a first reflective element M1. The first reflective element M1 is orientated such that the plane of incidence at the first reflective element forms an angle $\beta_1$ with the x-axis. It can be seen from FIG. 97B that the angle between the polarization plane 4004 and the plane of incidence at the first reflective element M1 is $\alpha_p+\beta_1$. The angle $\alpha_p+\beta_1$ between the polarization plane 4004 and the plane of incidence at the first reflective element M1 may be approximately 45°. In the embodiment depicted in FIGS. 97A and 97B the polarization angle $\alpha_p$ is approximately 15° and the angle $\beta_1$ is approximately 30°. The angle $\alpha_p+\beta_1$ is therefore approximately 45°. Since the angle $\alpha_p+\beta_1$ between the polarization plane 4004 and the plane of incidence at the first reflective element M1 is 45°, the s and p-polarized components which are incident on the first reflective element M1 have the same magnitude. Since the radiation which is incident on the first reflective element M1 is linearly polarized the s and p-polarized components are in phase with each other.

Figure 98:
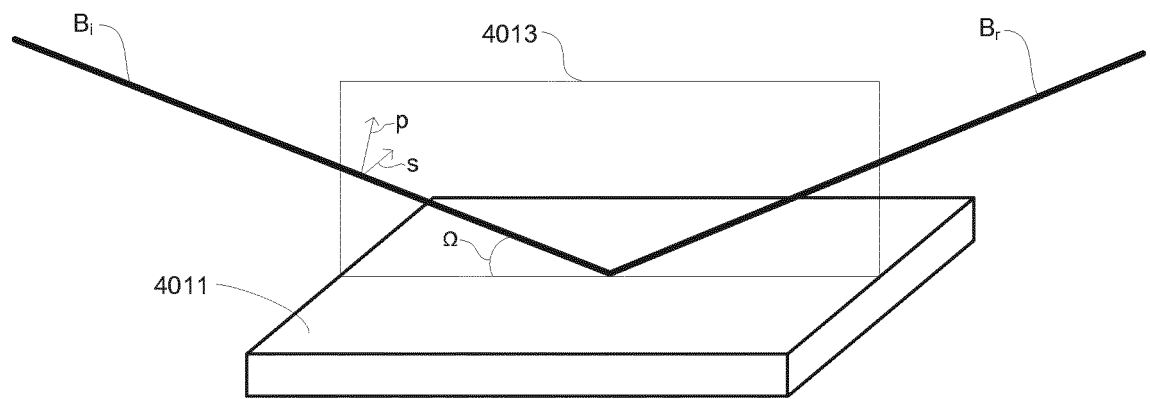
FIG. 98 is a schematic illustration of reflection of a radiation beam at a reflective element.

During a reflection at a reflective element the phase difference between the s and p-polarized components may change. A change in the phase difference between s and p-polarized components which occurs during a reflection at a reflective element may be referred to as a phase retardance ε. The phase retardance ε which occurs during a reflection at a reflective element depends on the complex refractive index of the reflective element and on the relative orientation of the reflective element and the incident radiation. FIG. 98 is a schematic illustration of an example of a reflection of a radiation beam at a reflective element 4011. An incident radiation beam $B_i$ is incident on the reflective element 4011 which results in a reflected radiation beam $B_r$ being reflected from the reflective element 4011. The incident radiation beam $B_i$ forms a grazing angle Ω with the surface of the reflective element 4011. Also shown in FIG. 98 is a plane of incidence 4013 in which both the incident radiation beam $B_i$ and the reflected radiation beam $B_r$ lie. The s and p-polarized components are depicted as being perpendicular and parallel to the plane of incidence 4013 respectively.

Figure 99:
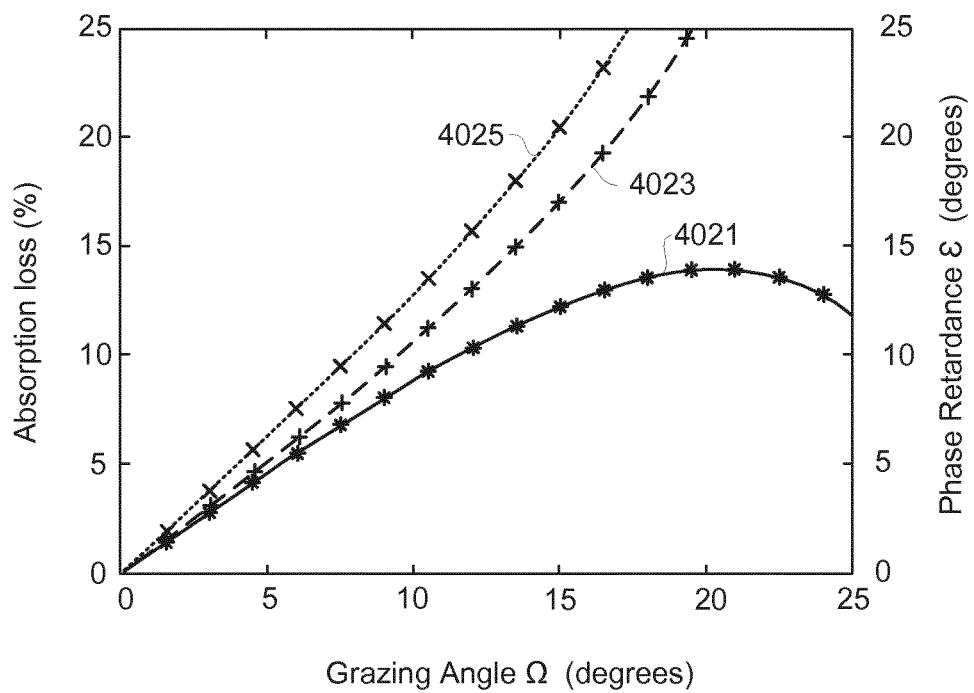
FIG. 99 is a representation of an absorption loss and phase retardance which occurs during a reflection of radiation at a reflective element as a function of a grazing angle at which the radiation is incident on the reflective element.

FIG. 99 is a representation of the phase retardance ε (in degrees) between the s and p-polarized components which occurs at the reflective element 4011 as a function of the grazing angle Ω of radiation which is incident on the reflective element 4011. The phase retardance ε is depicted in FIG. 99 with a solid line labeled 4021. Also shown in FIG. 99 is the percentage loss of radiation due to absorption at the reflective element 4021. The absorption loss for the p-polarized component is depicted with a dashed line labeled 4023. The absorption loss for the s-polarized component is depicted with a dotted line labeled 4025. The values in FIG. 99 were calculated for a reflective element 4011 having a complex refractive index of 0.87-0.017i. This value of the complex refractive index is representative of a mirror which is configured to reflect EUV radiation at a grazing incidence angle. In an embodiment the reflective element may be a mirror configured for reflection of EUV radiation which is coated with ruthenium. The refractive index of such a mirror at a wavelength of approximately 13.5 nm may be approximately 0.87-0.017i as is used to perform the calculations shown in FIG. 99.

In alternative embodiments a reflective element may be coated with a material other than ruthenium. For example, a reflective element may be coated with molybdenum. A reflective element which is coated with molybdenum may cause a similar phase retardance to that which is shown in FIG. 99. In alternative embodiments a reflective element may be coated with platinum, osmium, iridium, gold, zirconium, niobium or nickel. However a reflective element which is coated with platinum, osmium, iridium, gold, zirconium, niobium or nickel may cause less phase retardance than the phase retardance which is shown in FIG. 99.

It can be seen from FIG. 99 that the absorption loss of both s and p-polarized components increases with increasing grazing angle Ω. In some circumstances it is therefore advantageous to arrange a reflective element such that the grazing angle Ω is relatively small. It can also be seen from FIG. 99 that at relatively small grazing angles Ω (e.g. grazing angles which are less than approximately 10°) the phase retardance ε is approximately proportional to the grazing angle Ω. In the example which is shown in FIG. 99 the phase retardance ε is equal to approximately 0.92Ω (in units of degrees per degrees) for grazing angles of less than about 10°.

Referring again to FIGS. 97A and 97B the linearly polarized radiation beam B is incident on the first reflective element M1 such that the s and p-polarized components have the same magnitude. As was explained above with reference to FIGS. 98 and 99, reflection from the first reflective element M1 will cause a phase shift between the s and p-polarized components. For example, the reflection at the first reflective element M1 may introduce a phase difference between the s and p-polarized components which is approximately equal to the grazing angle Ω at the first reflective element M1. Since the radiation which is reflected from the first reflective element M1 has perpendicular linear polarization components which are not in phase with each other, the reflected radiation is no longer linearly polarized. Instead the radiation which is reflected from the first reflective element M1 is elliptically polarized.

Figure 100:
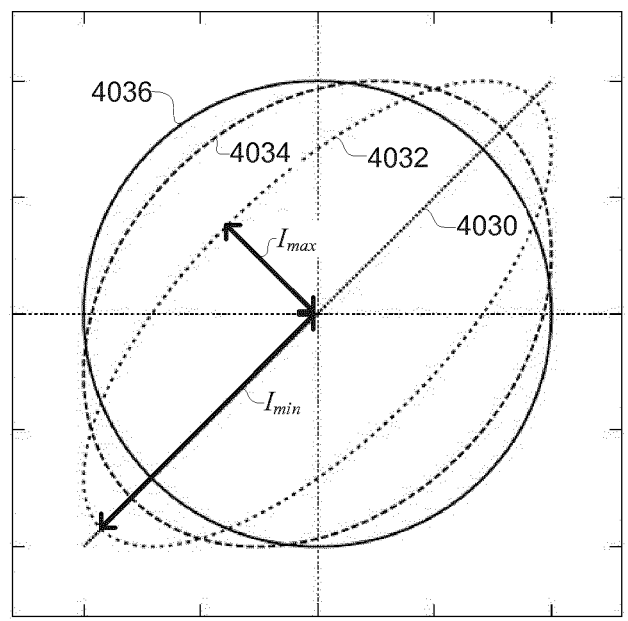
FIG. 100 is a representation of polarization states of a radiation beam.

Elliptical polarization is characterized by an ellipse which is traced out by the electric field vector of the radiation. FIG. 100 is a representation of several different polarization states of a radiation beam. The horizontal and vertical axes of FIG. 100 represent directions which extend perpendicular to the direction of propagation of the radiation beam. The shapes which are plotted on FIG. 100 represent the shape which the electric field vector of a radiation beam traces out in different polarization states. For example, a dotted line 4030 which is shown in FIG. 100 represents a linear polarization state in which the electric field vector is confined to a plane. A dotted line 4032 and a dashed line 4034 represent two elliptical polarization states in which the electric field vector traces out an ellipse. A solid line 4036 represents a circular polarization state in which the electric field vector traces out a circle.

A polarization state may be quantified with a polarization contrast C which is given by:

$$C = \frac{(I_{max} - I_{min})}{(I_{max} + I_{min})} \quad (15)$$

where $I_{max}$ is the maximum intensity of the electric field vector at different angles about a central axis of the radiation beam and $I_{min}$ is the minimum intensity of the electric field vector at different angles about the central axis of the radiation beam. That is, if the radiation beam were to be incident on an ideal polarizer and the ideal polarizer were to be rotated through 360° $I_{max}$ and $I_{min}$ are the maximum and minimum intensities of radiation which would be transmitted by the polarizer during its rotation. The maximum intensity of the electric field vector $I_{max}$ and the minimum intensity of the electric field $I_{min}$ for the elliptical polarization state 4032 are shown in FIG. 100.

For the linear polarization state 4030 which is depicted in FIG. 100, $I_{min}$=0 and thus the polarization contrast C is 1. For the circular polarization state 4036 which is depicted in FIG. 100 $I_{min}$=$I_{max}$ and thus the polarization contrast C is 0. As was described above a linear polarization state arises when there is no phase retardance between s and p-polarized components. A circular polarization state arises when there is a phase retardance ε of 90° between s and p-polarized components. An elliptical polarization state arises when there is a retardance ε of greater than 1 between s and p-polarized components. The elliptical polarization state 4032 which is shown in FIG. 100 arises when there is a phase retardance ε of 45° between s and p-polarized components. The elliptical polarization state 4034 which is shown in FIG. 100 arises when there is a phase retardance ε of 75° between s and p-polarized components.

In general if s and p-polarized components of a polarized radiation beam have equal magnitude then the polarization contrast C is related to the phase retardance ε between the s and p-polarized components by equation 16.

$$C = |\cos \varepsilon| \quad (16)$$

Referring again to FIGS. 97A and 97B the radiation which is reflected from the first reflective element M1 is elliptically polarized and therefore has a polarization contrast C which is less than 1. The first reflective element M1 therefore serves to decrease the polarization contrast C of the radiation which is reflected at the first reflective element M1.

The radiation which is reflected from the first reflective element M1 is incident on the second reflective element M2. The second reflective element M2 is orientated such that (similarly to the radiation which is incident on the first reflective element) the plane of incidence at the second reflective element M2 forms the angle $\beta_1$ with the x-axis. The plane of incidence at the second reflective element M2 is therefore in the same plane as the plane of incidence at the first reflective element M1. This correspondence between the plane of incidence at the first and second reflective elements M1, M2 means that the s and p-polarized components at the first reflective element M1 corresponds with the s and p-polarized components at the second reflective element M2. The s and p-polarized components which are incident on the second reflective element M2 therefore have a phase difference between them which is equal to the phase difference which was introduced between the s and p-polarized components at the first reflective element M1.

During the reflection of radiation at the second reflective element M2 a further phase retardance ε between the s and p-polarized components occurs. The phase retardance ε which is caused at the second reflective element M2 is dependent on the grazing angle Ω with which the radiation is incident on the second reflective element M2. The complex refractive index of the second reflective element M2 may be such that the phase retardance ε which is caused at the second reflective element M2 is approximately equal to the grazing angle Ω at the second reflective element M2. Since the s and p-polarized components at the second reflective element M2 correspond to the s and p-polarized components at the first reflective element M1, the phase retardance ε which occurs at the second reflective element M2 further increases the phase difference between s and p-polarized components. The second reflective element M2 therefore serves to further decrease the polarization contrast C of the radiation which is reflected by it.

Radiation which is reflected from the second reflective element M2 is incident on the third reflective element M3. The third reflective element M3 is orientated such that the plane of incidence at the third reflective element M3 forms an angle $\beta_2$ with the x-axis. In the embodiment which is shown in FIGS. 97A-97B the plane of incidence at the third reflective element M3 is perpendicular to the plane of incidence at the first reflective element M1 and is perpendicular to the plane of incidence at the second reflective element M2. The sum of the angles $\beta_1$ and $\beta_2$ is therefore approximately 90°. As was described above the angle $\beta_1$ is approximately 30° and the polarization angle $\alpha_p$ is approximately 15°. The angle $\beta_2$ is therefore approximately 60° and the angle $\beta_2$-$\alpha_p$ between the plane of incidence at the third reflective element M3 and the polarization angle $\alpha_p$ is approximately 45°.

Since the plane of incidence at the third reflective element M3 is perpendicular to the plane of incidence at the first and second reflective elements M1, M2, the s and p-polarized components at the third reflective element M3 are swapped relative to the s and p-polarized components at the first and second reflective elements M1, M2. That is the s-polarized component at the third reflective element M3 corresponds to the p-polarized component at the first and second reflective elements M1, M2 and the p-polarized component at the third reflective element M3 corresponds to the s-polarized component at the first and second reflective elements M1, M2. The phase retardance ε which occurs at the third reflective element M3 therefore acts in the opposite direction to the phase retardance ε which occurs at the first and second reflective elements M1, M2. The reflection at the third optical element M3 therefore serves to decrease the phase difference between s and p-polarized components which was introduced at the first and second reflective elements M1, M2. Reflection at the third reflective element M3 therefore serves to increase the polarization contrast C of the radiation which is reflected by it.

Radiation which is reflected from the third reflective element M3 is incident on the fourth reflective element M4. The fourth reflective element M4 is orientated such that the plane of incidence at the fourth reflective element lies in the same plane as the plane of incidence at the third reflective element M3. The plane of incidence at the fourth reflective element M4 therefore forms the angle $\beta_2$ with the x-axis. Since the plane of incidence at the fourth reflective element M4 lies in the same plane as the plane of incidence at the third reflective element M3 the s and p-polarized components at the third reflective element M3 correspond with the s and p-polarized components at the fourth reflective element M4. The phase retardance ε which occurs at the fourth reflective element M4 therefore acts in the same direction as at the third reflective element M3 and in the opposite direction as at the first and second reflective elements M1, M2.

In the embodiment of FIGS. 97A and 97B the sum of the grazing angles at the first and second reflective elements M1, M2 are approximately equal to the sum of the grazing angles Ω at the third and fourth reflective elements M3, M4. As was explained above, for reflections at small grazing angles Ω the phase retardance ε which occurs during a reflection is approximately proportional to the grazing angle Ω. The combined phase retardance ε which occurs at the first and second reflective elements M1, M2 is therefore approximately equal and opposite to the combined phase retardance ε which occurs at the third and fourth reflective elements M3, M4. That is, the reflections at the first and second reflective elements M1, M2 serve to decrease the polarization polarization contrast C of the radiation and the reflections at the third and fourth reflective elements M3, M4 serve to increase the polarization contrast C of the radiation by an approximately equal amount. The polarization of the radiation which is reflected from the fourth reflective element M4 is therefore approximately the same as the polarization of the radiation which is incident on the first reflective element M1.

The radiation which is reflected from the fourth reflective element M4 is incident on the bending optics 4005. The bending optics 4005 comprises four reflective elements 4005a-4005d which together serve to bend the branch radiation beam $B_1$ and direct it to the lithographic apparatus $LA_1$. The sum of the grazing angles Ω at each of the reflective elements 4005a-4005d which form the bending optics 4005 is approximately 45° which causes the branch radiation beam $B_1$ to be bent through an angle of approximately 90° by the bending optics 4005.

It can be seen from FIG. 97B that the plane of incidence at each of the reflective elements 4005a-4005d which form the bending optics 4005 forms the angle $\beta_2$ with the x-axis and lies in the same plane as the planes of incidence at the third and fourth reflective elements M3, M4. The s and p-components at the reflective elements 4005a-4005d which form the bending optics 4005 therefore correspond with the s and p-components at the third and fourth reflective elements M3 and M4. Each reflection at the reflective elements 4005a-4005d therefore causes a phase retardance ε which acts in the same direction as the phase retardance ε which is caused by reflections at the third and fourth reflective elements M3 and M4. The phase retardance ε which is caused by reflections at each of the reflective elements 4005a-4005d may, for example, be approximately equal to the grazing angles Ω with which radiation is incident on each reflective element 4005a-4005d. Since the sum of the grazing angles at each of the reflective elements 4005a-4005d which form the bending optics 4005 is approximately 45° then the phase retardance ε which is caused by the bending optics may be approximately 45°. The branch radiation beam $B_1$ which is output from the bending optics 4005 and is provided to the lithographic apparatus $LA_1$ therefore has perpendicularly polarized components which are approximately 45° out of phase with each other. The bending optics 4005 therefore serve to decrease the polarization contrast C of the branch radiation beam $B_1$ and results in elliptically polarized radiation being provided to the lithographic apparatus $LA_1$.

As was described above, the free electron laser FEL emits linearly polarized radiation which has a polarization contrast C of approximately 1. At least some of the radiation which is emitted from the free electron laser FEL is reflected by the first and second reflective elements M1, M2 which cause a phase retardance ε which serves to decrease the polarization polarization contrast C of the radiation which is reflected by them. Radiation which is reflected by the first and second reflective elements M1, M2 is incident on the third and fourth reflective elements M3, M4 which cause a phase retardance ε which serves to increase the polarization contrast C of the radiation which is reflected by them. The decrease in polarization contrast C which results from reflection by the first and second reflective elements M1, M2 is approximately equal to the increase in polarization contrast C which results from reflection by the third and fourth reflective elements M3, M4 such that radiation which is reflected from the fourth reflective element M4 is substantially linearly polarized and has a polarization contrast C of approximately 1. The bending optics 4005 causes a phase retardance ε of approximately 45° and which serves to decrease the polarization contrast C of the radiation which is reflected by it. The first, second, third and fourth reflective elements M1, M2, M3, M4 and the bending optics 4005 together form a beam delivery system BDS which directs radiation from a free electron laser FEL to a lithographic apparatus $LA_1$. The reflective elements which form the beam delivery system BDS alter the polarization state of the radiation such that the polarization contrast C of the branch radiation beam $B_1$ which is provided to the lithographic apparatus $LA_1$ is less than the polarization contrast C of the radiation beam B which is emitted from the free electron laser FEL.

In the embodiment which is depicted in FIGS. 97A-97B the reflective elements at which radiation is reflected on its optical path from the free electron laser FEL to the lithographic apparatus $LA_1$, are arranged such the plane of incidence at the reflective elements forms an angle of either $\beta_1$ or $\beta_2$ with the x-axis. A first group of reflective elements which comprises the first and second reflective elements M1, M2 are arranged such that the plane of incidence at the first group of reflective elements forms the angle $\beta_1$ with the x-axis. A second group of reflective elements which comprises the third and fourth reflective elements M3, M4 and the reflective elements 4005a-d which form the bending optics 4005 are arranged such that the plane of incidence at the second group of reflective elements forms the angle $\beta_2$ with the x-axis. The polarization plane 4004 is arranged relative to the x-axis (at the polarization angle $\alpha_p$) such that the angle between the planes of incidence at each of the reflective elements is approximately 45°. The first group of reflective elements are orientated such that the plane of incidence at each reflective element is orientated at an angle of +45° relative to the polarization plane 4004 and the second group of reflective elements are orientated such that the plane of incidence at each reflective element is orientated at an angle of −45° relative to the polarization plane 4004.

Arranging each of the reflective elements such that the planes of incidence form an angle of +45° or −45° relative to the polarization plane 4004 means that the s and p-polarized components which are incident on each of the reflective elements have approximately the same magnitude at each of the reflective elements. As was explained above the first group of reflective elements cause a phase retardance ε in a first direction and the second group of reflective elements cause a phase retardance in a second opposing direction. The total phase retardance ε which occurs as a result of reflection at each of the reflective elements on the optical path of radiation from the free electron laser FEL to the lithographic apparatus is equal to the difference between the phase retardance ε which is caused by reflections at the first group of optical elements and the phase retardance ε which is caused by reflections at the second group of optical elements.

In the example which was described above with reference to FIGS. 97A and 97B the difference between the phase retardance ε at the first group of reflective elements and the phase retardance ε at the second group of reflective elements is approximately 45°. Since the radiation which is emitted from the free electron laser FEL is linearly polarized this results in elliptically polarized radiation being provided to the lithographic apparatus $LA_1$. For some applications it is desirable to provide a branch radiation beam $B_1$ to a lithographic apparatus $LA_1$, which is substantially circularly polarized. This may be achieved, for example, by providing a greater number of reflective elements in the second group of reflective elements such that the radiation which is directed from the free electron laser FEL to the lithographic apparatus undergoes a greater number of reflections at reflective elements which have planes of incidence which are arranged at approximately −45° relative to the polarization plane 4004. Increasing the number of reflections which the radiation undergoes at reflective elements which have planes of incidence which are arranged at approximately −45° relative to the polarization plane 4004 will increase the total phase retardance ε which occurs along the optical path of the radiation. For example, the number of reflections which the radiation undergoes at reflective elements which have planes of incidence which are arranged at approximately −45° relative to the polarization plane 4004 may be increased such the total phase retardance ε which occurs along the optical path of the radiation approaches 90°. In such an embodiment the radiation which is received by the lithographic apparatus is substantially circularly polarized.

Additionally or alternatively the total phase retardance ε which occurs along the optical path of radiation from a free electron laser FEL to a lithographic apparatus $LA_1$, may be increased by increasing the grazing angles Ω at reflective elements which form the second group of reflective elements. As was described with reference to FIG. 99 at small grazing angles the phase retardance ε is approximately proportional to the grazing angle Ω. Increasing the grazing angle Ω at a reflective element may therefore increase the phase retardance ε which occurs at the reflective element. However it can be seen from FIG. 99 that the phase retardance ε only increases with increases in the grazing angle Ω over a limited range of grazing angles (e.g. grazing angles less than approximately 20°) and that increases in the grazing angle Ω beyond the limited range causes a decrease in the phase retardance ε. There may therefore be a limit as to how much the phase retardance ε can be increased by increasing the grazing angle Ω. Furthermore, it can also be seen from FIG. 99 that the percentage absorption of radiation at a reflective element increases with increases in the grazing angle Ω. Increasing the grazing angle Ω in order to increase the phase retardance ε will therefore increase the absorption of radiation at the reflective element and thus increase the amount of radiation which is lost to absorption along the optical path of radiation from a free electron laser FEL to a lithographic apparatus $LA_1$.

The optical path of radiation from a free electron laser FEL to a lithographic apparatus $LA_1$ which is depicted in FIGS. 97A and 97B is presented merely as an example in order to aid an understanding of the change in polarization which is brought about by reflection from a series of reflective elements. In practice a lithographic system LS11 may include more or fewer reflective elements than are shown in FIGS. 97A and 97B and the reflective elements may be orientated differently than are shown in FIGS. 97A and 97B. For example any of the reflective elements and arrangements of reflective elements which have been described throughout the description and which have been depicted in the figures may form part of an optical path of radiation from a free electron laser FEL to a lithographic apparatus.

In general, a beam delivery system comprising a plurality of reflective elements is arranged to receive radiation from a free electron laser and direct at least some of the radiation to a lithographic apparatus. The reflective elements are arranged such that an alteration of the polarization of the radiation which occurs as a result of reflection from the reflective elements serves to decrease the polarization contrast C such that the polarization contrast C of the radiation which is received by the lithographic apparatus $LA_1$ is less than the polarization contrast C of the radiation which is emitted from the free electron laser FEL. In some embodiments the reflective elements may be arranged such that the polarization of radiation which is emitted from the free electron laser FEL and the change in polarization which occurs as a result of reflection from reflective elements of a beam delivery system is such that a branch radiation beam $B_1$ which is provided to a lithographic apparatus is substantially circularly polarized.

It will be appreciated that whilst one or more of the reflective elements which form a beam delivery system may act to increase the polarization contrast C of radiation which is reflected from the one or more reflective elements, the net effect of the beam delivery system is to decrease the polarization contrast C of the radiation on its path from a free electron laser FEL to a lithographic apparatus $LA_1$.

In some embodiments the free electron laser FEL emits linearly polarized radiation whose polarization lies in a polarization plane 4004. A beam delivery system which is configured to direct at least some of the radiation emitted by the free electron laser FEL to a lithographic apparatus $LA_1$, may comprise a first group of reflective elements and a second group of reflective elements. The first group of reflective elements are each orientated such that the reflection of radiation at each reflective element defines a plane of incidence which forms an angle of approximately +45° with the plane of polarization 4004. The second group of reflective elements are each orientated such that the reflection of radiation at each reflective element defines a plane of incidence which forms an angle of approximately −45° with the plane of polarization 4004. Reflection of radiation at reflective elements which form the first group of reflective elements causes a phase retardance ε which acts in a first direction. Reflection of radiation at reflective elements which form the second group of reflective elements causes a phase retardance ε which acts in a second opposing direction. The total phase retardance ε which is caused by the beam delivery system is equal to the difference between the phase retardance ε which occurs at the first group of reflective elements and the phase retardance ε which occurs at the second group of reflective elements. The first group of reflective elements and the second group of reflective elements may be orientated such that the total phase retardance ε which is caused by the beam delivery system results in a branch radiation beam $B_1$ which has a desired polarization. For example the total phase retardance ε which is caused by the beam delivery system may be approximately 90° thereby resulting in a branch radiation beam $B_1$ which is circularly polarized.

In other embodiments the total phase retardance ε which is caused by the beam delivery system may be less than 90°. For example, the total phase retardance ε which is caused by the beam delivery system may be such that elliptically polarized radiation is provided to a lithographic apparatus $LA_1$. The elliptically polarized radiation which is provided to the lithographic apparatus $LA_1$ may have a relatively low polarization contrast C and has a lower polarization contrast C than the radiation which is emitted from the free electron laser FEL.

In the embodiments which have been described above reflection of radiation at reflective elements of a beam delivery system causes a decrease in the polarization contrast C of radiation on its optical path between a free electron laser FEL and a lithographic apparatus $LA_1$. This may, for example, allow a branch radiation beam $B_1$ which is substantially circularly polarized or elliptically polarized to be formed from a linearly polarized radiation beam which is emitted from a free electron laser FEL. A free electron laser FEL having a planar undulator which emits linearly polarized radiation may therefore be used as part of a radiation source SO for a lithographic system LS11 in which circularly or elliptically polarized radiation is provided to one or more lithographic apparatuses in the lithographic system LS11.

Using a free electron laser FEL which has a planar undulator in a radiation source SO for a lithographic system LS11 may be advantageous, for example when compared to using a free electron laser FEL which has a helical undulator. The design of a helical undulator is typically more complicated than the design of a planar undulator. For example, in a helical undulator magnets may be positioned around a large portion of the circumference of a beam pipe in which an electron beam propagates. This may provide a limited space in which other components of the undulator can be positioned. For example, an undulator may include components such as vacuum pumps for maintaining a vacuum in the beam pipe and/or components which are configured to manage thermal conditions in the undulator. The positioning of components in a helical undulator may therefore present significant engineering challenges. In comparison to a helical undulator, magnets in a planar undulator may be positioned in a single polarization plane 4003 as is shown, for example, in FIG. 97B. This may provide space around the remaining circumference of a beam pipe in which other components of an undulator may be positioned. Additionally or alternatively, the positioning and spacing of magnets in an undulator may be more critical and/or problematic in a helical undulator than in a planar undulator. The design and set up of a planar undulator may therefore be simplified in comparison to a helical undulator. A beam delivery system in which the reflective elements are configured to decrease the polarization contrast C of radiation on its optical path from a free electron laser to a lithographic apparatus may therefore be particularly advantageous in that it allows a planar undulator to be used whilst still providing a lithographic apparatus with circularly polarized or elliptically polarized radiation.

As has been described above with reference to various embodiments of a lithographic system LS11, a branch radiation beam $B_1$ which is received by a lithographic apparatus $LA_1$ may undergo several reflections at reflective elements on its optical path from a free electron laser FEL to the lithographic apparatus $LA_1$ and may undergo more reflections than are shown in the embodiment depicted in FIG. 97A-97C. An example optical path along which radiation may propagate between a free electron laser FEL and a lithographic apparatus in an embodiment of a lithographic system LS11 will now be described by way of example only.

In an embodiment a free electron laser FEL emits a main radiation beam B which is linearly polarized in a polarization plane 4004. The main radiation beam B is initially incident on a separation mirror (e.g. the reflective first optical element 1520 shown in FIG. 47) which is configured to separate the main radiation beam B from gamma radiation and/or neutrons which may also be emitted from the free electron laser FEL. The main radiation beam B is incident on the separation mirror at a grazing angle Ω of approximately 2°.

The main radiation beam B which is reflected from the separation mirror is incident on two reflective gratings (e.g. the mirror 90 shown in FIG. 10, the mirror 100 shown in FIG. 11 and/or the mirror 110 shown in FIG. 13) which are configured to split the main radiation beam B into a plurality of branch radiation beams. The reflective gratings are orientated such that they lie parallel to the polarization plane or perpendicular to the polarization plane such that radiation which is incident on the gratings consists only of either a p-polarized component or an s-polarized component. Such an orientation of a reflective grating may result in substantially no phase retardance ε being introduced at the gratings. Whilst alternative orientations of a reflective grating may be used, an orientation which is either perpendicular or parallel to the polarization plane may reduce the impact of a reflective grating on the polarization of radiation which is reflected from the grating. Such an arrangement may therefore simplify the design of a beam delivery system.

A branch radiation beam which is reflected from the gratings is incident on two shaping mirrors. One of the shaping mirrors has a concave shape and the other of the shaping mirrors has a convex shape. The shaping mirrors are configured to alter the cross-sectional shape of a branch radiation beam which is reflected from the gratings. For example, a branch radiation beam which is received from the gratings may have an elliptical cross-section. The shaping mirrors may alter the cross-sectional shape of the branch radiation beam such that after reflection from the shaping mirrors the branch radiation beam has a substantially circular cross-section. The shaping mirrors may, for example, be similar to the first optical element 2632 and the second optical element 2633 which are shown in FIG. 74. Whilst the first optical element 2632 and the second optical element 2633 are shown in FIG. 74 as shaping a main radiation beam B prior to splitting the main radiation beam B into branch radiation beams, it will be appreciated that similar optical elements may be used to shape a branch radiation beam after having been split off from a main radiation beam. The branch radiation beam may be incident on each of the shaping mirrors at a grazing angle $\Omega$ of approximately 3°. In an alternative embodiment the shaping mirrors may be cylindrically shaped such that they only curve in a single direction (as opposed to concave or convex mirrors which curve in two directions). In such an embodiment the branch radiation beam may be reflected at four shaping mirrors. However reflecting the branch radiation beam at four shaping mirrors may result in a greater loss of radiation due to absorption than reflecting the branch radiation beam at two shaping mirrors. Additionally reflecting the branch radiation beam at four shaping mirrors may result in a total phase retardance $\varepsilon$ at the shaping mirrors which is equal to zero, whereas reflecting the branch radiation beam at two shaping mirrors may result in a total phase retardance $\varepsilon$ at the shaping mirrors which is greater than zero.

The branch radiation beam which is reflected from the shaping mirrors is incident on two steering mirrors which are operable to control the position and direction of the branch radiation beam which is reflected from the steering mirrors. The steering mirrors may, for example, be similar to the grazing incidence steering mirror 3311 shown in FIG. 88. The branch radiation beam may be incident on each of the steering mirrors at a grazing angle $\Omega$ of approximately 3°.

The branch radiation beam which is reflected from the steering mirrors is incident on a bending optics (e.g. the bending optics 4005 shown in FIGS. 97A-97C). The bending optics comprises a plurality of reflective elements which are configured to bend the branch radiation beam through approximately 90°. The grazing angle $\Omega$ at which the branch radiation beam is incident on each of the reflective elements of the bending optics depends on the number of reflective elements which form the bending optics. For example, if the number of reflective elements which form the bending optics is decreased then the angle through which each reflective element deflects the branch radiation beam is increased in order to bend the branch radiation beam through 90°.

As was described above with reference to FIG. 99 the absorption loss of radiation which occurs during a reflection increases with increasing grazing angle $\Omega$. It may therefore be advantageous to decrease the grazing angle $\Omega$ at each reflective element in order to decrease the absorption loss of radiation at each reflective element. However if the grazing angle $\Omega$ at each reflective element is decreased then the number of reflective elements which are needed in order to bend the branch radiation beam through 90° is increased.

Since the bending optics bends the branch radiation beam through 90°, the sum of the grazing angles $\Omega$ at each reflective element of the bending optics is approximately 45°.

The branch radiation beam which is reflected from the bending optics is incident on two variable attenuation mirrors. For example, the branch radiation may be incident on the first mirror 2520 and the second mirror 2521 of the attenuation apparatus 2519 which is shown in FIG. 70*a*. The variable attenuation mirrors are configured to controllably attenuate the branch radiation beam such that the intensity of the branch radiation beam may be controlled. The branch radiation beam may be incident on each of the variable attenuation mirrors at a grazing angle $\Omega$ of approximately 5°.

Figure 89:
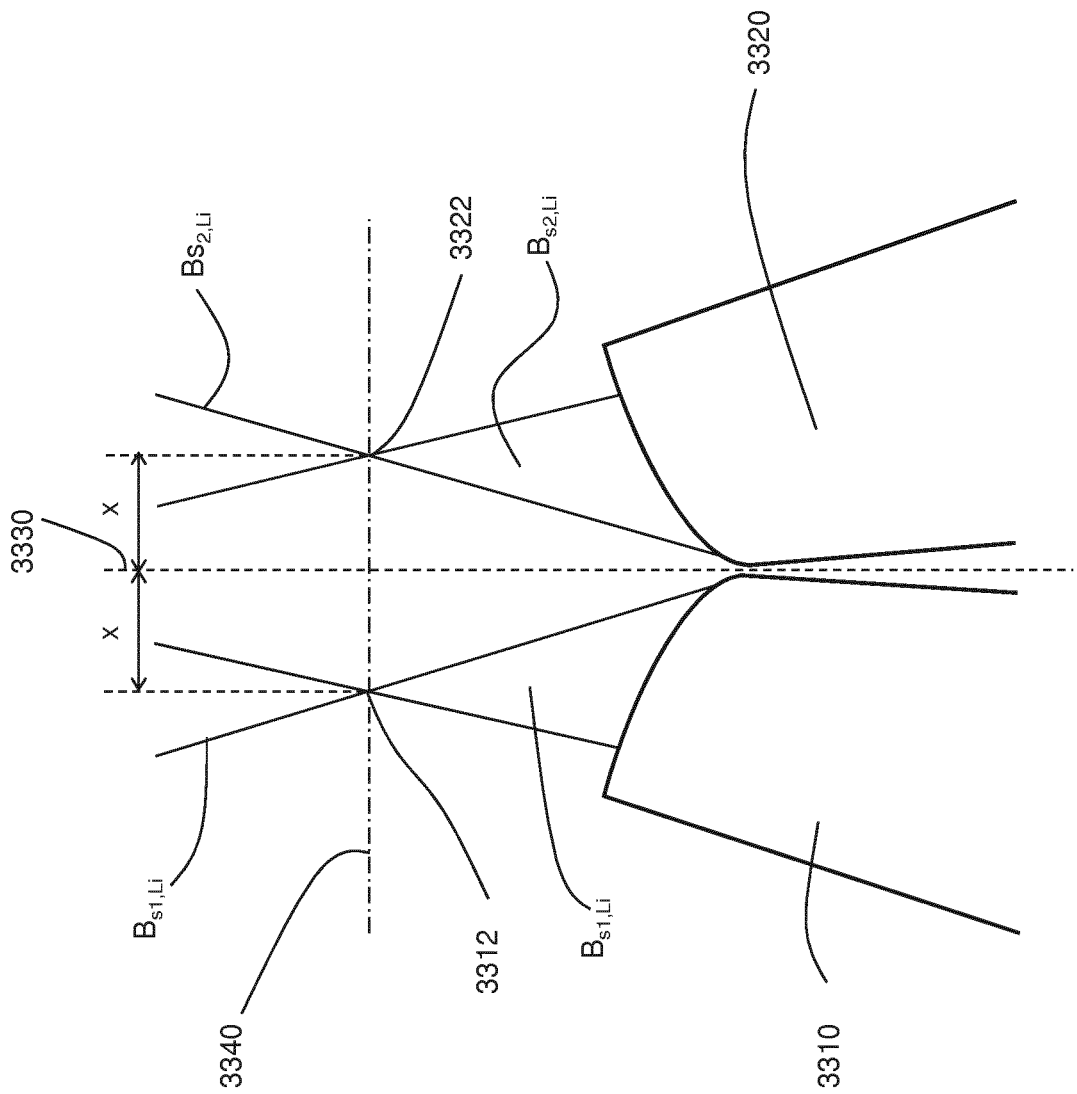
FIG. 89 is an enlarged view of a portion of the focusing unit of FIG. 88.

The branch radiation beam which is reflected from the variable attenuation mirrors is incident on a Wolter collector (e.g. the Wolter collector 3310 or 3320 shown in FIGS. 88 and 89). The branch radiation beam undergoes two reflections at the Wolter collector. The sum of grazing angles $\Omega$ at each reflection may be approximately 14°. The radiation which is output from the Wolter collector is provided to a lithographic apparatus.

During the example optical path of radiation from a free electron laser FEL to a lithographic apparatus which was described above, the sum of the grazing angles at each reflection which the radiation undergoes is approximately 72°. As was described above with reference to FIG. 99 the phase retardance $\varepsilon$ which occurs during a reflection at a small grazing angle $\Omega$ may be approximately equal to the grazing angle $\Omega$. In an embodiment each of the reflective elements along the optical path of the radiation may be orientated such that the plane of incidence at each of the reflective elements forms an angle of approximately 45° with the polarization plane 4004. In this embodiment the phase retardance $\varepsilon$ which is caused along the optical path of radiation from the free electron laser FEL to the lithographic apparatus is approximately 72° and the radiation which is received at the lithographic apparatus is elliptically polarized. Since the radiation which is emitted from the free electron laser FEL is linearly polarized (and therefore has a polarization contrast C of 1) the reflections of the radiation along its optical path to the lithographic apparatus act to decrease the polarization contrast C of the radiation. The polarization contrast C of the branch radiation beam which is provided to the lithographic apparatus is approximately 0.3.

In some embodiments it may be desirable to provide a lithographic apparatus with a branch radiation beam having a polarization contrast C which is less than a contrast threshold. For example, it may be desirable to provide a lithographic apparatus with a branch radiation beam having a polarization contrast C which is less than approximately 0.1. A polarization contrast C which is less than approximately 0.1 corresponds to a radiation beam having a phase retardance $\varepsilon$ which is between approximately 84° and 96°. In other embodiments the contrast threshold may be more or less than 0.1.

In the embodiment which was described above the polarization contrast C of the branch radiation beam which is provided to the lithographic apparatus is approximately 0.3. As was described above, for some applications it may be desirable to provide a branch radiation beam which has a polarization contrast C of less than 0.3. For example, it may be desirable to provide a branch radiation beam which has a polarization contrast C of less than 0.1. In order to further decrease the polarization contrast C of the branch radiation beam the number of reflective elements at which the branch radiation beam is reflected may be increased and the additional reflective elements may be configured to increase the phase retardance of the branch radiation beam. Additionally or alternatively the grazing angle Ω at one or more of the reflective elements may be increased in order to increase the phase retardance which occurs at the one or more reflective elements. However increasing the number of reflective elements at which the branch radiation beam is reflected and/or increasing the grazing angle Ω at one or more of the reflective elements may increase the amount of radiation which is absorbed at the reflective elements. Furthermore changing the number and/or the orientation of reflective elements at which the branch radiation beam is reflected may alter the position to which the branch radiation beam is directed and/or the direction of propagation of the branch radiation beam. Changing the number and/or the orientation of reflective elements may therefore require the position and/or the orientation of a lithographic apparatus to be changed such that it receives the branch radiation beam. It will be appreciated that in a lithographic system comprising a plurality of lithographic apparatuses changing the position and/or the orientation of lithographic apparatuses may be problematic.

In an alternative embodiment the polarization of the branch radiation beam which is provided to the lithographic apparatus may be controlled by controlling the polarization of the main radiation beam which is output from the free electron laser FEL. For example, the free electron laser FEL may output a main radiation beam which is elliptically polarized and has a phase retardance of approximately 18°. As was described above reflection of the radiation beam at the reflective elements causes a phase retardance of 72°. The combination of the phase retardance of the main radiation beam which is output from the free electron laser and the phase retardance which is caused by reflection at reflective elements therefore results in a substantially circularly polarized branch radiation beam which has phase retardance of approximately 90°.

In general, a beam delivery system comprising a plurality of reflective elements may be characterized in terms of a change in polarization which is caused by the beam delivery system. The change in polarization which is caused by a beam delivery system may be used to determine a polarization state which when input to the beam delivery system results in a branch radiation beam being output from the beam delivery system which has a desired polarization state.

Figure 101:
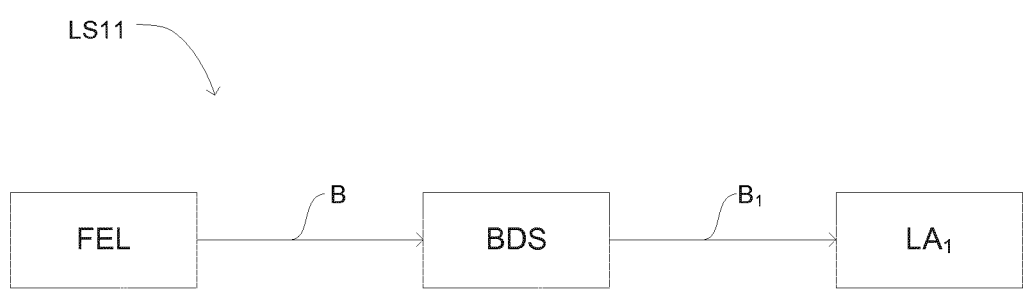
FIG. 101 is a schematic illustration of a lithographic system.

FIG. 101 is a schematic illustration of a lithographic system LS11. A free electron laser FEL emits a main radiation beam B. A beam delivery system BDS receives the main radiation beam B from the free electron laser FEL and directs a branch radiation beam $B_1$ to a lithographic apparatus $LA_1$. The branch radiation beam $B_1$ comprises at least some of the radiation beam B which is emitted from the free electron laser FEL. In practice the lithographic system LS11 may comprise a plurality of lithographic apparatuses and the beam delivery system BDS may be configured to split the main radiation beam B into a plurality of branch radiation beams and direct them to a plurality of lithographic apparatuses. However for the purposes of the following discussion only the path of a single branch radiation beam $B_1$ to a single lithographic apparatus $LA_1$ is considered.

In some embodiments the lithographic system LS11 may comprise a plurality of free electron lasers FEL whose outputs are combined to form the main radiation beam B. However for the purposes of the following discussion only a single free electron laser FEL is considered.

The polarization state of a radiation beam may be described in terms of a Jones vector J. A Jones vector J is a two component complex vector which describes the relative amplitude and relative phase of perpendicular components of the electric field vector of a radiation beam. For example, for a radiation beam propagating in a z-direction, the Jones vector J may describe the relative amplitude and relative phase of x and y-components of the electric field vector of the radiation beam. The polarization of the main radiation beam $B_1$ which is emitted from the free electron laser FEL and which is input to the beam delivery system BDS, may be charaterized with an input jones vector $J_{in}$. The change in the polarization of the branch radiation beam $B_1$ (relative to the main radiation beam B) which is caused by the beam delivery system BDS may be characterized with a Jones matrix M. The polarization of the branch radiation beam $B_1$ which is output from the beam delivery system BDS may be characterized with an output Jones matrix $J_{out}$. The output Jones matrix $J_{out}$ is given by equation 16.

$$J_{out}=MJ_{in} \qquad (16)$$

Figure 102A:
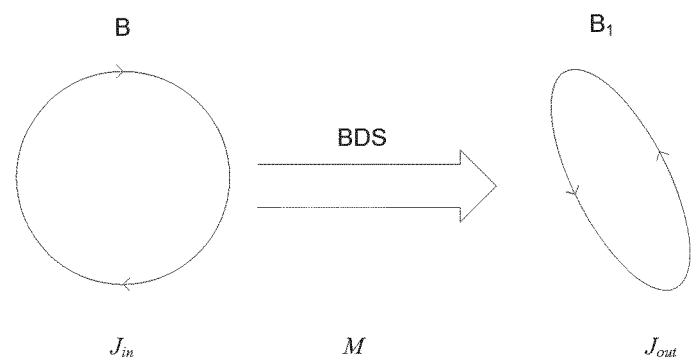
FIGS. 102A and 102B are representations of changes in polarization states which are caused by a beam delivery system of a lithographic system.

In order to control the polarization state of the branch radiation beam $B_1$ the Jones matrix M may be determined. FIG. 102A is a representation of the polarization states of the main radiation beam B and the branch radiation beam $\beta_1$. The main radiation beam B has a right-handed circular polarization state. The beam delivery system changes the polarization of radiation which propagates through it so as to provide a branch radiation beam $B_1$ which has a left-handed elliptical polarization state orientated as is shown in FIG. 102A. In this example, the polarization contrast C of the radiation which propagates through the beam delivery system BDS is undesirably increased by the beam delivery system BDS.

The change in polarization which is caused by the beam delivery system may be used to determine the Jones matrix M of the beam delivery system BDS. The determined Jones matrix M of the beam delivery system BDS may then be used to determine a polarization state of the main radiation beam B which results in a branch radiation beam $B_1$ having a desired polarization state. For example, it may be desired to provide a branch radiation beam $B_1$ having a right-handed circular polarization state. The Jones vector $J_{in}$ of a main radiation beam B which results in a branch radiation beam $B_1$ having a right-handed circular polarization state may be determined from:

$$J_{in}=M^{-1}J_{out} \qquad (17)$$

where $M^{-1}$ is the inverse of the Jones matrix M of the beam delivery system BDS and $J_{out}$ is the Jones vector of a branch radiation beam having the desired polarization state. The polarization state of the main radiation beam B which is emitted from the free electron laser FEL may be controlled such that is described by the Jones vector $J_{in}$ which is determined by equation 17 such that a branch radiation beam $B_1$ having the desired polarization state is output from the beam delivery system BDS.

Figure 102B:
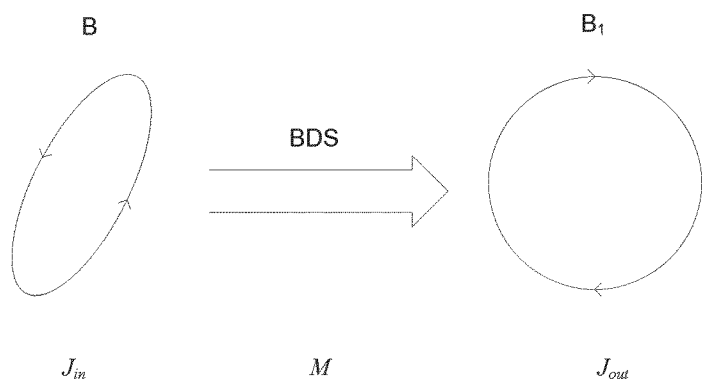

In the example which was shown in FIG. 102A a right-handed circular polarization state of the main radiation beam B was changed to a left-handed elliptical polarization state of the branch radiation beam $B_1$. A desired polarization state of the branch radiation beam $B_1$ may, for example, be a right-handed circular polarization state. By determining the Jones matrix M of the beam delivery system BDS of FIG. 102A, it may be found that inputting a main radiation beam B having a left-handed elliptical polarization state with a particular orientation to the beam delivery system BDS results in a branch radiation beam $B_1$ having the desired right-handed circular polarization state. FIG. 102B is a representation of the polarization states of the main radiation beam B and the branch radiation beam $B_1$ when a main radiation having a left-handed elliptical polarization state with a particular orientation is input to the beam delivery system BDS thereby resulting in a branch radiation beam $B_1$ having a right-handed circular polarization state. In the example shown in FIG. 102B the polarization contrast C of the radiation which propagates through the beam delivery system BDS is advantageously decreased by the beam delivery system BDS.

Figure 103:
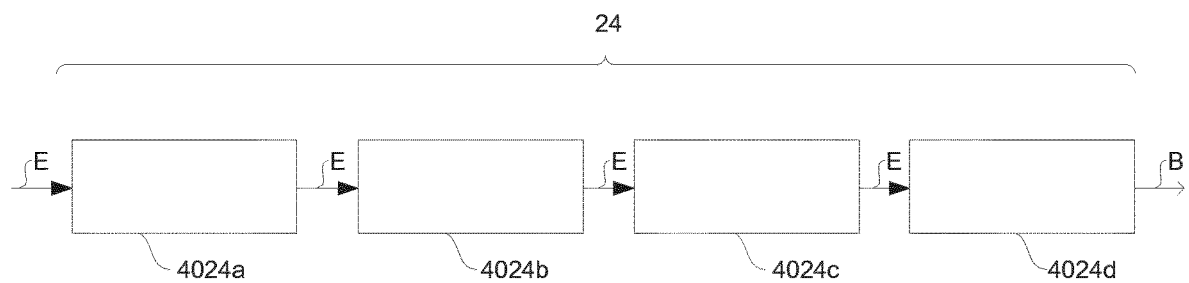
FIG. 103 is a schematic illustration of an undulator comprising a plurality of undulator sections.

An elliptical polarization state may be output from a free electron laser FEL as shown in FIG. 102B by forming an undulator of the free electron laser FEL from a combination of planar and helical undulator sections. FIG. 103 is a schematic illustration of an undulator 24 which may be used to provide a main radiation beam B having an elliptical polarization state. The undulator 24 comprises a plurality of undulator sections 4024a-4024d through which an electron beam B propagates. At least one of the undulator sections 4024a-4024d is a helical undulator section and at least one of the undulator sections 4024a-4024d is a planar undulator section.

In an embodiment, first, second and third undulator sections 4024a-4024c are helical undulator sections from which circularly polarized radiation is emitted. A fourth undulator section 4024d is a planar undulator section from which linearly polarized radiation is emitted. The circularly polarized radiation which is emitted from the first, second and third undulator sections 4024a-4024c passes through the planar undulator section 4024d. Some of the circularly polarized radiation may be absorbed by electrons in the planar undulator section 4024d and re-emitted as linearly polarized radiation. The combination of the helical undulator sections 4024a-4024c and the planar undulator section 4024d results in emission of a radiation beam B from the undulator 24 which is elliptically polarized.

The planar undulator section 4024d comprises magnets which lie in a polarization plane (not shown in FIG. 103). The polarization plane in the planar undulator section 4024d determines the orientation of the elliptical polarization of the radiation beam B. In particular the major axis of an ellipse which is traced out by the electric field vector of the radiation beam B is aligned with the polarization plane in the planar undulator section 4024d.

The polarization contrast C of the radiation beam B which is emitted from the undulator 24 depends on the relative gains of the radiation in the helical and planar undulator sections. Typically the gain of radiation in an undulator section increases with increases in the length of the undulator section. The polarization contrast C of the radiation beam B may therefore be controlled by controlling the relative lengths of the planar and helical undulator sections. For example, increasing the total length of the helical undulator sections 4024a-4024c relative to the length of the planar undulator section 4024d leads to a decrease in the polarization contrast C of the radiation beam B which is emitted from the undulator 24. Increasing the length of the planar undulator section 4024d relative to the total length of the helical undulator sections 4024a-4024c leads to an increase in the polarization contrast C of the radiation beam B which is emitted from the undulator 24.

Alternative embodiments of an undulator 24 may include more or fewer helical and/or planar undulator sections than the undulator 24 which is shown in FIG. 103.

The lithographic system LS11 which is depicted in FIG. 101 has been described above in the context of a single branch radiation beam $B_1$ which is provided to a single lithographic apparatus $LA_1$. However it will be appreciated that the beam delivery system BDS may splits the main radiation beam B into a plurality of branch radiation beams which are directed to a plurality of lithographic apparatuses. In some embodiments it may be desirable to provide the plurality of lithographic apparatuses with branch radiation beams which have substantially the same polarization state. In such embodiments it is therefore desirable that the beam delivery system BDS is configured to change the polarization state of each of the branch radiation beams in the substantially the same manner. That is, the Jones matrix M for each branch radiation beam is substantially the same. This allows a single main radiation beam B having a first polarization state to be split into a plurality of branch radiation beams which are provided to a plurality of lithographic apparatuses and which each have a second polarization state. In general the polarization contrast C of the second polarization state is less than the polarization contrast C of the first polarization state.

Embodiments of a lithographic system LS11 have been described above in which a main radiation beam B is emitted from a single free electron laser FEL. In other embodiments the main radiation beam B may comprise radiation which is emitted from a plurality of free electron lasers FEL which is combined to form the main radiation beam B. For example, an optical system 40 (e.g. the optical system 40 which is shown in FIGS. 4 and 5) may combine a plurality of radiation beams received from a plurality of free electron lasers FEL to form a main radiation beam B. In such an embodiment the polarization state of the main radiation beam B which is provided to a beam delivery system BDS depends on the polarization state of the radiation which is emitted from each of the free electron lasers FEL and any changes to the polarization of the radiation which may occur during the combination of the radiation into a main radiation beam B.

As has been described above the polarization state of a branch radiation beam $B_1$ which is provided to a lithographic apparatus $LA_1$ depends on the polarization state of a main radiation beam B and on any changes to the polarization state of radiation as it propagates through a beam delivery system BDS. It will be appreciated that the principles which have been described above with reference to various embodiments of a lithographic system LS11 may be used in order to design a lithographic system LS11 such that a branch radiation beam having a desired polarization state is provided to a lithographic apparatus.

Figure 104:
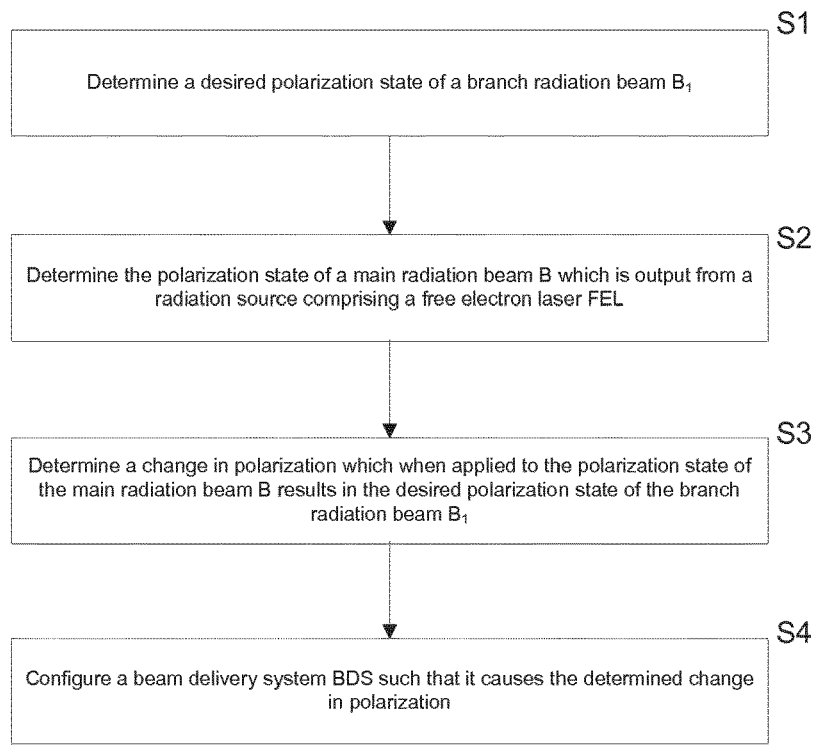
FIG. 104 is a flow chart representing a first method of configuring a lithographic system.

FIG. 104 is a flow chart of a first method of configuring a lithographic system LS11. At step 1 a desired polarization state of a branch radiation beam $B_1$ is determined. For example, it may be determined that it is desirable to provide a branch radiation beam $B_1$ which is circularly polarized.

At step 2 the polarization state of a main radiation beam B which is output from a radiation source is determined. The radiation source comprises at least one free electron laser FEL. For example, the radiation source may comprise a single free electron laser which emits the radiation beam B. Alternatively the radiation source may comprise a plurality of free electron lasers whose outputs are combined to form a main radiation beam B. The main radiation beam B may, for example, be linearly polarized. Alternatively the main radiation beam B may be elliptically polarized.

At step 3 a change in the polarization state of the main radiation beam B is determined which results in the desired polarization state of the branch radiation beam $B_1$. For example, a phase retardance may be determined which when applied to the main radiation beam B results in a branch radiation beam $B_1$ having a desired phase retardance.

At step 4 a beam delivery system BDS which delivers at least some of the radiation of the main radiation beam to form the branch radiation beam $B_1$ is configured such that the beam delivery system BDS causes the change in polarization which was determined at step 3. For example, reflective elements of the beam delivery system BDS may comprise a first group of reflective elements which have planes of incidence which are orientated at an angle of approximately +45° relative to a polarization plane of the main radiation beam B and a second group of reflective elements which have planes of incidence which are orientated at an angle of approximately −45° relative to the polarization plane such that at each reflective element s and p-polarized components have substantially the same magnitude. The first and second group of reflective elements may be orientated such that grazing angles Ω at each reflective element are such that the net phase retardance which is occurs along the optical path of radiation through the beam delivery system BDS is the phase retardance which was determined at step 3.

The first method of configuring a lithographic system LS11 therefore results in a beam delivery system BDS which is configured to change the polarization state of a main radiation beam so as to provide a branch radiation beam $B_1$ having a desired polarization.

Figure 105:
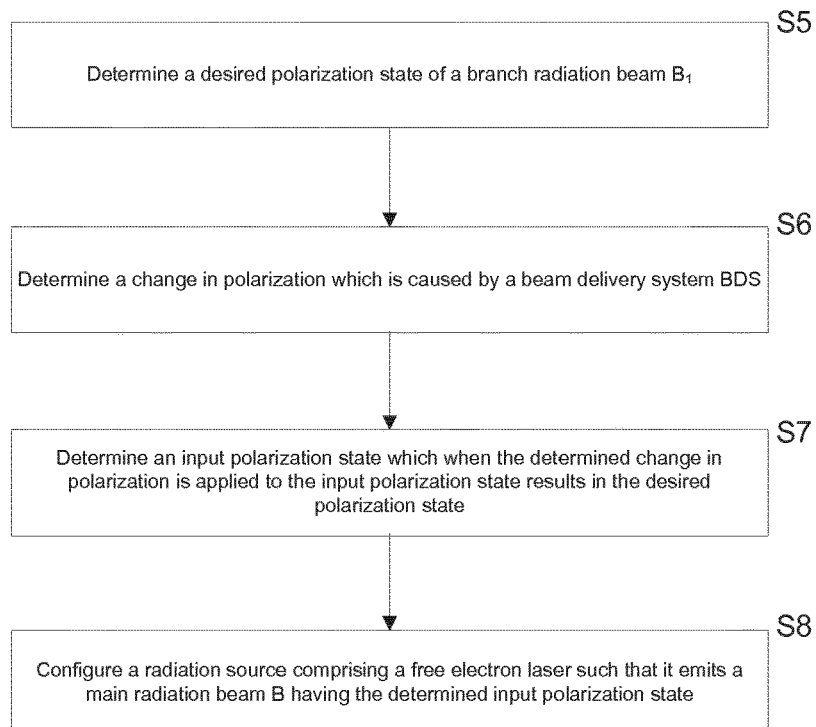
FIG. 105 is a flow chart representing a first method of configuring a lithographic system.

FIG. 105 is a flow chart of a second method of configuring a lithographic system LS11 in which a radiation source is configured so as to provide a main radiation beam whose polarization state, when changed by a beam delivery system, results in a branch radiation beam $B_1$ having a desired polarization.

At step 5 a desired polarization state of a branch radiation beam $B_1$ is determined. For example, it may be determined that it is desirable to provide a branch radiation beam $B_1$ which is circularly polarized.

At step 6 a change in polarization which is caused by a beam delivery system BDS is determined. For example, a phase retardance which is caused by a beam delivery system BDS may be determined. Additionally or alternatively a Jones matrix M which describes the change in polarization which is caused by the beam delivery system BDS may be determined. The change in polarization which is caused by the beam delivery system BDS may, for example, be determined theoretically by calculating the change in polarization which is caused by each reflective element of the beam delivery system BDS. Additionally or alternatively the change in polarization which is caused by the beam delivery system BDS may be determined experimentally. For example, a radiation beam of known polarization may be input to the beam delivery system BDS and the polarization of a radiation beam which is output from the beam delivery system BDS may be measured. The polarizations of the input and output beams may be compared in order to determine the change in polarization which is caused by the beam delivery system BDS.

At step 7 an input polarization state is determined which combined with the polarization change which was determined at step 6 results in a branch radiation beam $B_1$ having the desired polarization which was determined at step 5. For example, a Jones matrix M of the beam delivery system which was determined at step 6 may be inverted and combined and multiplied by an output Jones vector $J_{out}$ corresponding to the desired polarization state determined at step 5 in order to determine an input Jones vector $J_{in}$ accordance with equation 17.

At step 8 a radiation source is configured such that it emits a main radiation beam B having the input polarization state which was determined at step 7. The radiation source comprises at least one free electron laser FEL. The at least free electron laser FEL may comprise a plurality of undulator sections which together output a radiation beam having the determined input polarization state. For example, if the determined input polarization state is an elliptical polarization state then one or more helical undulator sections may be combined with one or more planar undulator sections such that the free electron laser FEL emits the determined elliptical polarization state.

In an embodiment the first method of configuring a lithographic system LS11 may be combined with the second method of configuring a lithographic system LS11. That is, both the radiation source and the beam delivery system BDS may be configured in order to provide a branch radiation beam $B_1$ having a desired polarization state.

Whilst embodiments have been described above in which a branch radiation beam $B_1$ is provided to a lithographic apparatus $LA_1$, a branch radiation beam $B_1$ may be provided to any tool. For example, a branch radiation beam may be provided to any lithographic tool which may comprise a lithographic apparatus, a mask inspection apparatus, or another form of lithographic tool. Any of the methods and apparatus which have been described above with reference to providing a lithographic apparatus with a branch radiation beam may therefore be equivalently used to provide any tool (e.g. a lithographic apparatus) with a branch radiation beam.

It will be appreciated that features described above with respect to one example embodiment may be combined with features described with respect to another example embodiment. For example, while a number of lithographic systems LS-LS11 have been described above, it will be appreciated that components of one lithographic system may be used with other lithographic systems even where such a combination is not explicitly described above. For example, while some lithographic systems comprise one beam delivery system BDS-BDS5, it will be appreciated that other beam delivery systems may be used with each lithographic system. More generally, it will be appreciated that components and arrangements described in a particular example embodiment may be used in other example embodiments.

Embodiments of a lithographic system may also include one or more mask inspection apparatus MIA and/or one or more Aerial Image Measurement Systems (AIMS). In some embodiments, the lithographic system may comprise two mask inspection apparatuses to allow for some redundancy. This may allow one mask inspection apparatus to be used when the other mask inspection apparatus is being repaired or undergoing maintenance. Thus, one mask inspection apparatus is always available for use. A mask inspection apparatus may use a lower power radiation beam than a lithographic apparatus. Further, it will be appreciated that radiation generated using a free electron laser of the type described herein may be used for applications other than lithography or lithography related applications.

The term "relativistic electrons" should be interpreted to mean electrons which relativistic energies, which they may obtain through acceleration by a particle accelerator. An electron may be considered to have a relativistic energy when its kinetic energy is comparable to or greater than its rest mass energy (511 keV). In practice a particle accelerator which forms part of a free electron laser may accelerate electrons to energies which are much greater than its rest mass energy. For example a particle accelerator may accelerate electrons to energies of >10 MeV, >100 MeV, >1 GeV or more.

Embodiments of the invention have been described in the context of free electron lasers which output an EUV radiation beam. However a free electron laser may be configured to output radiation having any wavelength. Some embodiments of the invention may therefore comprise a free electron which outputs a radiation beam which is not an EUV radiation beam.

The term "EUV radiation" may be considered to encompass electromagnetic radiation having a wavelength within the range of 4-20 nm, for example within the range of 13-14 nm. EUV radiation may have a wavelength of less than 10 nm, for example within the range of 4-10 nm such as 6.7 nm or 6.8 nm.

The lithographic apparatuses described herein may be used in the manufacture of ICs. Alternatively, the lithographic apparatuses described herein may have other applications. Possible other applications include the manufacture of integrated optical systems, guidance and detection patterns for magnetic domain memories, flat-panel displays, liquid-crystal displays (LCDs), thin-film magnetic heads, etc.

While specific embodiments of the invention have been described above, it will be appreciated that the invention may be practiced otherwise than as described. The descriptions above are intended to be illustrative, not limiting. Thus it will be apparent to one skilled in the art that modifications may be made to the invention as described without departing from the scope of the claims set out below.

The invention claimed is:

1. A beam splitting apparatus for use within a lithographic system, comprising:
a plurality of static mirrors each configured to receive a different part of a first radiation beam from a radiation source and reflect a respective portion of radiation along one of a plurality of directions to form a plurality of branch radiation beams for provision to two or more lithographic apparatuses,
wherein each lithographic apparatus is configured to receive a respective one of the plurality of branch radiation beams, direct the respective branch radiation beam onto a patterning device, and project a respective patterned beam onto a substrate,
wherein each lithographic apparatus is associated with a respective patterning device and a respective substrate such that patterning of plural substrates can be performed by the two or more lithographic apparatuses in parallel,
wherein the radiation source comprises a first free electron laser and a second free electron laser, and
wherein the first radiation beam is a composite radiation beam comprising radiation from at least one of the first and second free electron lasers.

2. The beam splitting apparatus of claim 1, wherein each of the plurality of directions provides a respective branch optical path, each branch optical path being associated with a respective one of the lithographic apparatuses.

3. The beam splitting apparatus of claim 2, wherein at least one branch optical path is associated with two or more of the plurality of static mirrors such that at least one of the plurality of branch radiation beams comprises a plurality of said reflected portions of radiation.

4. The beam splitting apparatus of claim 2, wherein each of the branch optical paths is associated with a respective plurality of the static mirrors such that each branch radiation beam comprises a plurality of said reflected portions.

5. The beam splitting apparatus of claim 1, wherein each static mirror is arranged to extend partially across a path of the first radiation beam.

6. The beam splitting apparatus claim 1, wherein at least some of the plurality of static mirrors are configured to reflect a solid area of the first radiation beam.

7. The beam splitting apparatus of claim 2, wherein at least two or more of the plurality of static mirrors comprise a reflective grating, wherein the reflective grating comprises a plurality of faces.

8. The beam splitting apparatus of claim 7, wherein each face of the reflective grating that is associated with a same one of the plurality of directions extends substantially parallel to a single silicon crystal plane of the reflective grating.

9. The beam splitting apparatus of claim 7, wherein the reflective grating is a macro-scale grating.

10. The beam splitting apparatus of claim 9, wherein the faces are arranged such that expansion of each reflected portion causes partial overlap of at least two reflected portions associated with one branch optical path at the one of the lithographic apparatuses associated with that one branch optical path.

11. The beam splitting apparatus of claim 10, wherein the faces are arranged such that the overlapping reflected portions provide a branch radiation beam having an intensity profile substantially the same as an intensity profile of the first radiation beam.

12. The beam splitting apparatus of claim 7, wherein the reflective grating comprises a first plurality of faces associated with a first branch optical path to provide a first branch radiation beam;
wherein each one of the first plurality of faces is arranged to reflect a respective part of the first radiation beam to form a respective sub-beam of the first branch radiation beam; and
wherein the first plurality of faces is arranged such that if a position of the first radiation beam changes in a plane perpendicular to a propagation direction of the first radiation beam, a power received by at least one of the first plurality of faces increases and a power received by at least one of the first plurality of faces decreases.

13. The beam splitting apparatus of claim 7, wherein the reflective grating is a micro-scale grating.

14. The beam splitting apparatus of claim 13, wherein the faces of the reflective grating are arranged such that portions of radiation reflected from the grating diffract to provide said plurality of branch radiation beams.

15. The beam splitting apparatus of claim 14, wherein the faces of the reflective grating are arranged such that each branch radiation beam has an intensity profile substantially similar to an intensity profile of the first radiation beam.

16. The beam splitting apparatus of claim 7, wherein the faces of the reflective grating have translational symmetry in at least one direction perpendicular to a direction of propagation of the first radiation beam.

17. The beam splitting apparatus of claim 7, wherein the beam splitting apparatus comprises expansion and/or flat-top forming optics, and wherein the reflective grating is disposed upstream of said expansion and/or flat-top forming optics.

18. The beam splitting apparatus of claim 7, wherein the reflective grating is arranged to receive the radiation beam from a flat mirror disposed between the radiation source and the reflective grating.

19. The beam splitting apparatus of claim 7, wherein the reflective grating is formed from etched silicon.

20. The beam splitting apparatus of claim 19, wherein the reflective grating comprises a reflective coating, the reflective coating comprising a material or composition selected for grazing incidence reflectivity of a desired wavelength.

21. The beam splitting apparatus of claim 7, further comprising a second reflective grating arranged to further split at least one of the branch radiation beams provided by the reflective grating.

22. The beam splitting apparatus of claim 1, wherein at least one of the static mirrors is provided with one or more apertures arranged to permit a portion of the first radiation beam not reflected by the at least one static mirror through the aperture towards a further one of the plurality of static mirrors.

23. The beam splitting apparatus of claim 1, wherein at least one of said static mirrors comprises a ring-shaped reflective surface arranged to reflect a portion of radiation along an associated branch optical path and to permit a portion of the first radiation beam through an aperture defined by the ring toward a further one of the plurality of static mirrors.

24. The beam splitting apparatus of claim 23, wherein said ring-shaped reflective surface is arranged such that if a position of the first radiation beam changes in a plane perpendicular to a propagation direction of the first radiation beam, a power received by at least one part of the ring-based reflective surface increases and a power received by at least a further part of the ring-based reflective surface decreases.

25. The beam splitting apparatus of claim 1, wherein at least one of the static mirrors comprises a first reflective surface and a second reflective surface joined along an edge, wherein the edge is arranged for placement within a radiation beam.

26. The beam splitting apparatus of claim 1, wherein at least one of the static mirrors is provided with active cooling.

27. The beam splitting apparatus of claim 1, further comprising: at least one diverging optical element arranged to increase the divergence of a radiation beam.

28. The beam splitting apparatus of claim 27, further comprising: a plurality of diverging optical elements, each arranged to increase the divergence of a respective one of the branch radiation beams.

29. A system comprising:
a radiation source configured to produce a main radiation beam, the radiation source comprising:
a first free electron laser; and
a second free electron laser;
a plurality of optical elements configured to:
receive at least one of a first radiation beam from the first free electron laser and a second radiation beam from the second free electron laser; and
output the main radiation beam;
a beam splitting apparatus configured to split the main radiation beam into a plurality of branch radiation beams, comprising:
a plurality of static mirrors each configured to:
receive a different part of the main radiation beam; and
reflect a respective portion of radiation along one of a plurality of directions to form the branch radiation beams; and
two or more lithographic apparatuses, wherein each lithographic apparatus is configured to receive a respective one of the plurality of branch radiation beams, direct the respective branch radiation beam onto a patterning device, and project a respective patterned beam onto a substrate,
wherein each lithographic apparatus is associated with a respective patterning device and a respective substrate such that patterning of plural substrates can be performed by the two or more lithographic apparatuses in parallel.

30. The system of claim 29, further comprising: a respective diverging optical element for each of the lithographic apparatuses.

31. The system of claim 30, wherein the beam splitting apparatus is configured such that at least two or more of the plurality of static mirrors comprise a reflective grating comprising a plurality of faces, and wherein each respective diverging optical element is downstream of the reflective grating.

32. The system of claim 30, wherein the diverging optical element comprises a convex, concave, and/or saddle shaped grazing incidence mirror.

33. The system of claim 29, further comprising: optics configured to modify a cross-sectional shape of a branch radiation beam.

34. The system of claim 33, wherein the optics comprise an array of mirrors arranged to split the branch radiation beam into a plurality of sub-beams and to combine the sub-beams together.

35. The system of claim 29, wherein the main radiation beam comprises EUV radiation.

36. The system of claim 29, further comprising: a mask inspection apparatus arranged to receive one of the branch radiation beams from the beam splitting apparatus.

37. A method comprising:
producing a main radiation beam using a radiation source wherein the radiation source comprises a first free electron laser and a second free electron laser, wherein the main radiation beam is a composite radiation beam comprising radiation from at least one of the first and second free electron lasers; and
directing the main radiation beam to a beam splitting apparatus,
wherein the beam splitting apparatus comprises a plurality of static mirrors each arranged to receive a different part of the main radiation beam and reflect a respective portion of radiation along one of a plurality of directions to form a plurality of branch radiation beams for provision to a first lithographic apparatus and a second lithographic apparatus,
wherein the first and second lithographic apparatuses are each configured to receive a respective one of the plurality of branch radiation beams, direct the respective branch radiation beam onto a patterning device, and project a respective patterned branch onto a substrate, and
wherein each lithographic apparatus is associated with a respective patterning device and a respective substrate such that patterning of plural substrates can be performed by the two or more lithographic apparatuses in parallel.

38. The method of claim 37, further comprising: directing each branch radiation beam to a respective lithographic apparatus.

* * * * *